United States Patent
von Geldern et al.

(10) Patent No.: US 11,667,606 B2
(45) Date of Patent: Jun. 6, 2023

(54) THYROMIMETICS

(71) Applicant: Autobahn Therapeutics, Inc., San Diego, CA (US)

(72) Inventors: Thomas von Geldern, Richmond, IL (US); Bradley Backes, San Francisco, CA (US)

(73) Assignee: AUTOBAHN THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/803,853

(22) Filed: Feb. 27, 2020

(65) Prior Publication Data

US 2021/0053917 A1 Feb. 25, 2021

Related U.S. Application Data

(60) Provisional application No. 62/953,100, filed on Dec. 23, 2019, provisional application No. 62/812,890, filed on Mar. 1, 2019.

(51) Int. Cl.
| | | |
|---|---|---|
| *C07D 205/04* | (2006.01) | |
| *C07C 59/68* | (2006.01) | |
| *C07C 69/734* | (2006.01) | |
| *C07C 235/34* | (2006.01) | |
| *C07C 235/38* | (2006.01) | |
| *C07C 317/46* | (2006.01) | |
| *C07D 203/16* | (2006.01) | |
| *C07D 207/08* | (2006.01) | |
| *C07D 213/55* | (2006.01) | |
| *C07D 239/26* | (2006.01) | |
| *C07D 307/54* | (2006.01) | |
| *C07D 333/24* | (2006.01) | |
| *C07D 333/28* | (2006.01) | |
| *A61P 5/14* | (2006.01) | |

(52) U.S. Cl.
CPC ............ *C07D 205/04* (2013.01); *A61P 5/14* (2018.01); *C07C 59/68* (2013.01); *C07C 69/734* (2013.01); *C07C 235/34* (2013.01); *C07C 235/38* (2013.01); *C07C 317/46* (2013.01); *C07D 203/16* (2013.01); *C07D 207/08* (2013.01); *C07D 213/55* (2013.01); *C07D 239/26* (2013.01); *C07D 307/54* (2013.01); *C07D 333/24* (2013.01); *C07D 333/28* (2013.01)

(58) Field of Classification Search
None
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,652,441 A | 3/1987 | Okada et al. |
| 4,675,189 A | 6/1987 | Kent et al. |
| 4,677,191 A | 6/1987 | Tanaka et al. |
| 4,723,027 A | 2/1988 | Stoutamire et al. |
| 4,728,721 A | 3/1988 | Yamamoto et al. |
| 4,741,897 A | 5/1988 | Andrews et al. |
| 4,917,893 A | 4/1990 | Okada et al. |
| 4,992,445 A | 2/1991 | Lawter et al. |
| 5,001,139 A | 3/1991 | Lawter et al. |
| 5,023,252 A | 6/1991 | Hseih |
| 5,466,569 A | 11/1995 | Eber et al. |
| 5,616,345 A | 4/1997 | Geoghegan et al. |
| 5,883,294 A | 3/1999 | Scanlan et al. |
| 6,054,485 A | 4/2000 | Schwartz et al. |
| 6,107,517 A | 8/2000 | Scanlan et al. |

(Continued)

FOREIGN PATENT DOCUMENTS

| | | |
|---|---|---|
| CN | 1882327 A | 12/2006 |
| CN | 101180097 A | 5/2008 |

(Continued)

OTHER PUBLICATIONS

Borngraeber et al. "Ligand Selectivity by Seeking Hydrophobicity in Thyroid Hormone Receptor" PNAS, 2003, vol. 100, No. 26, pp. 15358-15363.*

(Continued)

*Primary Examiner* — Joseph R Kosack
(74) *Attorney, Agent, or Firm* — Wilson Sonsini Goodrich & Rosati

(57) ABSTRACT

Compounds are provided having the structure of Formula (I):

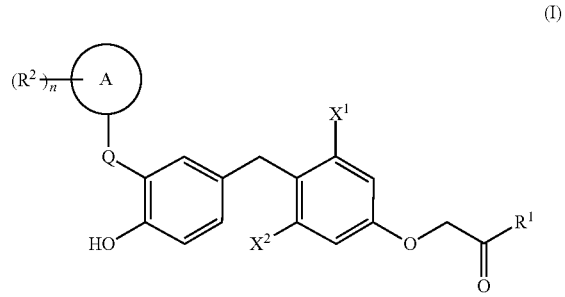

or a pharmaceutically acceptable isomer, racemate, hydrate, solvate, isotope, or salt thereof, wherein A, $X^1$, $X^2$, Q, $R^1$, $R^2$ and n are as defined herein. Such compounds function as thyromimetics and have utility for treating diseases such as neurodegenerative disorders and fibrotic diseases. Pharmaceutical compositions containing such compounds are also provided, as are methods of their use and preparation.

38 Claims, No Drawings

(56) References Cited

U.S. PATENT DOCUMENTS

| | | | |
|---|---|---|---|
| 6,236,946 | B1 | 5/2001 | Scanlan et al. |
| 7,288,571 | B2 | 10/2007 | Hangeland et al. |
| 7,302,347 | B2 | 11/2007 | Baxter et al. |
| 9,562,012 | B2 | 2/2017 | Tanis et al. |
| 9,701,650 | B2 | 7/2017 | Scanlan et al. |
| 10,130,643 | B2 | 11/2018 | Cable et al. |
| 10,226,438 | B2 | 3/2019 | Scanlan et al. |
| 10,392,356 | B2 | 8/2019 | Scanlan et al. |
| 10,544,075 | B2 | 1/2020 | Scanlan et al. |
| 10,870,616 | B2 | 12/2020 | Scanlan et al. |
| 11,104,654 | B2 | 8/2021 | Scanlan et al. |
| 11,325,886 | B2 | 5/2022 | Scanlan et al. |
| 2003/0203898 | A1 | 10/2003 | Haning et al. |
| 2003/0215434 | A1 | 11/2003 | Khan et al. |
| 2005/0282872 | A1 | 12/2005 | Hangeland et al. |
| 2007/0021407 | A1 | 1/2007 | Boyle et al. |
| 2008/0124280 | A1 | 5/2008 | Mousa et al. |
| 2008/0221170 | A1 | 9/2008 | Roberts et al. |
| 2009/0028925 | A1 | 1/2009 | Erion et al. |
| 2009/0062330 | A1 | 3/2009 | Kalafer et al. |
| 2009/0105347 | A1 | 4/2009 | Scanlan et al. |
| 2009/0232879 | A1 | 9/2009 | Cable et al. |
| 2009/0306225 | A1 | 12/2009 | Lichter et al. |
| 2009/0318514 | A1 | 12/2009 | Garcia Collazo et al. |
| 2010/0099608 | A1 | 4/2010 | Browning |
| 2010/0216771 | A1 | 8/2010 | Li |
| 2010/0303934 | A1 | 12/2010 | Soumyanath et al. |
| 2011/0178134 | A1 | 7/2011 | Jaehne et al. |
| 2012/0004166 | A1 | 1/2012 | Keil et al. |
| 2012/0245213 | A1 | 9/2012 | Mosinger et al. |
| 2013/0289024 | A1 | 10/2013 | Johansen et al. |
| 2014/0235676 | A1 | 8/2014 | Landreth |
| 2014/0288077 | A1 | 9/2014 | Fujii et al. |
| 2016/0081955 | A1 | 3/2016 | Scanlan et al. |
| 2016/0244418 | A1 | 8/2016 | Scanlan et al. |
| 2017/0007589 | A1 | 1/2017 | Ding et al. |
| 2017/0226154 | A1 | 8/2017 | Evans et al. |
| 2018/0057472 | A1 | 3/2018 | Scanlan et al. |
| 2019/0175531 | A1 | 6/2019 | Scanlan et al. |
| 2020/0181103 | A1 | 6/2020 | Scanlan et al. |
| 2020/0361849 | A1 | 11/2020 | Von Geldern et al. |
| 2020/0405669 | A1 | 12/2020 | Scanlan et al. |
| 2021/0002208 | A1 | 1/2021 | Scanlan |
| 2021/0087137 | A1 | 3/2021 | Scanlan et al. |

FOREIGN PATENT DOCUMENTS

| | | |
|---|---|---|
| CN | 101189248 A | 5/2008 |
| CN | 101547898 A | 9/2009 |
| CN | 101600450 A | 12/2009 |
| CN | 101610774 A | 12/2009 |
| CN | 101848712 A | 9/2010 |
| CN | 107848940 A | 3/2018 |
| EP | 3259246 A1 | 12/2017 |
| JP | 2002513422 A | 5/2002 |
| JP | 2003500483 A | 1/2003 |
| JP | 2004512303 A | 4/2004 |
| JP | 2004517037 A | 6/2004 |
| JP | 2008542301 A | 11/2008 |
| JP | 2008545711 A | 12/2008 |
| JP | 2012106996 A | 6/2012 |
| JP | 2016517884 A | 6/2016 |
| PE | 20180021 A1 | 1/2018 |
| RU | 2007148927 A | 7/2009 |
| WO | WO-9321146 A1 | 10/1993 |
| WO | WO-9900353 A1 | 1/1999 |
| WO | WO-0039077 A2 | 7/2000 |
| WO | WO-0073292 A1 | 12/2000 |
| WO | WO-0160784 A1 | 8/2001 |
| WO | 02/072539 A1 | 9/2002 |
| WO | WO-02081426 A1 | 10/2002 |
| WO | WO-2004043939 A1 | 5/2004 |
| WO | WO-2006031922 A2 | 3/2006 |
| WO | WO-2007110226 A1 | 10/2007 |
| WO | WO-2008125724 A1 | 10/2008 |
| WO | WO-2013006734 A1 | 1/2013 |
| WO | WO-2014078892 A1 | 5/2014 |
| WO | WO-2014178892 A1 | 11/2014 |
| WO | WO-2014178931 A1 | 11/2014 |
| WO | WO-2015188015 A1 | 12/2015 |
| WO | WO-2016134292 A1 | 8/2016 |
| WO | WO-2017015360 A1 | 1/2017 |
| WO | WO-2017201320 A1 | 11/2017 |
| WO | 2018/032012 A1 | 2/2018 |
| WO | WO-2018208707 A1 | 11/2018 |
| WO | WO-2019160980 A1 | 8/2019 |
| WO | WO-2020118564 A1 | 6/2020 |
| WO | WO-2020123861 A1 | 6/2020 |
| WO | WO-2020180624 A1 | 9/2020 |
| WO | WO-2021108549 A1 | 6/2021 |

OTHER PUBLICATIONS

Patani et al. "Bioisosterism: A Rational Approach in Drug Design" Chemical Reviews, 1996, vol. 96, pp. 3147-3176.*

PubChem SID 235918886 [https://pubchem.ncbi.nlm.nih.gov/substance/235918886] (2015).

Actis et al., Small molecule inhibitors of PCNA/PIP-box interaction suppress translesion DNA synthesis. Bioorg Med Chem. 21(7):1972-1977 (2013).

Alonso-Merino et al., Thyroid hormones inhibit TGF-beta signaling and attenuate fibrotic responses. Proc Natl Acad Sci U S A. 113(24):E3451-E3460 (2016).

Balkwill et al., Smoldering and polarized inflammation in the initiation and promotion of malignant disease. Cancer Cell 7(3):211-217 (2005).

Baxi et al., A selective thyroid hormone beta receptor agonist enhances human and rodent oligodendrocyte differentiation. Glia 62(9):1513-1529 (2014).

Baxter et al., Selective activation of thyroid hormone signaling pathways by GC-1: a new approach to controlling cholesterol and body weight. Trends Endocrinol Metab. 15(4):154-157 (2004).

Baxter et al., Selective modulation of thyroid hormone receptor action. J. Steroid Biochem. Mol. Bio. 76:31-42 (2001).

Berge et al. Pharmaceutical Salts. Journal of Pharmaceutical Sciences 66(1):1-19 (Jan. 1977).

Berkenstam et al., The thyroid hormone mimetic compound KB2115 lowers plasma LDL cholesterol and stimulates bile acid synthesis without cardiac effects in humans. Proc Natl Acad Sci U S A 105(2):663-667 (2008).

Bernal et al., Action of thyroid hormone in brain. J Endocrinol Invest. 25(3):268-288 (2002).

Bernal et al., Thyroid hormone receptors in brain development and function. Nat Clin Pract Endocrinol Metab. 3(3):249-259 (2007).

Biondi et al., Hypothyroidism as a risk factor for cardiovascular disease. Endocrine 24: 1-13 (2004).

Boger et al., Fatty acid amide hydrolase substrate specificity. Bioorg Med Chem Lett. 10(23):2613-2616 (2000).

Boymond et al., Preparation of highly functionalized grignard reagents by an iodine-magnesium exchange reaction and its application in solid-phase synthesis. Angew Chem Int Ed Engl. 37(12):1701-1703 (1998).

Calza et al., Thyroid hormone and remyelination in adult central nervous system: a lesson from an inflammatory-demyelinating disease. Brain Res Brain Res Rev. 48(2):339-346 (2005).

Chiellini et al., A high-affinity subtype-selective agonist ligand for the thyroid hormone receptor. Chemistry and Biology 5(6):299-306 (1998).

Chiellini et al., Synthesis and biological activity of novel thyroid hormone analogues: 5'-aryl substituted GC-1 derivatives. Bioorg Med Chem. 10(2):333-346 (2002).

Cravatt et al., Supersensitivity to anandamide and enhanced endogenous cannabinoid signaling in mice lacking fatty acid amide hydrolase. Proc Natl Acad Sci U S A 98(16):9371-9376 (2001).

Dell'Acqua et al., Functional and molecular evidence of myelin- and neuroprotection by thyroid hormone administration in experimental allergic encephalomyelitis. Neuropathol Appl Neurobiol. 38(5):454-470 (2012).

(56) References Cited

OTHER PUBLICATIONS

Devereaux et al., Increasing thyromimetic potency through halogen substitution. ChemMedChem. 11(21):2459-2465 (2016).
D'Intino et al., Triiodothyronine administration ameliorates the demyelination/remyelination ratio in a non-human primate model of multiple sclerosis by correcting tissue hypothyroidism. J Neuroendocrinol. 23(9):778-790 (2011).
Doran et al., The impact of P-glycoprotein on the disposition of drugs targeted for indications of the central nervous system: evaluation using the MDR1A/1B knockout mouse model. Drug Metab Dispos. 33(1):165-174 (2005).
Edgar et al., An efficient and selective method for the preparation of iodophenols. Journal of Organic Chemistry 55:5287-5291 (1990).
Engelen et al., X-linked adrenoleukodystrophy (X-ALD): clinical presentation and guidelines for diagnosis, follow-up and management. Orphanet J Rare Dis. 7:51 [1-14] (2012).
Erion et al., Targeting thyroid hormone receptor-beta agonists to the liver reduces cholesterol and triglycerides and improves the therapeutic index. Proc Natl Acad Sci U S A 104(39):15490-15495 (2007).
Ferrara et al., Ester-to-amide rearrangement of ethanolamine-derived prodrugs of sobetirome with increased blood-brain barrier penetration. Bioorg Med Chem. 25(10):2743-2753 (2017).
Fourcade et al., Thyroid hormone induction of the adrenoleukodystrophy-related gene (ABCD2). Mol. Pharmacol. 63:1296-1303 (2003).
Genin et al., Induction of the adrenoleukodystrophy-related gene (ABCD2) by thyromimetics. J Steroid Biochem Mol Biol. 116(1-2):37-43 (2009).
Gold et al. Understanding pathogenesis and therapy of multiple sclerosis via animal models: 70 years of merits and culprits in experimental autoimmune encephalomyelitis research. Brain 129:1953-1971 (2006).
Gould et al. Salt Selection for Basic Drugs. Int J. Pharm. 33:201-217 (1986).
Grover et al., Effects of the thyroid hormone receptor agonist GC-1 on metabolic rate and cholesterol in rats and primates: selective actions relative to 3,5,3'-triiodo-L-thyronine. Endocrinology 145(4):1656-1661 (2004).
Hafer-Macko et al., Immune attack on the Schwann cell surface in acute inflammatory demyelinating polyneuropathy. Ann. Neurol. 39:625-635 (1996).
Hangeland et al., Thyroid receptor ligands. Part 2: Thyromimetics with improved selectivity for the thyroid hormone receptor beta. Bioorg Med Chem Lett 14(13):3549-3553 (2004).
Hartley et al., A thyroid hormone-based strategy for correcting the biochemical abnormality in X-linked adrenoleukodystrophy. Endocrinology 158(5):1328-1338 (2017).
Johnson, Demyelinating diseases, in: The Infectious Etiology of Chronic Diseases: Defining the Relationship, Enhancing the Research, and Mitigating the Effects: Workshop Summary. Institute of Medicine (US) Forum on Microbial Threats; Knobler SL, O'Connor S, Lemon SM, et al., editors. Washington (DC): National Academies Press (US); 45-52 (2004).
Kavirajan et al., Efficacy and adverse effects of cholinesterase inhibitors and memantine in vascular dementia: a meta-analysis of randomised controlled trials. Lancet Neurol. 6(9):782-792 (2007).
Lee et al., Drug transporters in the central nervous system: brain barriers and brain parenchyma considerations. Pharmacological Review 53(4):569-596 (2001).
Link et al., Photo-caged agonists of the nuclear receptors RARgamma and TRbeta provide unique time-dependent gene expression profiles for light-activated gene patterning. Bioorg Med Chem. 12(22):5949-5959 (2004).
Lu et al., An expedient synthesis of benzyl 2,3,4-tri-O-benzyl-beta-D-glucopyranoside and benzyl 2,3,4-tri-O-benzyl-beta-D-mannopyranoside. Carbohydr Res. 340(6):1213-1217 (2005).
Mandal et al., Pd—C-induced catalytic transfer hydrogenation with triethylsilane. Journal of Organic Chemistry 72(17):6599-6601 (2007).
Massague. TGFbeta signalling in context. Nat Rev Mol Cell Biol. 13(10):616-630 (2012).
Meinig et al., Targeting fatty-acid amide hydrolase with prodrugs for CNS-selective therapy. ACS Chem Neurosci. 8(11):2468-2476 (2017).
Miller et al., Primary-progressive multiple sclerosis. Lance Neurol. 6:903-912 (2007).
Miyabara et al., Thyroid hormone receptor-beta-selective agonist GC-24 spares skeletal muscle type I to II fiber shift. Cell Tissue Res. 321(2):233-241 (2005).
Montalban et al. Primary progressive multiple sclerosis diagnostic criteria: a reappraisal. Mult Scler 15(12):1459-65 (2009).
Nguyen et al., Hammett analysis of selective thyroid hormone receptor modulators reveals structural and electronic requirements for hormone antagonists. J Am Chem Soc. 127(13):4599-4608 (2005).
Nguyen et al., Rational design and synthesis of a novel thyroid hormone antagonist that blocks coactivator recruitment. J Med Chem. 45(15):3310-3320 (2002).
Ocasio et al., Characterization of thyroid hormone receptor alpha (TRalpha)-specific analogs with varying inner- and outer-ring substituents. Bioorg Med Chem. 16(2):762-770 (2008).
Ocasio et al., Design and characterization of a thyroid hormone receptor alpha (TRalpha)-specific agonist. ACS Chem Biol. 1(9):585-593 (2006).
O'Shea et al., Characterization of skeletal phenotypes of TRalpha1 and TRbeta mutant mice: implications for tissue thyroid status and T3 target gene expression. Nucl Recept Signal 4:e011 [1-5] (2006).
Oppenheimer et al., Molecular basis of thyroid hormone-dependent brain development. Endocrine Reviews 18(4):462-475 (1997).
PCT/US2020/020199 International Search Report and Written Opinion dated May 14, 2020.
Penning et al., Structure-activity relationship studies on 1-[2-(4-Phenylphenoxy)ethyl]pyrrolidine (SC-22716), a potent inhibitor of leukotriene A(4) (LTA(4)) hydrolase. Journal of Medicinal Chemistry 43(4):721-735 (2000).
Placzek et al., New synthetic routes to thyroid hormone analogs: d(6)-sobetirome, (3)H-sobetirome, and the antagonist NH-3. Tetrahedron 71(35):5946-5951 (2015).
Placzek et al., Sobetirome prodrug esters with enhanced blood-brain barrier permeability. Bioorg Med Chem. 24(22):5842-5854 (2016).
Reichel et al., The role of blood-brain barrier studies in the pharmaceutical industry. Curr Drug Metab. 7(2):183-203 (2006).
Scanlan. Safety and Pharmacodynamic Study of Sobetirome in X-Linked Adrenoleukodystrophy (X-ALD), available online at ClinicalTrials.gov on Feb. 6, 2013, 3 pages (clinicaltrials.gov/ct2/show/NCT01787578?term=Scanlan&rank=1).
Scanlan. Sobetirome: a case history of bench-to-clinic drug discovery and development. Heart Fail Rev 15:177-182 (2010).
Shiohara et al., Discovery of novel indane derivatives as liver-selective thyroid hormone receptor beta (TRbeta) agonists for the treatment of dyslipidemia. Bioorg Med Chem 20(11):3622-3634 (2012).
Smith et al., Water soluble prodrug of a COX-2 selective inhibitor suitable for intravenous administration in models of cerebral ischemia. Bioorganic & Medicinal Chemistry Letters 15(13):3197-3200 (2005).
Takahashi et al., Characterisation of liver-specific distribution of a novel 1-benzyl-4-aminoindole-based thyroid hormone receptor beta agonist, SKL-13784: comparison with GC-1. Xenobiotica 46(2):108-116 [1-9] (2016; published online 2015).
Takahashi et al., In vivo evaluation of 1-benzyl-4-aminoindole-based thyroid hormone receptor beta agonists: importance of liver selectivity in drug discovery. Biol Pharm Bull. 37(7):1103-1108 (2014).
Takahashi et al., Synthesis and pharmacological characterization of 1-benzyl-4-aminoindole-based thyroid hormone receptor beta agonists. Bioorg Med Chem. 22(1):488-498 (2014).
Tancevski et al., The resurgence of thyromimetics as lipid-modifying agents. Curr Opin Investig Drugs 10(9):912-918 (2009).
Tangdenpaisal et al., Synthesis of the thyroid hormone analog GC-1 via Bi(OTf)3-catalyzed benzylation. Tetrahedron 70: 6789-6795 (2014).

(56) References Cited

OTHER PUBLICATIONS

Taub et al., Lipid lowering in healthy volunteers treated with multiple doses of MGL-3196, a liver-targeted thyroid hormone receptor-beta agonist. Atherosclerosis 230(2):373-380 (2013).
Thyroid. Abstract from poster presented at the 87th Annual Meeting of the American Thyroid Association (Oct. 18-22, 2017).
Trost et al., The thyroid hormone receptor-beta-selective agonist GC-1 differentially affects plasma lipids and cardiac activity. Endocrinology 141(9):3057-3064 (2000).
U.S. Department of Health and Human Services, Health Resources and Services Administration (HRSA), Orphan Drug Designations and Approvals List as of Sep. 3, 2013. http://www.hrsa.gov/opa/programrequirements/orphandrugsexclusion/ [originally accessed 2014/ updated Mar. 1, 2021].
Varga et al., Antitransforming growth factor-beta therapy in fibrosis: recent progress and implications for systemic sclerosis. Curr Opin Rheumatol. 20(6):720-728 (2008).
Vattakatuchery et al., Acetylcholinesterase inhibitors in cognitive impairment in Huntington's disease: A brief review. 3(3):62-64 (2013).
Ye et al., Thyroid receptor ligands. 1. Agonist ligands selective for the thyroid receptor beta1. J Med Chem. 46(9):1580-1588 (2003).
Yen, P., Physiological and molecular basis of thyroid hormone action. Physiological Reviews 81(3):1097-1142 (2001).
Yoshihara et al., A designed antagonist of the thyroid hormone receptor. Bioorg Med Chem Lett. 11(21):2821-2825 (2001).
Yoshihara et al., Structural determinants of selective thyromimetics. J Med Chem. 46(14):3152-3161 (2003).
Zhang et al., Thyroid hormone potentially benefits multiple sclerosis via facilitating remyelination. Mol Neurobiol. 53(7):4406-4416 (2016).

Malm et al., "Recent Advances in the Development of Agonists Selective for ß$_1$-Type Thyroid Hormone Receptor", pp. 79-86, 2007.
Meinig et al., "Structure-Activity Relationships of Central Nervous System Penetration by Fatty Acid Amide Hydrolase (FAAH)-Targeted Thyromimetic Prodrugs", pp. 111-116, 2019.
Ashraf et al., Synthesis, characterization and in vitro hydrolysis studies of ester and amide prodrugs of dexibuprofen. Medicinal Chemistry Research 21:3361-3368 (2012).
Krogsgaard-Larsen et al. Chapter 4: Design and application of prodrugs. Textbook of Drug Designing and Discovery, US, Taylor & Francis Inc (3rd Ed.) (pp. P460-P514).
Martin et al. The proliferating cell nuclear antigen regulates retinoic acid receptor transcriptional activity through direct protein-protein interaction. Nucleic Acids Res. 33(13):4311-21 (2005).
Tegeli et al. Synthesis and evaluation of amide prodrugs of mefenamic acid. International Journal of Chemical Sciences 12(3):1033-1043.
Valadares et al. Role of halogen bonds in thyroid hormone receptor selectivity: pharmacophore-based 3D-QSSR studies. J Chem Inf Model 49(11):2606-2616 (2009).
Bastin et al. Salt selection and optimisation procedures for pharmaceutical new chemical entities. Organic Process Research & Development 4.5:427-435 (2000).
Belikov. Pharmaceutical Chemistry: Manual. Moscow: MEDpress-inform (pp. 27-29) (2007).
Koenning et al., Myelin gene regulatory factor is required for maintenance of myelin and mature oligodendrocyte identity in the adult CNS. J Neurosci. 32(36):12528-12542 (2012).
PubChem SID 319635332 [https://pubchem.ncbi.nlm.nih.gov/substance/319635332] (2016).
U.S. Appl. No. 16/922,852 Office Action dated Mar. 15, 2022.
U.S. Appl. No. 16/969,793 Office Action dated Apr. 13, 2022.

* cited by examiner

THYROMIMETICS

BACKGROUND

Technical Field

The invention relates to thyromimetic compounds and to products containing the same, as well as to methods of their use and preparation.

Description of the Related Art

Thyroid hormone (TH) is a key signal for oligodendrocyte differentiation and myelin formation during development, and also stimulates remyelination in adult models of multiple sclerosis (MS) (Calzà et al., *Brain Res Revs* 48:339-346, 2005). However, TH is not an acceptable long-term therapy due to the limited therapeutic window in which remyelination can be achieved while avoiding the cardiotoxicity and bone demineralization associated with chronic hyperthyroidism. Some thyroid hormone analogs can activate thyroid hormone-responsive genes while avoiding the associated downsides of TH by exploiting molecular and physiological features of thyroid hormone receptors (Malm et al., *Mini Rev Med Chem* 7:79-86, 2007). These receptors are expressed in two major forms with heterogenous tissue distributions and overlapping but distinct sets of target genes (Yen, *Physiol Rev* 81:1097-1142, 2001). TRα is enriched in the heart, brain, and bone while TRβ is enriched in the liver (O'Shea et al., *Nucl Recept Signal* 4:e011, 2006).

It has also been reported that TH can inhibit the transforming growth factor beta (TGF-β) signaling, and, therefore, attenuate fibrotic responses (Alonso-Merino et al., *Proc Natl Acad Sci USA*. 113(24):E3451-60, 2016). TGF-β is a cytokine with pleiotropic effects in tissue homeostasis that plays a key role in pathological processes such as fibrosis (Massagué, *Nat Rev Mol Cell Biol*. 13(10):616-630, 2012). By inhibiting TGF-β signalling, TR ligands or agonists could have beneficial effects to block the progression of fibrotic diseases, such as idiopathic pulmonary fibrosis (IPF) or systemic sclerosis (Varga et al., *Curr Opin Rheumatol.* 20(6): 720-728, 2008).

Developing selective thyromimetics has been challenging due to the high sequence homology of thyroid hormone receptor subtypes; namely, only one amino acid residue on the internal surface of the ligand binding domain cavity varies between the α1 and β1 forms. Despite this challenge, several groups have reported TRβ-selective agonists. Scanlan et al. identified GC-1 (sobetirome) as one of the first potent analogs to demonstrate significant TRβ-selectivity in vitro (Chiellini et al., *Chem Biol* 5:299-306, 1998; Yoshihara et al., *J Med Chem* 46:3152-3161, 2003) and in vivo (Trost et al., *Endocrinology* 141:3057-3064, 2000; Grover et al., *Endocrinology* 145:1656-1661, 2004; Baxter et al., *Trends Endocrinol Metab* 15:154-157, 2004). As used herein, the term "sobetirome" refers to a synthetic diarylmethane derivative that was investigated clinically as a potential therapeutic for hypercholesterolemia (see U.S. Pat. No. 5,883,294, which is incorporated by reference herein). Other names for sobetirome found in the literature and regulatory filings include QRX-431 and GC-1. Metabasis employs a similar core with a novel liver-targeting prodrug strategy in MB07811 (Erion et al., *PNAS* 104(39), 15490-15495, 2007). Madrigal has reported TRβ-selective activity in vivo for MGL-3196 (Taub et al., *Atherosclerosis* 230(2):373-380, 2013). KaroBio has reported on eprotirome (KB2115; Berkenstam et al., *PNAS* 105(2):663-668, 2008) and KB-141 (Ye et al., *J Med Chem* 46:1580-1588, 2003), both of which demonstrate improved TRβ-selectivity in vitro. Further studies from this group highlight additional selective compounds (Hangeland et al., *BMCL* 14:3549-3553, 2004). Two TRβ-selective agonists, identified as SKL-12846 and SKL-13784, have been reported to accumulate in the liver and to reduce cholesterol levels in rodents (Takahashi et al., *BMC* 22(1):488-498, 2014; *Xenobiotica* 2015, 1-9). Kissei has also reported selective compounds (Shiohara et al., *BMC* 20(11), 3622-3634, 2012).

While progress has been made in this field, there remains a need in the art for further selective thyromimetic compounds, as well as to products containing the same, and for methods related to their use and preparation.

BRIEF SUMMARY

Disclosed herein are compounds according to Formula I:

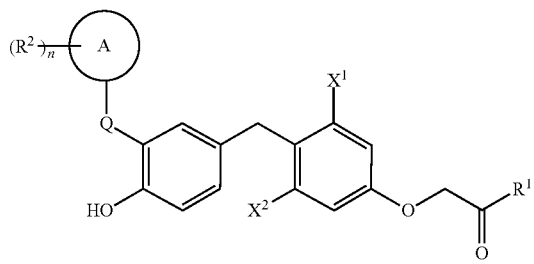

(I)

or a pharmaceutically acceptable isomer, racemate, hydrate, solvate, isotope, or salt thereof, wherein A, $X^1$, $X^2$, Q, $R^1$, $R^2$ and n are as defined below.

In an embodiment, a pharmaceutical composition is provided comprising a compound having the structure of Formula (I), or a pharmaceutically acceptable isomer, racemate, hydrate, solvate, isotope, or salt thereof, in combination with a pharmaceutically acceptable carrier, diluent, or excipient. In an embodiment, the pharmaceutical composition is for use in treating a neurodegenerative disorder including neurodegenerative disorders classified as a demyelinating disease such as X-linked adrenoleukodystrophy or multiple sclerosis. In another embodiment, the pharmaceutical composition is for use in treating a medical condition associated increased activity of TGF-β, such as a fibrotic disease.

In an embodiment, a method is provided for treating a neurodegenerative disorder in a subject in need thereof, comprising administering a compound having the structure of Formula (I), or a pharmaceutically acceptable salt or composition comprising the same. In some aspects, the neurodegenerative disorder can be classified as a demyelinating disease such as X-linked adrenoleukodystrophy or multiple sclerosis.

In another embodiment, a method is provided for treating a medical condition associated with over-expression of TGF-β in a subject in need thereof, comprising administering a compound having the structure of Formula (I), or a pharmaceutically acceptable salt or composition comprising the same. In some aspects, the medical condition associated with over-expression of TGF-β is a fibrotic disease.

DETAILED DESCRIPTION

As mentioned above, the invention relates to thyromimetic compounds, to products comprising the same, and to methods for their use and synthesis.

In one embodiment, compounds are provided having the structure of Formula (I):

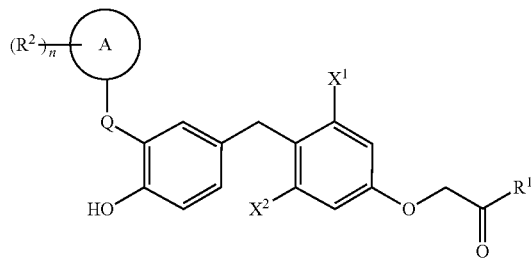

or a pharmaceutically acceptable isomer, racemate, hydrate, solvate, isotope, or salt thereof, wherein:
- $X^1$ is lower alkyl, lower haloalkyl, or halo;
- $X^2$ is lower alkyl, lower haloalkyl, or halo;
- $R^1$ is —$NR^{1a}R^{1b}$ or —$OR^{1c}$;
- $R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
- $R^{1c}$ is H, lower alkyl, carbocycle, heterocycle, carbocyclealkyl, or heterocyclealkyl;
- Q is a bond, —$C(R^3R^4)$— or —$\{C(R^3R^4)\}_2$—;
- A is aryl or heteroaryl;
- each $R^2$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
- each $R^3$ and $R^4$ are, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;
- n is 0-5; and
- $R^a$ and $R^b$ are each, independently, H, lower alkyl, or lower haloalkyl;
  - wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl; and
  - wherein $X^1$ is lower haloalkyl or halo when Q is —$CH_2$—, A is phenyl, $R^1$=—OH, and n is 0.

The acid compounds of the present invention ($R^1$=—$OR^{1c}$ and $R^{1c}$=H) are active agonists selectively activating the TRβ receptor. The amide compounds of the present invention ($R^1$=—$NR^{1a}R^{1b}$) may act as substrates for the specific hydrolase enzyme fatty acid-amide hydrolase (FAAH), which cleaves the amide, liberating the thyromimetic. Thus, prodrug conversion to drug is enhanced in tissues that express high levels of FAAH such as the central nervous system. The ester compounds of the present invention ($R^1$=—$OR^{1c}$ and $R^{1c}$≠H) are also prodrugs, typically processed through the action of esterases which may exist selectively in specific tissues.

As used herein, "lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of straight chain lower alkyl groups include, but are not limited to, methyl, ethyl, n-propyl, n-butyl, n-pentyl-, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

As used herein, "lower alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, butenyl, pentenyl, and hexenyl.

As used herein, "lower alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of lower alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.

"Cyano" refers to —CN.

"Lower haloalkyl" refers to a lower alkyl as defined above with one or more hydrogen atoms replaced with halogen. Examples of lower haloalkyl groups include, but are not limited to, —$CF_3$, —$CHF_2$, and the like.

"Lower alkoxy" refers to a lower alkyl as defined above joined by way of an oxygen atom (i.e., —O-(lower alkyl). Examples of lower alkoxy groups include, but are not limited to, methoxy, ethoxy, n-propoxy, n-butoxy, iso-propoxy, sec-butoxy, tert-butoxy, and the like.

"Lower haloalkoxy" refers to a lower haloalkyl as defined above joined by way of an oxygen atom (i.e., —O-(lower haloalkyl). Examples of lower haloalkoxy groups include, but are not limited to, —$OCF_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Cycloalkylalkyl" are alkyl groups as defined above in which a hydrogen or carbon bond of the alkyl group is replaced with a bond to a cycloalkyl group as defined above.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocyclyl," "carbocycle," or "carbocyclic" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Carbocyclealkyl" are alkyl groups as defined above in which a hydrogen or carbon bond of the alkyl group is replaced with a bond to a carbocycle group as defined above.

"Heterocyclyl," "heterocycle," or "heterocyclic" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclealkyl" are alkyl groups as defined above in which a hydrogen or carbon bond of the alkyl group is replaced with a bond to a heterocycle group as defined above.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

In one embodiment, compounds are provided having the structure of Formula (I-A):

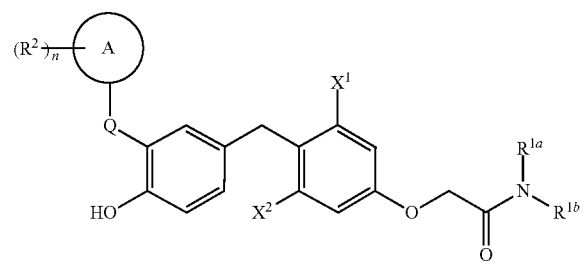

(I-A)

or a pharmaceutically acceptable isomer, racemate, hydrate, solvate, isotope, or salt thereof, wherein:
$X^1$ is lower alkyl, lower haloalkyl, or halo;
$X^2$ is lower alkyl, lower haloalkyl, or halo;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
Q is a bond, —$C(R^3R^4)$— or —$\{C(R^3R^4)\}_2$—;
A is aryl or heteroaryl;
each $R^2$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
each $R^3$ and $R^4$ are, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;
n is 0-5; and
$R^a$ and $R^b$ are each, independently, H, lower alkyl, or lower haloalkyl;
wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (I-B):

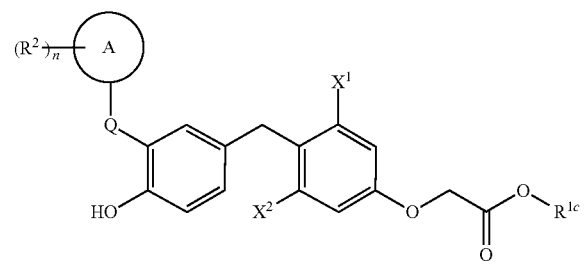

(I-B)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^{1c}$ is H, lower alkyl, carbocycle, heterocycle, carbocyclealkyl, or heterocyclealkyl;

Q is a bond, —C($R^3R^4$)— or —{C($R^3R^4$)}$_2$—;

A is aryl or heteroaryl;

each $R^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

each $R^3$ and $R^4$ are, independently, H, halo, cyano, lower alkyl, lower alkenyl, lower alkynyl, lower haloalkyl, —OR$^a$, —NR$^a$R$^b$, carbocycle, heterocycle, carbocyclealkyl, or heterocyclealkyl, or $R^3$ and $R^4$, together, form =O or =S;

n is 0-5; and $R^a$ and $R^b$ are each, independently, H, lower alkyl, or lower haloalkyl;

wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R'', —S(O)$_2$R' or —S(O)$_2$OR', wherein R' and R'' are each, independently, H, lower alkyl, or lower haloalkyl; and wherein $X^1$ is lower haloalkyl or halo when Q is —CH$_2$—, A is phenyl, $R^{1c}$ is H, and n is 0.

In one embodiment, compounds are provided having the structure of Formula (I-B), wherein A is heteroaryl and, in more specific embodiments, furanyl or thiophenyl.

In one embodiment, compounds are provided having the structure of Formula (II):

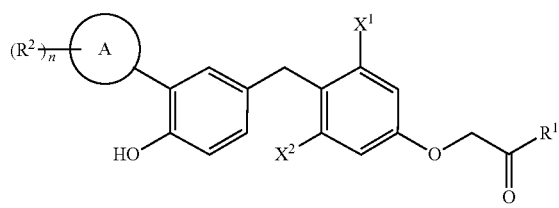

(II)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^1$ is —NR$^{1a}$R$^{1b}$ or —OR$^{1c}$;

$R^{1a}$ and $R^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

A is aryl or heteroaryl;

each $R^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and $R^a$ and $R^b$ are each, independently, H, lower alkyl, or lower haloalkyl;

wherein $R^{1a}$, $R^{1b}$, $R^{1c}$, $R^2$, $R^a$, and $R^b$ are each, independently, optionally substituted with one or more halo, cyano, —OR', —NR'R'', —S(O)$_2$R' or —S(O)$_2$OR', wherein R' and R'' are each, independently, H, lower alkyl, or lower haloalkyl.

In one embodiment, compounds are provided having the structure of Formula (II-A):

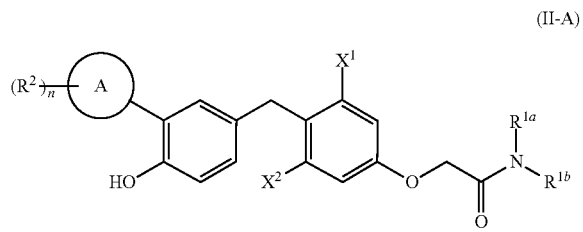

(II-A)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^{1a}$ and $R^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or $R^{1a}$ and $R^{1b}$ taken together with the nitrogen atom to which they are attached form heterocycle;

A is aryl or heteroaryl;

each $R^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and $R^a$ and $R^b$ are each, independently, H, lower alkyl, or lower haloalkyl;

wherein $R^{1a}$, $R^{1b}$, $R^{1c}$, $R^2$, $R^a$, and $R^b$ are each, independently, optionally substituted with one or more halo, cyano, —OR', —NR'R'', —S(O)$_2$R' or —S(O)$_2$OR', wherein R' and R'' are each, independently, H, lower alkyl, or lower haloalkyl.

In one embodiment, compounds are provided having the structure of Formula (II-B):

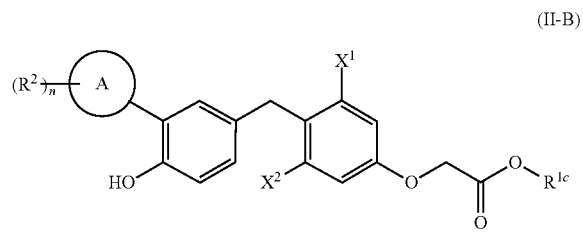

(II-B)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^{1c}$ is H, lower alkyl, carbocycle, heterocycle, carbocyclealkyl, or heterocyclealkyl;

A is aryl or heteroaryl;

each $R^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and

R$^a$ and R$^b$ are each, independently, H, lower alkyl, or lower haloalkyl;

wherein R$^{1a}$, R$^{1b}$, R$^{1c}$, R$^2$, R$^a$, and R$^b$ are each, independently, optionally substituted with one or more halo, cyano, —OR', —NR'R", —S(O)$_2$R' or —S(O)$_2$OR', wherein R' and R" are each, independently, H, lower alkyl, or lower haloalkyl.

In one embodiment, compounds are provided having the structure of Formula (III):

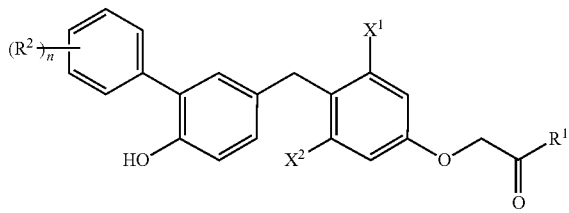

(III)

or a pharmaceutically acceptable isomer, racemate, hydrate, solvate, isotope, or salt thereof, wherein:

X$^1$ is lower alkyl, lower haloalkyl, or halo;
X$^2$ is lower alkyl, lower haloalkyl, or halo;
R$^1$ is —NR$^{1a}$R$^{1b}$ or —OR$^{1c}$;
R$^{1a}$ and R$^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or R$^{1a}$ and R$^{1b}$ taken together with the nitrogen atom to which they are attached form heterocycle;

R$^{1c}$ is H, lower alkyl, carbocycle, heterocycle, carbocyclealkyl, or heterocyclealkyl;

each R$^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and

R$^a$ and R$^b$ are each, independently, H, lower alkyl, or lower haloalkyl;

wherein R$^{1a}$, R$^{1b}$, R$^{1c}$, R$^2$, R$^a$, and R$^b$ are each, independently, optionally substituted with one or more halo, cyano, —OR', —NR'R", —S(O)$_2$R' or —S(O)$_2$OR', wherein R' and R" are each, independently, H, lower alkyl, or lower haloalkyl.

In one embodiment, compounds are provided having the structure of Formula (III-A):

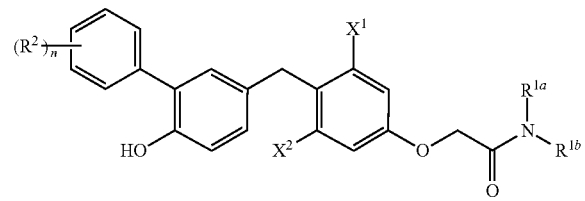

(III-A)

or a pharmaceutically acceptable isomer, racemate, hydrate, solvate, isotope, or salt thereof, wherein:

X$^1$ is lower alkyl, lower haloalkyl, or halo;
X$^2$ is lower alkyl, lower haloalkyl, or halo;
R$^{1a}$ and R$^{1b}$ are each, independently, H, lower alkyl, lower alkenyl, lower alkynyl, —OR$^a$, —NR$^a$R$^b$, carbocycle, carbocyclealkyl, heterocycle, or heterocyclealkyl, or R$^{1a}$ and R$^{1b}$ taken together with the nitrogen atom to which they are attached form heterocycle;

each R$^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and

R$^a$ and R$^b$ are each, independently, H, lower alkyl, or lower haloalkyl;

wherein R$^{1a}$, R$^{1b}$, R$^{1c}$, R$^2$, R$^a$, and R$^b$ are each, independently, optionally substituted with one or more halo, cyano, —OR', —NR'R", —S(O)$_2$R' or —S(O)$_2$OR', wherein R' and R" are each, independently, H, lower alkyl, or lower haloalkyl.

In one embodiment, compounds are provided having the structure of Formula (III-B):

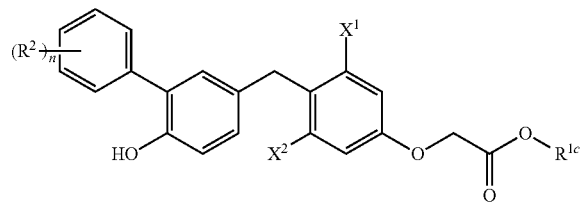

(III-B)

or a pharmaceutically acceptable isomer, racemate, hydrate, solvate, isotope, or salt thereof, wherein:

X$^1$ is lower alkyl, lower haloalkyl, or halo;
X$^2$ is lower alkyl, lower haloalkyl, or halo;
R$^{1c}$ is H, lower alkyl, carbocycle, heterocycle, carbocyclealkyl, or heterocyclealkyl;

each R$^2$ is, independently, halo, cyano, lower alkyl, lower alkenyl, lower alkynyl, lower haloalkyl, carbocycle, heterocycle, carbocyclealkyl, heterocyclealkyl, —OR$^a$, —NR$^a$R$^b$, —C(O)R$^a$, —C(O)OR$^a$, —C(O)NR$^a$R$^b$, —NR$^a$C(O)R$^b$, —S(O)$_2$R$^a$, or —S(O)$_2$OR$^a$;

n is 0-5; and

R$^a$ and R$^b$ are each, independently, H, lower alkyl, or lower haloalkyl;

wherein R$^{1a}$, R$^{1b}$, R$^{1c}$, R$^2$, R$^a$, and R$^b$ are each, independently, optionally substituted with one or more halo, cyano, —OR', —NR'R", —S(O)$_2$R' or —S(O)$_2$OR', wherein R' and R" are each, independently, H, lower alkyl, or lower haloalkyl.

In a more specific embodiment, compounds are provided having the structure of any one of above Formulas (I), (I-A), (I-B), (II), (II-A), (II-B), (III), (III-A), or (III-B), or a pharmaceutically acceptable isomer, racemate, hydrate, solvate, isotope, or salt thereof, wherein n is 1-5 and one R$^2$ is R$^{2a}$ substituted at the 3-position of ring A.

In one embodiment, compounds are provided having the structure of Formula (IV):

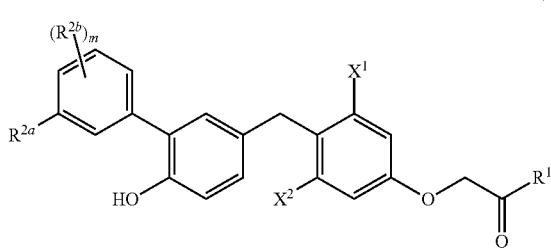

(IV)

or a pharmaceutically acceptable isomer, racemate, hydrate, solvate, isotope, or salt thereof, wherein:
  $X^1$ is lower alkyl, lower haloalkyl, or halo;
  $X^2$ is lower alkyl, lower haloalkyl, or halo;
  $R^1$ is —$NR^{1a}R^{1b}$ or —$OR^{1c}$;
  $R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
  $R^{1c}$ is H, lower alkyl, carbocycle, heterocycle, carbocyclealkyl, or heterocyclealkyl;
  $R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  m is 0-4; and
  $R^a$ and $R^b$ are each, independently, H, lower alkyl, or lower haloalkyl;
    wherein $R^{1a}$, $R^{1b}$, $R^{1c}$, $R^{2a}$, $R^{2b}$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (IV-A):

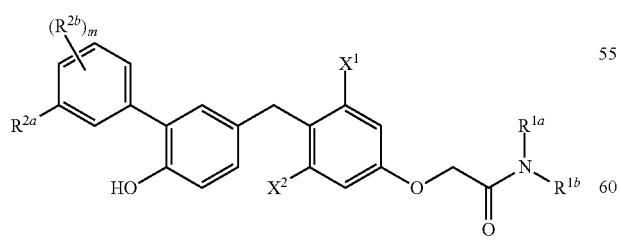

(IV-A)

or a pharmaceutically acceptable isomer, racemate, hydrate, solvate, isotope, or salt thereof, wherein:
  $X^1$ is lower alkyl, lower haloalkyl, or halo;
  $X^2$ is lower alkyl, lower haloalkyl, or halo;
  $R^{1a}$ and $R^{1b}$ bare each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
  $R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  m is 0-4; and
  $R^a$ and $R^b$ are each, independently, H, lower alkyl, or lower haloalkyl;
    wherein $R^{1a}$, $R^{1b}$, $R^{1c}$, $R^{2a}$, $R^{2b}$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (IV-B):

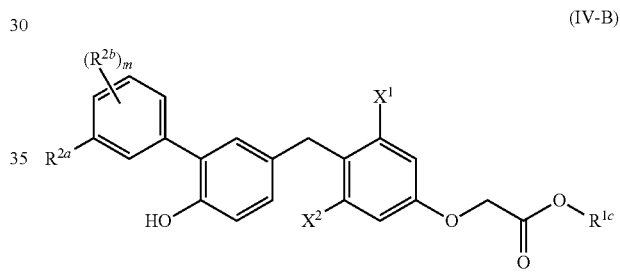

(IV-B)

or a pharmaceutically acceptable isomer, racemate, hydrate, solvate, isotope, or salt thereof, wherein:
  $X^1$ is lower alkyl, lower haloalkyl, or halo;
  $X^2$ is lower alkyl, lower haloalkyl, or halo;
  $R^{1c}$ is H, lower alkyl, carbocycle, heterocycle, carbocyclealkyl, or heterocyclealkyl;
  $R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
  m is 0-4; and
  $R^a$ and $R^b$ are each, independently, H, lower alkyl, or lower haloalkyl;
    wherein $R^{1a}$, $R^{1b}$, $R^{1c}$, $R^{2a}$, $R^{2b}$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (V):

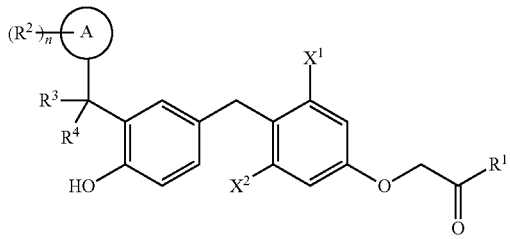

(V)

or a pharmaceutically acceptable isomer, racemate, hydrate, solvate, isotope, or salt thereof, wherein:
 $X^1$ is lower alkyl, lower haloalkyl, or halo;
 $X^2$ is lower alkyl, lower haloalkyl, or halo;
 $R^1$ is —$NR^{1a}R^{1b}$ or —$OR^{1c}$;
 $R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
 $R^{1c}$ is H, lower alkyl, carbocycle, heterocycle, carbocyclealkyl, or heterocyclealkyl;
 A is aryl or heteroaryl;
 each $R^2$ is, independently, halo, cyano, lower alkyl, lower alkenyl, lower alkynyl, lower haloalkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
 $R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;
 n is 0-5; and
 $R^a$ and $R^b$ are each, independently, H, lower alkyl, or lower haloalkyl;
  wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl; and
  wherein $X^1$ is lower haloalkyl or halo when $R^3$ and $R^4$ are each H, A is phenyl, $R^1$ is —OH, and n is 0.

In one embodiment, compounds are provided having the structure of Formula (V), wherein A is heteroaryl and, in more specific embodiments, furanyl or thiophenyl.

In one embodiment, compounds are provided having the structure of Formula (V-A):

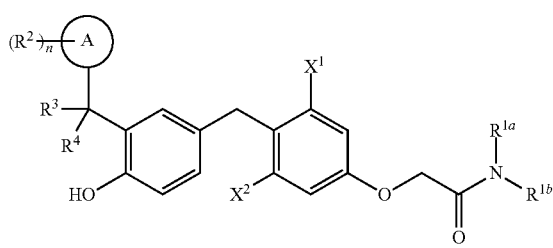

(V-A)

or a pharmaceutically acceptable isomer, racemate, hydrate, solvate, isotope, or salt thereof, wherein:
 $X^1$ is lower alkyl, lower haloalkyl, or halo;
 $X^2$ is lower alkyl, lower haloalkyl, or halo;
 $R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
 A is aryl or heteroaryl;
 each $R^2$ is, independently, halo, cyano, lower alkyl, lower alkenyl, lower alkynyl, lower haloalkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
 $R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;
 n is 0-5; and
 $R^a$ and $R^b$ are each, independently, H, lower alkyl, or lower haloalkyl;
  wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (V-B):

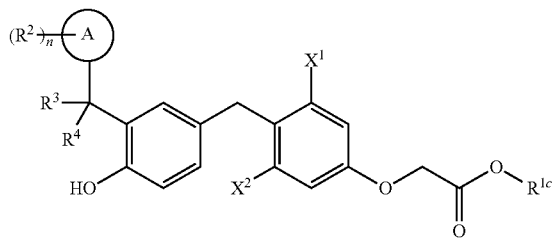

(V-B)

or a pharmaceutically acceptable isomer, racemate, hydrate, solvate, isotope, or salt thereof, wherein:
 $X^1$ is lower alkyl, lower haloalkyl, or halo;
 $X^2$ is lower alkyl, lower haloalkyl, or halo;
 $R^{1c}$ is H, lower alkyl, carbocycle, heterocycle, carbocyclealkyl, or heterocyclealkyl;
 A is aryl or heteroaryl;
 each $R^2$ is, independently, halo, cyano, lower alkyl, lower alkenyl, lower alkynyl, lower haloalkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
 $R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;
 n is 0-5; and
 $R^a$ and $R^b$ are each, independently, H, lower alkyl, or lower haloalkyl;
  wherein $R^{1a}$, $R^{1b}$, $R^{1c}$, $R^2$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl; and
  wherein $X^1$ is lower haloalkyl or halo when $R^3$ and $R^4$ are each H, A is phenyl, $R^{1c}$ is H, and n is 0.

In one embodiment, compounds are provided having the structure of Formula (VI):

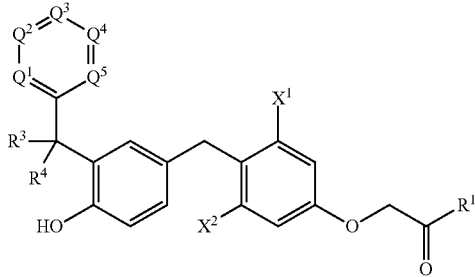

(VI)

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^2$, or N;

$X^1$ is lower alkyl, lower haloalkyl, or halo;

$X^2$ is lower alkyl, lower haloalkyl, or halo;

$R^1$ is $-NR^{1a}R^{1b}$ or $-OR^{1c}$;

$R^{1a}$ and $R^{1b}$ are each, independently, H, lower alkyl, lower alkenyl, lower alkynyl, $-OR^a$, $-NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

each $R^2$ is, independently, halo, cyano, lower alkyl, lower alkenyl, lower alkynyl, lower haloalkyl, $-OR^a$, $-NR^aR^b$, $-C(O)R^a$, $-C(O)OR^a$, $-C(O)NR^aR^b$, $-NR^aC(O)R^b$, $-S(O)_2R^a$, or $-S(O)_2OR^a$;

$R^3$ and $R^4$ are each, independently, H, halo, cyano, lower alkyl, lower alkenyl, lower alkynyl, lower haloalkyl, $-OR^a$, $-NR^aR^b$, carbocycle, heterocycle, carbocyclealkyl, or heterocyclealkyl, or $R^3$ and $R^4$, together, form =O or =S; and $R^a$ and $R^b$ are each, independently, H, lower alkyl, or lower haloalkyl;

wherein $R^{1a}$, $R^{1b}$, $R^{1c}$, $R^2$, $R^3$, $R^4$, $R^a$, and $R^b$ are each, independently, optionally substituted with one or more halo, cyano, $-OR'$, $-NR'R''$, $-S(O)_2R'$ or $-S(O)_2OR'$, wherein R' and R" are each, independently, H, lower alkyl, or lower haloalkyl; and wherein $X^1$ is lower haloalkyl or halo when $R^3$ and $R^4$ are each H, $R^1$ is —OH, and $Q^1$, $Q^2$, $Q^3$, $Q^4$, and $Q^5$ are each CH.

In one embodiment, compounds are provided having the structure of Formula (VI-A):

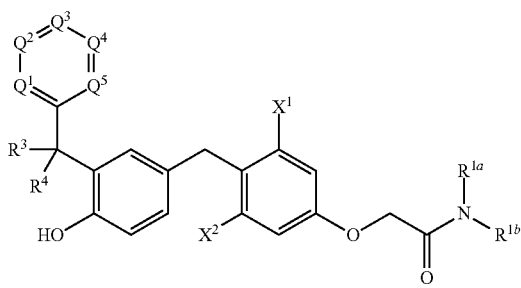

(VI-A)

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^2$, or N;

$X^1$ is lower alkyl, lower haloalkyl, or halo;

$X^2$ is lower alkyl, lower haloalkyl, or halo;

$R^{1a}$ and $R^{1b}$ are each, independently, H, lower alkyl, lower alkenyl, lower alkynyl, $-OR^a$, $-NR^aR^b$, carbocycle, carbocyclealkyl, heterocycle, or heterocyclealkyl, or $R^{1a}$ and $R^{1b}$ taken together with the nitrogen atom to which they are attached form heterocycle;

each $R^2$ is, independently, halo, cyano, lower alkyl, lower alkenyl, lower alkynyl, lower haloalkyl, $-OR^a$, $-NR^aR^b$, $-C(O)R^a$, $-C(O)OR^a$, $-C(O)NR^aR^b$, $-NR^aC(O)R^b$, $-S(O)_2R^a$, or $-S(O)_2OR^a$;

$R^3$ and $R^4$ are each, independently, H, halo, cyano, lower alkyl, lower alkenyl, lower alkynyl, lower haloalkyl, $-OR^a$, $-NR^aR^b$, carbocycle, heterocycle, carbocyclealkyl, or heterocyclealkyl, or $R^3$ and $R^4$, together, form =O or =S; and $R^a$ and $R^b$ are each, independently, H, lower alkyl, or lower haloalkyl;

wherein $R^{1a}$, $R^{1b}$, $R^{1c}$, $R^2$, $R^3$, $R^4$, $R^a$, and $R^b$ are each, independently, optionally substituted with one or more halo, cyano, $-OR'$, $-NR'R''$, $-S(O)_2R'$ or $-S(O)_2OR'$, wherein R' and R" are each, independently, H, lower alkyl, or lower haloalkyl.

In one embodiment, compounds are provided having the structure of Formula (VI-B):

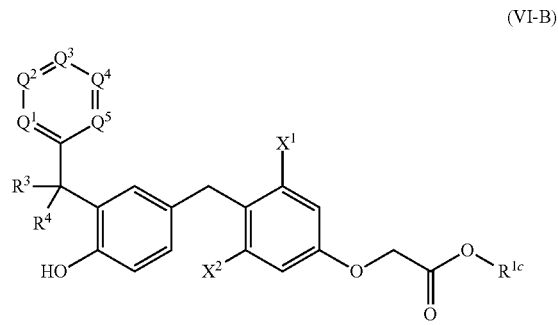

(VI-B)

or a pharmaceutically acceptable isomer, racemate, hydrate, solvate, isotope, or salt thereof, wherein:

$Q^1$, $Q^2$, $Q^3$, $Q^4$, and $Q^5$ are each, independently, CH, $CR^2$, or N;

$X^1$ is lower alkyl, lower haloalkyl, or halo;

$X^2$ is lower alkyl, lower haloalkyl, or halo;

$R^{1c}$ is H, lower alkyl, carbocycle, heterocycle, carbocyclealkyl, or heterocyclealkyl;

each $R^2$ is, independently, halo, cyano, lower alkyl, lower alkenyl, lower alkynyl, lower haloalkyl, $-OR^a$, $-NR^aR^b$, $-C(O)R^a$, $-C(O)OR^a$, $-C(O)NR^aR^b$, $-NR^aC(O)R^b$, $-S(O)_2R^a$, or $-S(O)_2OR^a$;

$R^3$ and $R^4$ are each, independently, H, halo, cyano, lower alkyl, lower alkenyl, lower alkynyl, lower haloalkyl, $-OR^a$, $-NR^aR^b$, carbocycle, heterocycle, carbocyclealkyl, or heterocyclealkyl, or $R^3$ and $R^4$, together, form =O or =S; and $R^a$ and $R^b$ are each, independently, H, lower alkyl, or lower haloalkyl;

wherein $R^{1a}$, $R^{1b}$, $R^{1c}$, $R^2$, $R^3$, $R^4$, $R^a$, and $R^b$ are each, independently, optionally substituted with one or more halo, cyano, $-OR'$, $-NR'R''$, $-S(O)_2R'$ or $-S(O)_2OR'$, wherein R' and R" are each, independently, H, lower alkyl, or lower haloalkyl; and wherein X¹ is lower haloalkyl or halo when R³ and R⁴ are each H, R¹ᶜ is H, and Q¹, Q², Q³, Q⁴, and Q⁵ are each CH.

In one embodiment, compounds are provided having the structure of Formula (VII):

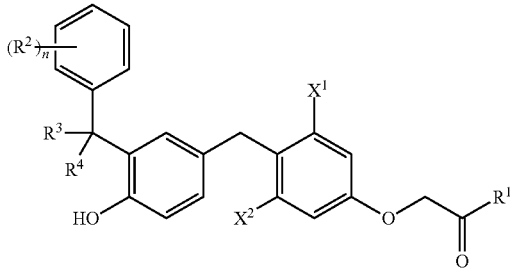

(VII)

or a pharmaceutically acceptable isomer, racemate, hydrate, solvate, isotope, or salt thereof, wherein:
X¹ is lower alkyl, lower haloalkyl, or halo;
X² is lower alkyl, lower haloalkyl, or halo;
R¹ is —NR¹ᵃR¹ᵇ, —OR¹ᶜ or heterocycle;
R¹ᵃ and R¹ᵇ are each, independently, H, lower alkyl, lower alkenyl, lower alkynyl, —ORᵃ, —NRᵃRᵇ, carbocycle, carbocyclealkyl, heterocycle, or heterocyclealkyl, or R¹ᵃ and R¹ᵇ taken together with the nitrogen atom to which they are attached form heterocycle;
R¹ᶜ is H, lower alkyl, carbocycle, heterocycle, carbocyclealkyl, or heterocyclealkyl;
each R² is, independently, halo, cyano, lower alkyl, lower alkenyl, lower alkynyl, lower haloalkyl, —ORᵃ, —NRᵃRᵇ, —C(O)Rᵃ, —C(O)ORᵃ, —C(O)NRᵃRᵇ, —NRᵃC(O)Rᵇ, —S(O)₂Rᵃ, or —S(O)₂ORᵃ;
R³ and R⁴ are each, independently, H, halo, cyano, lower alkyl, lower alkenyl, lower alkynyl, lower haloalkyl, —ORᵃ, —NRᵃRᵇ, carbocycle, heterocycle, carbocyclealkyl, or heterocyclealkyl, or R³ and R⁴, together, form =O or =S;
n is 0-5; and
Rᵃ and Rᵇ are each, independently, H, lower alkyl, or lower haloalkyl;
wherein R¹ᵃ, R¹ᵇ, R¹ᶜ, R², R³, R⁴, Rᵃ, and Rᵇ are each, independently, optionally substituted with one or more halo, cyano, —OR', —NR'R", —S(O)₂R' or —S(O)₂OR', wherein R' and R" are each, independently, H, lower alkyl, or lower haloalkyl; and
wherein X¹ is lower haloalkyl or halo when R³ and R⁴ are each H, R¹ is —OH, and n is 0.

In one embodiment, compounds are provided having the structure of Formula (VII-A):

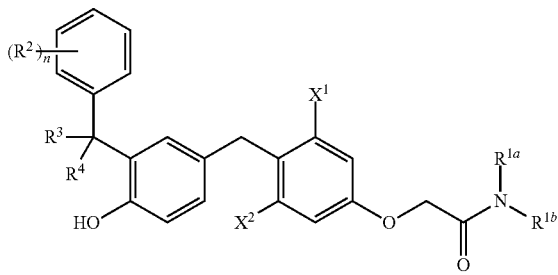

(VII-A)

or a pharmaceutically acceptable isomer, racemate, hydrate, solvate, isotope, or salt thereof, wherein:
X¹ is lower alkyl, lower haloalkyl, or halo;
X² is lower alkyl, lower haloalkyl, or halo;
R¹ᵃ and R¹ᵇ are each, independently, H, lower alkyl, lower alkenyl, lower alkynyl, —ORᵃ, —NRᵃRᵇ, carbocycle, carbocyclealkyl, heterocycle, or heterocyclealkyl, or R¹ᵃ and R¹ᵇ taken together with the nitrogen atom to which they are attached form heterocycle;
each R² is, independently, halo, cyano, lower alkyl, lower alkenyl, lower alkynyl, lower haloalkyl, —ORᵃ, —NRᵃRᵇ, —C(O)Rᵃ, —C(O)ORᵃ, —C(O)NRᵃRᵇ, —NRᵃC(O)Rᵇ, —S(O)₂Rᵃ, or —S(O)₂ORᵃ;
R³ and R⁴ are each, independently, H, halo, cyano, lower alkyl, lower alkenyl, lower alkynyl, lower haloalkyl, —ORᵃ, —NRᵃRᵇ, carbocycle, heterocycle, carbocyclealkyl, or heterocyclealkyl, or R³ and R⁴, together, form =O or =S;
n is 0-5; and
Rᵃ and Rᵇ are each, independently, H, lower alkyl, or lower haloalkyl;
wherein R¹ᵃ, R¹ᵇ, R¹ᶜ, R², R³, R⁴, Rᵃ, and Rᵇ are each, independently, optionally substituted with one or more halo, cyano, —OR', —NR'R", —S(O)₂R' or —S(O)₂OR', wherein R' and R" are each, independently, H, lower alkyl, or lower haloalkyl.

In one embodiment, compounds are provided having the structure of Formula (VII-B):

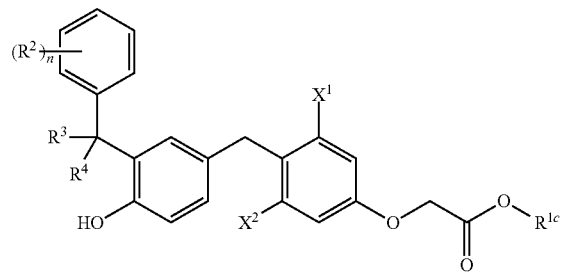

(VII-B)

or a pharmaceutically acceptable isomer, racemate, hydrate, solvate, isotope, or salt thereof, wherein:
X¹ is lower alkyl, lower haloalkyl, or halo;
X² is lower alkyl, lower haloalkyl, or halo;
R¹ᶜ is H, lower alkyl, carbocycle, heterocycle, carbocyclealkyl, or heterocyclealkyl;
each R² is, independently, halo, cyano, lower alkyl, lower alkenyl, lower alkynyl, lower haloalkyl, —ORᵃ, —NRᵃRᵇ, —C(O)Rᵃ, —C(O)ORᵃ, —C(O)NRᵃRᵇ, —NRᵃC(O)Rᵇ, —S(O)₂Rᵃ, or —S(O)₂ORᵃ;
R³ and R⁴ are each, independently, H, halo, cyano, lower alkyl, lower alkenyl, lower alkynyl, lower haloalkyl, —ORᵃ, —NRᵃRᵇ, carbocycle, heterocycle, carbocyclealkyl, or heterocyclealkyl, or R³ and R⁴, together, form =O or =S;
n is 0-5; and
Rᵃ and Rᵇ are each, independently, H, lower alkyl, or lower haloalkyl;
wherein R¹ᵃ, R¹ᵇ, R¹ᶜ, R², R³, R⁴, Rᵃ, and Rᵇ are each, independently, optionally substituted with one or more halo, cyano, —OR', —NR'R", —S(O)₂R' or —S(O)₂OR', wherein R' and R" are each, independently, H, lower alkyl, or lower haloalkyl; and
wherein X¹ is lower haloalkyl or halo when R³ and R⁴ are each H, R¹ is —OH, and n is 0.

In one embodiment, compounds are provided having the structure of Formula (VIII):

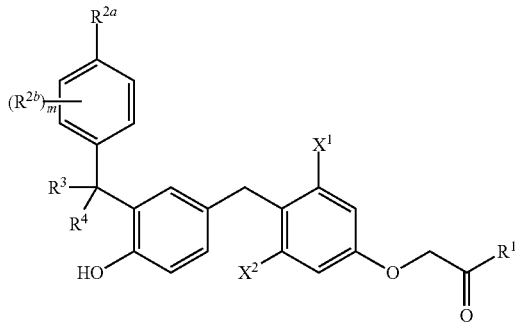

(VIII)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^1$ is —$NR^{1a}R^{1b}$ or —$OR^{1c}$;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{1c}$ is H, lower alkyl, carbocycle, heterocycle, carbocyclealkyl, or heterocyclealkyl;

$R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

m is 0-4; and $R^a$ and $R^b$ are each, independently, H, lower alkyl, or lower haloalkyl;

wherein $R^{1a}$, $R^{1b}$, $R^{1c}$, $R^{2a}$, $R^{2b}$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (VIII-A):

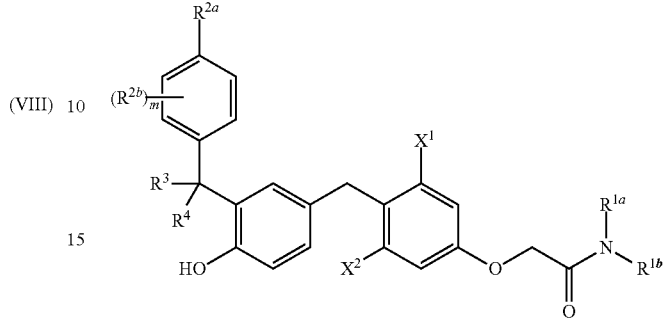

(VIII-A)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;

$R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

m is 0-4; and $R^a$ and $R^b$ are each, independently, H, lower alkyl, or lower haloalkyl;

wherein $R^{1a}$, $R^{1b}$, $R^{1c}$, $R^{2a}$, $R^{2b}$, $R^3$, $R^4$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

In one embodiment, compounds are provided having the structure of Formula (VIII-B):

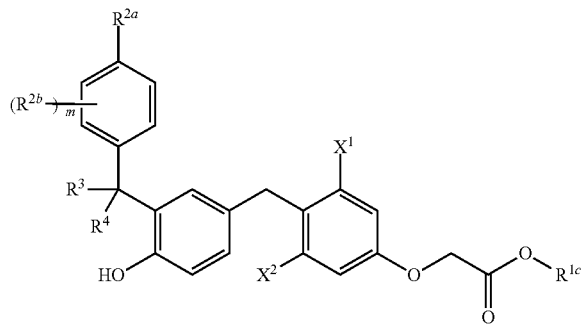

(VIII-B)

or a pharmaceutically acceptable isomer, racemate, hydrate, solvate, isotope, or salt thereof, wherein:

$X^1$ is lower alkyl, lower haloalkyl, or halo;

$X^2$ is lower alkyl, lower haloalkyl, or halo;

$R^{1c}$ is H, lower alkyl, carbocycle, heterocycle, carbocyclealkyl, or heterocyclealkyl;

$R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;

$R^3$ and $R^4$ are each, independently, H, halo, cyano, lower alkyl, lower alkenyl, lower alkynyl, lower haloalkyl, —$OR^a$, —$NR^aR^b$, carbocycle, heterocycle, carbocyclealkyl, or heterocyclealkyl, or $R^3$ and $R^4$, together, form =O or =S;

m is 0-4; and $R^a$ and $R^b$ are each, independently, H, lower alkyl, or lower haloalkyl;

wherein $R^{1a}$, $R^{1b}$, $R^{1c}$, $R^2$, $R^{2b}$, $R^3$, $R^4$, $R^a$, and $R^b$ are each, independently, optionally substituted with one or more halo, cyano, —OR', —NR'R'', —$S(O)_2$R' or —$S(O)_2$OR', wherein R' and R'' are each, independently, H, lower alkyl, or lower haloalkyl.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is H.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is carbocycle.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is cyclopropyl or cyclobutyl.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is lower alkyl.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is lower haloalkyl.

In a more specific embodiment, compounds are provided having the structure of any one of above Formulas (I), (I-A), (I-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^3$ is —$OR^a$, and in a further embodiment $R^a$ is H.

In a more specific embodiment, compounds are provided having the structure of any one of above Formulas (I), (I-A), (II), (II-A), (III), (III-A), (IV), (IV-A), (V), (V-A), (VI), (VI-A), (VII), (VII-A), (VIII), or (VIII-A), or a pharmaceutically acceptable isomer, racemate, hydrate, solvate, isotope, or salt thereof, wherein $R^{1a}$ is lower alkyl.

In a more specific embodiment, compounds are provided having the structure of any one of above Formulas (I), (I-A), (II), (II-A), (III), (III-A), (IV), (IV-A), (V), (V-A), (VI), (VI-A), (VII), (VII-A), (VIII), or (VIII-A), or a pharmaceutically acceptable isomer, racemate, hydrate, solvate, isotope, or salt thereof, wherein $R^{1a}$ is methyl.

In a more specific embodiment, compounds are provided having the structure of any one of above Formulas (I), (I-A), (II), (II-A), (III), (III-A), (IV), (IV-A), (V), (V-A), (VI), (VI-A), (VII), (VII-A), (VIII), or (VIII-A), or a pharmaceutically acceptable isomer, racemate, hydrate, solvate, isotope, or salt thereof, wherein $R^{1b}$ is H.

In a more specific embodiment, compounds are provided having the structure of any one of above Formulas (I), (I-B), (II), (II-B), (III), (III-B), (IV), (IV-B), (V), (V-B), (VI), (VI-B), (VII), (VII-B), (VIII), or (VIII-B), or a pharmaceutically acceptable isomer, racemate, hydrate, solvate, isotope, or salt thereof, wherein $R^{1c}$ is H.

In a more specific embodiment, compounds are provided having the structure of any one of above Formulas (I), (I-B), (II), (II-B), (III), (III-B), (IV), (IV-B), (V), (V-B), (VI), (VI-B), (VII), (VII-B), (VIII), or (VIII-B), or a pharmaceutically acceptable isomer, racemate, hydrate, solvate, isotope, or salt thereof, wherein $R^{1c}$ is lower alkyl.

In a more specific embodiment, compounds are provided having the structure of any one of above Formulas (I), (I-B), (II), (II-B), (III), (III-B), (IV), (IV-B), (V), (V-B), (VI), (VI-B), (VII), (VII-B), (VIII), or (VIII-B), or a pharmaceutically acceptable isomer, racemate, hydrate, solvate, isotope, or salt thereof, wherein $R^{1c}$ is methyl or ethyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is lower alkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is methyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is lower alkenyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is halo.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is Cl or Br.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is Cl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is Br.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is lower haloalkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^1$ is —$CF_3$.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is lower alkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is methyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is halo.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is Cl or Br.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is Cl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is Br.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is lower haloalkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $X^2$ is —$CF_3$.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is lower alkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is lower alkyl substituted with —OR', and in further embodiments R' is H or R' is lower alkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is lower haloalkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is —$OR^a$, and in further embodiments $R^a$ is lower alkyl or $R^a$ is lower haloalkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^{2a}$ is —$C(O)R^a$, and in further embodiments $R^a$ is lower alkyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is —$NR^aC(O)R^b$, and in further embodiments $R^a$ is H and $R^b$ is lower alkyl or $R^b$ is methyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is —$C(O)OR^a$, and in further embodiments $R^a$ is lower alkyl or $R^a$ is methyl or ethyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is —$S(O)_2R^a$, and in further embodiments $R^a$ is lower alkyl or $R^a$ is methyl.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is halo, and in further embodiments $R^{2a}$ or at least one $R^2$ is F.

In a more specific embodiment, compounds are provided having the structure of any one of above Formulas (I), (I-A), (I-B), (II), (II-A), (II-B), (III), (III-A), (III-B), (IV), (IV-A), (IV-B), (V), (V-A), (V-B), (VI), (VI-A), (VI-B), (VII), (VII-A), (VII-B), (VIII), (VIII-A), or (VIII-B), or a pharmaceutically acceptable isomer, racemate, hydrate, solvate, isotope, or salt thereof, wherein $R^{2a}$ or at least one $R^2$ is cyano.

Representative compounds of Formula (I), and Formulas (II) through (VIII) as applicable, include the compounds listed in Table 1 below, as well as pharmaceutically acceptable salts thereof. To this end, representative compounds are identified herein by their respective "Compound Number", which is sometimes abbreviated as "Compound No.", "Cmpd. No." or "No."

TABLE 1

Representative Compounds

| Compound Number | Structure |
|---|---|
| 1 | 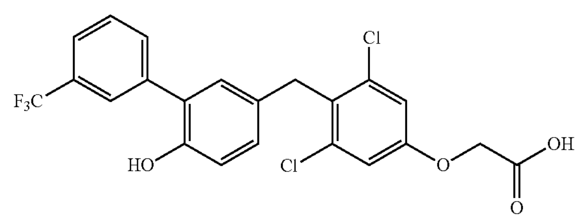 [SMILES: O=C(O)COc1cc(Cl)c(Cc2ccc(O)c(-c3cccc(C(F)(F)F)c3)c2)c(Cl)c1] |
| 2 | 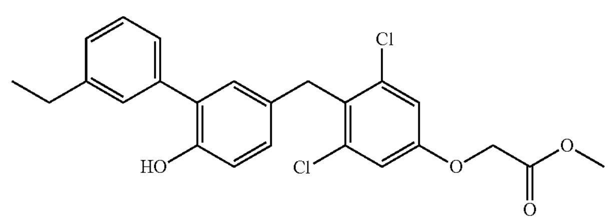 [SMILES: CCc1cccc(-c2cc(Cc3c(Cl)cc(OCC(=O)OC)cc3Cl)ccc2O)c1] |
| 3 | 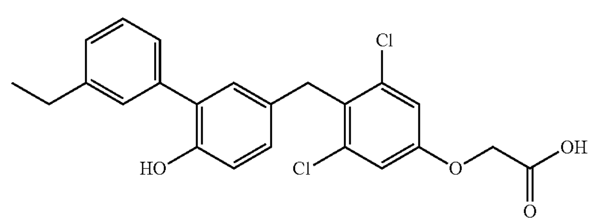 [SMILES: CCc1cccc(-c2cc(Cc3c(Cl)cc(OCC(=O)O)cc3Cl)ccc2O)c1] |
| 4 | 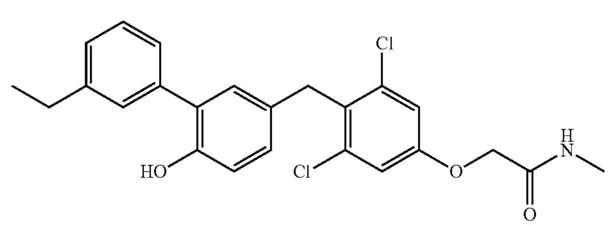 [SMILES: CCc1cccc(-c2cc(Cc3c(Cl)cc(OCC(=O)NC)cc3Cl)ccc2O)c1] |

TABLE 1-continued

Representative Compounds

| Compound Number | Structure |
|---|---|
| 5 | 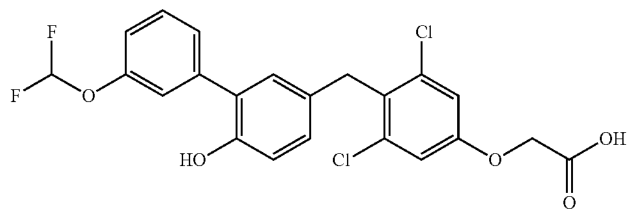 [SMILES: O=C(O)COc1cc(Cl)c(Cc2ccc(O)c(-c3cccc(OC(F)F)c3)c2)c(Cl)c1] |
| 6 | 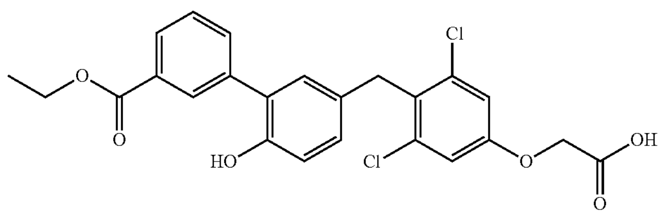 [SMILES: CCOC(=O)c1cccc(-c2cc(Cc3c(Cl)cc(OCC(=O)O)cc3Cl)ccc2O)c1] |
| 7 | 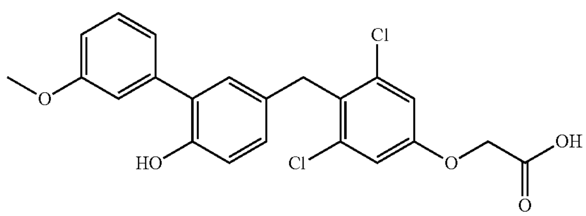 [SMILES: COc1cccc(-c2cc(Cc3c(Cl)cc(OCC(=O)O)cc3Cl)ccc2O)c1] |
| 8 | 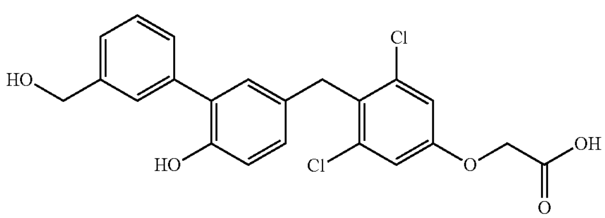 [SMILES: O=C(O)COc1cc(Cl)c(Cc2ccc(O)c(-c3cccc(CO)c3)c2)c(Cl)c1] |
| 9 | 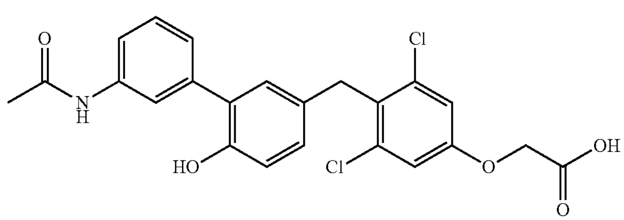 [SMILES: CC(=O)Nc1cccc(-c2cc(Cc3c(Cl)cc(OCC(=O)O)cc3Cl)ccc2O)c1] |
| 10 | 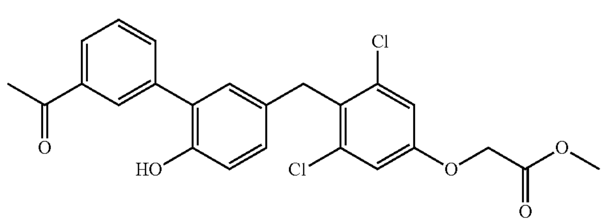 [SMILES: COC(=O)COc1cc(Cl)c(Cc2ccc(O)c(-c3cccc(C(C)=O)c3)c2)c(Cl)c1] |
| 11 | 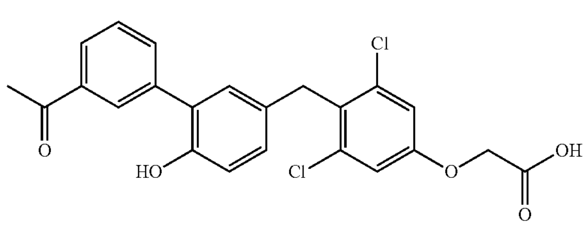 [SMILES: CC(=O)c1cccc(-c2cc(Cc3c(Cl)cc(OCC(=O)O)cc3Cl)ccc2O)c1] |

TABLE 1-continued

Representative Compounds

| Compound Number | Structure |
|---|---|
| 12 | 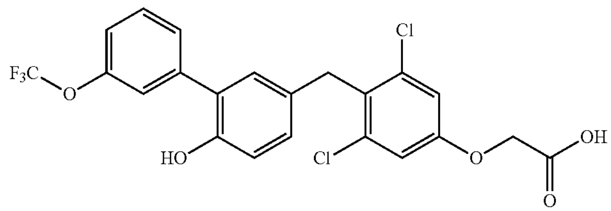 |
| 13 | 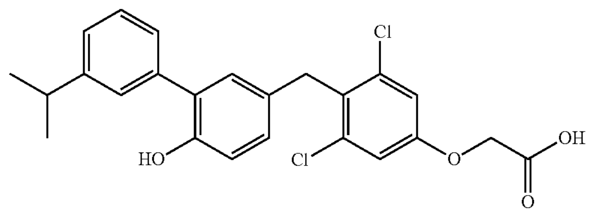 [SMILES: CC(C)c1cccc(-c2cc(Cc3c(Cl)cc(OCC(=O)O)cc3Cl)ccc2O)c1] |
| 14 | 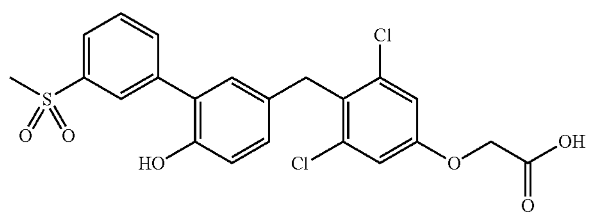 [SMILES: CS(=O)(=O)c1cccc(-c2cc(Cc3c(Cl)cc(OCC(=O)O)cc3Cl)ccc2O)c1] |
| 15 | 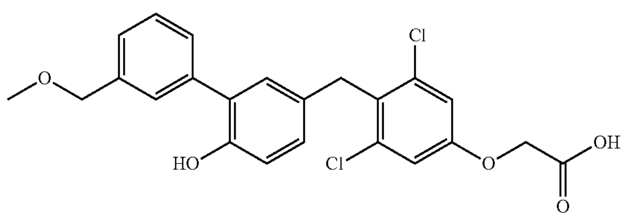 |
| 16 | 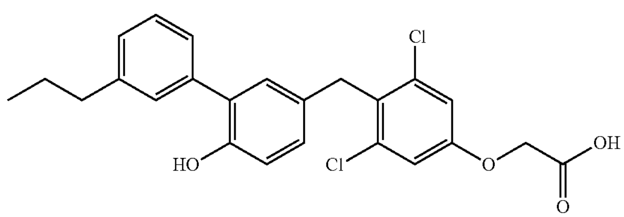 [SMILES: CCCc1cccc(-c2cc(Cc3c(Cl)cc(OCC(=O)O)cc3Cl)ccc2O)c1] |
| 17 | 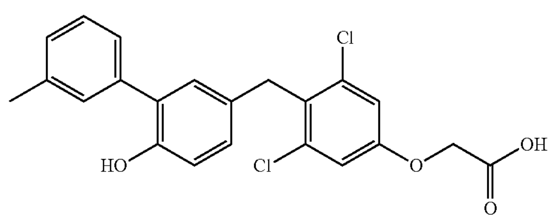 [SMILES: Cc1cccc(-c2cc(Cc3c(Cl)cc(OCC(=O)O)cc3Cl)ccc2O)c1] |
| 18 | 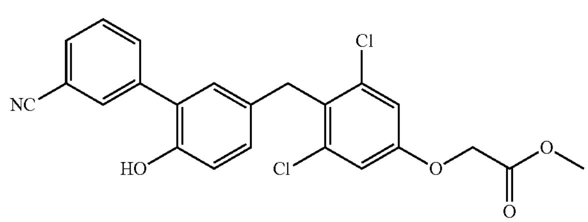 [SMILES: COC(=O)COc1cc(Cl)c(Cc2ccc(O)c(-c3cccc(C#N)c3)c2)c(Cl)c1] |

TABLE 1-continued

Representative Compounds

| Compound Number | Structure |
|---|---|
| 19 | 3'-cyano-biphenyl-CH2-(2,6-dichloro-4-(OCH2COOH))phenyl with 2-OH |
| 20 | 3'-vinyl-biphenyl-CH2-(2,6-dichloro-4-(OCH2COOCH3))phenyl with 2-OH |
| 21 | 3'-vinyl-biphenyl-CH2-(2,6-dichloro-4-(OCH2COOH))phenyl with 2-OH |
| 22 | 3'-isopropenyl-biphenyl-CH2-(2,6-dichloro-4-(OCH2COOH))phenyl with 2-OH |
| 23 | 3'-formyl-biphenyl-CH2-(2,6-dichloro-4-(OCH2COOCH3))phenyl with 2-OH |
| 24 | 3'-ethynyl-biphenyl-CH2-(2,6-dichloro-4-(OCH2COOCH3))phenyl with 2-OH |
| 25 | 3'-ethynyl-biphenyl-CH2-(2,6-dichloro-4-(OCH2COOH))phenyl with 2-OH |

TABLE 1-continued

Representative Compounds

| Compound Number | Structure |
|---|---|
| 26 | 3'-(2,2,2-trifluoroethyl)-biphenyl with chlorophenoxyacetic acid |
| 27 | 3'-(1,1,2,2,2-pentafluoroethyl)-biphenyl with methyl chlorophenoxyacetate |
| 28 | 3'-(1,1,2,2,2-pentafluoroethyl)-biphenyl with chlorophenoxyacetic acid |
| 29 | 3'-chloro-biphenyl with chlorophenoxyacetic acid |
| 30 | 3'-chloro-biphenyl with methyl chlorophenoxyacetate |
| 31 | 3'-chloro-biphenyl with N-methyl chlorophenoxyacetamide |
| 32 | 3'-chloro-biphenyl with N,N-dimethyl chlorophenoxyacetamide |

TABLE 1-continued

Representative Compounds

| Compound Number | Structure |
|---|---|
| 33 | (structure) |
| 34 | (structure) |
| 35 | (structure) |
| 36 | (structure) |
| 37 | (structure) |
| 38 | (structure) |

TABLE 1-continued

Representative Compounds

| Compound Number | Structure |
|---|---|
| 39 | 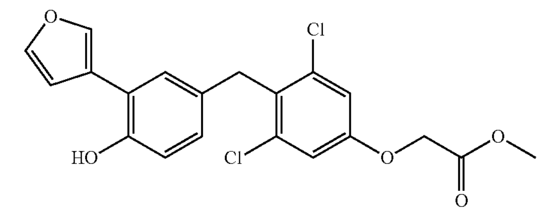 [SMILES: COC(=O)COc1cc(Cl)c(Cc2ccc(O)c(-c3ccoc3)c2)c(Cl)c1] |
| 40 | 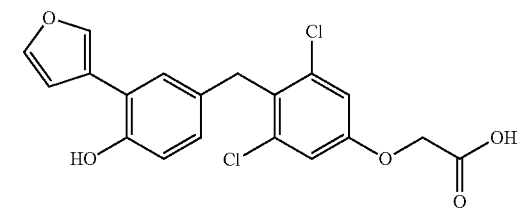 [SMILES: O=C(O)COc1cc(Cl)c(Cc2ccc(O)c(-c3ccoc3)c2)c(Cl)c1] |
| 41 | 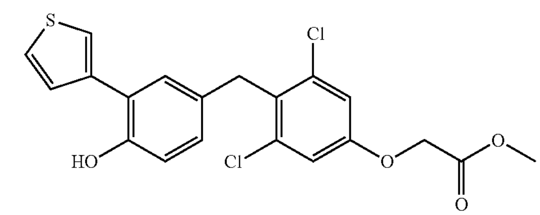 [SMILES: COC(=O)COc1cc(Cl)c(Cc2ccc(O)c(-c3ccsc3)c2)c(Cl)c1] |
| 42 | 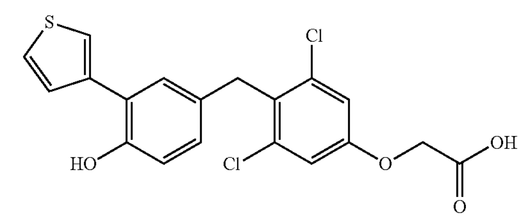 [SMILES: O=C(O)COc1cc(Cl)c(Cc2ccc(O)c(-c3ccsc3)c2)c(Cl)c1] |
| 43 | 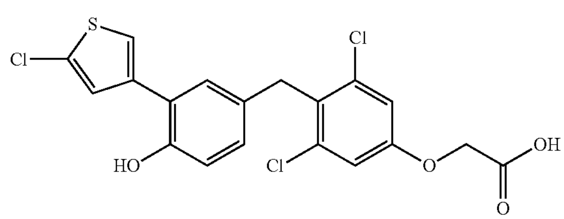 [SMILES: O=C(O)COc1cc(Cl)c(Cc2ccc(O)c(-c3csc(Cl)c3)c2)c(Cl)c1] |
| 44 | 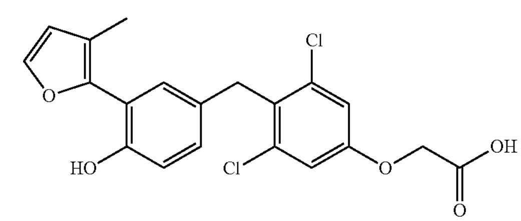 [SMILES: Cc1ccoc1-c1cc(Cc2c(Cl)cc(OCC(=O)O)cc2Cl)ccc1O] |
| 45 | 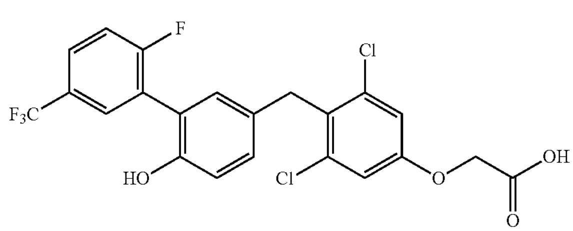 [SMILES: O=C(O)COc1cc(Cl)c(Cc2ccc(O)c(-c3cc(C(F)(F)F)ccc3F)c2)c(Cl)c1] |

TABLE 1-continued

Representative Compounds

| Compound Number | Structure |
|---|---|
| 46 | (structure: 2'-fluoro-5'-trifluoromethyl-6-hydroxybiphenyl linked via CH₂ to 2,6-dichloro-4-(O-CH₂-C(=O)Cl)phenyl) |
| 46 | (structure: 2'-fluoro-5'-trifluoromethyl-6-hydroxybiphenyl linked via CH₂ to 2,6-dichloro-4-(O-CH₂-C(=O)NHCH₃)phenyl) |
| 47 | (structure: 2'-fluoro-5'-trifluoromethyl-6-hydroxybiphenyl linked via CH₂ to 2,6-dichloro-4-(O-CH₂-C(=O)N(CH₃)₂)phenyl) |
| 48 | (structure: 4'-fluoro-3'-trifluoromethyl-6-hydroxybiphenyl linked via CH₂ to 2,6-dichloro-4-(O-CH₂-COOH)phenyl) |
| 49 | (structure: 3'-trifluoromethyl-2'-fluoro-6-hydroxybiphenyl linked via CH₂ to 2,6-dichloro-4-(O-CH₂-COOH)phenyl) |
| 50 | (structure: 3'-fluoro-5'-trifluoromethyl-6-hydroxybiphenyl linked via CH₂ to 2,6-dichloro-4-(O-CH₂-COOH)phenyl) |

US 11,667,606 B2
41                                           42
TABLE 1-continued
Representative Compounds
| Compound Number | Structure |
|---|---|
| 51 | 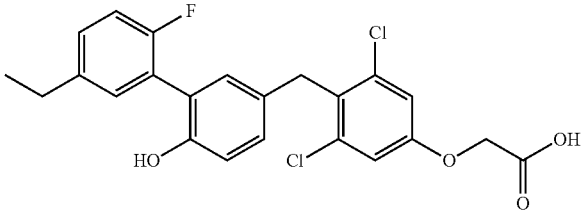 [SMILES: CCc1ccc(F)c(-c2cc(Cc3c(Cl)cc(OCC(=O)O)cc3Cl)ccc2O)c1] |
| 52 | 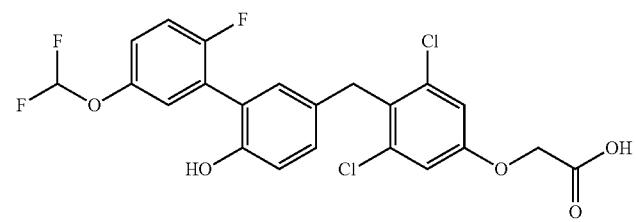 [SMILES: O=C(O)COc1cc(Cl)c(Cc2ccc(O)c(-c3cc(OC(F)F)ccc3F)c2)c(Cl)c1] |
| 53 | 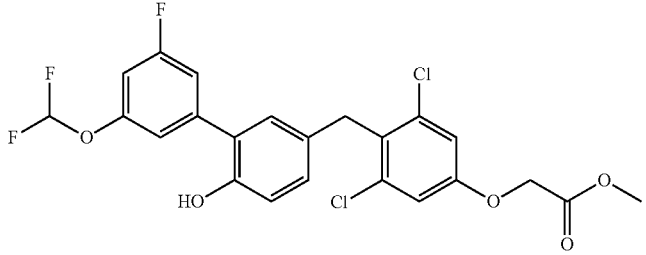 [SMILES: COC(=O)COc1cc(Cl)c(Cc2ccc(O)c(-c3cc(F)cc(OC(F)F)c3)c2)c(Cl)c1] |
| 54 | 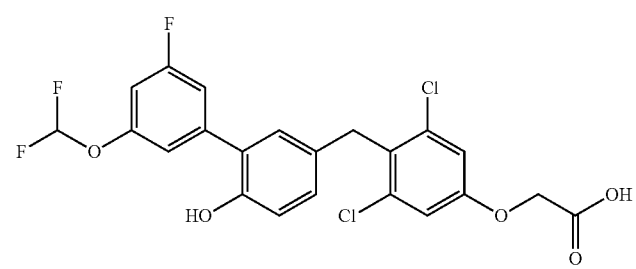 [SMILES: O=C(O)COc1cc(Cl)c(Cc2ccc(O)c(-c3cc(F)cc(OC(F)F)c3)c2)c(Cl)c1] |
| 55 | 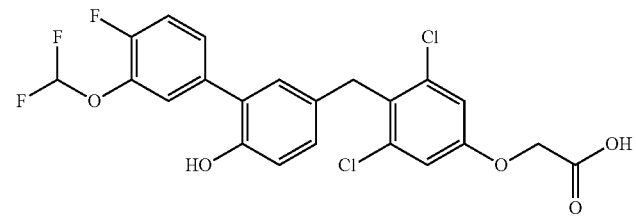 [SMILES: O=C(O)COc1cc(Cl)c(Cc2ccc(O)c(-c3ccc(F)c(OC(F)F)c3)c2)c(Cl)c1] |
| 56 | 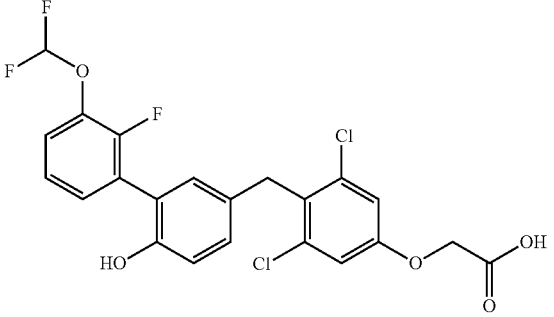 [SMILES: O=C(O)COc1cc(Cl)c(Cc2ccc(O)c(-c3cccc(OC(F)F)c3F)c2)c(Cl)c1] |

TABLE 1-continued

Representative Compounds

| Compound Number | Structure |
|---|---|
| 57 | 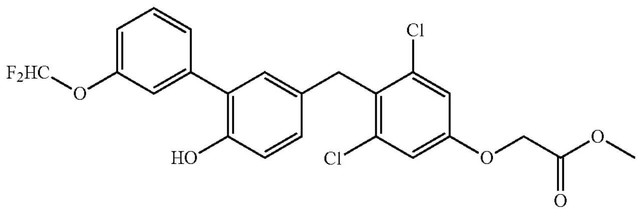 [SMILES: COC(=O)COc1cc(Cl)c(Cc2ccc(O)c(-c3cccc(OC(F)F)c3)c2)c(Cl)c1] |
| 58 | 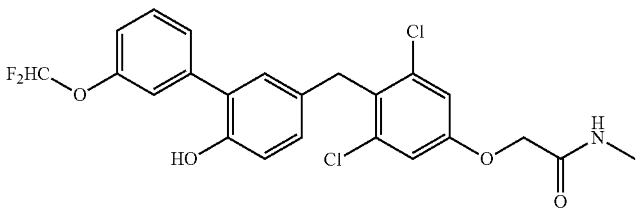 [SMILES: CNC(=O)COc1cc(Cl)c(Cc2ccc(O)c(-c3cccc(OC(F)F)c3)c2)c(Cl)c1] |
| 59 | 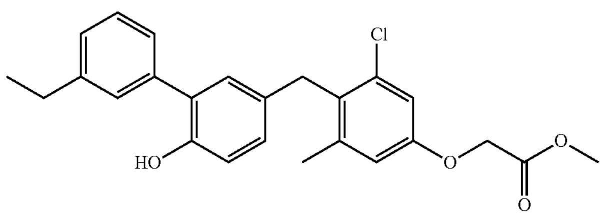 [SMILES: CCc1cccc(-c2cc(Cc3c(C)cc(OCC(=O)OC)cc3Cl)ccc2O)c1] |
| 60 | 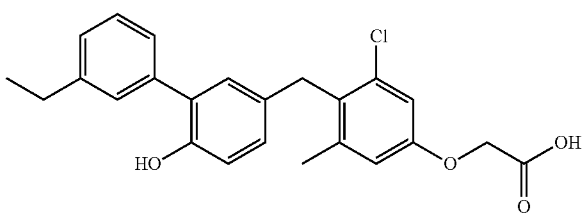 [SMILES: CCc1cccc(-c2cc(Cc3c(C)cc(OCC(=O)O)cc3Cl)ccc2O)c1] |
| 61 | 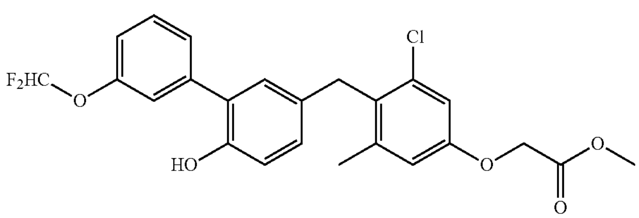 [SMILES: COC(=O)COc1cc(C)c(Cc2ccc(O)c(-c3cccc(OC(F)F)c3)c2)c(Cl)c1] |
| 62 | 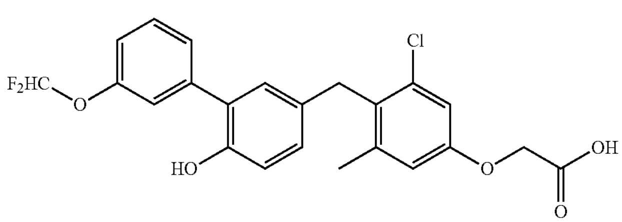 [SMILES: Cc1cc(OCC(=O)O)cc(Cl)c1Cc1ccc(O)c(-c2cccc(OC(F)F)c2)c1] |
| 63 | 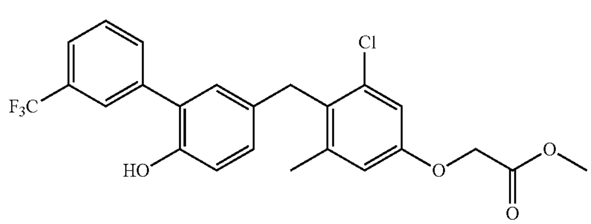 [SMILES: COC(=O)COc1cc(C)c(Cc2ccc(O)c(-c3cccc(C(F)(F)F)c3)c2)c(Cl)c1] |

TABLE 1-continued

Representative Compounds

| Compound Number | Structure |
|---|---|
| 64 | 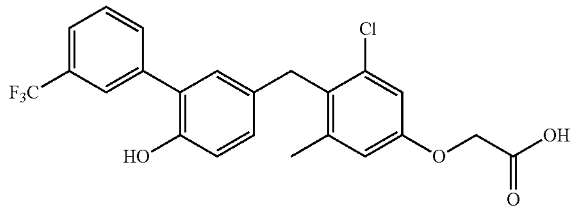 [SMILES: Cc1cc(OCC(=O)O)cc(Cl)c1Cc1ccc(O)c(-c2cccc(C(F)(F)F)c2)c1] |
| 65 | 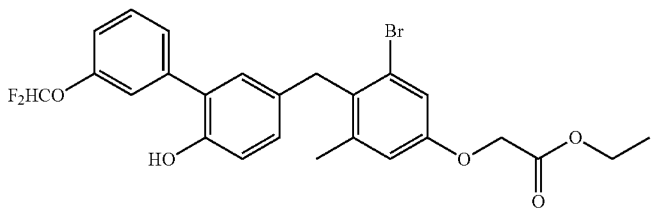 [SMILES: CCOC(=O)COc1cc(C)c(Cc2ccc(O)c(-c3cccc(OC(F)F)c3)c2)c(Br)c1] |
| 66 | 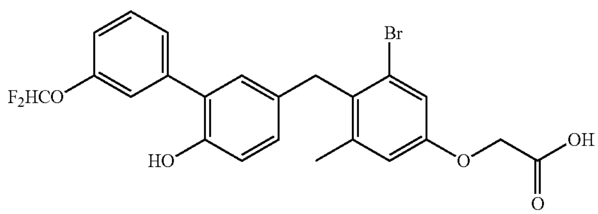 [SMILES: Cc1cc(OCC(=O)O)cc(Br)c1Cc1ccc(O)c(-c2cccc(OC(F)F)c2)c1] |
| 67 | 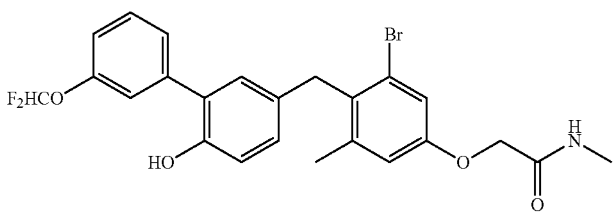 [SMILES: CNC(=O)COc1cc(C)c(Cc2ccc(O)c(-c3cccc(OC(F)F)c3)c2)c(Br)c1] |
| 68 | 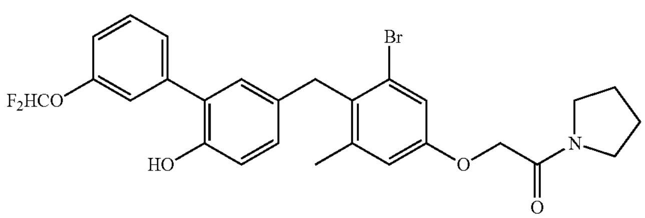 [SMILES: Cc1cc(OCC(=O)N2CCCC2)cc(Br)c1Cc1ccc(O)c(-c2cccc(OC(F)F)c2)c1] |
| 69 | 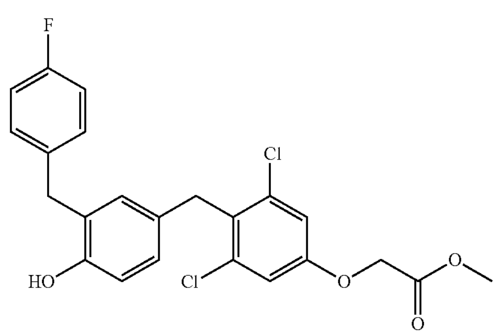 [SMILES: COC(=O)COc1cc(Cl)c(Cc2ccc(O)c(Cc3ccc(F)cc3)c2)c(Cl)c1] |

TABLE 1-continued

Representative Compounds

| Compound Number | Structure |
|---|---|
| 70 | 2-(3,5-dichloro-4-(4-hydroxy-3-(4-fluorobenzyl)benzyl)phenoxy)acetic acid |
| 71 | 2-(3,5-dichloro-4-(4-hydroxy-3-(4-fluorobenzyl)benzyl)phenoxy)-N-methylacetamide |
| 72 | methyl 2-(3,5-dichloro-4-(4-hydroxy-3-(1-(4-fluorophenyl)ethyl)benzyl)phenoxy)acetate |
| 73 | 2-(3,5-dichloro-4-(4-hydroxy-3-(1-(4-fluorophenyl)ethyl)benzyl)phenoxy)acetic acid |

TABLE 1-continued

Representative Compounds

| Compound Number | Structure |
|---|---|
| 74 | 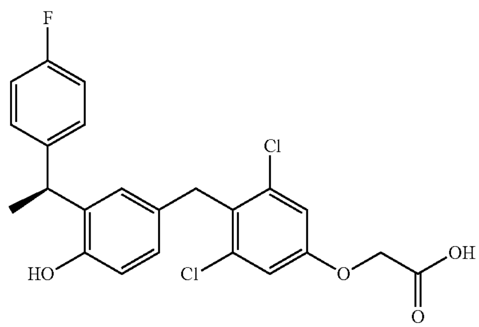 |
| 75 | 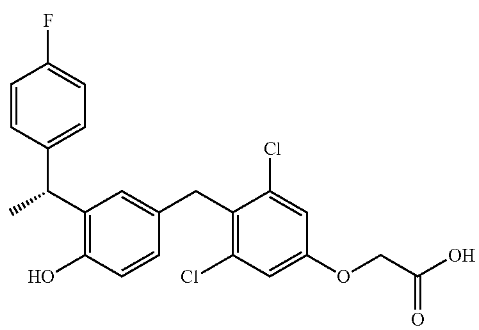 [SMILES: CC(c1ccc(F)cc1)c1cc(Cc2c(Cl)cc(OCC(=O)O)cc2Cl)ccc1O] |
| 76 | 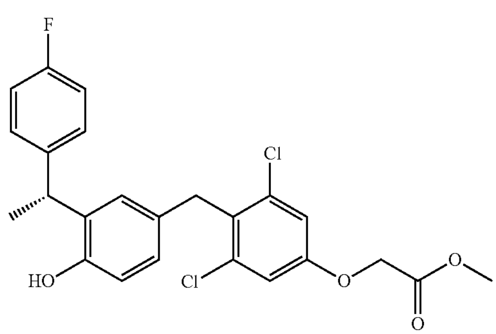 |
| 77 | 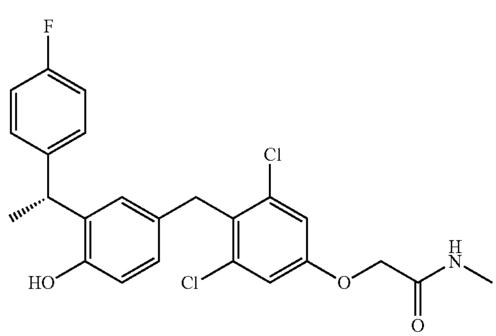 [SMILES: C[C@H](c1ccc(F)cc1)c1cc(Cc2c(Cl)cc(OCC(=O)N(C)C)cc2Cl)ccc1O] |

TABLE 1-continued
Representative Compounds
| Compound Number | Structure |
|---|---|
| 78 | 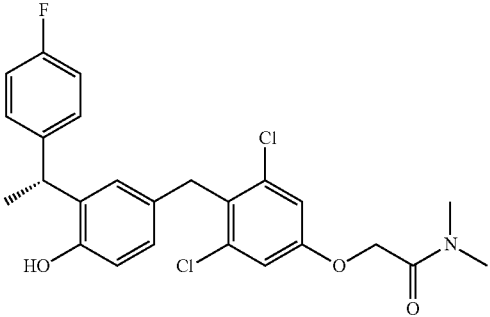 |
| 79 | 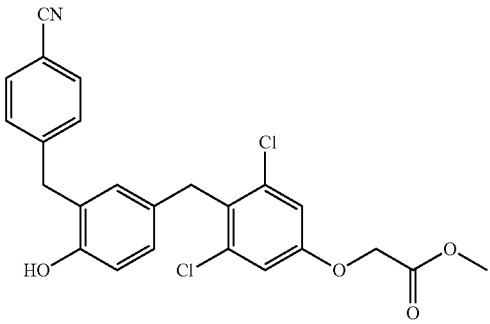 [SMILES: COC(=O)COc1cc(Cl)c(Cc2ccc(O)c(Cc3ccc(C#N)cc3)c2)c(Cl)c1] |
| 80 | 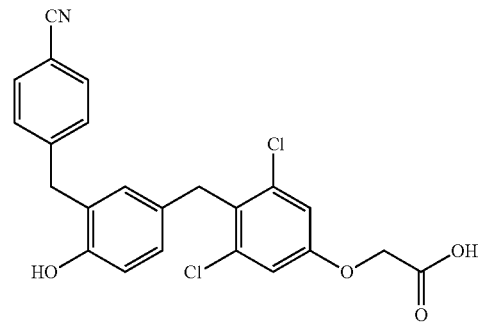 [SMILES: N#Cc1ccc(Cc2cc(Cc3c(Cl)cc(OCC(=O)O)cc3Cl)ccc2O)cc1] |
| 81 | 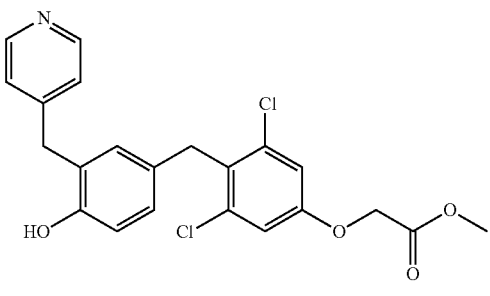 [SMILES: COC(=O)COc1cc(Cl)c(Cc2ccc(O)c(Cc3ccncc3)c2)c(Cl)c1] |
| 82 | 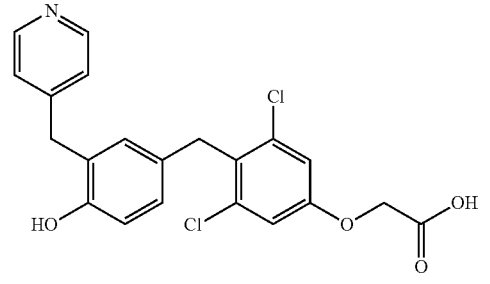 [SMILES: O=C(O)COc1cc(Cl)c(Cc2ccc(O)c(Cc3ccncc3)c2)c(Cl)c1] |

TABLE 1-continued
Representative Compounds
| Compound Number | Structure |
|---|---|
| 83 | 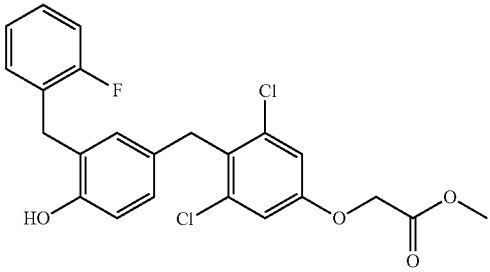 [SMILES: COC(=O)COc1cc(Cl)c(Cc2ccc(O)c(Cc3ccccc3F)c2)c(Cl)c1] |
| 84 | 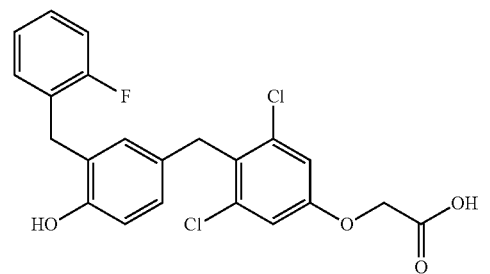 [SMILES: O=C(O)COc1cc(Cl)c(Cc2ccc(O)c(Cc3ccccc3F)c2)c(Cl)c1] |
| 85 | 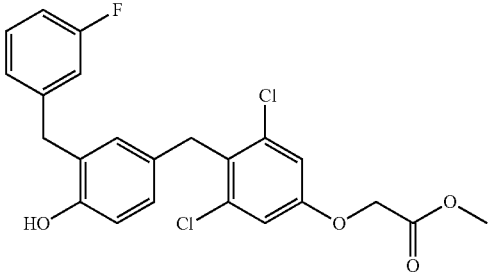 [SMILES: COC(=O)COc1cc(Cl)c(Cc2ccc(O)c(Cc3cccc(F)c3)c2)c(Cl)c1] |
| 86 | 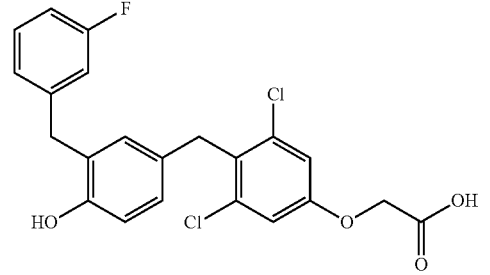 [SMILES: O=C(O)COc1cc(Cl)c(Cc2ccc(O)c(Cc3cccc(F)c3)c2)c(Cl)c1] |
| 87 | 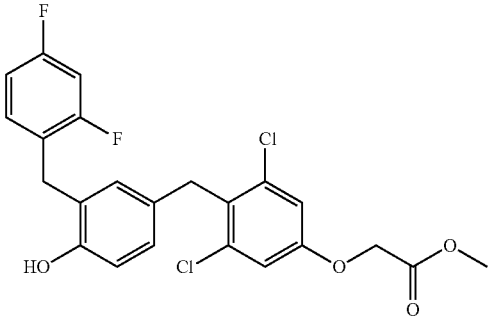 [SMILES: COC(=O)COc1cc(Cl)c(Cc2ccc(O)c(Cc3ccc(F)cc3F)c2)c(Cl)c1] |

TABLE 1-continued

Representative Compounds

| Compound Number | Structure |
|---|---|
| 88 | *(2,4-difluorobenzyl)-substituted phenol linked via CH₂ to 2,6-dichloro-4-(carboxymethoxy)phenyl)* |
| 89 | *(4-chlorobenzyl)-substituted phenol linked via CH₂ to 2,6-dichloro-4-(methoxycarbonylmethoxy)phenyl* |
| 90 | *(4-chlorobenzyl)-substituted phenol linked via CH₂ to 2,6-dichloro-4-(carboxymethoxy)phenyl* |
| 91 | *(4-methylbenzyl)-substituted phenol linked via CH₂ to 2,6-dichloro-4-(methoxycarbonylmethoxy)phenyl* |

TABLE 1-continued

Representative Compounds

| Compound Number | Structure |
|---|---|
| 92 | (4-methylbenzyl)-substituted phenol linked via CH2 to 2,6-dichloro-4-(carboxymethoxy)phenyl |
| 93 | (pyrimidin-5-ylmethyl)-substituted phenol linked via CH2 to 2,6-dichloro-4-(methoxycarbonylmethoxy)phenyl |
| 94 | (pyrimidin-5-ylmethyl)-substituted phenol linked via CH2 to 2,6-dichloro-4-(carboxymethoxy)phenyl |
| 95 | [4-(2,2,2-trifluoroethyl)benzyl]-substituted phenol linked via CH2 to 2,6-dichloro-4-(methoxycarbonylmethoxy)phenyl |

TABLE 1-continued
Representative Compounds
| Compound Number | Structure |
| --- | --- |
| 96 | 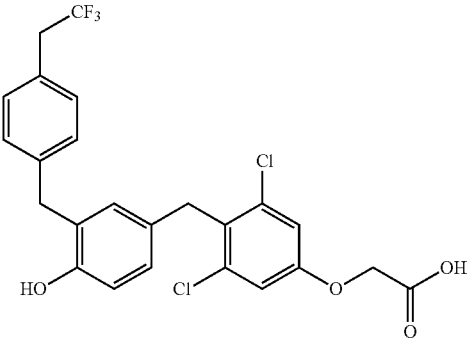 [SMILES: O=C(O)COc1cc(Cl)c(Cc2ccc(O)c(Cc3ccc(CC(F)(F)F)cc3)c2)c(Cl)c1] |
| 97 | 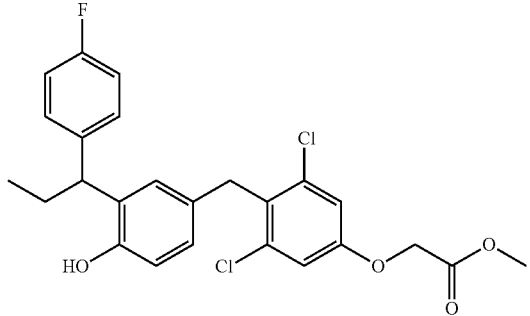 [SMILES: CCC(c1ccc(F)cc1)c1cc(Cc2c(Cl)cc(OCC(=O)OC)cc2Cl)ccc1O] |
| 98 | 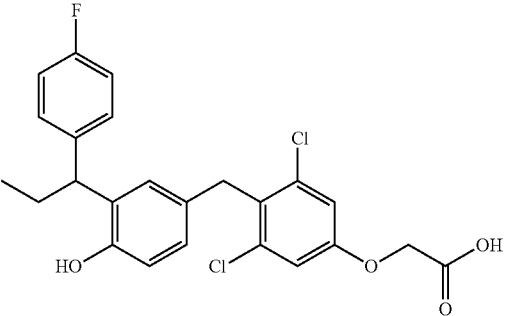 [SMILES: CCC(c1ccc(F)cc1)c1cc(Cc2c(Cl)cc(OCC(=O)O)cc2Cl)ccc1O] |
| 99 | 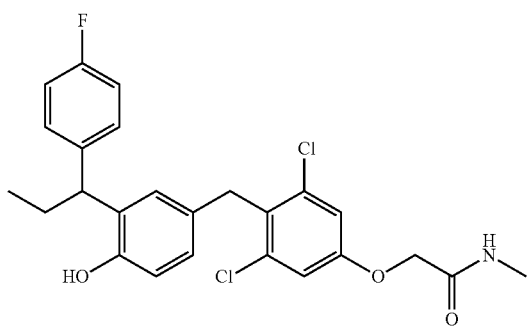 |

TABLE 1-continued
Representative Compounds
| Compound Number | Structure |
|---|---|
| 100 | 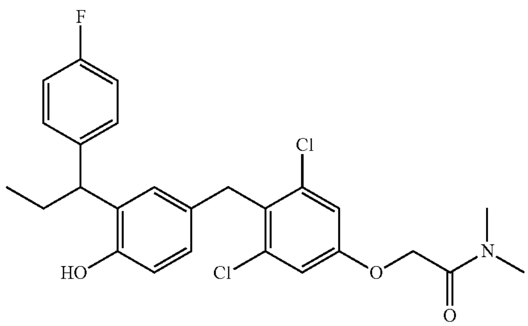 [SMILES: CCC(c1ccc(F)cc1)c1cc(Cc2c(Cl)cc(OCC(=O)N(C)C)cc2Cl)ccc1O] |
| 101 | 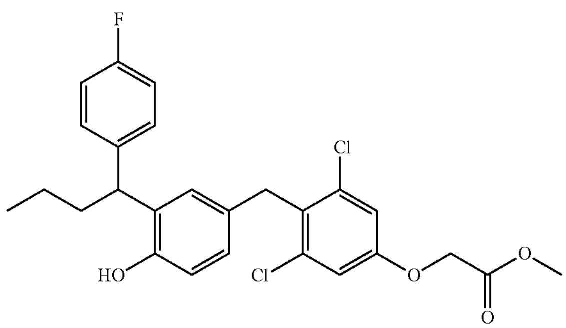 [SMILES: CCCC(c1ccc(F)cc1)c1cc(Cc2c(Cl)cc(OCC(=O)OC)cc2Cl)ccc1O] |
| 102 | 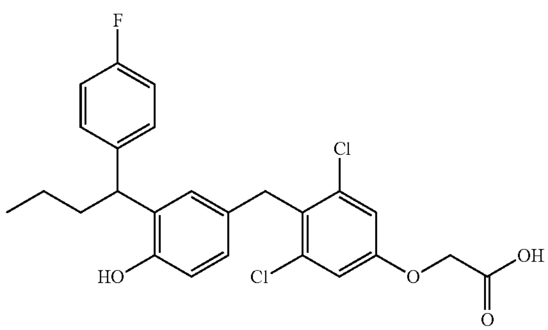 [SMILES: CCCC(c1ccc(F)cc1)c1cc(Cc2c(Cl)cc(OCC(=O)O)cc2Cl)ccc1O] |
| 103 | 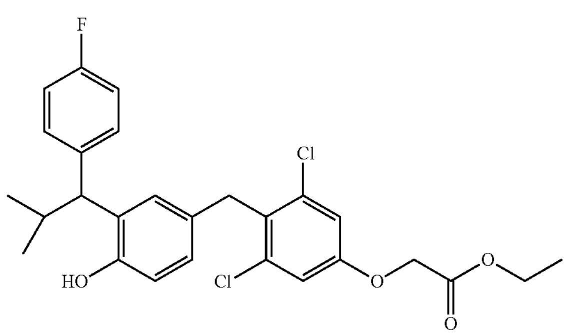 [SMILES: CCOC(=O)COc1cc(Cl)c(Cc2ccc(O)c(C(c3ccc(F)cc3)C(C)C)c2)c(Cl)c1] |
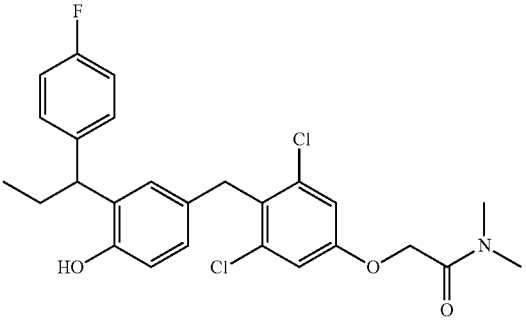

TABLE 1-continued
Representative Compounds
| Compound Number | Structure |
|---|---|
| 104 | 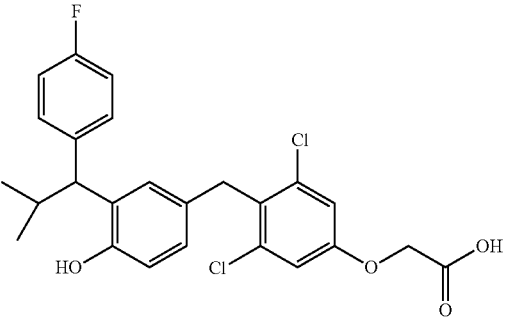 [SMILES: CC(C)C(c1ccc(F)cc1)c1cc(Cc2c(Cl)cc(OCC(=O)O)cc2Cl)ccc1O] |
| 105 | 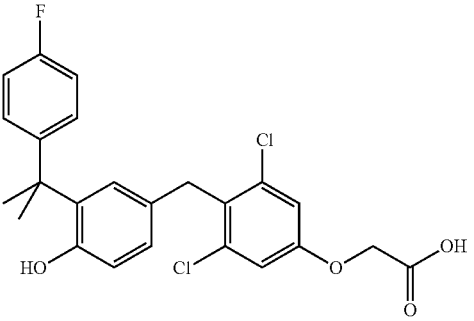 [SMILES: CC(C)(c1ccc(F)cc1)c1cc(Cc2c(Cl)cc(OCC(=O)O)cc2Cl)ccc1O] |
| 106 | 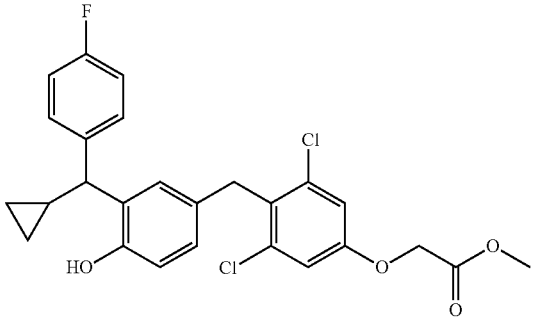 [SMILES: COC(=O)COc1cc(Cl)c(Cc2ccc(O)c(C(c3ccc(F)cc3)C3CC3)c2)c(Cl)c1] |
| 107 | 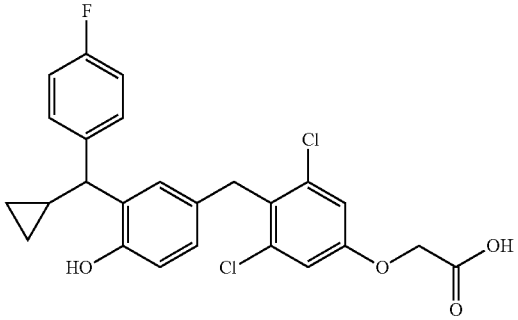 [SMILES: O=C(O)COc1cc(Cl)c(Cc2ccc(O)c(C(c3ccc(F)cc3)C3CC3)c2)c(Cl)c1] |

TABLE 1-continued
Representative Compounds
| Compound Number | Structure |
|---|---|
| 108 | 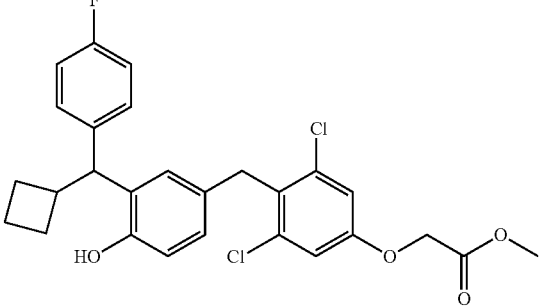 |
| 109 | 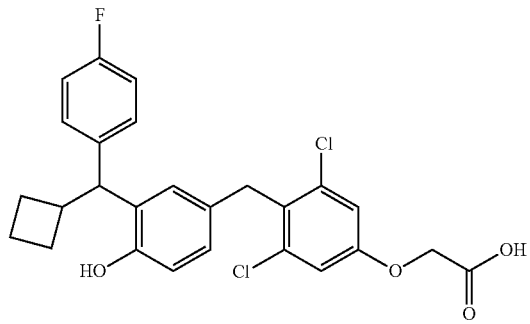 [SMILES: O=C(O)COc1cc(Cl)c(Cc2ccc(O)c(C(c3ccc(F)cc3)C3CCC3)c2)c(Cl)c1] |
| 110 | 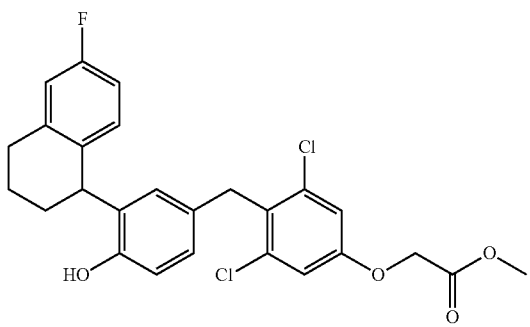 [SMILES: COC(=O)COc1cc(Cl)c(Cc2ccc(O)c(C3CCCc4cc(F)ccc43)c2)c(Cl)c1] |
| 111 | 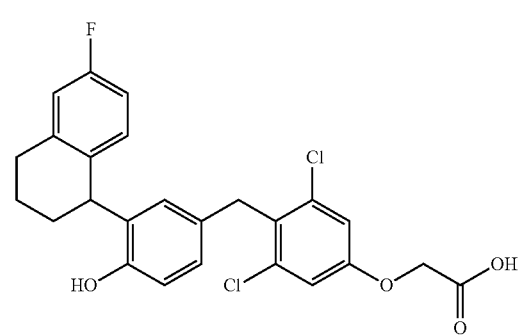 [SMILES: O=C(O)COc1cc(Cl)c(Cc2ccc(O)c(C3CCCc4cc(F)ccc43)c2)c(Cl)c1] |

TABLE 1-continued

Representative Compounds

| Compound Number | Structure |
|---|---|
| 112 | (5-fluoro-2,3-dihydro-1H-inden-1-yl substituted phenol linked via CH₂ to 2,6-dichloro-4-(methoxycarbonylmethoxy)phenyl) |
| 113 | (5-fluoro-2,3-dihydro-1H-inden-1-yl substituted phenol linked via CH₂ to 2,6-dichloro-4-(carboxymethoxy)phenyl) |
| 114 | (4-fluorobenzyl substituted phenol linked via CH₂ to 3-chloro-5-methyl-4-(methoxycarbonylmethoxy)phenyl) |
| 115 | (4-fluorobenzyl substituted phenol linked via CH₂ to 3-chloro-5-methyl-4-(carboxymethoxy)phenyl) |

TABLE 1-continued
Representative Compounds
| Compound Number | Structure |
|---|---|
| 116 | 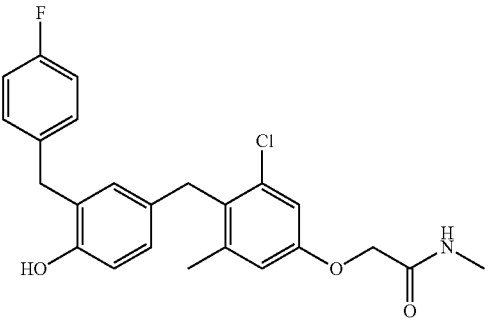 [SMILES: COC(=O)COc1cc(C)c(Cc2ccc(O)c(Cc3ccc(F)cc3)c2)c(Cl)c1] |
| 117 | 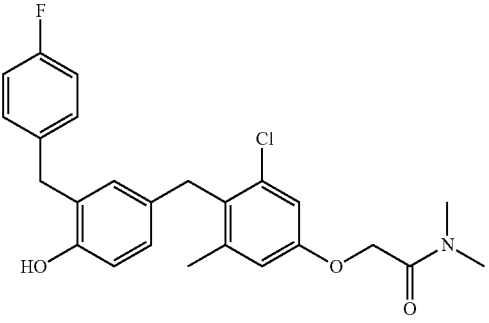 [SMILES: Cc1cc(OCC(=O)N(C)C)cc(Cl)c1Cc1ccc(O)c(Cc2ccc(F)cc2)c1] |
| 118 | 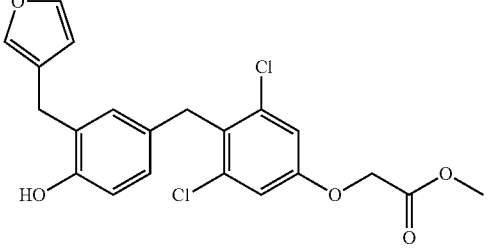 |
| 119 | 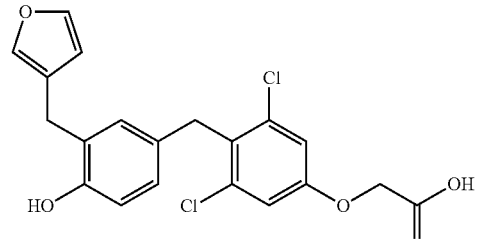 |
| 120 | 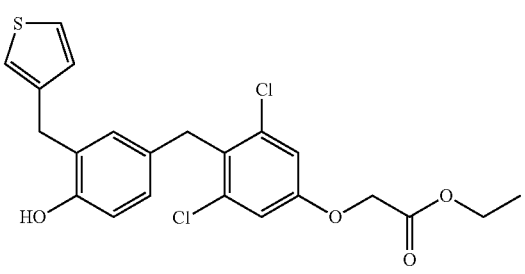 [SMILES: CCOC(=O)COc1cc(Cl)c(Cc2ccc(O)c(Cc3ccsc3)c2)c(Cl)c1] |

TABLE 1-continued

| Compound Number | Structure |
|---|---|
| 121 | (3-thienylmethyl-hydroxyphenyl)methyl-dichlorophenoxyacetic acid |
| 122 | (2-thienylmethyl-hydroxyphenyl)methyl-dichlorophenoxyacetic acid ethyl ester |
| 123 | (2-thienylmethyl-hydroxyphenyl)methyl-dichlorophenoxyacetic acid |
| 124 | [1-(4-fluorophenyl)-2,2,2-trifluoroethyl-hydroxyphenyl]methyl-dichlorophenoxyacetic acid ethyl ester |
| 125 | [1-(4-fluorophenyl)-2,2,2-trifluoroethyl-hydroxyphenyl]methyl-dichlorophenoxyacetic acid |

TABLE 1-continued
Representative Compounds
| Compound Number | Structure |
|---|---|
| 126 | 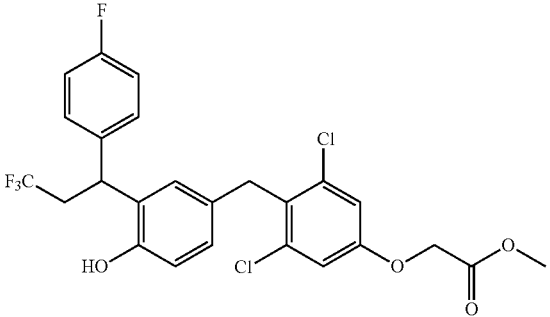 [SMILES: COC(=O)COc1cc(Cl)c(Cc2ccc(O)c(C(CC(F)(F)F)c3ccc(F)cc3)c2)c(Cl)c1] |
| 127 | 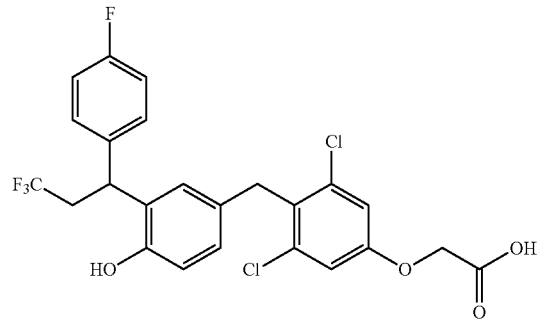 [SMILES: O=C(O)COc1cc(Cl)c(Cc2ccc(O)c(C(CC(F)(F)F)c3ccc(F)cc3)c2)c(Cl)c1] |
| 128 | 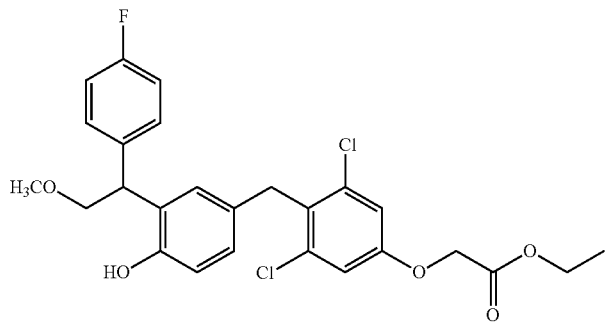 [SMILES: CCOC(=O)COc1cc(Cl)c(Cc2ccc(O)c(C(COC)c3ccc(F)cc3)c2)c(Cl)c1] |
| 129 | 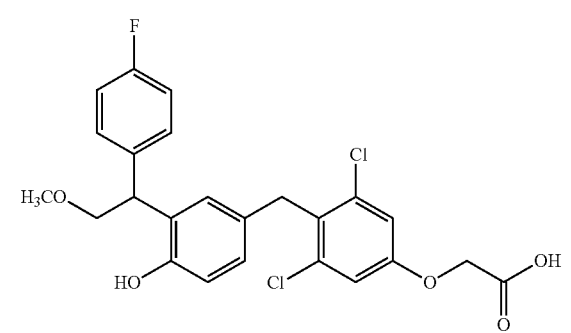 |

US 11,667,606 B2
TABLE 1-continued
Representative Compounds
| Compound Number | Structure |
|---|---|
| 130 | 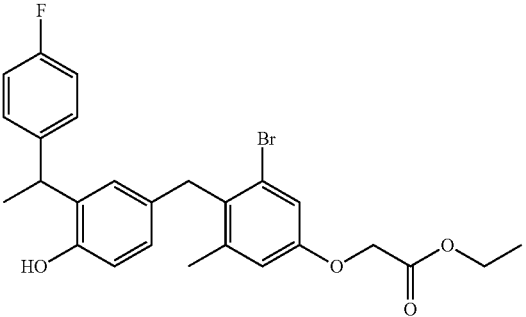 [SMILES: CCOC(=O)COc1cc(C)c(Cc2ccc(O)c(C(C)c3ccc(F)cc3)c2)c(Br)c1] |
| 131 | 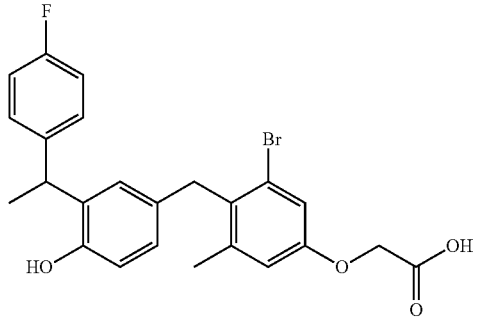 [SMILES: Cc1cc(OCC(=O)O)cc(Br)c1Cc1ccc(O)c(C(C)c2ccc(F)cc2)c1] |
| 132 | 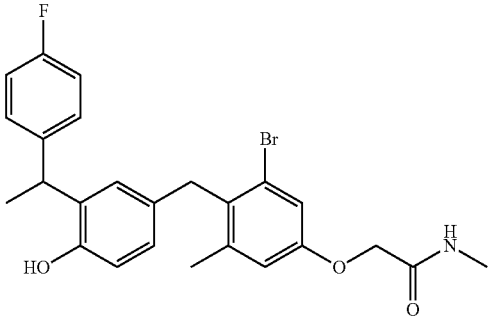 [SMILES: CNC(=O)COc1cc(C)c(Cc2ccc(O)c(C(C)c3ccc(F)cc3)c2)c(Br)c1] |
| 133 | 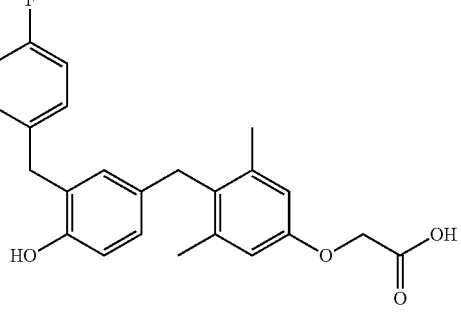 |
| 134 | 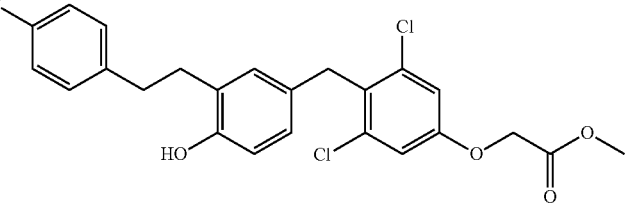 |

TABLE 1-continued

Representative Compounds

| Compound Number | Structure |
|---|---|
| 135 | 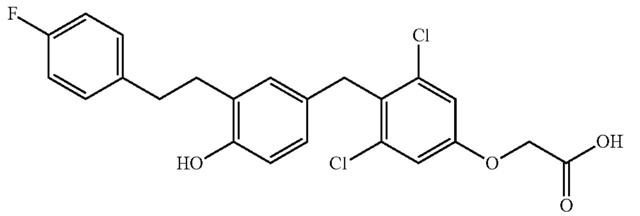 [SMILES: O=C(O)COc1cc(Cl)c(Cc2ccc(O)c(CCc3ccc(F)cc3)c2)c(Cl)c1] |
| 136 | 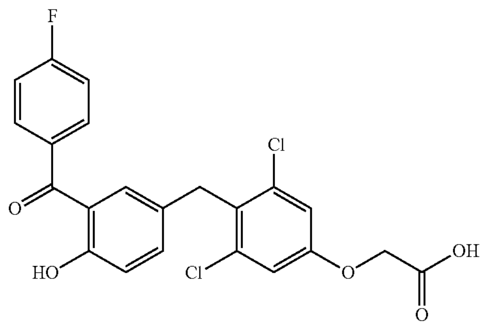 [SMILES: O=C(O)COc1cc(Cl)c(Cc2ccc(O)c(C(=O)c3ccc(F)cc3)c2)c(Cl)c1] |
| 137 | 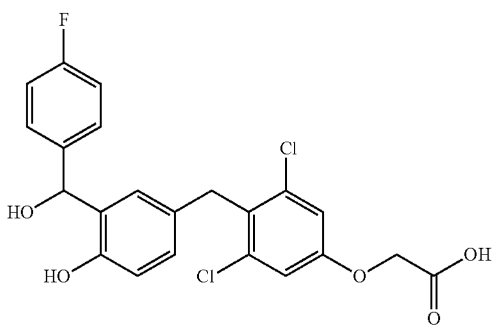 [SMILES: O=C(O)COc1cc(Cl)c(Cc2ccc(O)c(C(O)c3ccc(F)cc3)c2)c(Cl)c1] |
| 138 | 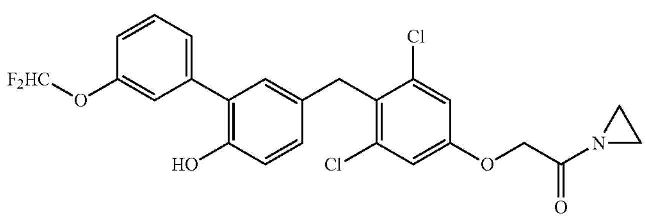 [SMILES: O=C(COc1cc(Cl)c(Cc2ccc(O)c(-c3cccc(OC(F)F)c3)c2)c(Cl)c1)N1CC1] |
| 139 | 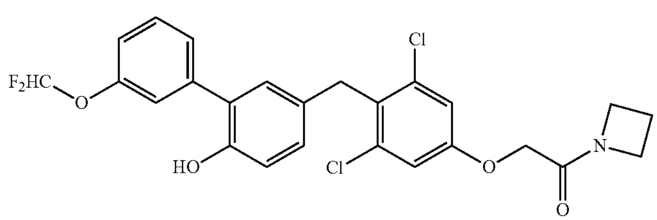 [SMILES: O=C(COc1cc(Cl)c(Cc2ccc(O)c(-c3cccc(OC(F)F)c3)c2)c(Cl)c1)N1CCC1] |
| 140 | 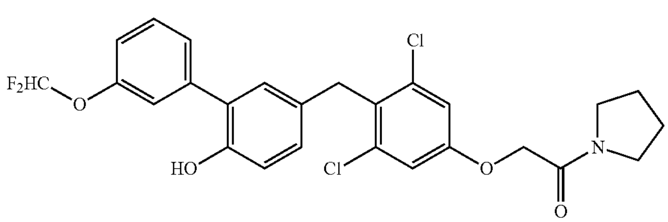 [SMILES: O=C(COc1cc(Cl)c(Cc2ccc(O)c(-c3cccc(OC(F)F)c3)c2)c(Cl)c1)N1CCCC1] |

TABLE 1-continued
Representative Compounds
| Compound Number | Structure |
|---|---|
| 141 | 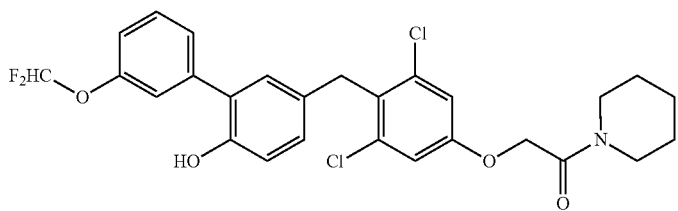 [SMILES: O=C(COc1cc(Cl)c(Cc2ccc(O)c(-c3cccc(OC(F)F)c3)c2)c(Cl)c1)N1CCCCC1] |
| 142 | 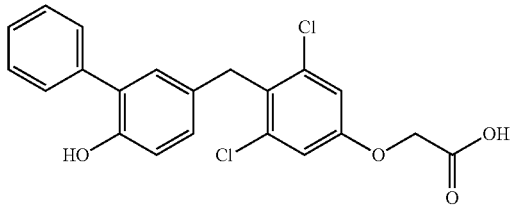 [SMILES: O=C(O)COc1cc(Cl)c(Cc2ccc(O)c(-c3ccccc3)c2)c(Cl)c1] |
| 143 | 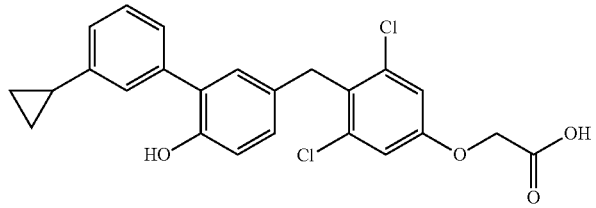 [SMILES: O=C(O)COc1cc(Cl)c(Cc2ccc(O)c(-c3cccc(C4CC4)c3)c2)c(Cl)c1] |
| 144 | 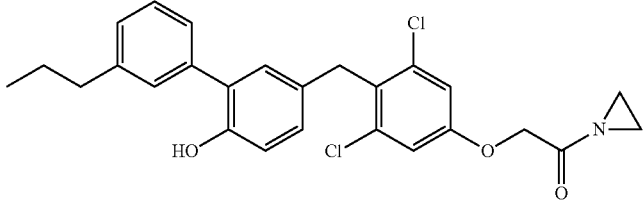 [SMILES: CCCc1cccc(-c2cc(Cc3c(Cl)cc(OCC(=O)N4CC4)cc3Cl)ccc2O)c1] |
| 145 | 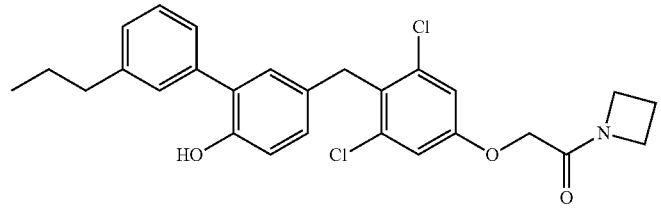 [SMILES: CCCc1cccc(-c2cc(Cc3c(Cl)cc(OCC(=O)N4CCC4)cc3Cl)ccc2O)c1] |
| 146 | 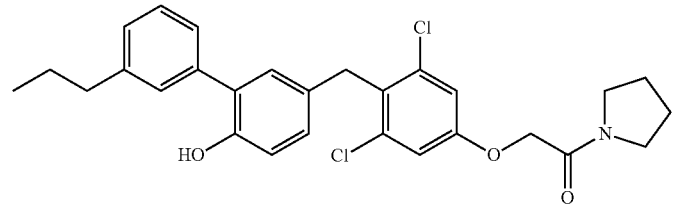 [SMILES: CCCc1cccc(-c2cc(Cc3c(Cl)cc(OCC(=O)N4CCCC4)cc3Cl)ccc2O)c1] |
| 147 | 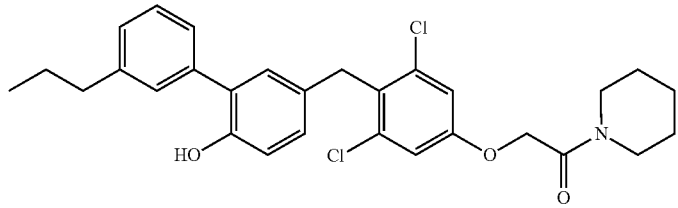 [SMILES: CCCc1cccc(-c2cc(Cc3c(Cl)cc(OCC(=O)N4CCCCC4)cc3Cl)ccc2O)c1] |

TABLE 1-continued

Representative Compounds

| Compound Number | Structure |
|---|---|
| 148 | 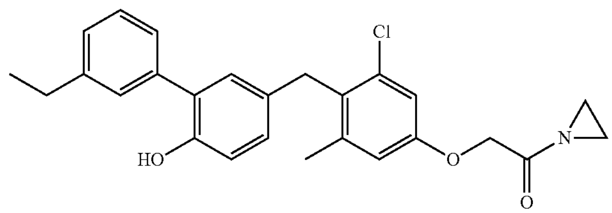 [SMILES: CCc1cccc(-c2cc(Cc3c(C)cc(OCC(=O)N4CC4)cc3Cl)ccc2O)c1] |
| 149 | 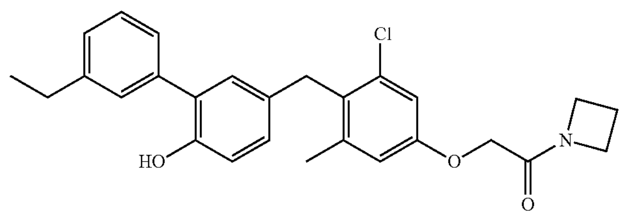 [SMILES: CCc1cccc(-c2cc(Cc3c(C)cc(OCC(=O)N4CCC4)cc3Cl)ccc2O)c1] |
| 150 | 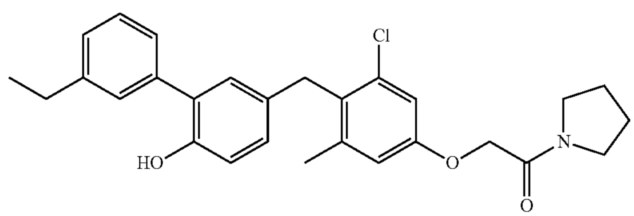 [SMILES: CCc1cccc(-c2cc(Cc3c(C)cc(OCC(=O)N4CCCC4)cc3Cl)ccc2O)c1] |
| 151 | 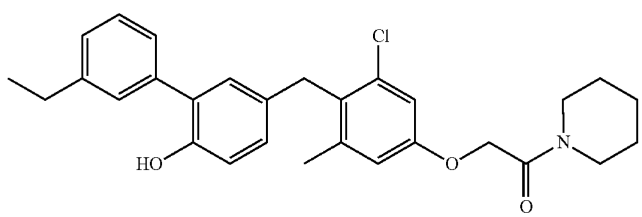 [SMILES: CCc1cccc(-c2cc(Cc3c(C)cc(OCC(=O)N4CCCCC4)cc3Cl)ccc2O)c1] |
| 152 | 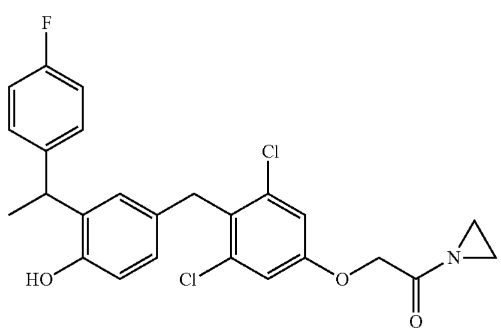 [SMILES: CC(c1ccc(F)cc1)c1cc(Cc2c(Cl)cc(OCC(=O)N3CC3)cc2Cl)ccc1O] |
| 153 | 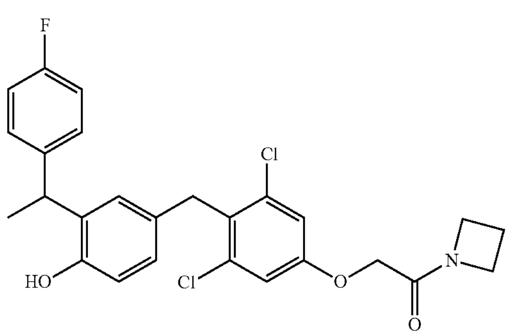 [SMILES: CC(c1ccc(F)cc1)c1cc(Cc2c(Cl)cc(OCC(=O)N3CCC3)cc2Cl)ccc1O] |

TABLE 1-continued
Representative Compounds
| Compound Number | Structure |
|---|---|
| 154 | 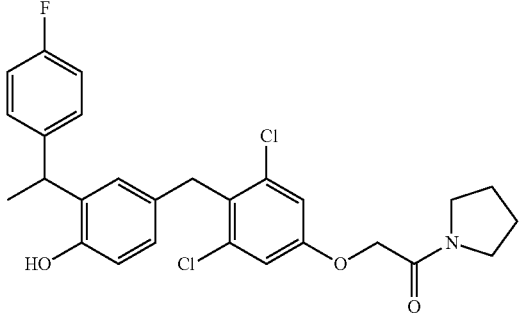 [SMILES: CC(c1ccc(F)cc1)c1cc(Cc2c(Cl)cc(OCC(=O)N3CCCC3)cc2Cl)ccc1O] |
| 155 | 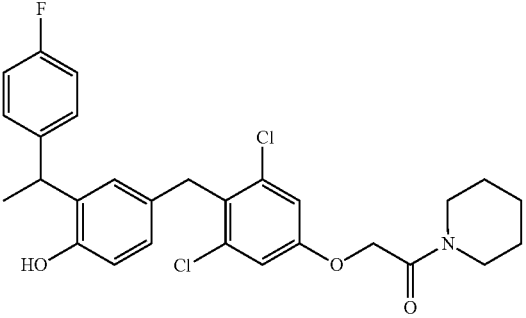 [SMILES: CC(c1ccc(F)cc1)c1cc(Cc2c(Cl)cc(OCC(=O)N3CCCCC3)cc2Cl)ccc1O] |
| 156 | 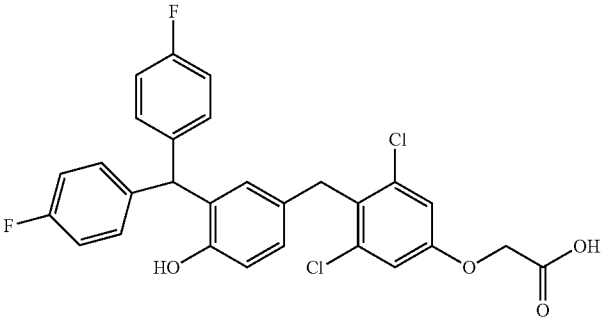 [SMILES: O=C(O)COc1cc(Cl)c(Cc2ccc(O)c(C(c3ccc(F)cc3)c3ccc(F)cc3)c2)c(Cl)c1] |
| 157 | 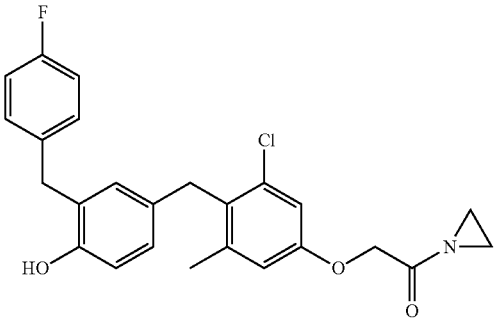 [SMILES: Cc1cc(OCC(=O)N2CC2)cc(Cl)c1Cc1ccc(O)c(Cc2ccc(F)cc2)c1] |

TABLE 1-continued
Representative Compounds
| Compound Number | Structure |
|---|---|
| 158 | 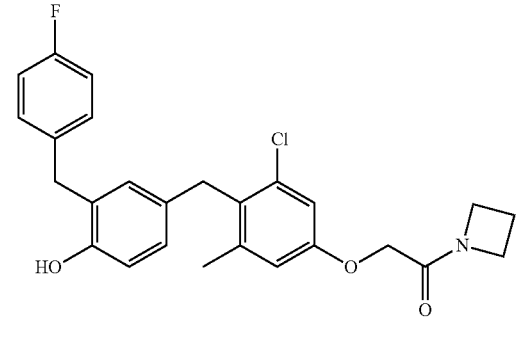 [SMILES: Cc1cc(OCC(=O)N2CCC2)cc(Cl)c1Cc1ccc(O)c(Cc2ccc(F)cc2)c1] |
| 159 | 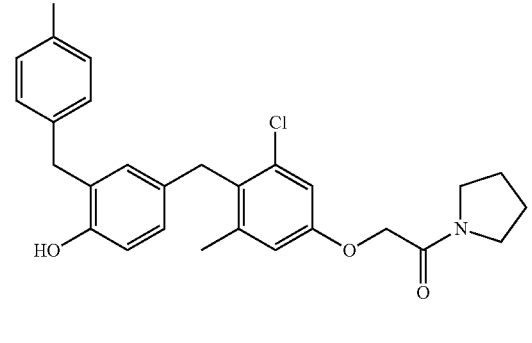 |
| 160 | 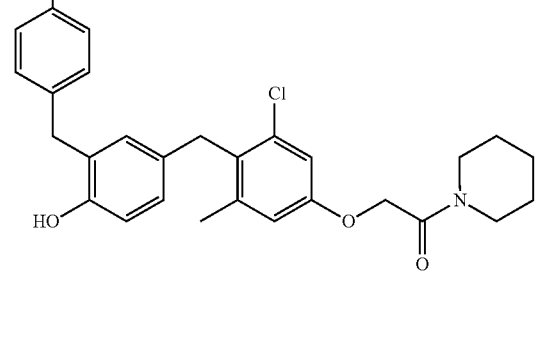 |
| 161 | 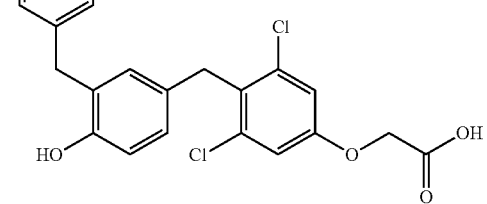 |

TABLE 1-continued
Representative Compounds
| Compound Number | Structure |
|---|---|
| 162 | 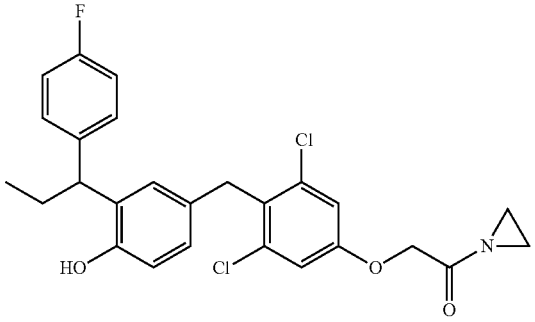 [SMILES: CCC(c1ccc(F)cc1)c1cc(Cc2c(Cl)cc(OCC(=O)N3CC3)cc2Cl)ccc1O] |
| 163 | 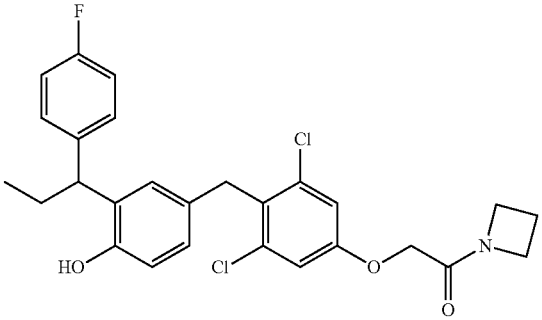 [SMILES: CCC(c1ccc(F)cc1)c1cc(Cc2c(Cl)cc(OCC(=O)N3CCC3)cc2Cl)ccc1O] |
| 164 | 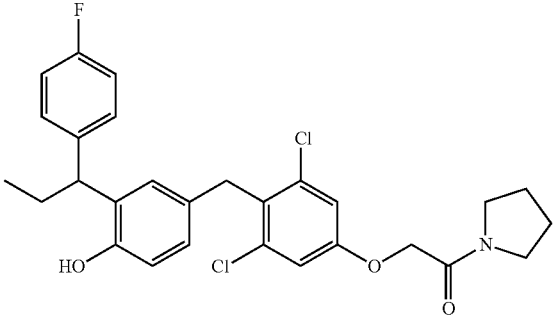 [SMILES: CCC(c1ccc(F)cc1)c1cc(Cc2c(Cl)cc(OCC(=O)N3CCCC3)cc2Cl)ccc1O] |
| 165 | 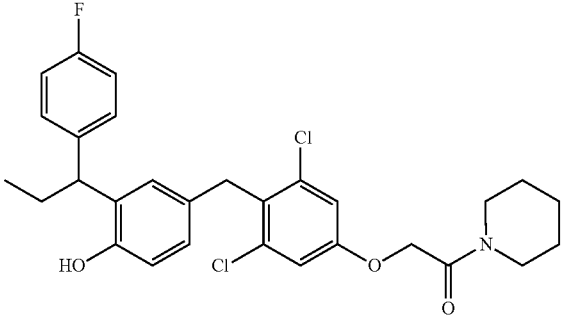 [SMILES: CCC(c1ccc(F)cc1)c1cc(Cc2c(Cl)cc(OCC(=O)N3CCCCC3)cc2Cl)ccc1O] |

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quarternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In certain embodiments, the invention provides a pharmaceutical composition comprising a compound of the invention together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the *Physicians' Desk Reference*, incorporated herein by reference.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In another embodiment, a method of treating a subject having a neurodegenerative disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the neurodegenerative disease is a demyelinating disease. In another embodiment, the demyelinating disease is a chronic demyelinating disease. In yet another embodiment, the demyelinating disease is or is associated with a X-linked genetic disorder, leukodystrophy, dementia, tauopathy, or ischaemic stroke. In another embodiment, the demyelinating disease is or is associated with adult Refsum disease, Alexander disease, Alzheimer's disease, Balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), infantile Refsum disease, Krabbe disease, Leber hereditary optic neuropathy, Marburg multiple sclerosis, Marchiafava-Bignami disease, metachromatic leukodystrophy, multifocal motor neuropathy, paraproteinemic demyelinating polyneuropathy, Pelizaeus-Merzbacher disease, peroneal muscular atrophy, progressive multifocal leukoencephalopathy, transverse myelitis, tropical spastic paraparesis, van der Knaap disease, or Zellweger syndrome. In one embodiment, the demyelinating disease is or is associated with multiple sclerosis, MCT8 deficiency, X-linked adrenoleukodystrophy (ALD), amyotrophic lateral sclerosis (ALS), Alzheimer's disease, frontotemporal dementia, or lacunar stroke.

As used herein, the term "neurodegenerative disease" refers to any type of disease that is characterized by the progressive deterioration of the nervous system.

As used herein, the term "demyelinating disease" refers to any disease or medical condition of the nervous system in which myelin is damaged or lost, or in which the growth or development of the myelin sheath is impaired. Demyelination inhibits the conduction of signals in the affected nerves, causing impairment in sensation, movement, cognition, or other functions for which nerves are involved. Demyelinating diseases have a number of different causes and can be hereditary or acquired. In some cases, a demyelinating disease is caused by an infectious agent, an autoimmune response, a toxic agent or traumatic injury. In other cases, the cause of the demyelinating disease is unknown ("idiopathic") or develops from a combination of factors.

As used herein, the term "leukodystrophy" refers to a group of diseases that affects the growth or development of the myelin sheath.

As used herein, the term "leukoencephalopathy" refers to any of a group of diseases affecting the white substance of the brain; can refer specifically to several diseases including, for example, "leukoencephalopathy with vanishing white matter" and "toxic leukoencephalopathy." Leukoencephalopathies are leukodystrophy-like diseases.

As used herein, the term "tauopathy" refers to tau-related disorders or conditions, e.g., Alzheimer's Disease (AD), Progressive Supranuclear Palsy (PSP), Corticobasal Degeneration (CBD), Pick's Disease (PiD), Argyrophilic grain disease (AGD), Frontotemporal dementia and Parkinsonism associated with chromosome 17 (FTDP-17), Parkinson's disease, stroke, traumatic brain injury, mild cognitive impairment and the like.

As used herein, the terms "multiple sclerosis" and "MS" refer to a slowly progressive CNS disease characterized by disseminated patches of demyelination in the brain and spinal cord, resulting in multiple and varied neurological symptoms and signs, usually with remissions and exacerbation. The cause of MS is unknown but an immunological abnormality is suspected. An increased family incidence suggests genetic susceptibility, and women are somewhat more often affected than men. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary-progressive multiple sclerosis (PPMS) presents initially in the progressive form. A clinically isolated syndrome is the first neurologic episode, which is caused by inflammation/demyelination at one or more sites in the CNS. Progressive-relapsing multiple sclerosis (PRMS) is a rare form of MS (5%) characterized by a steadily worsening disease state from onset, with acute relapses but no remissions.

In yet another embodiment, a method of treating a subject having a X-linked genetic disorder is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the X-linked genetic disorder is MCT8 deficiency or X-linked adrenoleukodystrophy (ALD).

In another embodiment, a method of treating a subject having a leukodystrophy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the leukodystrophy is adrenoleukodystrophy (ALD), adrenomyeloneuropathy (AMN), cerebral form of adrenoleukodystrophy (cALD), metachromatic leukodystrophy (MLD), Canavan's disease, or Krabbe disease (globoid leukodystrophy). As used herein, the term "adrenomyeloneuropathy" or "AMN" refers to an adult variant of X-linked adrenoleukodystrophy, characterized by ABCD1 gene mutation, that results in impaired peroxisome function with accumulation of very long chain fatty acids (VLCFA) and demyelination.

In one embodiment, a method of treating a subject having a tauopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the tauopathy is Alzheimer's disease, frontotemporal dementia, primary age-related tauopathy (PART), Pick's disease, or frontotemporal dementia and parkinsonism linked to chromosome 17 (FTDP-17).

In yet another embodiment, a method of treating a subject having an ischaemic stroke is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ischaemic stroke is lacunar stroke (also called "lacunar infarct"). In another embodiment, the present method is used to treat a subject suffering from a lacunar stroke syndrome (LACS).

In another embodiment, a method of treating a subject having adult Refsum disease, infantile Refsum disease, Alexander disease, Alzheimer's disease, balo concentric sclerosis, Canavan disease, central pontine myelinolysis (CPM), cerebral palsy, cerebrotendineous xanthomatosis, chronic inflammatory demyelinating polyneuropathy (CIDP), Devic's syndrome, diffuse myelinoclastic sclerosis, encephalomyelitis, idiopathic inflammatory demyelinating disease (IIDD), Krabbe disease, Leber hereditary optic neuropathy, leukodystrophy, Marburg multiple sclerosis, Marchiafava-Bignami disease, metachromatic leukodystrophy (MLD), multifocal motor neuropathy (MMN), multiple sclerosis (MS), paraproteinemic demyelinating polyneuropathy, Pelizaeus-Merzbacher disease (PMD), progressive multifocal leukoencephaalopathy (PML), tropical spastic paraparesis (TSP), X-linked adrenoleukodystrophy (X-ALD, ALO, or X-linked ALO), or Zellweger syndrome is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In one embodiment, the demyelinating disease is multiple sclerosis. In another embodiment, the demyelinating disease is X-linked adrenoleukodystrophy (ALD).

In another embodiment, a method of treating a subject having an amyotrophic lateral sclerosis (ALS) disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the ALS is sporadic or familial ALS, or ALS with Superoxide dismutase-1 mutation.

In one embodiment, a method of treating a subject having a medical condition associated with increased activity of TGF-β is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the medical condition associated with increased activity of TGF-β is a fibrotic disease. In another embodiment, the fibrotic disease is or is associated with nonalcoholic steatohepatitis (NASH), idiopathic pulmonary fibrosis (IPF), systemic scleroderma, or Alport syndrome. As used herein, the term "Alport syndrome" refers to a hereditary disorder caused by mutations in the a3a4a5(IV) collagen network genes resulting in structural defects in the glomerular basement membrane (GBM) early during development leading subsequently to the breakdown of the filtration barrier, development of renal fibrosis and kidney failure.

As used herein, the term "fibrotic disease" refers to a condition, disease or disorder that is amenable to treatment by administration of a compound having anti-fibrotic activity. Fibrotic diseases include, but are not limited to, pulmonary fibrosis, including idiopathic pulmonary fibrosis (IPF) and pulmonary fibrosis from a known etiology, liver fibrosis, and renal-fibrosis. Other exemplary fibrotic diseases include musculoskeletal fibrosis, cardiac fibrosis, post-surgical adhesions, scleroderma, glaucoma, and skin lesions such as keloids.

In another embodiment, a method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having IPF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pleuroparenchymal fibroelastosis, unclassifiable idiopathic interstitial pneumonias, hypersensitivity pneumonitis, radiation-induced lung injury, progressive massive fibrosis—pneumoconiosis, bronchiectasis, byssinosis, chronic respiratory disease, chronic obstructive pulmonary disease (COPD), emphysema, pulmonary arterial hypertension (PAH), or Cystic fibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scleroderma/systemic sclerosis, graft versus host disease, hypertrophic scars, keloids, nephrogenic systemic fibrosis, *porphyria* cutanea *tarda*, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents. GvHD induced fibrosis, *Scleredema adultorum*, Lipodermatosclerosis, or Progeroid disorders (progeria, acrogeria, Werner's syndrome) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having atrial fibrosis, endomyocardial fibrosis, cardiac fibrosis, *atherosclerosis*, restenosis, or arthrofibrosis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having mediastinal fibrosis, myelofibrosis, post-polycythermia vera myelofibrosis, or post essential thrombocythemia is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having endometrial fibrosis, uterine fibroids, or Peyronie's disease is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having macular degeneration, diabetic retinopathy, retinal fibrovascular diseases, or vitreal retinopathy is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

In another embodiment, a method of treating a subject having scarring associated with trauma (surgical complications, chemotherapeutics drug-induced fibrosis, radiation induced fibrosis) is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof.

As used herein, the term "administration" refers to providing a compound, a prodrug of a compound, or a pharmaceutical composition comprising the compound or prodrug as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment.

The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "chronic" refers to a medical disorder or condition that persists over time or is frequently recurring.

Compounds having the structure of Formulas (I), (II), (III), (IV), (V), and (VI) can be synthesized using standard synthetic techniques known to those skilled in the art. For example, compounds of the present invention can be synthesized using appropriately modified synthetic procedures set forth in WO 2014/178892, WO 2014/178931, WO 2016/134292, WO 2017/201320, WO 2018/032012, and Schemes 1-7 below.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

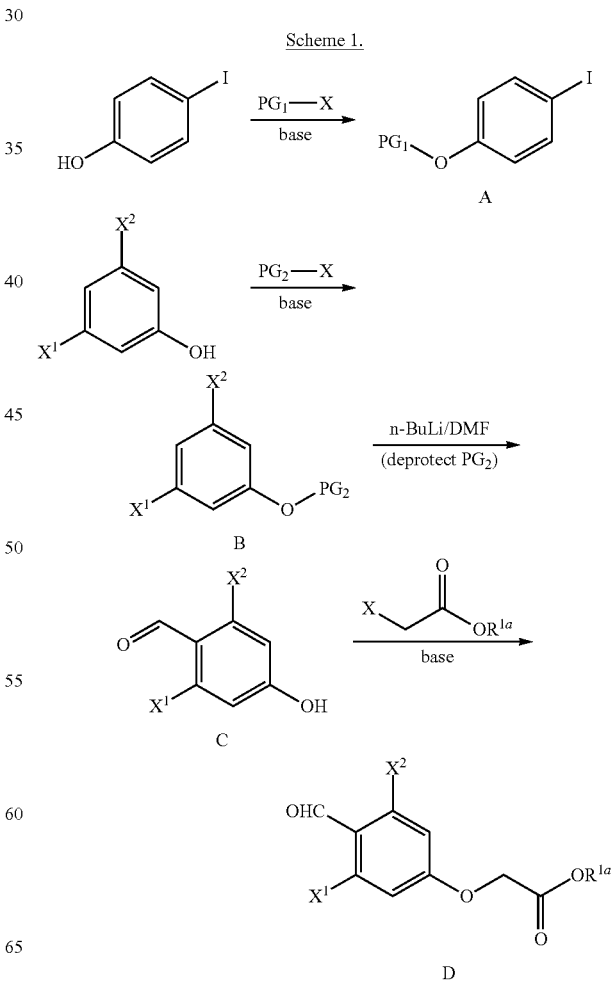

-continued

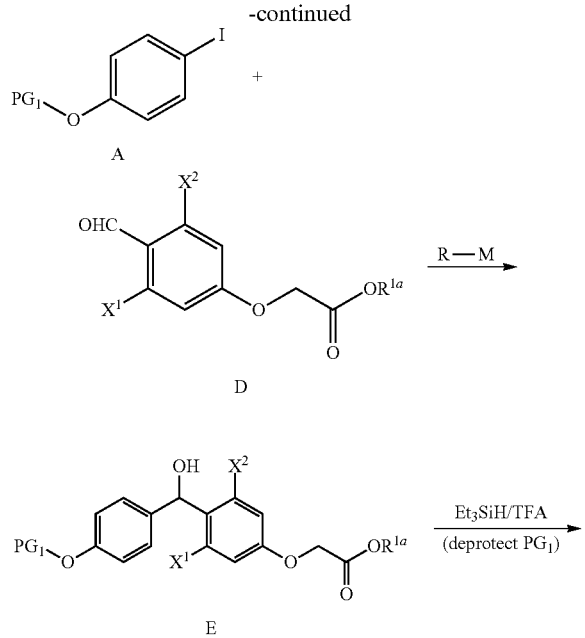

Compounds of the present invention can be prepared according to Scheme 1. Commercially available 4-Iodophenol is protected through treatment with an alkylating agent like methoxymethyl chloride, or benzyl bromide, or triisopropylsilyl chloride, or the like, using a base like sodium hydride or triethylamine or the like, in a solvent like THF or DMF or the like, to give the protected phenol A. A 3,5-disubstituted phenol is similarly protected using an orthogonal protecting group to give B. Compound B is deprotonated at the 4-position using n-butyllithium or n-butylmagnesium bromide or the like, and the resultant anion is condensed with a formylating agent like DMF or the like, to give the aldehyde C. In the case that protecting group $PG_2$ is acid sensitive, the free phenol may be liberated during an acidic workup; alternatively $PG_2$ may be cleaved in a separate step. The phenol moiety of C is alkylated with a protected acetic acid equivalent like methyl chloroacetate or t-butyl bromoacetate or the like, in a solvent like THF or DMF or acetone or the like, using a base like potassium carbonate or sodium hydride or the like, to give ester D.

Iodide A is transmetallated using isopropylmagnesium bromide or s-butyllithium or the like, in a solvent like THF or DME or the like, and the resultant anion is condensed with aldehyde D to give diarylmethanol species E. Deoxygenation of E using a hydride source like triethylsilane or the like, in an acidic solvent like TFA or aqueous HCl or the like, produces diarylmethane species F. In the case that $PG_1$ is an acid-sensitive protecting (e.g. MOM or the like), the deoxygenated product is isolated directly as the phenol. Alternatively $PG_1$ may be removed in a separate step. Phenol F is then reacted with a substituted benzyl alcohol or benzyl halide G, for example p-fluorobenzyl chloride or 1-(1-chloroethyl)-4-fluoro-benzene or 2,4-difluorobenzyl alcohol or the like, in the presence of a Lewis acid like Zinc chloride or Aluminum chloride or boron trifluoride etherate or the like, to give a 3'-benzylated product like ester H.

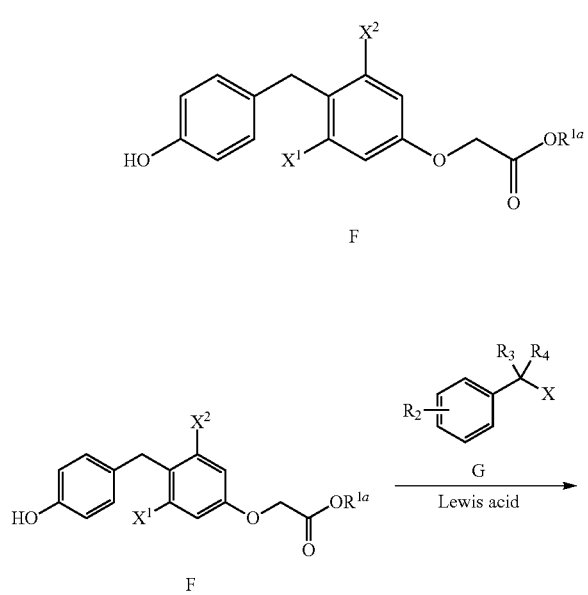

Scheme 2.

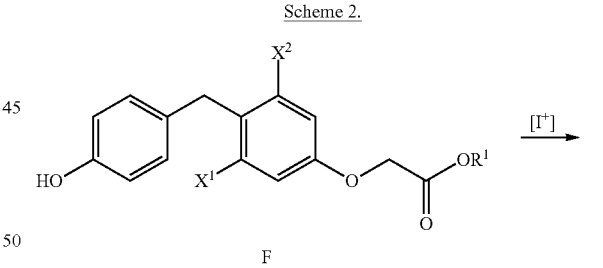

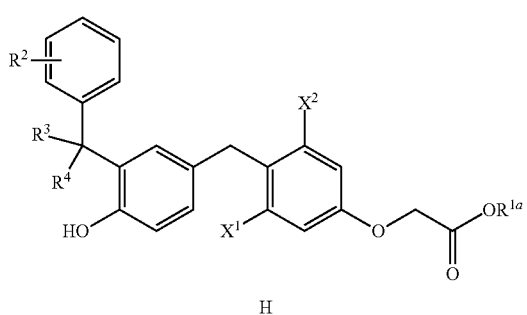

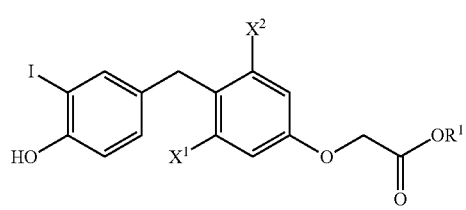

101
-continued

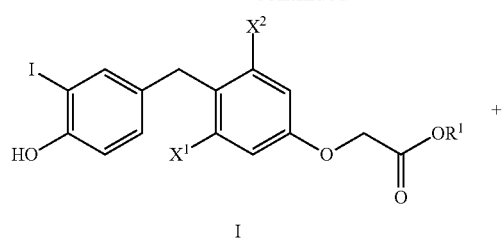

I

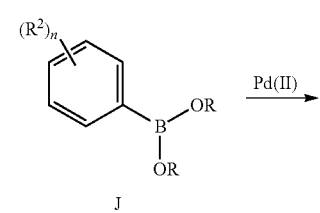

J

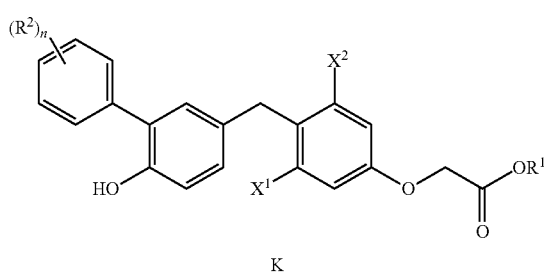

K

As described in Scheme 2, ortho-iodination of phenol F, for example using N-iodosuccinimide or solid iodine or the like, provides key Intermediate I. To prepare compounds of the present invention, I is reacted with a meta-substituted boronic acid (or boronate) J under various Suzuki conditions to provide esters K of the present invention.

Scheme 3

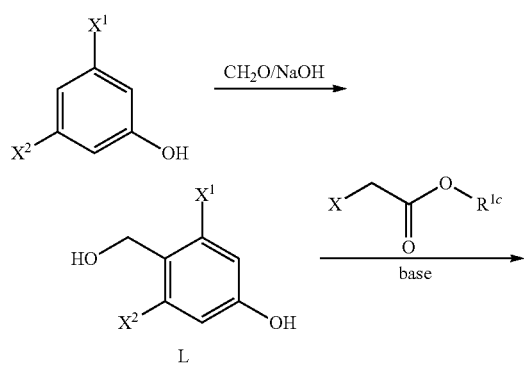

102
-continued

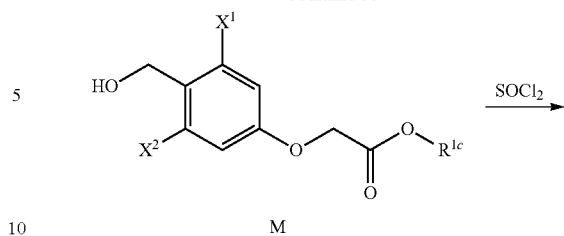

M

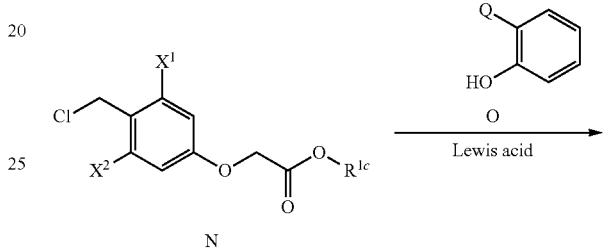

N

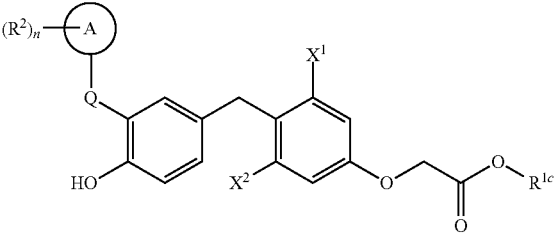

P

Referring to Scheme 3, a disubstituted phenol (for example, 3,5-dichlorophenol or 3-methyl-5-chlorophenol or 3-methyl-5-bromo-phenol, or the like) is reacted with a formaldehyde equivalent (for example, aqueous formaldehyde or paraformaldehyde or dimethoxymethane or the like) to give a hydroxymethyl derivative (L), which is subsequently reacted with an activated acetate moiety (for example ethyl chloroacetate or methyl bromoacetate or the like) in the presence of base, selectively at the phenolic oxygen, to provide Intermediate (M). The hydroxymethyl group is activated (for example, through reaction with thionyl chloride or oxalyl chloride or p-toluenesulfonylchloride or the like) to give a chloromethyl derivative (N) (or the corresponding tosylate, or mesylate, or bromomethyl analog, or the like), which is condensed with a 2-substituted phenol (O) in the presence of a Lewis acid (like zinc chloride, or aluminum chloride, or the like) to give an ester (P).

Scheme 4.

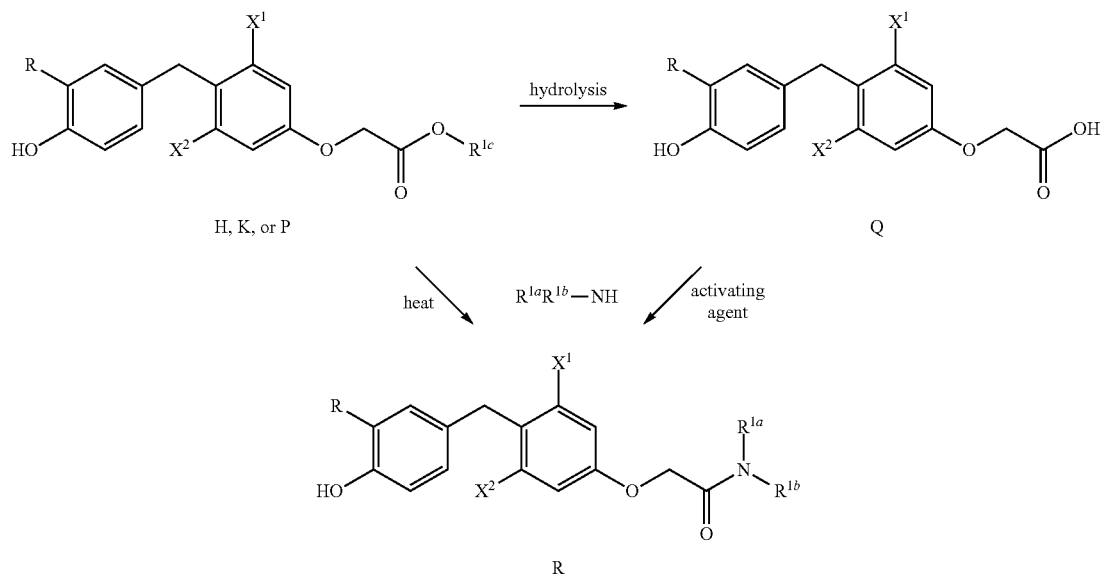

As shown in Scheme 4, hydrolysis of the ester group of (H), (K), or (P), for example using aqueous sodium hydroxide (if $R^1$ is methyl) or TFA (if $R^1$ is t-butyl) provides acids (Q) of the present invention. If desired, acid (Q) can be converted to an amide (R) by condensing with the corresponding amine (for example methylamine or propylamine or 2-sulfonylethylamine or the like) in the presence of a coupling agent like DDC or EDCI or the like, or by forming an activated intermediate (for example the corresponding acid chloride) using thionyl chloride or the like. Alternatively, if desired, either esters (H), (K), or (P), or acids (Q) may be heated with an amine $R^{1a}R^{1b}NH_2$, for example methylamine or propylamine or 2-sulfonylethylamine or the like, to give amides (R) of the present invention.

Scheme 6.

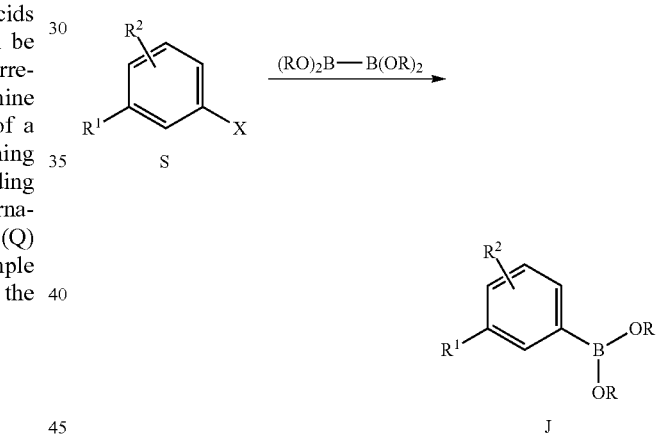

Scheme 5.

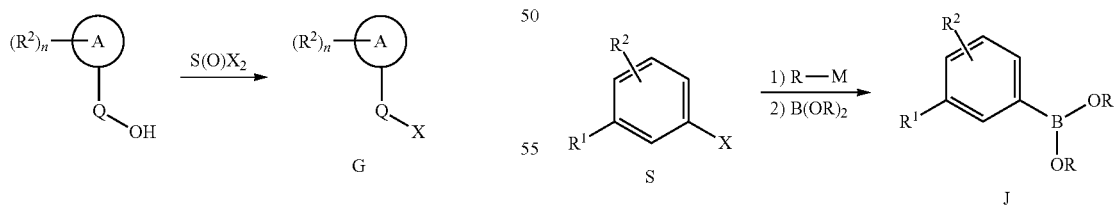

Benzyl alcohols or halides (G) as used in Scheme 1 may be sourced from commercial vendors, or may be prepared as in Scheme 5. For example, a benzyl alcohol like 1-(4-fluorophenyl) ethanol or the like, is combined with an agent like thionyl chloride or phosphorus tribromide or the like, to give the corresponding benzyl halide (G).

Arylboronic acids or esters (J) as employed in Scheme 2 may be sourced commercially, or may be prepared as described in Scheme 6. Aryl halides (S) may be reacted with di(pinacolato)diboron or a similar reagent, using a palladium catalyst or the like, to give (J). Alternatively (S) may be metallated using isopropylmagnesium bromide or n-butyl-lithium or the like, then reacted with a trialkoxyborate or the like, to provide (J).

Scheme 7.

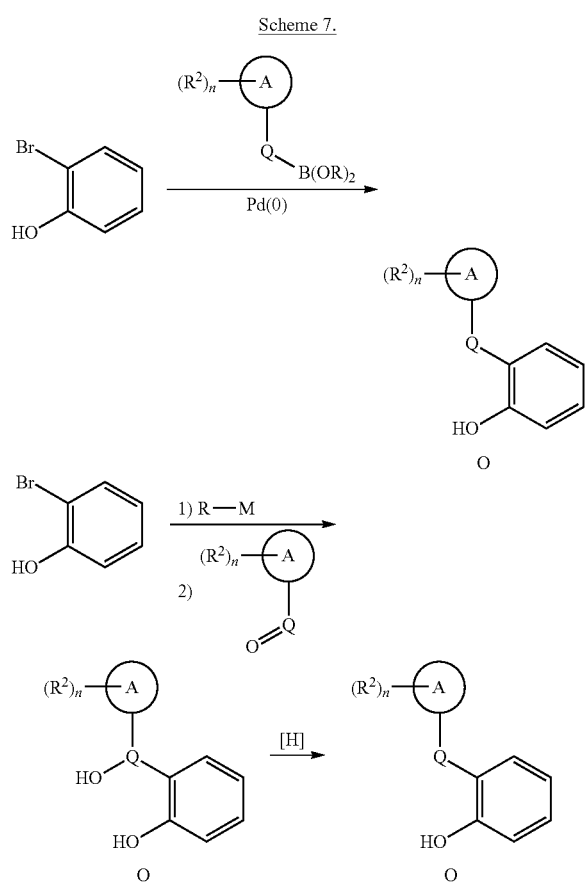

Substituted phenols (O) as employed in Scheme 3 may be prepared as indicated in Scheme 7. A 2-halophenol like 2-bromophenol or the like may be condensed with a boronic acid or ester (J) under Suzuki conditions in the presence of a palladium catalyst or the like, to give 2-substituted phenol (O). Alternatively 2-bromophenol may be metallated using isopropylmagnesium bromide or n-butyllithium or the like, then condensed with an aldehyde or ketone (T), to give an intermediate like (U). Deoxygenation of (U) under hydrogenolysis conditions, using hydrogen gas in the presence of a palladium or platinum catalyst or the like, or under reductive-deoxygenation conditions in the presence of a reducing agent triethylsilane or the like, in the presence of an acid like TFA or the like, produces substituted phenol (O).

EXAMPLES

The invention is further illustrated by the following examples. The examples below are non-limiting are merely representative of various aspects of the invention. Solid and dotted wedges within the structures herein disclosed illustrate relative stereochemistry, with absolute stereochemistry depicted only when specifically stated or delineated.

General Methods

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent.

In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

All the starting materials and reagents are commercially available and were used as is. $^1$H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad. Preparative HPLC purification was performed by reverse phase HPLC using gradients of acetonitrile in aqueous TFA or an equivalent HPLC system such as Methanol in aqueous ammonium acetate.

Chemical names were generated using the ChemDraw naming software (Version 17.0.0.206) by PerkinElmer Informatics, Inc. In some cases, generally accepted names of commercially available reagents were used in place of names generated by the naming software.

Intermediate A1

Synthesis of 1-Iodo-4-(methoxymethoxy)benzene (Intermediate A1)

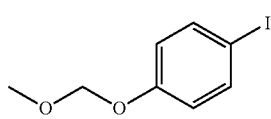

A solution of 4-iodophenol (50 g, 227 mmol) in THF (400 mL) was cooled to 0° C. Sodium hydride (60% in mineral oil) (10.9 g, 273 mmol) was added in portions. The mixture was stirred at 0° C. for 20 min. Chloromethyl methyl ether (21.96 g, 273 mmol) was added dropwise. The mixture was stirred at rt for 2 h. The mixture was poured into ice water (600 mL) and extracted with EtOAc (200 mL*3). The combined organic phase was washed with brine (200 mL), dried over $Na_2SO_4$, and concentrated in vacuo to afford Intermediate A1 (60 g, 227 mmol, 99% yield) as a colourless liquid.

TLC: EtOAc/pet. ether=1/10 (v/v), Rf=0.95
$^1$H NMR: (400 MHz, DMSO-$d_6$) δ 7.63-7.59 (m, 2H), 6.89-6.84 (m, 2H), 5.17 (s, 2H), 3.36 (s, 3H).

Intermediate A2

Synthesis of (3,5-Dichlorophenoxy)-triisopropyl-silane (Compound A2)

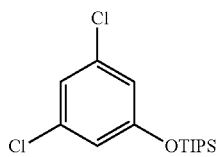

A solution of 3,5-dichlorophenol (35.0 g, 215 mmol) and imidazole (21.93 g, 322 mmol) in DCM (400 mL) was cooled to 0° C. Chloro(triisopropyl)silane (45.5 g, 236 mmol) was added. The mixture was stirred at rt for 2 h. Water (200 mL) was added and the resultant mixture was extracted with DCM (100 mL*3). The combined DCM phase was washed with brine (200 mL), dried over $Na_2SO_4$ and concentrated in vacuo to afford Intermediate A2 (68 g, 213 mmol, 99.2% yield) as a light yellow liquid.

TLC: EtOAc/pet. ether=1/20 (v/v), Rf=0.95
$^1$H NMR: (400 MHz, DMSO-$d_6$) δ 7.21 (t, J=1.8 Hz, 1H), 6.89 (d, J=1.8 Hz, 2H), 1.29-1.23 (m, 3H), 1.06 (d, J=7.4 Hz, 18H).

Intermediate A3

Synthesis of 2,6-Dichloro-4-hydroxy-benzaldehyde (Intermediate A3)

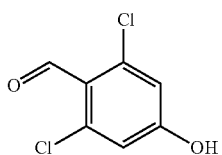

A solution of Intermediate A2 (70 g, 219 mmol) in THF (600 mL) was cooled to −70° C. n-Butyllithium (96.5 mL, 241 mmol, 2.5 M in THF) was added dropwise at −70° C. The solution was stirred at −70° C. for 45 min. DMF (20.83 g, 285 mmol) was added dropwise. The mixture was stirred at −70° C. for 3 h. The reaction mixture was warmed to −10° C., quenched with 1N HCl (440 mL), stirred at rt for 15 min and then extracted with EtOAc (300 mL*2). The combined organic phase was washed with brine (500 mL), dried over $Na_2SO_4$ and concentrated in vacuo. The residue was washed with hexane and dried to afford Intermediate A3 (28.5 g, 149 mmol, 68.1% yield) as a white solid.

TLC: EtOAc/pet. ether=1/5 (v/v), Rf=0.5
$^1$H NMR: (400 MHz, DMSO-$d_6$) δ 10.25 (s, 1H), 6.94 (s, 2H).

Intermediate A4

Synthesis of methyl 2-(3,5-dichloro-4-formyl-phenoxy)acetate (Intermediate A4)

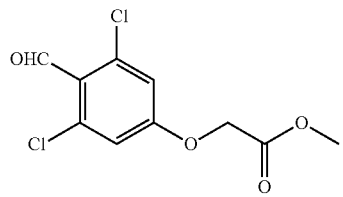

To a solution of Intermediate A3 (18.2 g, 95.3 mmol) in acetone (180 mL) was added methyl 2-chloroacetate (12.4 g, 114 mmol) and potassium carbonate (26.34 g, 191 mmol). The reaction mixture was heated to 60° C. and stirred for 2 h. Water (100 mL) was added and the resultant mixture was extracted with EtOAc (50 mL*3). The combined organic phase was washed with brine (100 mL), dried over $Na_2SO_4$ and concentrated in vacuo to afford Intermediate A4 (25.0 g, 95.1 mmol, 99.9% yield) as a yellow solid.

TLC: EtOAc/pet. ether=1/5 (v/v), Rf=0.45
$^1$H NMR: (400 MHz, DMSO-$d_6$) δ 10.28 (s, 1H), 7.28 (s, 2H), 5.04 (s, 2H), 3.72 (s, 3H).

Intermediate A5

Synthesis of methyl 2-(3,5-dichloro-4-(hydroxy(4-(methoxymethoxy)phenyl)methyl) phenoxy)acetate (Intermediate A5)

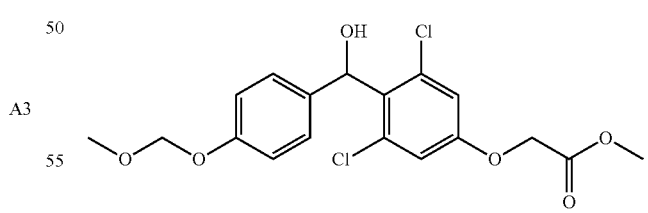

A solution of Intermediate A1 (50 g, 189 mmol) in THF (250 mL) was cooled to −20° C. Isopropyl magnesium chloride (20.8 g, 202 mmol, 1.0M in THF) was added dropwise. The mixture was stirred at rt for 2 h, then cooled to −67° C. A solution of Intermediate A4 (33.2 g, 126 mmol) in THF (250 mL) was added dropwise at −67° C. The mixture was stirred at −67° C. for 2 h. Reaction was quenched by the addition of saturated aqueous $NH_4Cl$ solution (100 mL). The mixture was extracted with EtOAc (100 mL*3). The combined organic phase was washed with brine (200 mL), dried over Na$_2$SO$_4$, concentrated in vacuo and purified by silica gel column chromatography (EtOAc/pet. ether=1/50 to 1/10) to afford Intermediate A5 (12.0 g, 29.9 mmol, 23.7% yield) as a white solid.

TLC: EtOAc/pet. ether=1/5 (v/v), Rf=0.3

$^1$H NMR: (400 MHz, DMSO-d$_6$) δ 7.16 (d, J=8.3 Hz, 2H), 7.07 (s, 2H), 6.94 (d, J=8.7 Hz, 2H), 6.36 (d, J=4.9 Hz, 1H), 6.01 (d, J=4.9 Hz, 1H), 5.14 (s, 2H), 4.91 (s, 2H), 3.71 (s, 3H), 3.35 (s, 3H).

Intermediate A6

Synthesis of methyl 2-[3,5-dichloro-4-[(4-hydroxyphenyl)methyl]phenoxy]acetate (Intermediate A6)

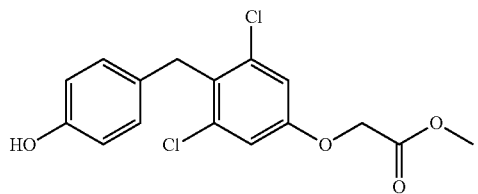

A6

To a solution of Intermediate A5 (10.0 g, 24.9 mmol) in DCM (100 mL) at rt was added triethylsilane (11.6 g, 100 mmol, 15.9 mL). The solution was cooled to 0° C. TFA (85.3 g, 748 mmol, 57.6 mL) was added dropwise. The mixture was stirred at rt for 2 h. The mixture was concentrated in vacuo. The residue was washed with hexane (10 mL) and dried to afford Intermediate A6 (6.86 g, 20.1 mmol, 80.7% yield) as a white solid.

TLC: Pet. ether/EtOAc=1/5 (v/v), Rf=0.32

$^1$H NMR: (400 MHz, DMSO-d$_6$) δ 9.16 (s, 1H), 7.14 (s, 2H), 6.91 (d, J=8.3 Hz, 2H), 6.65 (d, J=8.4 Hz, 2H), 4.89 (s, 2H), 4.05 (s, 2H), 3.71 (s, 3H).

Intermediate A7

Synthesis of methyl 2-(3,5-dichloro-4-(4-hydroxy-3-iodobenzyl)phenoxy)acetate (Intermediate A7)

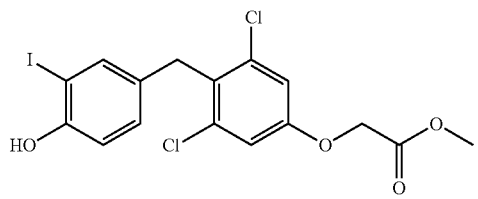

A7

A solution of Intermediate A6 (2.0 g, 5.86 mmol) and p-Toluenesulfinic acid (183 mg, 1.17 mmol) in DCM (20 mL) was cooled to 0° C. N-iodosuccinimide (1.32 g, 5.86 mmol) was added in portions. The mixture was stirred at 0° C. for 4 h. Water (15 mL) was added and the mixture was extracted with DCM (10 mL*2). The combined organic phase was washed with brine (15 mL), dried over Na$_2$SO$_4$, and concentrated in vacuo to afford Intermediate A7 (2.4 g, 5.14 mmol, 87.7% yield) as an orange solid.

TLC: Pet. ether/EtOAc=1/5 (v/v), Rf=0.32

$^1$H NMR: (400 MHz, DMSO-d$_6$) δ 10.15 (s, 1H), 7.40 (d, J=2.1 Hz, 1H), 7.17 (s, 2H), 6.96-6.90 (m, 1H), 6.78 (d, J=8.3 Hz, 1H), 4.90 (s, 2H), 4.05 (s, 2H), 3.71 (s, 3H).

Intermediate A8

Synthesis of 3,5-Dichloro-4-(hydroxymethyl)phenol (Intermediate A8)

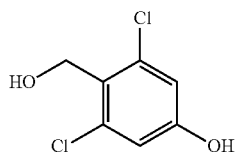

A8

To a solution of NaOH (6.7 g, 169 mmol) in water (20 mL) was added 3,5-dichlorophenol (25.0 g, 153 mmol). The mixture was heated to 45° C. and 36% aqueous formaldehyde (12.4 g, 153 mmol) was added dropwise slowly. The mixture was stirred at 45° C. for 2 h, then cooled to rt. The pH was adjusted to ~3-4 with 1N HCl, and the mixture was stirred at rt for 20 min. The solid was filtered, washed with water (50 mL) and dried to afford Intermediate A8 (11.5 g, 59.6 mmol, 39% yield) as an off-white solid.

TLC: EtOAc/pet. ether 1/3, Rf 0.36

$^1$H NMR: (400 MHz, DMSO-d$_6$) δ 10.02 (s, 1H), 6.82 (s, 2H), 4.98 (s, 1H), 4.57 (d, J=2.1 Hz, 2H)

Intermediate A9

Synthesis of methyl 2-[3,5-dichloro-4-(hydroxymethyl)phenoxy]acetate (Intermediate A9)

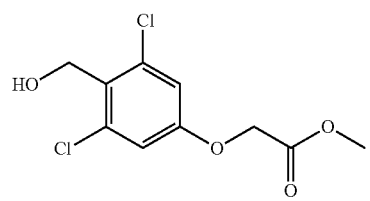

A9

To a solution of Intermediate A8 (3.0 g, 15.5 mmol) in acetone (40 mL) were added potassium carbonate (3.22 g, 23.3 mmol) and methyl 2-chloroacetate (2.02 g, 18.6 mmol). The mixture was refluxed for 2 h. The mixture was cooled to rt, diluted with water (120 mL), and extracted with EtOAc (80 mL*3). The combined organic phase was washed with brine (200 mL), dried over Na$_2$SO$_4$, and concentrated in vacuo. The residue was purified by silica gel column chromatography (pet. ether/EtOAc=20/1 to 5/1) to afford Intermediate A9 (2.0 g, 7.54 mmol, 48.5% yield) as a white solid.

TLC: EtOAc/pet. ether 1/5, Rf 0.28

$^1$H NMR: (400 MHz, DMSO-d$_6$) δ 7.10 (s, 2H), 5.08 (t, J=5.3 Hz, 1H), 4.91 (s, 2H), 4.61 (d, J=5.3 Hz, 2H), 3.70 (s, 3H).

Intermediate A10

Synthesis of methyl 2-[3,5-dichloro-4-(chloromethyl)phenoxy]acetate (Intermediate A10)

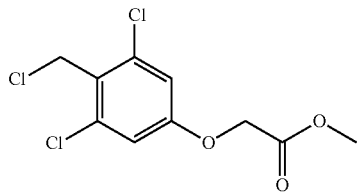

To a mixture of Intermediate A9 (1.0 g, 3.77 mmol) in DCM (10 mL) was added thionyl chloride (0.67 g, 5.66 mmol). The mixture was stirred at rt for 1 h, then was concentrated in vacuo to afford crude Intermediate A10 (1.0 g, 3.53 mmol, 93.5% yield) as a light yellow solid.

TLC: EtOAc/pet. ether ⅕, Rf 0.72

$^1$H NMR: (400 MHz, DMSO-d$_6$) δ 7.21 (s, 2H), 4.94 (s, 2H), 4.85 (s, 2H), 3.71 (s, 3H).

Intermediate A11

Synthesis of ethyl 2-(3,5-dichloro-4-(hydroxymethyl)phenoxy)acetate (Intermediate A11)

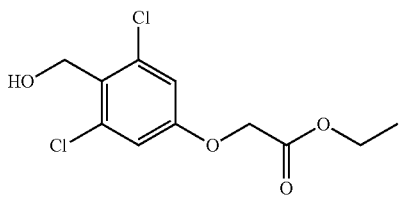

To a solution of Intermediate A8 (13.0 g, 67.4 mmol) in DMF (120 mL) at rt were added ethyl 2-bromoacetate (11.25 g, 67.4 mmol) and K$_2$CO$_3$ (11.17 g, 80.8 mmol). The mixture was stirred at rt for 2 h, then diluted with water (200 mL), and extracted with EtOAc (100 mL*3). The combined organic phase was washed with water (100 mL*3) and brine (200 mL), dried over Na$_2$SO$_4$, and concentrated in vacuo. The crude product was purified by silica gel column chromatography (pet. ether/EtOAc=5/1) to afford Intermediate A11 (15 g, 79% yield) as an off-white solid.

TLC: EtOAc/pet. ether=⅕ (v/v), Rf=0.42

$^1$H NMR: (400 MHz, DMSO-d$_6$) δ 7.09 (s, 2H), 5.09 (t, J=5.2 Hz, 1H), 4.88 (s, 2H), 4.60 (d, J=5.2 Hz, 2H), 4.17 (q, J=7.1 Hz, 2H), 1.21 (t, J=7.1 Hz, 3H).

Intermediate A12

Synthesis of ethyl 2-(3,5-dichloro-4-(chloromethyl)phenoxy)acetate (Intermediate A12)

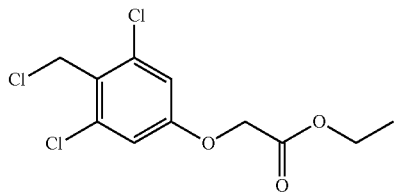

To a reaction mixture of Intermediate A11 (15.0 g, 3.77 mmol) in DCM (150 mL) at 0° C. was added dropwise thionyl chloride (9.59 g, 80.6 mmol). The mixture was stirred at rt for 1 h, diluted with DCM (100 mL), and concentrated in vacuo to afford Intermediate A12 (15.0 g, 93.5% yield) as a light yellow solid.

TLC: EtOAc/pet. ether=⅕ (v/v), Rf=0.72

$^1$H NMR: (400 MHz, DMSO-d$_6$) δ 7.20 (s, 2H), 4.92 (s, 2H), 4.86 (s, 2H), 4.17 (q, J=7.2 Hz, 2H), 1.21 (t, J=7.1 Hz, 3H).

Intermediate A13

Synthesis of 3-chloro-4-(hydroxymethyl)-5-methyl-phenol (Intermediate A13)

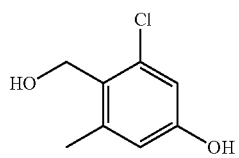

To a mixture of 3-chloro-5-methyl-phenol (3.55 g, 24.9 mmol) in water (10 mL) at rt was added NaOH (1.10 g, 27.4 mmol). The mixture was heated to 45° C., then aqueous formaldehyde (0.75 g, 24.9 mmol, 37%) was added dropwise. The resultant mixture was stirred at 45° C. for 2 h. The mixture was cooled to rt, then acidified with HCl (3N) to pH~3 and extracted with EtOAc (10 mL*3). The combined organic phase was washed with brine (15 mL), dried over Na$_2$SO$_4$, and concentrated in vacuo. The crude product was purified by silica gel column chromatography (pet. ether/EtOAc=50/1 to 5/1) to afford Intermediate A13 (0.76 g, 4.40 mmol, 17.7% yield) as an off-white solid.

TLC: EtOAc/pet. ether=1/1 (v/v), Rf=0.8

$^1$H NMR: (400 MHz, DMSO-d$_6$) δ 9.68 (s, 1H), 6.62 (d, J=2.4 Hz, 1H), 6.56 (d, J=2.4 Hz, 1H), 4.73 (t, J=5.2 Hz, 1H), 4.49 (d, J=5.2 Hz, 2H), 2.31 (s, 3H).

Intermediate A14

Synthesis of 2-[3-Chloro-4-(hydroxymethyl)-5-methyl-phenoxy]acetate (Intermediate A14)

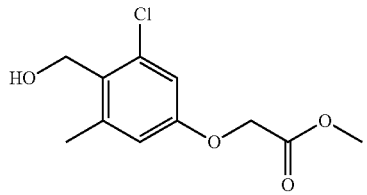

To a solution of Intermediate A13 (0.66 g, 3.82 mmol) in acetone (10 mL) at rt were added cesium carbonate (1.87 g, 5.74 mmol), sodium iodide (57 mg, 380 umol) and methyl 2-chloroacetate (540 mg, 4.97 mmol). The mixture was stirred at rt for 4 h. Water (30 mL) was added, and the mixture was extracted with EtOAc (10 mL*3). The combined organic phase was washed with brine (20 mL), dried over $Na_2SO_4$ and concentrated in vacuo. The crude product was purified by silica gel column chromatography (pet. ether/EtOAc=100/1 to 5/1) to afford Intermediate A14 (280 mg, 1.14 mmol, 29.9% yield) as a white solid.

TLC: EtOAc/pet. ether=½ (v/v), Rf=0.67

$^1$H NMR: (400 MHz, DMSO-$d_6$) δ 6.84 (d, J=2.6 Hz, 1H), 6.78 (d, J=2.6 Hz, 1H), 4.85-4.81 (m, 3H), 4.53 (d, J=4.9 Hz, 2H), 3.69 (s, 2H), 2.37 (s, 3H).

Intermediate A15

Synthesis of 2-[3-chloro-4-(chloromethyl)-5-methyl-phenoxy]acetate (Intermediate A15)

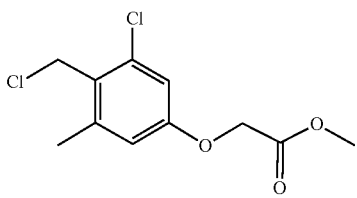

To a solution of Intermediate A14 (360 mg, 1.47 mmol) in DCM (6 mL) at rt was added thionyl chloride (263 mg, 2.21 mmol). The mixture was stirred at rt for 1 h, then concentrated in vacuo to afford Intermediate A15 (300 mg, 1.14 mmol, 77.5% yield) as a yellow solid.

TLC: EtOAc/pet. ether=½ (v/v), Rf=0.8

$^1$H NMR: (400 MHz, DMSO-$d_6$) δ 6.96 (d, J=2.4 Hz, 1H), 6.87 (d, J=2.4 Hz, 1H), 4.86 (s, 2H), 4.82 (s, 2H), 3.71 (s, 3H), 2.41 (s, 3H).

Intermediate A16

Synthesis of 3-bromo-4-(hydroxymethyl)-5-methylphenol (Intermediate A16)

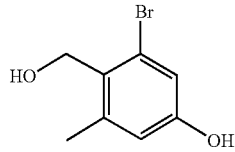

To a solution of 3-bromo-5-methyl-phenol (15 g, 80.2 mmol) and NaOH (3.5 g, 88.2 mmol) in water (100 mL) at 45° C. was added dropwise aqueous formaldehyde (6.5 g, 80.2 mmol). The reaction was heated to 45° C. overnight. The reaction mixture was acidified to pH~6-7 with 1N HCl, and extracted with EtOAc (50 mL*3); the combined organic phase was washed with brine (50 mL), dried over $Na_2SO_4$, and concentrated in vacuo. The crude product was purified by silica gel column chromatography (EtOAc/pet. ether=1/20 to ⅕) to afford Intermediate A16 (3.0 g, 14% yield) as an off-white solid.

TLC: EtOAc/pet. ether=⅕ (v/v), Rf=0.41

$^1$H NMR: (400 MHz, DMSO-$d_6$) δ 9.67 (s, 1H), 6.80 (d, J=2.5 Hz, 1H), 6.60 (d, J=2.4 Hz, 1H), 4.73 (t, J=5.1 Hz, 1H), 4.51 (d, J=5.1 Hz, 2H), 2.30 (s, 3H).

Intermediate A17

Synthesis of ethyl 2-(3-bromo-4-(hydroxymethyl)-5-methylphenoxy)acetate (Intermediate A17)

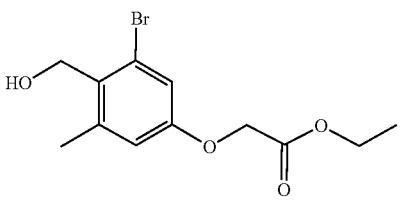

To a solution of Intermediate A16 (3.0 g, 13.8 mmol) in DMF (20 mL) at rt were added $K_2CO_3$ (2.3 g, 16.56 mmol), and ethyl 2-bromoacetate (2.5 g, 15.2 mmol); the mixture was stirred at rt for 2 h. Water (100 mL) was added and the resultant mixture was extracted with EtOAc (40 mL*3). The combined organic phase was washed with brine (100 mL), dried over $Na_2SO_4$, and concentrated in vacuo; the residue was purified by reversed-phase column chromatography to afford Intermediate A17 (2.7 g, 64% yield).

TLC: EtOAc/pet. ether=⅕ (v/v), Rf=0.44

$^1$H NMR: (400 MHz, DMSO-$d_6$) δ 6.99 (d, J=2.7 Hz, 1H), 6.82 (dd, J=2.7, 0.7 Hz, 1H), 4.84 (t, J=5.1 Hz, 1H), 4.81 (s, 2H), 4.79 (s, 2H), 4.55 (d, J=5.2 Hz, 2H), 4.17 (q, J=7.1 Hz, 2H), 2.39 (s, 3H), 1.21 (t, J=7.1 Hz, 3H).

Intermediate A18

Synthesis of ethyl 2-(3-bromo-4-(chloromethyl)-5-methylphenoxy)acetate (Intermediate A18)

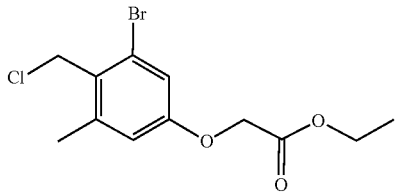

To a solution of Intermediate A17 (2.8 g, 9.24 mmol) in DCM (10 mL) at rt was added thionyl chloride (2.19 g, 18.48 mmol); the resulting mixture was stirred at rt for 1 h. The reaction was concentrated in vacuo to afford Intermediate A18 (2.9 g, 97% yield).

TLC: EtOAc/pet. ether=1/5 (v/v), Rf=0.6

$^1$H NMR: (400 MHz, DMSO-d$_6$) δ 7.10 (d, J=2.7 Hz, 1H), 6.90 (d, J=2.7 Hz, 1H), 4.83 (d, J=1.3 Hz, 4H), 4.17 (q, J=7.1 Hz, 2H), 2.42 (s, 3H), 1.21 (t, J=7.1 Hz, 3H).

Intermediate A19

Synthesis of tert-butyl 2-(4-formyl-3,5-dimethylphenoxy)acetate (Intermediate A19)

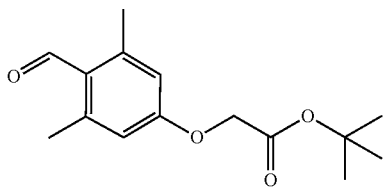

To a solution of 2,6-dimethyl-4-hydroxybenzaldehyde (30 g, 0.20 mol) and tert-butyl bromoacetate (35 mL, 0.25 mol) in DMF (600 mL) at rt was added cesium carbonate (130 g, 0.40 mol). The reaction was stirred at rt for 3 h. The reaction mixture was diluted with EtOAc (1000 mL) and filtered. The filtrate was washed with water (1000 mL*3), and brine (500 mL*2), then dried over Na$_2$SO$_4$, and concentrated in vacuo to afford Intermediate A19 (47 g, 89% yield) as a white solid.

TLC: EtOAc/pet. ether=1/20

$^1$H NMR: (400 MHz, CDCl$_3$) δ 10.48 (s, 1H), 6.58 (s, 2H), 4.55 (s, 2H), 2.60 (s, 6H), 1.49 (s, 9H).

Intermediate A20

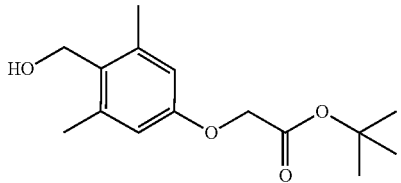

To a solution of Intermediate A19 (1.00 g, 3.78 mmol) in methanol (30 mL) at 0° C. was added NaBH$_4$ (0.14 g, 3.8 mmol) in portions. The reaction was stirred at rt for 1 h. The reaction mixture was quenched with water (50 mL), extracted with EtOAc (50 mL*3), dried over Na$_2$SO$_4$, and concentrated in vacuo to afford Intermediate A20 (0.9 g, 89% yield) as a colorless oil.

TLC: EtOAc/pet. ether=1/10 (v/v)

$^1$H NMR: (400 MHz, DMSO) δ 6.53 (d, J=7.6 Hz, 2H), 4.57 (d, J=7.6 Hz, 2H), 4.40 (s, 2H), 4.32 (s, 1H), 2.30 (d, J=7.6 Hz, 6H), 1.43 (d, J=7.8 Hz, 9H).

Intermediate A21

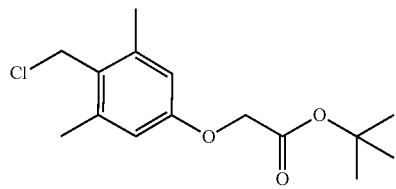

To a solution of Intermediate A20 (0.9 g, 3.38 mmol) in DCM (20 mL) at rt was added thionyl chloride (0.44 g, 3.72 mmol); the resultant solution was stirred at rt for 30 min. The reaction mixture was concentrated in vacuo to afford Intermediate A21 (0.9 g, 93% yield) as white solid.

TLC: EtOAc/pet. ether=1/10 (v/v)

$^1$H NMR: (400 MHz, DMSO) δ 6.61 (s, 2H), 4.75 (s, 2H), 4.61 (s, 2H), 2.31 (d, J=13.6 Hz, 6H), 1.42 (s, 9H).

Intermediate B1

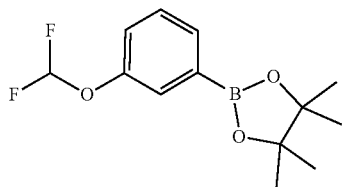

A mixture of (3-bromophenyl)-difluoromethyl ether (3.0 g, 13.4 mmol), bis(pinacolato)diboron (6.8 g, 26.9 mmol), Pd(dppf)Cl₂ (984 mg, 1.35 mmol) and KOAc (4.0 g, 40.4 mmol) in dry 1,4-dioxane (30 mL) was stirred at 85° C. overnight. The resultant solution of Intermediate B1 was used without further purification.

TLC: EtOAc/pet. ether=½ (v/v), Rf=0.2

Intermediate B2

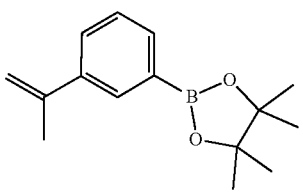

A mixture of 3'-bromo-1-methylstyrene (500 mg, 2.54 mmol), Pd(dppf)Cl₂ (186 mg, 0.25 mmol), bis(pinacolato)diboron (1.29 g, 5.07 mmol) and KOAc (748 mg, 7.62 mmol) in 1,4-dioxane (10 mL) was stirred at 80° C. for 4 h. The mixture was filtered through a pad of silica gel, concentrated to dryness and purified by silica gel column chromatography (pet. ether/EtOAc=20/1) to afford Intermediate B2 (400 mg, 65%) as a yellow solid.

TLC: EtOAc/pet. ether=⅕ (v/v), Rf=0.87

¹H NMR: (400 MHz, DMSO-d₆) δ 7.76-7.72 (m, 1H), 7.65-7.62 (m, 1H), 7.63-7.58 (m, 1H), 7.41-7.34 (m, 1H), 5.39 (dd, J=1.7, 0.8 Hz, 1H), 5.11 (t, J=1.5 Hz, 1H), 2.11 (s, 3H), 1.30 (s, 12H).

Intermediate B3

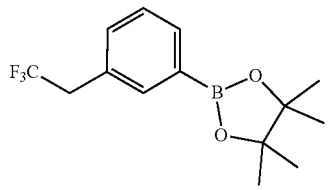

A mixture of 3-(2,2,2-trifluoroethyl)-1-bromobenzene (500 mg, 2.09 mmol), Pd(dppf)Cl₂ (153 mg, 0.21 mmol), bis(pinacolato)diboron (1.06 g, 4.18 mmol) and KOAc (616 mg, 6.28 mmol) in 1,4-dioxane (10 mL) was stirred at 80° C. for 4 h. The mixture was filtered through a pad of silica gel, concentrated to dryness, and purified by silica gel column chromatography (pet. ether/EtOAc=20/1) to afford Intermediate B3 (400 mg, 84%) as a colorless oil.

TLC: EtOAc/pet. ether=⅕ (v/v), Rf=0.88

Intermediate B4

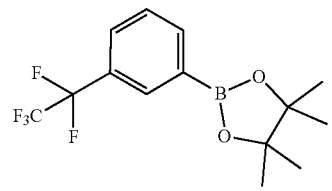

To a mixture of 3-pentafluoroethyl-bromobenzene (400 mg, 1.45 mmol), bis(pinacolato)diboron (406 mg, 1.60 mmol) and Pd(dppf)Cl₂ (53 mg, 0.07 mmol) in 1,4-dioxane (10 mL) was added potassium acetate (430 mg, 4.36 mmol). The mixture was heated to 100° C. for 3 h. The mixture was cooled to rt and filtered. The filtrate was concentrated in vacuo to afford crude Intermediate B4 (468 mg, 99% yield), which was used without further purification.

TLC: Pet. ether/EtOAc=10/1 (v/v), Rf=0.9

Intermediate B5

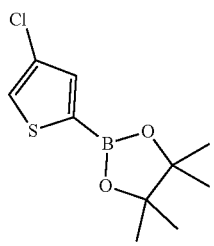

To a solution of 3-chlorothiophene (237 mg, 2.0 mmol) in hexane (3 mL) were added 4,4'-di-tert-butyl-2,2'-bipyridine (16 mg, 60 umol), 4,4,5,5-tetramethyl-1,3,2-dioxaborolane (128 mg, 1.0 mmol), and (1,5-cyclooctadiene)(methoxy)iridium(I) dimer (40 mg, 60 umol). The reaction was stirred at rt for 1 h. The reaction mixture was concentrated in vacuo and Intermediate B5 was used without further purification.

Intermediate B6

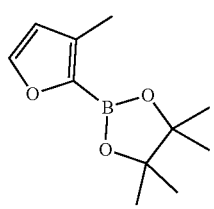

To a solution of 3-methylfuran (400 mg, 4.87 mmol) in THF (10 mL) were added bis(pinacolato)diboron (1.23 g, 4.87 mmol), (1,5-cyclooctadiene)(methoxy)iridium(I) dimer (65 mg, 97.4 umol), and 4,4'-di-tert-butyl-2,2'-bipyridine (33 mg, 122 umol). The mixture was heated to reflux for 2 h, then cooled to rt and concentrated in vacuo to afford Intermediate B6 as a mixture with the 2,4-substituted isomer. This mixture was used without further purification.

TLC: EtOAc/pet. ether=1/5 (v/v), Rf=0.30

Intermediate B7

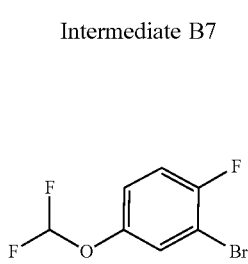

A mixture of sodium chlorodifluoroacetate (1.0 g, 5.2 mmol), 3-bromo-4-fluorophenol (1.60 g, 10.5 mmol) and K₂CO₃ (868 mg, 6.3 mmol) in DMF (10 mL) was stirred at 100° C. for 2 h. The mixture was cooled to rt. Concentrated HCl (1.5 ml) and water (3 mL) were added and the mixture was stirred at rt for 1 h. The mixture was cooled to 0° C. NaOH (4M, 5 mL) and water (25 mL) were added, and the mixture was extracted with Et₂O (5 mL*3). The organic layer was washed with brine (15 ml), dried over Na₂SO₄ and purified by silica gel column chromatography (pet. ether/EtOAc=200/1 to 100/1) to afford Intermediate B7 (150 mg, 11% yield) as a colorless oil.

TLC: Pet. ether/EtOAc=100/1 (v/v), Rf=0.55

$^1$H NMR: (400 MHz, DMSO-$d_6$) δ 7.62 (dd, J=6.0, 3.2 Hz, 1H), 7.46 (t, J=8.8 Hz, 1H), 7.28 (dt, J=9.2, 3.6 Hz, 1H), 7.24 (t, J=73.6 Hz, 1H).

$^{19}$F NMR: (376 MHz, DMSO-$d_6$) δ −82.81, −112.84.

Intermediate B8

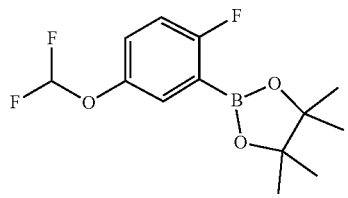

To a mixture of Intermediate B7 (150 mg, 622 umol), bis(pinacolato)diboron (175 mg, 684 umol) and Pd(dppf)Cl₂·CH₂Cl₂ (25 mg, 31 umol) in 1,4-dioxane (5.0 mL) at rt was added potassium acetate (183 mg, 1.8 mmol). The mixture was heated to 110° C. for 3 h. The mixture was cooled to rt and filtered. The filtrate was concentrated in vacuo to afford crude Intermediate B8 (175 mg, 97% yield) which was used without further purification.

TLC: EtOAc/pet. ether=1/10 (v/v), Rf=0.65

Intermediate B9

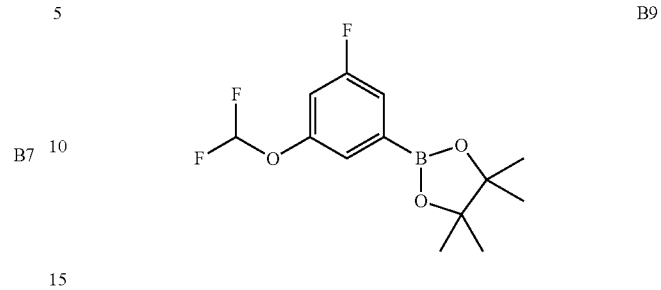

A mixture of (3-bromo-5-fluorophenyl)-difluoromethyl ether (120 mg, 0.50 mmol), KOAc (146 mg, 1.50 mmol), bis(pinacolato)diboron (189 mg, 0.75 mmol) and Pd(dppf)Cl₂ (18 mg, 0.03 mmol) in 1,4-dioxane (3 mL) was stirred at 85° C. for 2 h under N₂ atmosphere. The crude solution of Intermediate B9 was used without further purification.

TLC: pet. ether/EtOAc=20/1 (v/v), Rf=0.65

Intermediate B10

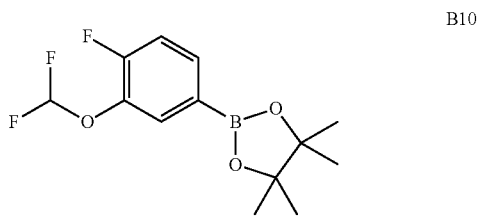 [SMILES: CC1(C)OB(c2ccc(F)c(OC(F)F)c2)OC1(C)C]

A mixture of (3-bromo-6-fluorophenyl)-difluoromethyl ether (300 mg, 1.2 mmol), bis(pinacolato)diboron (348 mg, 1.4 mmol), Pd(dppf)Cl₂ (91 mg, 0.1 mmol) and KOAc (365 mg, 3.6 mmol) in 1,4-dioxane (3 mL) was stirred at 80° C. overnight. The mixture was filtered and concentrated in vacuo to afford Intermediate B10 (330 mg, 95% yield) as a black oil which was used without further purification.

TLC: Pet. ether/EtOAc=10/1 (v/v), Rf=0.8

LCMS: RT=4.324 min; [M+1]=289.1

Intermediate B11

Synthesis of 1-bromo-3-(difluoromethoxy)-2-fluorobenzene (Intermediate B11)

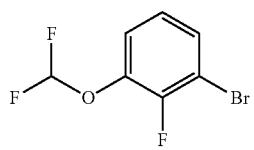

A mixture of sodium chlorodifluoroacetate (1.0 g, 5.2 mmol), 3-bromo-2-fluorophenol (1.60 g, 10.47 mmol) and K₂CO₃ (868 mg, 6.3 mmol) in DMF (10 mL) was stirred at 100° C. for 2 h. The mixture was cooled to rt. Concentrated HCl (1.5 ml) and water (3 mL) were added, and the mixture was stirred at rt for 1 h. The mixture was cooled to 0° C. and NaOH (4 M, 5 ml) and H₂O (25 mL) were added. The mixture was extracted with Et₂O (5 mL*3). The combined organic phase was washed with brine (15 ml), dried over Na₂SO₄ and purified by silica gel column chromatography (pet. ether/EtOAc=200/1 to 100/1) to afford Intermediate B11 (800 mg, 47% yield) as a colorless oil.

TLC: Pet. ether/EtOAc=100/1 (v/v), Rf=0.55

¹H NMR: (400 MHz, DMSO-d₆) δ 7.66-7.60 (m, 1H), 7.42 (t, J=8.0 Hz, 1H), 7.303 (t, J=15.6 Hz, 1H), 7.24 (td, J=8.4, 1.6 Hz, 1H).

¹⁹F NMR: (376 MHz, DMSO-d₆) δ −82.56 (d, J=3.6 Hz), −124.68.

Intermediate B12

Synthesis of 2-(3-(difluoromethoxy)-2-fluorophenyl)-4,4,5,5-tetramethyl-1,3,2-dioxaborolane (Intermediate B12)

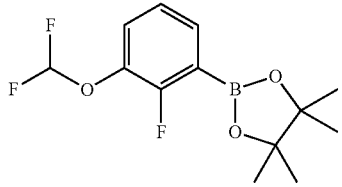

B12

To a solution of Intermediate B11 (400 mg, 1.7 mmol), bis(pinacolato)diboron (1.25 g, 4.93 mmol) and Pd(dppf)Cl₂·CH₂Cl₂ (457 mg, 1.8 mmol) in 1,4-dioxane (5.0 mL) at rt was added potassium acetate (500 mg, 5.1 mmol). The mixture was heated to 110° C. for 3 h. The mixture was cooled to room temperature and filtered. The filtrate was concentrated in vacuo to afford crude Intermediate B12 (470 mg, 95% yield) which was used without further purification.

TLC: EtOAc/pet. ether=1/10 (v/v), Rf=0.65

Intermediate C1

Synthesis of 3'-(difluoromethoxy)-[1,1'-biphenyl]-2-ol (Intermediate C1)

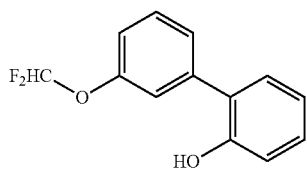

C1

A mixture of Intermediate B1 (3.5 g, 13 mmol), 2-bromophenol (1.5 g, 8.67 mmol), Pd(dppf)Cl₂ (634 mg, 0.87 mmol) and K₂CO₃ (3.6 g, 26 mmol) in 1,4-dioxane (30 mL) and water (3 mL) was stirred at 90° C. overnight. Water (50 mL) was added, and the mixture was extracted with EtOAc (30 mL*2). The combined organic phase was washed with brine (50 mL), dried over Na₂SO₄, and concentrated in vacuo. The residue was purified by silica gel column chromatography (Pet. ether/EtOAc=20/1 to 5/1, v/v) to afford Intermediate C1 (700 mg, 34% yield) as a yellow oil.

TLC: EtOAc/pet. ether=1/5 (v/v), Rf=0.54

LCMS: RT=2.551 min; [M−1]=235.0

Intermediate C2

Synthesis of 3'-ethyl-[1,1'-biphenyl]-2-ol (Intermediate C2)

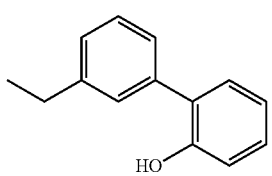

C2

A mixture of 2-bromophenol (660 mg, 3.81 mmol), (3-ethylphenyl)boronic acid (630 mg, 4.20 mmol), Na₂CO₃ (809 mg, 7.63 mmol) and Pd(dppf)Cl₂ (278 mg, 381 umol) in 1,4-Dioxane (10 mL)/water (2 mL) was stirred at 85° C. for 2 h under N₂ atmosphere. The mixture was concentrated and purified by silica gel column chromatography (pet. ether/EtOAc=100/1, v/v) to give Intermediate C2 (600 mg, 79% yield) as a yellow oil.

TLC: EtOAc/pet. ether=1/5 (v/v), Rf=0.35

¹H NMR: (400 MHz, DMSO) δ 9.43 (s, 1H), 7.41-7.07 (m, 6H), 6.92 (d, J=7.7 Hz, 1H), 6.86 (t, J=7.4 Hz, 1H), 2.64 (q, J=7.6 Hz, 2H), 1.21 (t, J=6.8 Hz, 3H).

Intermediate C3

Synthesis of 3'-(trifluoromethyl)-[1,1'-biphenyl]-2-ol (Intermediate C3)

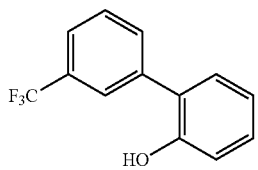

C3

A mixture of 2-bromophenol (500 mg, 2.89 mmol), 3-trifluoromethyl-phenylboronic acid (659 mg, 3.47 mmol), Pd(dppf)Cl₂ (211 mg, 289 umol) and K₂CO₃ (1.20 g, 8.67 mmol) in water (1 mL) and 1,4-dioxane (5 mL) was stirred at 90° C. overnight. Water (30 mL) was added, and the mixture was extracted with EtOAc (20 mL*2). The combined organic layer was washed with brine (30 mL), dried over Na₂SO₄, concentrated in vacuo and purified by silica gel column chromatography (pet. ether/EtOAc=20/1) to afford Intermediate C3 (600 mg, 87% yield) as a yellow oil.

TLC: EtOAc/pet. ether=1/5 (v/v), Rf=0.37

¹H NMR: (400 MHz, DMSO-d₆) δ 9.75 (s, 1H), 7.93-7.82 (m, 2H), 7.72-7.62 (m, 2H), 7.32 (dd, J=7.6, 1.8 Hz, 1H), 7.24-7.20 (m, 1H), 6.98 (dd, J=8.2, 1.2 Hz, 1H), 6.91 (td, J=7.4, 1.2 Hz, 1H).

Intermediate C4

Synthesis of
4-(hydroxy(2-hydroxyphenyl)methyl)benzonitrile
(Intermediate C4)

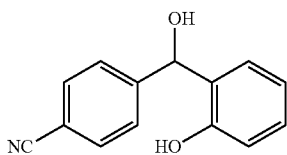

C4

A solution of 2-bromophenol (2.0 g, 11.6 mmol) in diethyl ether (20 mL) was cooled to −78° C. n-BuLi (2.5 M) (25.5 mmol) was added dropwise. The mixture was warmed to room temperature and stirred for 2 h. The mixture was cooled to −78° C. A solution of 4-cyanobenzaldehyde (1.7 g, 12.7 mmol) in THF (6 mL) was added dropwise. The mixture was stirred at −78° C. for 1 h and warmed to rt. The reaction was quenched with saturated aqueous NH$_4$Cl solution (20 mL) and extracted with EtOAc (10 mL*3). The combined organic phase was washed with brine (15 mL), dried over Na$_2$SO$_4$, concentrated in vacuo and purified by silica gel column chromatography (EtOAc/pet. ether=1/50 to 1/5) to afford Intermediate C4 (1.7 g, 65% yield) as a white solid.

TLC: EtOAc/pet. ether=1/5 (v/v), Rf=0.20

$^1$H NMR: (400 MHz, DMSO-d$_6$) δ 9.56 (s, 1H), 7.76-7.69 (m, 2H), 7.59-7.53 (m, 2H), 7.35 (dd, J=8.0, 1.6 Hz, 1H), 7.05 (td, J=7.6, 1.6 Hz, 1H), 6.81-6.77 (m, 2H), 6.04 (d, J=4.4 Hz, 1H), 5.93 (d, J=4.0 Hz, 1H).

Intermediate C5

Synthesis of 4-(2-hydroxybenzyl)benzonitrile
(Intermediate C5)

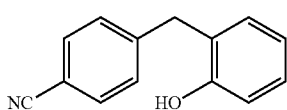

C5

To a solution of Intermediate C4 (1.7 g, 7.5 mmol) in DCM (20 mL) was added Et$_3$SiH (3.5 g, 30.7 mmol). The mixture was cooled to 0° C. and TFA (26.3 g, 231 mmol) was added dropwise. The mixture was stirred at rt for 2 h. Water (20 mL) was added and the resultant mixture was extracted with DCM (10 mL*3). The combined organic phase was washed with brine (15 mL), dried over Na$_2$SO$_4$, and concentrated in vacuo; the residue was washed with hexane (10 mL) to afford Intermediate C5 (1.2 g, 76% yield) as a white solid.

TLC: EtOAc/pet. ether=1/5 (v/v), R$_f$=0.45

$^1$H NMR: (400 MHz, DMSO-d$_6$) δ 9.47 (s, 1H), 7.72 (d, J=8.2 Hz, 2H), 7.40 (d, J=8.4 Hz, 2H), 7.12-7.02 (m, 2H), 6.81 (d, J=7.6 Hz, 1H), 6.74 (t, J=7.4 Hz, 1H), 3.95 (s, 2H).

Intermediate C6

Synthesis of 2-(hydroxy(pyridin-4-yl)methyl)phenol
(Intermediate C6)

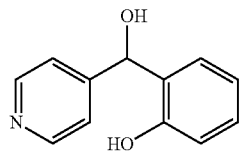

C6

A solution of 2-bromophenol (2.0 g, 11.6 mmol) in ether (20 mL) was cooled to −70° C.; n-BuLi (25.5 mmol, 10 mL of 2.5M) was added dropwise. The mixture was stirred at −70° C. for 2 h. Isonicotinaldehyde (1.4 g, 12.7 mmol) in THF (5 mL) was added dropwise. The mixture was stirred at −70° C. for 1 h. Reaction was quenched with saturated aqueous NH$_4$Cl (15 mL); the pH was adjusted to pH~7 with HCl (1N). The resultant mixture was extracted with EtOAc (30 mL*2); the combined organic phase was washed with brine (50 mL), dried over Na$_2$SO$_4$, and concentrated in vacuo. The residue was purified by silica gel column chromatography (DCM:MeOH=100:1 to 20:1) to afford Intermediate C6 (1.2 g, 51% yield) as a white solid.

TLC: DCM/MeOH=15/1 (v/v), Rf=0.3

$^1$H NMR: (400 MHz, DMSO-d$_6$) δ 9.56 (s, 1H), 8.46-8.43 (m, 2H), 7.34 (d, J=6.2 Hz, 3H), 7.07-7.02 (m, 1H), 6.81-6.75 (m, 2H), 5.97 (s, 1H), 5.89 (d, J=4.4 Hz, 1H).

Intermediate C7

Synthesis of 2-(pyridin-4-ylmethyl)phenol
(Intermediate C7)

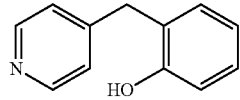

C7

To a solution of Intermediate C6 (1.2 g, 5.96 mmol) in DCM (15 mL) at 0° C. were added Et$_3$SiH (2.8 g, 23.8 mmol) and TFA (2.7 g, 23.8 mmol). The mixture was stirred at rt for 1 h, then concentrated in vacuo. Water (15 mL) was added, the mixture was adjusted to pH~7 with NaHCO$_3$ (2N) and extracted with EtOAc (50 mL*2). The combined organic phase was washed with brine (100 mL), dried over Na$_2$SO$_4$, and concentrated in vacuo. The residue was purified by silica gel column chromatography (DCM:MeOH=100:1 to 30:1) to afford Intermediate C7 (530 mg, 48% yield) as a yellow oil.

TLC: DCM/MeOH=10/1 (v/v), Rf=0.7

$^1$H NMR: (400 MHz, DMSO-d$_6$) δ 9.45 (s, 1H), 8.43-8.38 (m, 2H), 7.21-7.17 (m, 2H), 7.11-7.02 (m, 2H), 6.81 (dd, J=8.2, 1.2 Hz, 1H), 6.75 (dd, J=7.4, 1.2 Hz, 1H), 3.87 (s, 2H).

Intermediate C8

Synthesis of pyrimidine-5-carbaldehyde (Intermediate C8)

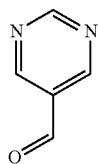

C8

To a solution of pyrimidine-5-methanol (2.0 g, 18.1 mmol) in chloroform (30 mL) at rt was added $MnO_2$ (15.6 g, 181 mmol). The mixture was stirred at 50° C. overnight. The reaction mixture was cooled to rt, then filtered, and the filtrate was concentrated in vacuo to give a crude product which was purified by silica gel column chromatography (pet. ether/EtOAc=2/1, v/v) to afford Intermediate C8 (800 mg, 40% yield) as a white solid.

TLC: EtOAc/pet. ether=1/10 (v/v), Rf=0.44

$^1$H NMR: (400 MHz, DMSO) δ 10.15 (s, 1H), 9.45 (s, 1H), 9.26 (s, 2H).

Intermediate C9

Synthesis of 2-(hydroxy(pyrimidin-5-yl)methyl)phenol (Intermediate C9)

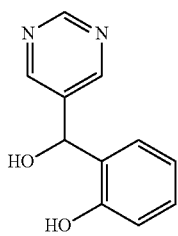

C9

To a solution of 2-bromophenol (1.28 g, 7.40 mmol) in THF (30 mL) at −70° C. was added n-BuLi (16 mmol, 6.51 mL of 2.5M). The mixture was stirred at rt for 30 min and then cooled to −70° C. Intermediate C8 (800 mg, 7.40 mmol) was added at −70° C.; the mixture was warmed slowly to rt and stirred for 16 h. The reaction was quenched with water (50 mL); the pH was adjusted to pH~6-7 with 2N HCl and the resultant mixture was extracted with EtOAc (50 mL*3). The combined organic phase was washed with brine (50 mL), dried over $Na_2SO_4$ and concentrated in vacuo. The residue was purified by silica gel column chromatography (pet. ether/EtOAc=½, v/v) to afford Intermediate C9 (800 mg, 53% yield) as a white solid.

TLC: EtOAc/pet. ether=1/10 (v/v), Rf=0.4

$^1$H NMR: (400 MHz, DMSO) δ 9.60 (s, 1H), 9.02 (s, 1H), 8.70 (s, 2H), 7.48 (m, 1H), 7.09 (m, 1H), 6.84 (t, J=7.4 Hz, 1H), 6.77 (d, J=8.0 Hz, 1H), 6.04 (d, J=4.4 Hz, 1H), 5.98 (d, J=4.4 Hz, 1H).

Intermediate C10

Synthesis of 2-(pyrimidin-5-ylmethyl)phenol (Intermediate C10)

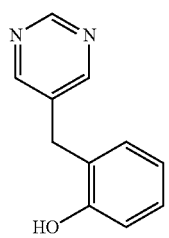

C10

To a solution of Intermediate C9 (800 mg, 3.95 mmol) in DCM (10 mL) at 0° C. were added $Et_3SiH$ (1.84 g, 15.8 mmol) and TFA (118 mmol, 9.0 mL). The mixture was stirred at rt for 0.5 h. The reaction was concentrated in vacuo and extracted with chloroform/isopropyl alcohol (30 mL/10 mL*3). The combined organic phase was dried over $Na_2SO_4$, concentrated in vacuo and purified by silica gel column chromatography (DCM/MeOH=20/1, v/v) to give Intermediate C10 (1.0 g, 100% yield) as a white solid.

TLC: EtOAc/pet. ether=1/10 (v/v), Rf=0.5

$^1$H NMR: (400 MHz, DMSO) δ 9.57 (s, 1H), 9.00 (s, 1H), 8.66 (s, 2H), 7.16 (m, 1H), 7.06 (d, J=1.7 Hz, 1H), 6.81 (d, J=8.0 Hz, 1H), 6.76 (d, J=7.4 Hz, 1H), 3.88 (s, 2H).

Intermediate C11

Synthesis of methyl 4-(2,2,2-trifluoroethyl)benzoate (Intermediate C11)

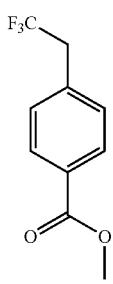

C11

A mixture of (4-carbomethoxyphenyl)boron pinacolate (1.0 g, 3.82 mmol), 1,1,1-trifluoro-2-iodo-ethane (1.6 g, 7.6 mmol), $Pd_2(dba)_3$ (175 mg, 191 umol), xantphos (221 mg, 382 umol), CuCi (38 mg, 382 umol) and CsF (1.74 g, 11.5 mmol) in 1,4-dioxane (10 mL) and water (1 mL) was stirred under $N_2$ atmosphere at 65° C. overnight. The mixture was cooled to rt and filtered; the filtrate was concentrated in vacuo. The residue was dissolved in DCM (100 mL), washed with $H_2O$ (50 mL), and brine (50 mL), then dried over $Na_2SO_4$. The solution was concentrated in vacuo, and purified by silica gel column chromatography (pet. ether/

EtOAc=10/1) to afford Intermediate C11 (330 mg, 40% yield) as a light yellow solid.

TLC: EtOAc/pet. ether=⅕ (v/v), Rf=0.82

¹H NMR: (400 MHz, DMSO-d₆) δ 7.97 (d, J=8.1 Hz, 2H), 7.52 (d, J=7.9 Hz, 2H), 3.86 (s, 3H), 3.78 (q, J=11.6 Hz, 2H).

Intermediate C12

Synthesis of (4-(2,2,2-trifluoroethyl)phenyl)methanol (Intermediate C12)

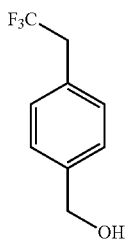

To a solution of Intermediate C11 (330 mg, 1.51 mmol) in dry THF (6 mL) at 0° C. was added LiAlH₄ (69 mg, 1.82 mmol); the mixture was stirred at 0° C. for 1 h. Saturated NH₄Cl (aq) solution (5 mL) was added and the resultant mixture was extracted with DCM (5 mL*2). The organic layer was dried over Na₂SO₄ and concentrated in vacuo to afford Intermediate C12 (250 mg, 87% yield) as a light yellow solid.

TLC: EtOAc/pet. ether=⅕ (v/v), Rf=0.49

¹H NMR: (400 MHz, DMSO-d₆) δ 7.33-7.29 (m, 4H), 5.18 (t, J=5.7 Hz, 1H), 4.49 (d, J=5.7 Hz, 2H), 3.61 (q, J=11.7 Hz, 2H).

Intermediate C13

Synthesis of 1-(chloromethyl)-4-(2,2,2-trifluoroethyl)benzene (Intermediate C13)

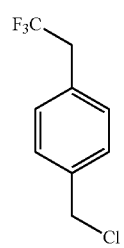

To a solution of Intermediate C12 (250 mg, 1.31 mmol) in DCM (4 mL) was added thionyl chloride (235 mg, 1.97 mmol). The mixture was stirred at RT for 2 h. The mixture was concentrated to dryness to afford Intermediate C13 (250 mg, 92% yield) as a light yellow solid.

TLC: EtOAc/pet. ether=⅕ (v/v), Rf=0.78

¹H NMR: (400 MHz, DMSO-d₆) δ 7.45 (d, J=7.9 Hz, 2H), 7.37 (d, J=7.9 Hz, 2H), 4.76 (s, 2H), 3.66 (q, J=11.6 Hz, 2H).

Intermediate C14

Synthesis of 2-(1-(4-fluorophenyl)-1-hydroxypropyl)phenol (Intermediate C14)

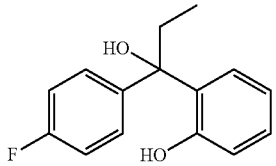

A solution of 2-bromophenol (3.41 g, 19.7 mmol) in THF (40 mL) at −30° C. was added dropwise n-BuLi (2.5 M, 17.35 mL). After 2 h, the mixture was cooled to −50° C. and (4-fluorophenyl)-ethyl ketone (3.0 g, 19.7 mmol) was added dropwise. The mixture was stirred at rt overnight, then diluted with NH₄Cl aqueous (30 mL), acidified with HCl (1N) to pH=6-7, and extracted with EtOAc (30 mL*3). The combined organic phase was washed with brine (30 mL), dried over Na₂SO₄, and concentrated in vacuo. The crude product was purified by silica gel column chromatography (pet. ether/EtOAc=20/1 to 5/1) to afford Intermediate C14 (2.1 g, 43% yield) as a yellow oil.

TLC: EtOAc/pet. ether=⅕ (v/v), Rf=0.36

¹H NMR: (400 MHz, DMSO-d₆) δ 9.58 (s, 1H), 7.41-7.30 (m, 3H), 7.11-7.02 (m, 3H), 6.80 (td, J=7.6, 1.3 Hz, 1H), 6.67 (dd, J=8.0, 1.3 Hz, 1H), 6.19 (s, 1H), 2.42 (dq, J=14.4, 7.3 Hz, 1H), 2.14 (dq, J=14.3, 7.2 Hz, 1H), 0.77 (t, J=7.2 Hz, 3H).

Intermediate C15

Synthesis of 2-(1-(4-fluorophenyl)propyl)phenol (Intermediate C15)

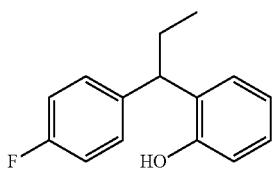

To a solution of Intermediate C14 (2.10 g, 8.53 mmol) in DCM (20 mL) at rt was added Et₃SiH (3.97 g, 34 mmol). The mixture was cooled to 0° C. and TFA (29.17 g, 256 mmol) was added dropwise. The mixture was stirred at rt for 3 h, diluted with DCM (20 mL) and concentrated in vacuo. The crude product was purified by silica gel column chromatography (pet. ether/EtOAc=50/1 to 10/1) to afford Intermediate C15 (1.7 g, 86% yield) as a yellow oil.

TLC: EtOAc/pet. ether=⅕ (v/v), Rf=0.60

¹H NMR: (400 MHz, DMSO-d₆) δ 9.31 (s, 1H), 7.31-7.22 (m, 2H), 7.17 (dd, J=8.0, 1.6 Hz, 1H), 7.10-7.01 (m, 2H), 6.97 (td, J=7.5, 1.7 Hz, 1H), 6.75 (dd, J=7.8, 6.6 Hz, 2H), 4.16 (t, J=7.9 Hz, 1H), 2.01-1.89 (m, 2H), 0.80 (t, J=7.3 Hz, 3H).

Intermediate C16

Synthesis of 2-(1-(4-fluorophenyl)-1-hydroxybutyl)phenol (Intermediate C16)

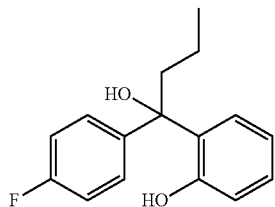

C16

A solution of 2-bromophenol (2.0 g, 11.6 mmol) in THF (20 mL) was cooled to −78° C. n-BuLi (10.2 mL of 2.5 M; 25.5 mmol) was added dropwise. The mixture was stirred at rt for 2 h, then cooled to −78° C. A solution of (4-fluorophenyl)-n-propyl ketone (1.7 g, 12.7 mmol) in THF (6 mL) was added dropwise. The mixture was stirred at −78° C. for 1 h and then warmed to 70° C. and stirred overnight. The reaction was quenched with saturated aqueous $NH_4Cl$ solution (20 mL) and extracted with EtOAc (10 mL*3). The combined organic phase was washed with brine (15 mL), dried over $Na_2SO_4$, concentrated in vacuo and purified by silica gel column chromatography (EtOAc/pet. ether=1/50 to 1/10) to afford Intermediate C16 (750 mg, 25% yield) as a white solid.

TLC: EtOAc/pet. ether=1/10 (v/v), Rf=0.20
LCMS: RT=4.018 min; [M−1]=259.0

Intermediate C17

Synthesis of 2-(1-(4-fluorophenyl)butyl)phenol (Intermediate C17)

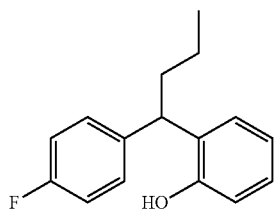

C17

To a solution of Intermediate C16 (750 mg, 2.9 mmol) in DCM (10 mL) was added $Et_3SiH$ (1.3 g, 11.4 mmol). The mixture was cooled to 0° C. and TFA (9.8 g, 85.5 mmol) was added dropwise. The mixture was stirred at rt for 2 h. Water (20 mL) was added and the resultant mixture was extracted with DCM (10 mL*3). The combined organic phase was washed with brine (15 mL), dried over $Na_2SO_4$, and concentrated in vacuo. The residue was washed with hexane (10 mL) to afford Intermediate C17 (1.2 g, 76% yield) as a white solid.

TLC: EtOAc/pet. ether=1/10 (v/v), $R_f$=0.6
$^1$H NMR: (400 MHz, DMSO) δ 9.35 (s, 1H), 7.28 (dd, J=8.4, 6.0 Hz, 2H), 7.17 (t, J=9.2 Hz, 1H), 7.05 (t, J=8.8 Hz, 2H), 6.97 (m, 1H), 6.80-6.71 (m, 2H), 4.30 (t, J=8.0 Hz, 1H), 1.99-1.84 (m, 2H), 1.20 (td, J=14.0, 7.2 Hz, 2H), 0.88 (t, J=7.2 Hz, 2H).

Intermediate C18

Synthesis of 2-(1-(4-fluorophenyl)-1-hydroxy-2-methylpropyl)phenol (Intermediate C18)

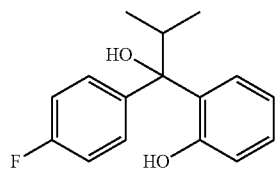

C18

To a solution of 2-bromophenol (691 mg, 4.00 mmol) in dry THF (5 mL) at −50° C. was added dropwise n-BuLi (8.79 mmol, 3.52 mL of 2.5M). The mixture was warmed to room temperature and stirred for 1 h to give Solution A. In parallel, a mixture of (4-fluorophenyl)-isopropyl ketone (332 mg, 2.00 mmol) and $ZnCl_2$ (1 mL, 1.00 mmol) was stirred at room temperature for 1 h and then added dropwise to Solution A. The resultant mixture was stirred at room temperature for 2 h, then reaction was quenched by the addition of saturated $NH_4Cl$ aqueous solution (15 mL). The mixture was acidified to pH~4-5 with 1N HCl, then extracted with DCM (15 mL*2). The combined organic layer was dried over $Na_2SO_4$, concentrated in vacuo, and purified by reversed-phase column chromatography to afford Intermediate C18 (350 mg, 67% yield) as a colorless oil.

TLC: EtOAc/pet. ether=1/5 (v/v), Rf=0.48
$^1$H NMR: (400 MHz, Chloroform-d) δ 8.78 (s, 1H), 7.40-7.33 (m, 2H), 7.15-7.11 (m, 2H), 7.02-6.93 (m, 2H), 6.86-6.77 (m, 2H), 2.81-2.72 (m, 1H), 1.10 (d, J=6.8 Hz, 3H), 0.82 (d, J=6.7 Hz, 3H).

Intermediate C19

Synthesis of 2-(1-(4-fluorophenyl)-2-methylpropyl)phenol (Intermediate C19)

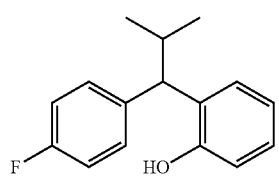

C19

A mixture of Intermediate C18 (250 mg, 960 umol) and 5% Pd/C (250 mg) in THF (10 mL) was stirred at 60° C. overnight. The mixture was cooled to rt and filtered, then concentrated to dryness to afford the Intermediate C19 (200 mg, 85% yield).

TLC: EtOAc/pet. ether=1/5 (v/v), Rf=0.66
$^1$H NMR: (400 MHz, DMSO-$d_6$) δ 9.39 (s, 1H), 7.36-7.30 (m, 3H), 7.06-7.01 (m, 2H), 6.95-6.91 (m, 1H), 6.75-6.71 (m, 2H), 3.88 (d, J=11.3 Hz, 1H), 2.58-2.51 (m, 1H), 0.79 (dd, J=14.9, 6.4 Hz, 6H).

Intermediate C20

Synthesis of 2-(cyclopropyl(4-fluorophenyl)(hydroxy)methyl)phenol (Intermediate C20)

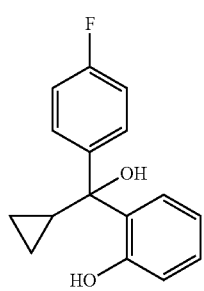

A solution of 2-bromophenol (1.58 g, 9.13 mmol) in THF (30 mL) was cooled to −70° C., and n-BuLi (20 mmol, 8.0 mL of 2.5 M) was added dropwise. The mixture was stirred at rt for 30 min, then cooled to −70° C.; 4-fluorophenyl cyclopropyl ketone (1.50 g, 9.13 mmol) in THF (3 mL) was added dropwise. The mixture was stirred at rt for 16 h. The reaction was quenched with water (50 mL); the mixture was adjusted to pH~6-7 with 2N HCl and extracted with EtOAc (50 mL*3). The combined organic phase was washed with brine (50 mL), dried over Na$_2$SO$_4$ and concentrated in vacuo. The residue was purified by silica gel column chromatography (pet. ether/EtOAc=20/1, v/v) to afford Intermediate C20 (2.0 g, 87% yield) as a white solid.

TLC: EtOAc/pet. ether=1/10 (v/v), Rf=0.4
LCMS: (RT=3.74 min; [M−1]=257.0)

Intermediate C21

Synthesis of 2-(cyclopropyl(4-fluorophenyl)methyl)phenol (Intermediate C21)

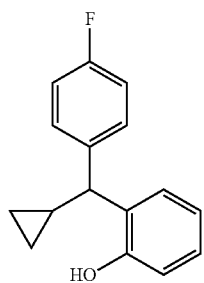

To a solution of Intermediate C20 (1.0 g, 3.87 mmol) in DCM (10 mL) at 0° C. were added Et$_3$SiH (1.8 g, 15.5 mmol) and TFA (116 mmol, 8.6 mL). The mixture was stirred at rt for 30 min. The mixture was concentrated in vacuo; water (10 mL) was added, and the mixture was extracted with DCM (30 mL*3). The combined organic phase was dried over Na$_2$SO$_4$, concentrated in vacuo and purified by silica gel column chromatography (pet. ether/EtOAc=20/1, v/v) to afford Intermediate C21 (400 mg, 25% yield, 60% purity) as a white solid.

TLC: EtOAc/pet. ether=1/10 (v/v), Rf=0.5
$^1$H NMR: (400 MHz, DMSO) δ 9.24 (s, 1H), 7.36-7.23 (m, 3H), 7.10-6.95 (m, 3H), 6.76 (m, 2H), 3.48 (d, J=10.0 Hz, 1H), 0.53 (m, 2H), 0.25 (m, 1H), 0.12 (m, 1H).

Intermediate C22

Synthesis of cyclobutyl(4-fluorophenyl)methanol (Intermediate C22)

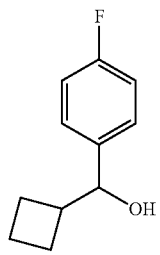

To a mixture of 4-fluorobenzaldehyde (2 g, 16.1 mmol), 1-bromocyclobutane (2.4 g, 17.7 mmol) and Mg (1.0 g, 40.3 mmol) in THF (20 mL) at rt was added I2 (1.61 mmol). The mixture was refluxed for 4 h. Water (40 mL) was added and the mixture was extracted with EtOAc (20 mL*3). The combined organic phase was washed with brine (5 mL), dried over Na$_2$SO$_4$, concentrated in vacuo and purified by silica gel column chromatography (pet. ether/EtOAc=50/1 to 5/1) to afford Intermediate C22 (2.0 g, 69% yield) as a light yellow liquid.

TLC: EtOAc/pet.ether=1/5 (v/v), Rf=0.25
$^1$H NMR: (400 MHz, Chloroform-d) δ 7.25-7.19 (m, 2H), 6.99-6.90 (m, 2H), 4.49 (d, J=8.0 Hz, 1H), 2.52 (h, J=8.0 Hz, 1H), 2.04-1.70 (m, 6H).

Intermediate C23

Synthesis of cyclobutyl(4-fluorophenyl)methanone (Intermediate C23)

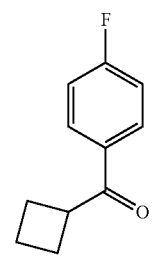

To a solution of Intermediate C22 (1.5 g, 8.32 mmol) in DCM (20 mL) was added Dess-Martin periodinane (4.2 g, 10.0 mmol). The mixture was stirred at rt for 2 h. Water (30 mL) was added and the resultant mixture was extracted with DCM (15 mL*3). The combined organic phase was washed with brine (20 mL), dried over Na$_2$SO$_4$ and concentrated in vacuo to afford Intermediate C23 (1.4 g, 94% yield) as a colorless liquid.

TLC: EtOAc/pet.ether=⅕ (v/v), R$_f$=0.7

$^1$H NMR: (400 MHz, Chloroform-d) δ 7.87-7.79 (m, 2H), 7.03 (t, J=8.6 Hz, 2H), 3.88 (p, J=8.0 Hz, 1H), 2.40-2.26 (m, 2H), 2.26-2.15 (m, 2H), 2.07-1.93 (m, 1H), 1.83 (m, 1H).

Intermediate C24

Synthesis of 2-(cyclobutyl(4-fluorophenyl)(hydroxy)methyl)phenol (Intermediate C24)

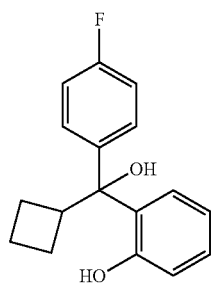

To a solution of Intermediate C23 (1 g, 5.61 mmol) in THF (10 mL) at rt was added ZnCl$_2$ (2.8 mL, 1.3 mmol); the mixture was stirred at rt for 30 min (Solution A). Separately, a solution of 2-bromophenol (1.2 g, 6.73 mmol) in THF (2.5 mL) was cooled to −78° C., n-BuLi (2.5 M, in THF) (7.4 mL, 18.5 mmol) was added, and the solution was stirred at rt for 1 h (Solution B). Solution B was cooled to −78° C., and Solution A was added. The resultant mixture was stirred at −78° C. for 2 h. Water (20 mL) was added and the mixture was extracted with EtOAc (10 mL*3). The combined organic phase was washed with brine (5 mL), dried over Na$_2$SO$_4$, concentrated in vacuo and purified by reversed-phase column chromatography (MeCN/H$_2$O) to afford Intermediate C24 (800 mg, 52% yield) as a light yellow oil.

TLC: EtOAc/pet.ether=⅕ (v/v), R$_f$=0.50

LCMS: RT=4.030 min; [M−1]=271.1

Intermediate C25

Synthesis of 2-(cyclobutyl(4-fluorophenyl)methyl)phenol (Intermediate C25)

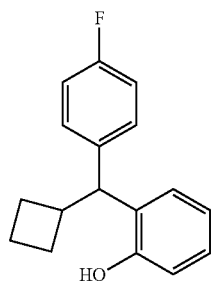

A solution of Intermediate C24 (800 mg, 3.0 mmol) and Et$_3$SiH (1.37 g, 11.75 mmol, 1.88 mL) in DCM (8 mL) was cooled to 0° C. TFA (10.1 g, 88.5 mmol) was added dropwise. The mixture was stirred at rt for 2 h. Water (20 mL) was added and the mixture was extracted with DCM (10 mL*3). The combined organic phase was washed with brine (15 mL), dried over Na$_2$SO$_4$, concentrated in vacuo and purified by silica gel column chromatography (pet. ether/EtOAc=50/1 to 10/1) to afford Intermediate C25 (650 mg, 86% yield) as a light yellow oil.

TLC: EtOAc/pet. ether=⅕ (v/v), R$_f$=0.45

$^1$H NMR: (400 MHz, DMSO-d$_6$) δ 9.28 (s, 1H), 7.23 (dd, J=8.4, 5.8 Hz, 2H), 7.17 (d, J=7.0 Hz, 1H), 7.02 (t, J=8.9 Hz, 2H), 6.97 (t, J=7.6 Hz, 1H), 6.74 (t, J=7.0 Hz, 2H), 4.25 (d, J=11.4 Hz, 1H), 3.15-3.04 (m, 1H), 1.97-1.85 (m, 2H), 1.83-1.72 (m, 2H), 1.72-1.63 (m, 1H), 1.56 (q, J=8.0, 16.0 Hz, 1H).

Intermediate C26

Synthesis of 6-fluoro-1-(2-hydroxyphenyl)-1,2,3,4-tetrahydronaphthalen-1-ol (Intermediate C26)

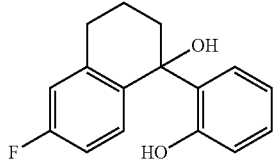

To a Solution A of 2-bromophenol (1.4 g, 8.3 mmol) in THF (15 mL) at −78° C. was added dropwise n-BuLi (2.5 M, 7.3 mL). The mixture was stirred at rt for 1 h. To a Solution B of 6-fluoro-1-tetralone (1.5 g, 9.14 mmol) in THF (3 mL) was added ZnCl$_2$ (1M, 3.3 mL). The mixture was stirred at rt for 30 min. Solution A was cooled to −78° C., solution B was added dropwise. The mixture was stirred at −78° C. for 2 h. Water (30 mL) was added and the resultant mixture was extracted with EtOAc (15 mL*3). The combined organic phase was washed with brine (30 mL), dried over Na$_2$SO$_4$, concentrated in vacuo and purified by reversed-phase column chromatography (MeCN/H$_2$O) to afford Intermediate C26 (220 mg, 10% yield) as a brown oil.

TLC: EtOAc/pet. ether=1/10 (v/v), Rf=0.20

LCMS: RT=3.835 min; [M−1]=257.0

Intermediate C27

Synthesis of 2-(6-fluoro-1,2,3,4-tetrahydronaphthalen-1-yl)phenol (Intermediate C27)

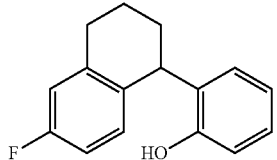

A solution of Intermediate C26 (220 mg, 852 umol) and Et$_3$SiH (396 mg, 3.41 mmol) in DCM (4 mL) was cooled to 0° C. TFA (2.91 g, 25.6 mmol) was added dropwise. The solution was stirred at rt for 2 h. The reaction was quenched with water (20 mL) and extracted with DCM (10 mL*3).

The combined organic phase was washed with brine (10 mL), dried over Na$_2$SO$_4$, concentrated in vacuo and purified by silica gel column chromatography (pet. ether/EtOAc=50/1 to 10/1) to afford Intermediate C27 (110 mg, 53% yield) as a light yellow oil.

TLC: EtOAc/pet. ether=⅕ (v/v), R$_f$=0.6

Intermediate C28

Synthesis of 6-fluoro-1-(2-hydroxyphenyl)-2,3-dihydro-1H-inden-1-ol (Intermediate C28)

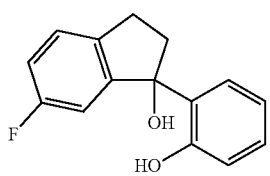

To a solution A of 2-bromophenol (1.0 g, 5.8 mmol) in THF (15 mL) at −78° C. was added n-BuLi (12.8 mmol, 5.1 mL of 2.5M). The mixture was stirred at rt for 1 h. To a solution B of 6-fluoro-1-indanone (1.0 g, 6.4 mmol) in THF (3 mL) at rt was added ZnCl$_2$ (1 M, 2.3 mL). The mixture was stirred at rt for 30 min. Solution A was cooled to −78° C., solution B was added. The reaction mixture was stirred at −78° C. for 2 h. Water (20 mL) was added and the pH was adjusted to pH~6-7 with 1N HCl. The mixture was extracted with EtOAc (10 mL*3). The combined organic phase was washed with brine (30 mL), dried over Na$_2$SO$_4$, concentrated in vacuo and purified by reversed-phase column chromatography (MeCN/H$_2$O) to afford Intermediate C28 (180 mg, 11% yield) as a yellow oil.

TLC: EtOAc/pet. ether=1/10 (v/v), Rf=0.20

LCMS: RT=3.661 min; [M−1]=243.0

Intermediate C29

Synthesis of 2-(6-fluoro-2,3-dihydro-1H-inden-1-yl)phenol (Intermediate C29)

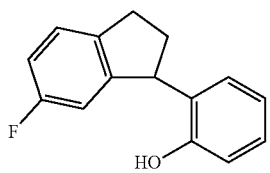

A solution of Intermediate C28 (220 mg, 852 umol) and Et$_3$SiH (396 mg, 3.41 mmol) in DCM (4 mL) was cooled to 0° C. TFA (2.91 g, 25.6 mmol) was added dropwise. The solution was stirred at rt for 2 h. The reaction was quenched with water (10 mL) and extracted with DCM (5 mL*3). The combined organic phase was washed with brine (10 mL), dried over Na$_2$SO$_4$, concentrated in vacuo and purified by silica gel column chromatography (pet. ether/EtOAc=50/1 to 10/1) to afford Intermediate C29 (130 mg, 63% yield) as a light yellow oil.

TLC: EtOAc/pet. ether=⅕ (v/v), R$_f$=0.6

LCMS: RT=3.997 min; [M−1]=227.0

Intermediate C30

Synthesis of 2-((4-fluorophenyl)(hydroxy)methyl)phenol (Intermediate C30)

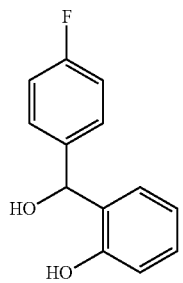

To a solution of 2-bromophenol (4.18 g, 24.2 mmol) in THF (40 mL) at −30° C. was added dropwise n-BuLi (2.5 M in hexanes) (29.0 mmol, 11.6 mL). After 0.5 h, 4-fluorobenzaldehyde (3.0 g, 24.2 mmol) in THF (10 mL) was added dropwise. The mixture was stirred for 1 h, then quenched with saturated aqueous NH$_4$Cl (50 mL), acidified with 1N HCl to pH~6-7 and extracted with EtOAc (10 mL*3). The combined organic phase was washed with brine (15 mL), dried over Na$_2$SO$_4$, and concentrated in vacuo. The crude product was purified by silica gel column chromatography (pet. ether/EtOAc=20/1 to 5/1) to afford Intermediate C30 (2.47 g, 46% yield) as a yellow oil.

TLC: EtOAc/pet. ether=⅕ (v/v), Rf=0.36

$^1$H NMR: (400 MHz, DMSO-d$_6$) δ 9.43 (s, 1H), 7.36 (td, J=5.6, 2.4 Hz, 3H), 7.14-6.97 (m, 3H), 6.82-6.70 (m, 2H), 5.96 (d, J=4.2 Hz, 1H), 5.72 (d, J=4.3 Hz, 1H).

Intermediate C31

Synthesis of 2-(4-fluorobenzyl)phenol (Intermediate C31)

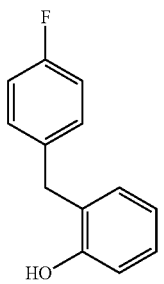

To a solution of Intermediate C30 (2.47 g, 11.3 mmol) in DCM (25 mL) at rt was added Et$_3$SiH (5.26 g, 45.3 mmol). The mixture was stirred at 0° C. for 10 min, then TFA (38.7 g, 340 mmol) was added dropwise. The mixture was stirred at rt for 3 h, diluted with DCM (20 mL) and concentrated in vacuo. The crude product was purified by silica gel column chromatography (pet. ether/EtOAc=50/1 to 10/1) to afford Intermediate C31 (1.86 g, 81% yield) as a yellow oil.

TLC: EtOAc/pet. ether=⅕ (v/v), R$_f$=0.64

$^1$H NMR: (400 MHz, DMSO-d$_6$) δ 9.39 (s, 1H), 7.25-7.20 (m, 2H), 7.10-6.98 (m, 4H), 6.81-6.78 (m, 1H), 6.71 (td, J=7.4, 1.3 Hz, 1H), 3.84 (s, 2H).

Intermediate C32

Synthesis of 2-(hydroxy(thiophen-3-yl)methyl)phenol (Intermediate C32)

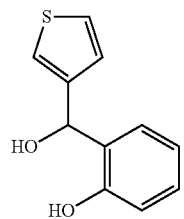

C32

To a solution of 2-bromophenol (1.0 g, 5.78 mmol) in THF (10 mL) at −78° C. was added n-BuLi (14.5 mmol, 5.8 mL of 2.5M); the mixture was stirred at −78° C. for 1 h. Thiophene-3-carboxaldehyde (1.3 g, 11.6 mmol) in THF (5 mL) at −78° C. was added to the resultant solution. The mixture was stirred at −78° C. for 2 h. The reaction mixture was quenched with water (20 mL) and the pH of the solution was adjusted to pH~6-7 with 1N HCl. The resultant mixture was extracted with EtOAc (20 mL*2). The combined organic phase was washed with brine (20 mL), dried over Na$_2$SO$_4$, concentrated in vacuo and purified by reversed-phase column chromatography to afford Intermediate C32 (850 mg, 71% yield) as yellow solid.

TLC: Pet. ether/EtOAc=5/1 (v/v), Rf=0.4

LCMS: RT=2.809 min, [M−1]=205.1

$^1$H NMR: (400 MHz, DMSO-d$_6$) δ 9.41 (s, 1H), 7.37 (dd, J=4.8, 2.8 Hz, 1H), 7.34 (dd, J=8.0, 1.6 Hz, 1H), 7.18 (dt, J=3.2, 1.2 Hz, 1H), 7.06-6.98 (m, 2H), 6.79-6.75 (m, 2H), 6.01 (d, J=4.4 Hz, 1H), 5.68 (d, J=4.8 Hz, 1H).

Intermediate C33

Synthesis of 2-(thiophen-3-ylmethyl)phenol (Intermediate C33)

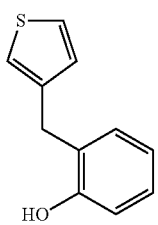

C33

To a solution of Intermediate C32 (550 mg, 2.67 mmol) in DCM (15 mL) at 0° C. were added Et$_3$SiH (930 mg, 8.0 mmol) and TFA (3.0 g, 26.7 mmol); the mixture was stirred at rt for 2 h. The reaction was concentrated and purified by reversed-phase column chromatography to afford Intermediate C33 (230 mg, 45% yield).

TLC: Pet. ether/EtOAc=5/1 (v/v), Rf=0.59

$^1$H NMR: (400 MHz, DMSO-d$_6$) δ 9.38 (s, 1H), 7.40 (dd, J=4.8, 3.2 Hz, 1H), 7.10-7.08 (m, 1H), 7.02-6.98 (m, 2H), 6.96 (dd, J=4.8, 1.6 Hz, 1H), 6.83-6.77 (m, 1H), 6.70 (td, J=7.2, 1.2 Hz, 1H), 3.84 (s, 2H).

Intermediate C34

Synthesis of 2-(hydroxy(thiophen-2-yl)methyl)phenol (Intermediate C34)

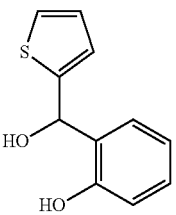

C34

To a solution of 2-bromophenol (2.0 g, 11.6 mmol) in THF (20 mL) at −78° C. was added n-BuLi (28.9 mmol, 12 mL of 2.5M); the mixture was stirred at −78° C. for 1 h. Thiophene-2-carbaldehyde (2.6 g, 23.1 mmol) was added and the mixture was stirred at −78° C. for 2 h. The reaction mixture was quenched with water (20 mL), the pH was adjusted to pH~6-7 with 1N HCl, and the mixture was extracted with EtOAc (20 mL*2). The combined organic phase was washed with brine (30 mL), dried over Na$_2$SO$_4$, and concentrated in vacuo; the residue was purified by reversed-phase column chromatography to afford Intermediate C34 (2.0 g, 83% yield) as a yellow solid.

TLC: EtOAc/pet. ether=⅕ (v/v), Rf=0.4

$^1$H NMR: (400 MHz, DMSO-d$_6$) δ 9.47 (s, 1H), 7.39 (dd, J=7.6, 1.6 Hz, 1H), 7.32 (dd, J=4.8, 1.2 Hz, 1H), 7.05 (dd, J=7.6, 1.6 Hz, 1H), 6.88 (dd, J=4.8, 3.6 Hz, 1H), 6.83-6.75 (m, 3H), 6.17 (d, J=4.8 Hz, 1H), 5.98 (d, J=4.8 Hz, 1H).

Intermediate C35

Synthesis of 2-(thiophen-2-ylmethyl)phenol (Intermediate C35)

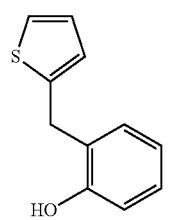

C35

To a solution of Intermediate C34 (2.0 g, 9.70 mmol) in DCM (20 mL) at 0° C. were added Et₃SiH (3.4 g, 29.1 mmol) and TFA (11.1 g, 97.0 mmol); the mixture was stirred at rt for 1 h. The reaction mixture was concentrated in vacuo and purified by reversed-phase column chromatography to afford Intermediate C35 (700 mg, 37% yield).

TLC: EtOAc/pet. ether=⅕ (v/v), Rf=0.7

¹H NMR: (400 MHz, DMSO-d₆) δ 9.47 (s, 1H), 7.26 (dd, J=5.2, 1.2 Hz, 1H), 7.11-6.98 (m, 2H), 6.90 (dd, J=5.2, 3.2 Hz, 1H), 6.86-6.77 (m, 2H), 6.72 (td, J=7.2, 1.2 Hz, 1H), 4.03 (s, 2H).

Intermediate C36

Synthesis of 2-(2,2,2-trifluoro-1-(4-fluorophenyl)-1-hydroxyethyl)phenol (Intermediate C36)

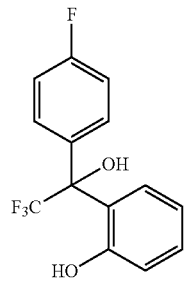

C36

To a mixture of 2-bromophenol (2.2 g, 12.5 mmol) in THF (30 mL) under N₂ atmosphere at −70° C. was added dropwise n-Butyllithium (26.0 mmol, 10.4 mL of 2.5M). The mixture was stirred at rt for h. (4-Fluorophenyl)-trifluoromethyl ketone (2.0 g, 10.4 mmol) was added at 0° C. The mixture was stirred at rt for 3 h. The mixture was quenched with saturated aqueous NH₄Cl solution (30 mL). The mixture was acidified with 2M HCl to pH ~5-6, then extracted with EtOAc (15 mL*2). The organic phase was washed with water (30 mL*2), then brine (30 mL), concentrated in vacuo and purified by reversed-phase column chromatography to afford Intermediate C36 (1.0 g, 34% yield) as a white solid.

TLC: EtOAc/pet. ether=⅕ (v/v), Rf=0.48

¹H NMR: (400 MHz, DMSO-d₆) δ 9.62 (s, 1H), 7.42-7.34 (m, 3H), 7.24-7.14 (m, 3H), 6.87 (td, J=7.6, 1.3 Hz, 1H), 6.79 (dd, J=8.1, 1.2 Hz, 1H).

Intermediate C37

Synthesis of 2-(2,2,2-trifluoro-1-(4-fluorophenyl)ethyl)phenol (Intermediate C37)

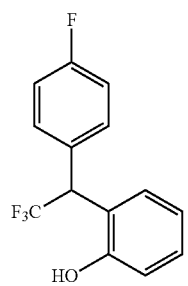

C37

A mixture of Intermediate C36 (1.0 g, 3.49 mmol), NaI (4.2 g, 28.0 mmol), TMSCl (2.3 g, 21.0 mmol) in acetonitrile (10 mL) was microwaved at 120° C. for 2 h. The mixture was cooled to rt and concentrated to dryness; the residue was purified by Prep-TLC to afford Intermediate C37 (300 mg, 32% yield) as a colorless oil.

TLC: EtOAc/pet. ether=⅕ (v/v), Rf=0.66

¹H NMR: (400 MHz, DMSO-d₆) δ 9.89 (s, 1H), 7.45-7.40 (m, 3H), 7.23-7.13 (m, 3H), 6.91-6.82 (m, 2H), 5.33 (q, J=10.8 Hz, 1H).

Intermediate C38

Synthesis of 2-(3,3,3-trifluoro-1-(4-fluorophenyl)propyl)phenol (Intermediate C38)

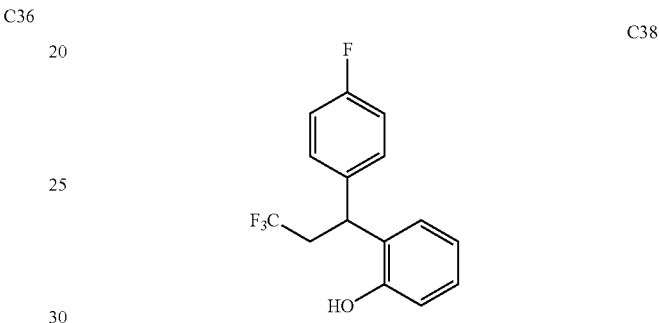

To a mixture of 4-fluorostyrene (200 mg, 1.6 mmol), Tognis reagent (792 mg, 2.4 mmol) and 2-hydroxyphenyl-boronic acid (452 mg, 3.3 mmol) in DMA (10.0 mL) was added Cu(CH₃CN)₄PF₆ (61 mg, 164 umol). The mixture was stirred at 40° C. for 1 h. Water (10 mL) was added and the resultant mixture was extracted with EtOAc (5 mL*3). The combined organic phase was washed with brine (20 mL), dried over Na₂SO₄, concentrated in vacuo and purified by silica gel column chromatography (pet. ether/EtOAc=50/1 to 10/1) to afford Intermediate C38 (360 mg, 77% yield) as a yellow oil.

TLC: EtOAc/Pet. ether-⅕ (v/v), Rf=0.3
LCMS: RT=1.569 min, [M−1]:283.1

Intermediate C39

Synthesis of 1-(4-fluorophenyl)-2-methoxyethan-1-one (Intermediate C39)

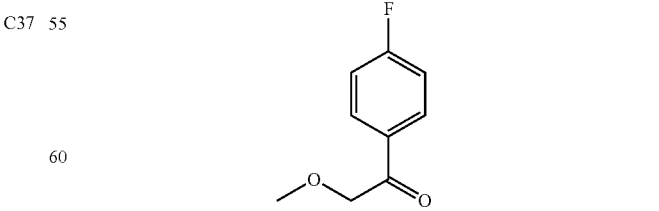

To a solution of 4-fluoroacetophenone (2.0 g, 14.5 mmol) in MeOH (60 mL) at rt were added TsNHNH₂ (2.7 g, 14.5 mmol), TBHP (7.8 g, 86.9 mmol) and TBAI (1.1 g, 2.89 mmol). The mixture was stirred at rt overnight. Water (100 mL) was added, and the resultant mixture was extracted with EtOAc (50 mL*2). The organic phase was washed with brine (20 mL*2) dried over Na₂SO₄, and concentrated in vacuo. The crude product was purified by silica gel column chromatography (EtOAc/pet. ether=1/100-1/10) to afford Intermediate C39 (1.7 g, 70% yield) as a yellow liquid.

TLC: EtOAc/pet. ether=1/5 (v/v), Rf=0.49.

¹H NMR: (400 MHz, DMSO-d₆) δ 8.04-7.96 (m, 2H), 7.40-7.32 (m, 2H), 4.77 (s, 2H), 3.35 (s, 3H).

Intermediate C40

Synthesis of 2-(1-(4-fluorophenyl)-1-hydroxy-2-methoxyethyl)phenol (Intermediate C40)

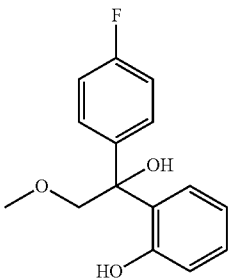

C40

To a solution of 2-bromophenol (3.0 g, 17.3 mmol) in THF (30 mL) at −78° C. was added n-BuLi (38.2 mmol, 15 mL of 2.5M); the mixture was stirred at rt for 1 h. A solution of Intermediate C39 (1.9 g, 11.6 mmol) in THF (5 mL) at −78° C. was added to the reaction. The mixture was stirred at −5° C. overnight. Water (100 mL) was added dropwise to the reaction mixture, which was then acidified to pH~6-7 with 2N HCl and extracted with EtOAc (30 mL*2). The organic phase was concentrated and purified by reversed-phase column chromatography to afford Intermediate C40 (800 mg, 28% yield) as a yellow liquid.

TLC: EtOAc/pet. ether=1/5 (v/v), Rf=0.39

¹H NMR (400 MHz, DMSO-d₆) δ 9.45 (s, 1H), 7.39-7.32 (m, 2H), 7.29 (dd, J=8.0, 2.0 Hz, 1H), 7.12-7.05 (m, 3H), 6.79 (td, J=7.6, 1.2 Hz, 1H), 6.70 (dd, J=8.0, 1.2 Hz, 1H), 6.40 (s, 1H), 3.98-3.88 (m, 2H), 3.29 (s, 3H).

Intermediate C41

Synthesis of 2-(1-(4-fluorophenyl)-2-methoxyethyl)phenol (Intermediate C41)

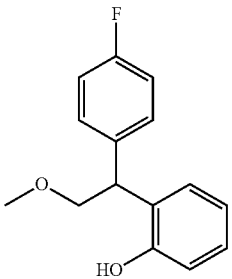

C41

To a solution of Intermediate C40 (400 mg, 1.53 mmol) in MeOH (8 mL) at rt was added Pd/C (400 mg, 5% w/w); the mixture was stirred at 50° C. for 3d. The reaction was filtered, concentrated in vacuo and purified by Prep-TLC to afford Intermediate C41 (90 mg, 24% yield) as a white solid.

TLC: EtOAc/pet. ether=1/5 (v/v), Rf=0.50

¹H NMR: (400 MHz, DMSO-d₆) δ 9.40 (s, 1H), 7.31-7.23 (m, 2H), 7.11-7.04 (m, 3H), 7.00 (td, J=7.6, 1.6 Hz, 1H), 6.80-6.69 (m, 2H), 4.56 (t, J=7.6 Hz, 1H), 3.86-3.75 (m, 2H), 3.23 (s, 3H).

Intermediate C42

Synthesis of 2-(1-(4-fluorophenyl)-1-hydroxyethyl)phenol (Intermediate C42)

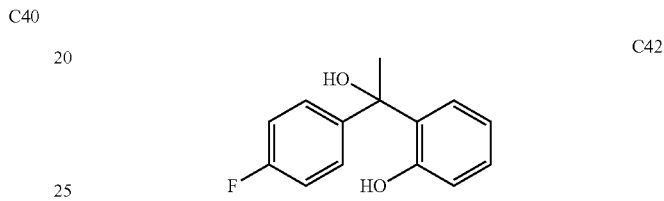

C42

2-Bromophenol (20.0 g, 116 mmol) in THF (100 mL) was cooled to −78° C. n-BuLi (232 mmol, 92.5 mL of 2.5M) was added. The mixture was stirred at rt for 1 h and was then cooled to −78° C. 4-fluoroacetophenone (16.0 g, 116 mmol) in TH (10 mL) was added. The mixture was stirred at rt for 16 h. The reaction mixture was acidified to pH~6-7 with 2N HCl and then was extracted with EtOAc (50 mL*3). The combined organic phase was washed with brine (100 mL), dried over Na₂SO₄, concentrated in vacuo and purified by reversed-phase column chromatography to afford Intermediate C42 (2.0 g, 7.3% yield).

TLC: EtOAc/pet. ether=1/5 (v/v), Rf=0.3

LCMS: RT=3.46 min; [M−1]=231.1

Intermediate C43

Synthesis of 2-(1-(4-fluorophenyl)ethyl)phenol (Intermediate C43)

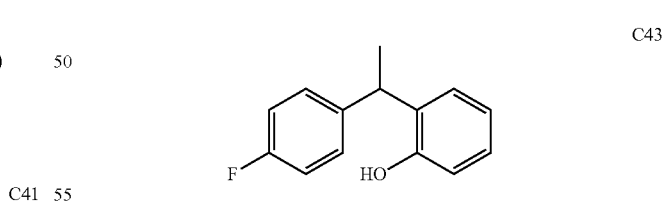

C43

To a solution of Intermediate C42 (5.7 g, 24.5 mmol) in DCM (50 mL) at 0° C. were added Et₃SiH (11.4 g, 98.0 mmol) and TFA (84.0 g, 735 mmol). The mixture was stirred at rt for 2 h. The reaction was concentrated in vacuo and purified by silica gel column chromatography (pet. ether/EtOAc=10/1) to afford Intermediate C43 (5.0 g, 94.3% yield).

TLC: EtOAc/pet. ether=1/5 (v/v), Rf=0.25

¹H NMR: (400 MHz, DMSO) δ 9.33 (s, 1H), 7.28-7.19 (m, 2H), 7.12-7.02 (m, 3H), 6.99 (m, 1H), 6.79-6.71 (m, 2H), 4.44 (d, J=7.3 Hz, 1H), 1.49 (d, J=7.3 Hz, 3H).

Intermediate C44

Synthesis of 2-(2-(4-fluorophenyl)-1-hydroxyethyl)phenol (Intermediate C44)

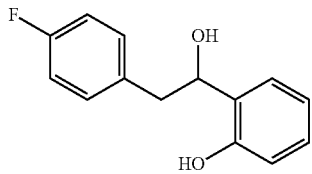

C44

A solution of 2-bromophenol (571 mg, 3.3 mmol) in THF (5 mL) was cooled to −78° C. n-BuLi (2.5M in THF) (7.3 mmol, 3.2 mL) was added dropwise. The mixture was stirred at rt for 30 min, then cooled to −78° C. A solution of 4-fluorophenylacetaldehyde (500 mg, 3.6 mmol) in THF (5 mL) was added dropwise. The mixture was stirred at −78° C. for 1 h. The reaction was quenched with saturated aqueous NH$_4$Cl solution (10 mL) and extracted with EtOAc (5 mL*3). The combined organic phase was washed with brine (15 mL), dried over Na$_2$SO$_4$, concentrated in vacuo and purified by silica gel column chromatography (EtOAc/pet. ether=1/50 to 1/20) to afford Intermediate C44 (200 mg, 24% yield) as a colorless oil.

TLC: EtOAc/pet. ether=1/10 (v/v), Rf=0.20

Intermediate C45

Synthesis of 2-(4-fluorophenethyl)phenol (Intermediate C45)

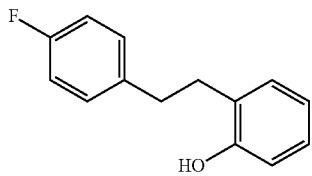

C45

To a solution of Intermediate C44 (200 mg, 0.9 mmol) in DCM (4 mL) was added Et$_3$SiH (418 mg, 3.6 mmol). The mixture was cooled to 0° C. and TFA (3.1 g, 27 mmol) was added dropwise. The mixture was stirred at rt for 2 h. Water (10 mL) was added and the resultant mixture was extracted with DCM (5 mL*3). The combined organic phase was washed with brine (15 mL), dried over Na$_2$SO$_4$, concentrated in vacuo and purified by Prep-TLC (EtOAc/pet. ether=1/10) to afford Intermediate C45 (120 mg, 65% yield) as a white solid.

TLC: EtOAc/pet. ether=1/10 (v/v), R$_f$=0.6

$^1$H NMR: (400 MHz, DMSO) δ 9.29 (s, 1H), 7.26-7.19 (m, 1H), 7.11-7.05 (m, 1H), 7.03-6.97 (m, 1H), 6.78 (d, J=8.0 Hz, 1H), 6.68 (dt, J=7.6, 1.2 Hz, 1H), 2.84-2.74 (m, 1H).

Intermediate D1

Synthesis of 1-(1-chloroethyl)-4-fluorobenzene (Intermediate D1)

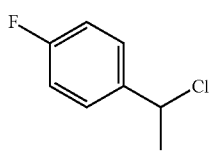

D1

To a solution of 1-(4-fluorophenyl)-1-ethanol (1.00 g, 7.13 mmol) in DCM (10 mL) at rt was added thionyl chloride (1.27 g, 10.7 mmol). The mixture was stirred for 1 h and was concentrated in vacuo to afford Intermediate D1 (1.13 g, 7.12 mmol, 99% yield).

TLC: EtOAc/pet. ether=3/1 (v/v), Rf=0.54

$^1$H NMR: (400 MHz, DMSO-d$_6$) δ 7.56-7.50 (m, 2H), 7.20-7.16 (m, 2H), 5.36 (q, J=6.8 Hz, 1H), 1.78 (d, J=6.8 Hz, 3H).

Intermediate D2

Synthesis of 1-(2-chloropropan-2-yl)-4-fluorobenzene (Intermediate D2)

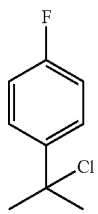

D2

A solution of 2-(4-F-phenyl)-2-propanol (500 mg, 3.24 mmol) and SOCl$_2$ (579 mg, 4.86 mmol) in DCM (5 mL) was stirred at room temperature overnight. The mixture was concentrated to dryness to afford crude Intermediate D2 (500 mg, 89% yield) as a colorless oil.

TLC: EtOAc/pet. ether=1/5 (v/v), Rf=0.57

$^1$H NMR: (400 MHz, DMSO-d$_6$) δ 7.68-7.62 (m, 2H), 7.22-7.17 (m, 2H), 1.96 (s, 6H).

Intermediate D3

Synthesis of furan-3-ylmethanol (Intermediate D3)

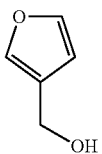

D3

To a solution of furan-3-carboxaldehyde (200 mg, 2.08 mmol) in THF (2 mL) at 0° C. was added NaBH$_4$ (95 mg, 2.50 mmol). The mixture was stirred at 0° C. for 2 h, then quenched with water (10 mL) and extracted with EtOAc (10 mL). The organic layer was washed with water (10 mL), then brine (10 mL), dried over Na$_2$SO$_4$, and concentrated to dryness to afford Intermediate D3 (150 mg, 73% yield) as a colorless oil.

TLC: EtOAc/pet. ether=1/10 (v/v), Rf=0.49

$^1$H NMR: (400 MHz, DMSO-d$_6$) δ 7.58 (t, J=1.7 Hz, 1H), 7.53-7.50 (m, 1H), 6.45-6.41 (m, 1H), 4.93 (t, J=5.6 Hz, 1H), 4.33 (dd, J=5.6, 1.0 Hz, 2H).

Intermediate D4

Synthesis of 3-(chloromethyl)furan (Intermediate D4)

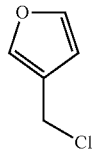

D4

To a solution of Intermediate D3 (200 mg, 2.04 mmol) in DCM (2 mL) was added thionyl chloride (364 mg, 3.06 mmol). The mixture was stirred at 0° C. for 2 h. The mixture was concentrated to dryness to afford Intermediate D4 (150 mg, 63% yield) as a colorless solid.

TLC: EtOAc/pet. ether=1/10 (v/v), Rf=0.78

Example 1

Synthesis of 2-(3,5-dichloro-4-((6-hydroxy-3'-(trifluoromethyl)-[1,1'-biphenyl]-3-yl)methyl)phenoxy)acetic Acid (Compound 1)

1

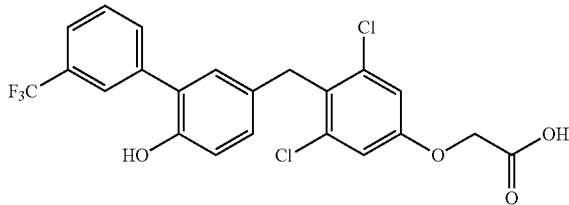 [SMILES: O=C(O)COc1cc(Cl)c(Cc2ccc(O)c(-c3cccc(C(F)(F)F)c3)c2)c(Cl)c1]

To a solution of Intermediate A7 (300 mg, 642 umol), 3-trifluoromethylphenylboronic acid (183 mg, 963 umol) and Pd(dppf)Cl$_2$ (47.0 mg, 64.2 umol) in dioxane (5 mL) at rt was added sodium bicarbonate (1 mL, 2 M in water). The mixture was heated to 70° C. and stirred for 3 h. The mixture was cooled to rt. NaOH (1.9 mL, 1.0 M in water) was added and the mixture was stirred at rt for 30 min. The reaction was quenched with water (5 mL), acidified to pH~4-5 with aqueous HCl (1M) and extracted with EtOAc (3 mL*3). The combined organic phase was washed with brine (5 mL), dried over Na$_2$SO$_4$, concentrated in vacuo and purified by prep-TLC (DCM/MeOH=10/1) to afford Compound 1 (20 mg, 42.4 umol, 6.6% yield) as a white solid.

TLC: DCM/MeOH=10/1 (v/v), Rf=0.15

$^1$H NMR: (400 MHz, DMSO-d$_6$) δ 9.65 (s, 1H), 7.84 (s, 1H), 7.76 (d, J=5.5 Hz, 1H), 7.64 (d, J=5.5 Hz, 2H), 7.15 (s, 1H), 7.11 (s, 2H), 6.98-6.84 (m, 2H), 4.74 (s, 2H), 4.13 (s, 2H).

Example 2

Synthesis of methyl 2-(3,5-dichloro-4-((3'-ethyl-6-hydroxy-[1,1'-biphenyl]-3-yl)methyl)phenoxy)acetate (Compound 2)

2

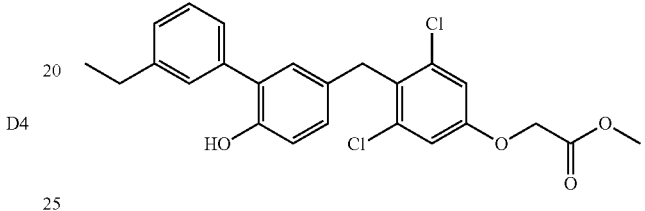

A mixture of 3-ethylphenylboronic acid (101 mg, 0.64 mmol), Intermediate A7 (300 mg, 0.57 mmol), 2N NaHCO$_3$ (1 mL, 1.92 mmol) and Pd(dppf)Cl$_2$ (47 mg, 0.06 mmol) in 1,4-dioxane (5 mL) was stirred at 70° C. for 8 h under N$_2$ atmosphere. The mixture was concentrated in vacuo. The residue was purified by reverse-phase column chromatography to afford Compound 2 (57 mg, 19% yield) as a yellow oil.

TLC: Pet. ether/EtOAc=1/5 (v/v), Rf=0.45

$^1$H NMR: (400 MHz, DMSO) δ 9.33 (s, 1H), 7.27 (m, 3H), 7.15 (s, 2H), 7.12 (d, J=7.0 Hz, 1H), 7.02 (s, 1H), 6.89 (d, J=8.3 Hz, 1H), 6.82 (d, J=8.3 Hz, 1H), 4.89 (s, 2H), 4.11 (s, 2H), 3.71 (s, 3H), 2.63 (q, J=7.5 Hz, 2H), 1.22-1.14 (m, 3H).

Example 3

Synthesis of 2-(3,5-dichloro-4-((3'-ethyl-6-hydroxy-[1,1'-biphenyl]-3-yl)methyl)phenoxy)acetic Acid (Compound 3)

3

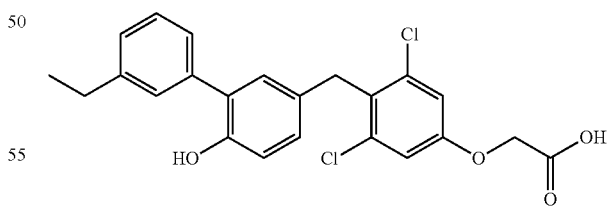

To a solution of Intermediate A7 (200 mg, 428 umol), 3-ethylphenylboronic acid (96 mg, 642 umol) and Pd(dppf)Cl$_2$ (31 mg, 43 umol) in dioxane (5 mL) at rt was added sodium bicarbonate (642 uL, 2M in water). The mixture was heated to 70° C. and stirred overnight. The mixture was cooled to rt. NaOH (1.3 mL, 1M in water) was added and the resultant mixture was stirred for 30 min. The reaction was quenched with water (10 mL), acidified to pH~4-5 with aqueous HCl (1 M) and extracted with EtOAc (5 mL*3). The combined organic phase was washed with brine (10 mL), dried over Na$_2$SO$_4$, concentrated in vacuo and purified by prep-HPLC to afford Compound 3 (30 mg, 67 umol, 15.7% yield) as a white solid.

TLC: DCM/MeOH=10/1 (v/v), Rf=0.26

$^1$H NMR: (400 MHz, DMSO-d$_6$) δ 9.34 (s, 1H), 7.35-7.22 (m, 3H), 7.13 (d, J=2.2 Hz, 1H), 7.10 (s, 2H), 7.03 (d, J=2.2 Hz, 1H), 6.88 (dd, J=8.3, 2.2 Hz, 1H), 6.83 (d, J=8.3 Hz, 1H), 4.75 (s, 2H), 4.11 (s, 2H), 2.62 (q, J=7.6 Hz, 2H), 1.19 (t, J=7.6 Hz, 3H).

Example 4

Synthesis of 2-(3,5-dichloro-4-((3'-ethyl-6-hydroxy-[1,1'-biphenyl]-3-yl)methyl)phenoxy)-N-methylacetamide (Compound 4)

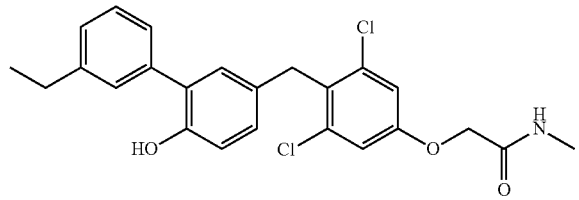

To a solution of Compound 2 (57 mg, 0.13 mmol) in THF (2 mL) at rt was added 1N aqueous MeNH$_2$ (1.3 mL, 1.30 mmol); the resulting mixture was stirred at 75° C. overnight. The reaction was concentrated in vacuo and purified by prep-TLC (DCM/MeOH=20/1, v/v) to give Compound 4 (37 mg, 65% yield) as a light yellow oil.

TLC: Pet. ether/EtOAc=⅕ (v/v), Rf=0.4

$^1$H NMR: (400 MHz, DMSO) δ 9.34 (s, 1H), 8.05 (d, J=4.7 Hz, 1H), 7.31-7.22 (m, 3H), 7.14 (s, 2H), 7.13-7.10 (m, 1H), 7.02 (d, J=2.3 Hz, 1H), 6.89 (m, 1H), 6.82 (d, J=8.3 Hz, 1H), 4.53 (s, 2H), 4.11 (s, 2H), 2.64 (d, J=4.6 Hz, 3H), 2.63-2.58 (m, 2H), 1.19 (t, J=7.6 Hz, 3H).

LCMS: RT=4.10 min; [M+1]=443.

Example 5

Synthesis of 2-(3,5-dichloro-4-((3'-(difluoromethoxy)-6-hydroxy-[1,1'-biphenyl]-3-yl)methyl)phenoxy)acetic Acid (Compound 5)

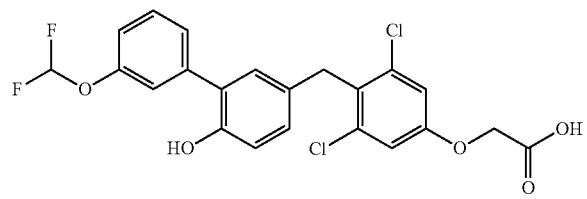 [SMILES: O=C(O)COc1cc(Cl)c(Cc2ccc(O)c(-c3cccc(OC(F)F)c3)c2)c(Cl)c1]

To a solution of Intermediate B1 (173 mg, 642 umol), Intermediate A7 (300 mg, 642 umol), and Pd(dppf)Cl$_2$ (23 mg, 32 umol) in 1,4-dioxane (10 mL) at rt was added NaHCO$_3$ (0.96 mL, 2M in water). The mixture was heated to 70° C. and stirred overnight. The reaction was cooled to rt. NaOH (1.25 mL, 1N in water) was added and the mixture was stirred at rt for 30 min. The reaction was quenched with water (10 mL), acidified to pH~4-5 with aqueous HCl (1 M) and extracted with EtOAc (10 mL*2). The combined organic phase was washed with brine (10 mL), dried over Na$_2$SO$_4$, concentrated in vacuo and purified by prep-HPLC to afford Compound 5 (40 mg, 85.2 umol, 20% yield) as a white solid.

TLC. DCM/MeOH=10/1 (v/v), Rf=0.2

$^1$H NMR: (400 MHz, DMSO-d$_6$) δ 13.10 (s, 1H), 9.55 (s, 1H), 7.45-7.42 (t, J=8.0 Hz, 1H), 7.24 (t, J=74.0 Hz, 1H), 7.37-7.28 (m, 2H), 7.12 (s, 1H), 7.12-7.05 (m, 3H), 6.92 (dd, J=8.4, 2.3 Hz, 1H), 6.86 (d, J=8.3 Hz, 1H), 4.77 (s, 2H), 4.12 (s, 2H).

Example 6

Synthesis of 2-(3,5-dichloro-4-((3'-(ethoxycarbonyl)-6-hydroxy-[1,1'-biphenyl]-3-yl)methyl)phenoxy)acetic Acid (Compound 6)

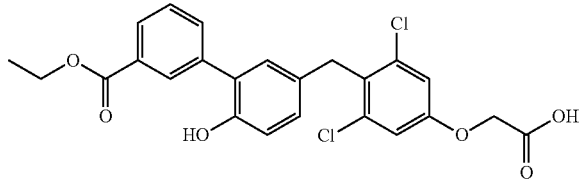

To a mixture of Intermediate A7 (200 mg, 428 umol), 3-ethoxycarbonylphenylboronic acid (125 mg, 644 umol) and Pd(dppf)Cl$_2$·CH$_2$Cl$_2$ (35 mg, 43 umol) in 1,4-dioxane (3.0 mL) at rt was added aqueous NaHCO$_3$ (2M, 0.5 mL). The mixture was heated to 70° C. overnight. The reaction mixture was cooled to rt. NaOH (1M, 0.4 mL) was added and the resultant mixture was stirred for 30 min. The reaction was quenched with water (10 mL), acidified to pH~4-5 with aqueous HCl (1M) and extracted with EtOAc (5 mL*3). The combined organic phase was washed with brine (10 mL), dried over Na$_2$SO$_4$, concentrated in vacuo and purified by prep-HPLC to afford Compound 6 (30 mg, 14% yield) as a white solid.

TLC: MeOH/DCM=1/10 (v/v), Rf=0.20

LCMS: RT=3.997 min; [M−1]=472.8

$^1$H NMR: (400 MHz, DMSO) δ 9.58 (s, 1H), 8.10 (s, 1H), 7.88 (d, J=7.6 Hz, 1H), 7.74 (d, J=7.4 Hz, 1H), 7.54 (t, J=7.6 Hz, 1H), 7.12 (s, 1H), 7.09 (d, J=1.8 Hz, 1H), 6.94 (d, J=8.4 Hz, 1H), 6.87 (d, J=8.4 Hz, 1H), 4.77 (s, 1H), 4.33 (dd, J=14.2, 7.0 Hz, 1H), 4.13 (s, 1H), 1.33 (t, J=7.0 Hz, 1H).

Example 7

Synthesis of 2-(3,5-dichloro-4-((6-hydroxy-3'-methoxy-[1,1'-biphenyl]-3-yl)methyl)phenoxy)acetic Acid (Compound 7)

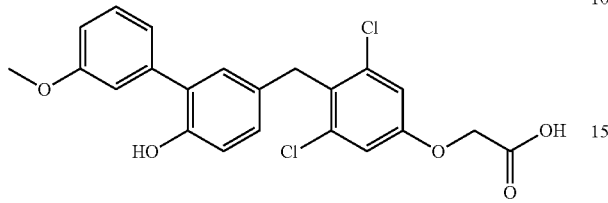

7

To a mixture of Intermediate A7 (250 mg, 540 umol), 3-methoxyphenylboronic acid (122 mg, 800 umol) and Pd(dppf)Cl$_2$·CH$_2$Cl$_2$ (39 mg, 54 umol) in 1,4-dioxane (5.0 mL) at rt was added aqueous NaHCO$_3$ (2M, 0.5 mL). The mixture was heated to 70° C. and stirred overnight. The reaction mixture was cooled to rt; LiOH.H$_2$O (67 mg, 1.6 mmol) was added and the mixture was stirred for 30 min. The reaction was quenched with water (10 mL), acidified to pH~4-5 with aqueous HCl (1M) and extracted with EtOAc (5 mL*3). The combined organic phase was washed with brine (10 mL), dried over Na$_2$SO$_4$, concentrated in vacuo and purified by Prep-HPLC to afford Compound 7 (30 mg, 29% yield) as a white solid.

TLC: MeOH/DCM=1/10 (v/v), Rf=0.20
LCMS: RT=3.887 min; [M−1]=430.8
$^1$H NMR: (400 MHz, DMSO) δ 13.11 (s, 1H), 9.40 (s, 1H), 7.29 (dd, J=10.2, 6.0 Hz, 1H), 7.12 (s, 1H), 7.05-7.00 (m, 1H), 6.93-6.89 (m, 1H), 6.85 (dd, J=14.0, 5.0 Hz, 1H), 4.77 (s, 1H), 4.11 (s, 1H), 3.76 (s, 1H).

Example 8

Synthesis of 2-(3,5-dichloro-4-((6-hydroxy-3'-(hydroxymethyl)-[1,1'-biphenyl]-3-yl)methyl)phenoxy)acetic Acid (Compound 8)

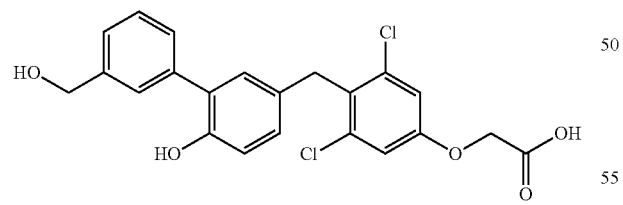

8

A mixture of Intermediate A7 (200 mg, 428 umol), 3-hydroxymethyl-phenylboronic acid (78 mg, 514 umol), Pd(dppf)Cl$_2$ (31 mg, 43 umol) and NaHCO$_3$ (aq) (1 M, 1 mL) in 1,4-dioxane (3 mL) was stirred at 75° C. overnight. The mixture was cooled to rt, LiOH.H$_2$O (54 mg, 1.3 mmol) was added, and the mixture was stirred at rt for 30 min. Water (10 mL) was added, the pH was adjusted to pH~4-5 with 1N HCl, and the mixture was extracted with EtOAc (10 mL*2). The combined organic phase was washed with brine (30 mL), dried over Na$_2$SO$_4$, and concentrated in vacuo. The residue was purified by Prep-HPLC to afford Compound 8 (50 mg, 27% yield) as a light yellow solid.

TLC: EtOAc/pet. ether=1/5 (v/v), Rf=0
LCMS: RT=3.298 min; [M−1]=430.8/432.8
$^1$H NMR: (400 MHz, DMSO-d$_6$) δ 13.13 (s, 1H), 9.35 (s, 1H), 7.42 (s, 1H), 7.34-7.29 (m, 2H), 7.24-7.19 (m, 1H), 7.11 (s, 2H), 7.03 (d, J=2.0 Hz, 1H), 6.89 (dd, J=8.4, 2.2 Hz, 1H), 6.83 (d, J=8.4 Hz, 1H), 5.17 (s, 1H), 4.75 (s, 2H), 4.51 (s, 2H), 4.11 (s, 2H).

Example 9

Synthesis of 2-(4-((3'-acetamido-6-hydroxy-[1,1'-biphenyl]-3-yl)methyl)-3,5-dichlorophenoxy)acetic Acid (Compound 9)

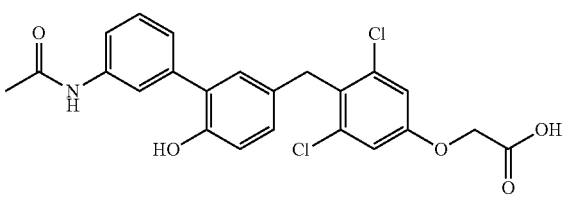 [SMILES: CC(=O)Nc1cccc(-c2cc(Cc3c(Cl)cc(OCC(=O)O)cc3Cl)ccc2O)c1]

9

To a mixture of Intermediate A7 (200 mg, 428 umol), 3-acetamido-phenylboronic acid (115 mg, 642 umol) and Pd(dppf)Cl$_2$·CH$_2$Cl$_2$ (39 mg, 54 umol) in 1,4-dioxane (5.0 mL) at rt was added aqueous NaHCO$_3$ (2M, 0.5 mL). The mixture was heated to 70° C. and stirred overnight. The reaction was cooled to rt; LiOH.H$_2$O (55 mg, 1.3 mmol) was added and the resultant mixture was stirred for 30 min. The reaction was quenched by addition of water (10 mL); the mixture was acidified to pH~4-5 with aqueous HCl (1M) and extracted with EtOAc (5 mL*3). The combined organic phase was washed with brine (10 mL), dried over Na$_2$SO$_4$, concentrated in vacuo and purified by Prep-HPLC to afford Compound 9 (10 mg, 5% yield) as a white solid.

TLC: MeOH/DCM=1/10 (v/v), Rf=0.15
LCMS: RT=3.276 min; [M−1]=457.9
$^1$H NMR: (400 MHz, DMSO-d$_6$) δ 9.94 (s, 1H), 8.86 (s, 1H), 7.19 (dd, J=4.4, 2.0 Hz, 4H), 6.65 (d, J=8.4 Hz, 1H), 6.48 (d, J=8.4 Hz, 1H), 6.19 (d, J=8.4 Hz, 1H), 6.07 (d, J=8.4 Hz, 1H), 5.24-5.21 (m, 1H), 4.93 (d, J=3.6 Hz, 4H), 4.69 (dd, J=2.4, 1.1 Hz, 1H), 4.05 (s, 2H), 3.97 (s, 2H), 3.72 (d, J=0.8 Hz, 4H), 2.45 (s, 2H), 2.23 (s, 3H), 1.93 (s, 3H).

Example 10

Synthesis of methyl 2-(4-((3'-acetyl-6-hydroxy-[1,1'-biphenyl]-3-yl)methyl)-3,5-dichlorophenoxy)acetate (Compound 10)

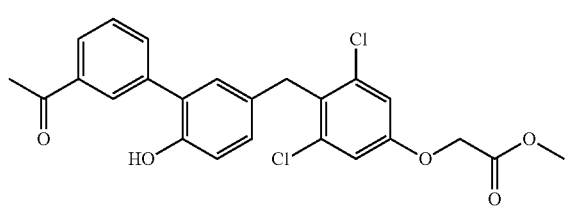

10

To a solution of Intermediate A7 (200 mg, 0.43 mmol) in 1,4-dioxane (3 mL) at rt was added 3-acetylphenylboronic acid (106 mg, 0.65 mmol), Pd(dppf)Cl₂ (29 mg, 0.04 mmol) and NaHCO₃ (2N) (1.29 mmol, 0.6 mL). The mixture was stirred at 85° C. overnight, then diluted with EtOAc (20 mL) and filtered. The filtrate was washed with brine (30 mL), dried over Na₂SO₄ and concentrated in vacuo. The residue was purified by Prep-HPLC to afford Compound 10 (17 mg, 9% yield) as a white solid.

TLC: Pet. ether/EtOAc=5/1 (v/v), Rf=0.6

Example 11

Synthesis of 2-(4-((3'-acetyl-6-hydroxy-[1,1'-biphenyl]-3-yl)methyl)-3,5-dichlorophenoxy)acetic Acid (Compound 11)

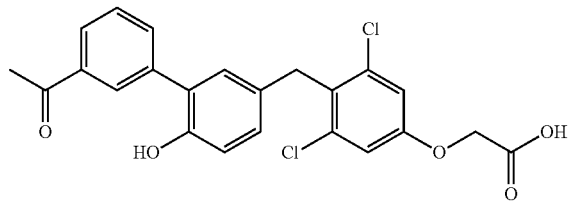

To a solution of Compound 10 (17 mg, 0.04 mmol) in THF (3 mL) and water (2 mL) was added LiOH.H₂O (5 mg, 0.12 mmol). The mixture was stirred at rt for 2 h. The pH was adjusted to ~4 with 1N HCl, and the resultant mixture was extracted with EtOAc (20 mL*2). The organic layer was washed with brine (20 mL), dried over Na₂SO₄ and concentrated in vacuo. The residue was purified by Prep-HPLC to afford Compound 11 (8 mg, 44% yield) as a white solid.

TLC: DCM/MeOH=10/1 (v/v), Rf=0.1

LCMS: RT=3.744 min; [M−1]=442.8

¹H NMR: (400 MHz, DMSO-d₆) δ 9.76 (s, 1H), 8.05 (s, 1H), 7.88 (d, J=7.8 Hz, 1H), 7.73 (d, J=7.8 Hz, 1H), 7.54 (t, J=7.6 Hz, 1H), 7.11 (s, 1H), 6.94 (d, J=16.0 Hz, 4H), 4.28 (s, 2H), 4.11 (s, 2H), 2.60 (s, 3H).

Example 12

Synthesis of 2-(3,5-dichloro-4-((6-hydroxy-3'-(trifluoromethoxy)-[1,1'-biphenyl]-3-yl)methyl)phenoxy)acetic Acid (Compound 12)

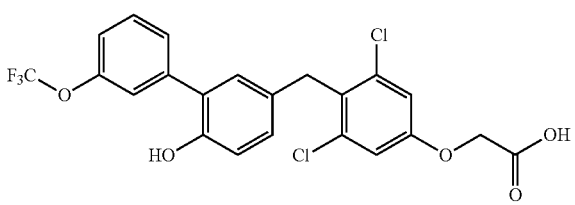 [SMILES: O=C(O)COc1cc(Cl)c(Cc2ccc(O)c(-c3cccc(OC(F)(F)F)c3)c2)c(Cl)c1]

A solution of Intermediate A7 (200 mg, 0.43 mmol), Pd(dppf)Cl₂ (35 mg, 0.64 mmol), NaHCO₃ (108 mg, 1.28 mmol), and 3-trifluoromethoxyphenylboronic acid (132 mg, 0.64 mmol) in H₂O (0.5 mL) and 1,4-dioxane (5 mL) was refluxed overnight. The mixture was cooled to rt; LiOH.H₂O (54 mg, 1.28 mmol) was added, and the resultant mixture was stirred at rt for 30 min. Water (10 mL) was added, and the mixture was extracted with ether (10 mL*2); the aqueous phase was adjusted to pH~3 with HCl (1N), and then re-extracted with EtOAc (10 mL*2). The combined EtOAc phase was washed with brine (5 mL), dried over Na₂SO₄, concentrated in vacuo and purified by Prep-HPLC (MeCN/H₂O) to afford Compound 12 (5 mg, 2% yield) as a white solid.

TLC: Pet. ether/EtOAc=5/1 (v/v), Rf=0.1

LCMS: RT=4.21 min; [M−1]=485

¹H NMR: (400 MHz, DMSO-d₆) δ 13.13 (s, 1H), 9.66 (s, 1H), 7.53-7.47 (m, 4H), 7.28 (d, J=7.8 Hz, 1H), 7.11 (d, J=3.8 Hz, 3H), 6.95-6.91 (m, 1H), 6.87 (d, J=8.4 Hz, 1H), 4.73 (s, 2H), 4.12 (s, 2H).

Example 13

Synthesis of 2-(3,5-dichloro-4-((6-hydroxy-3'-isopropyl-[1,1'-biphenyl]-3-yl)methyl)phenoxy)acetic Acid (Compound 13)

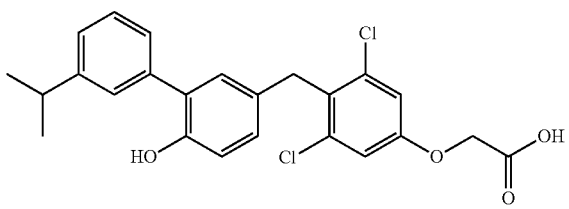

To a mixture of Intermediate A7 (200 mg, 428 umol), 3-isopropylphenylboronic acid (105 mg, 642 umol) and Pd(dppf)Cl₂·CH₂Cl₂ (39 mg, 54 umol) in 1,4-dioxane (5.0 mL) at rt was added aqueous NaHCO₃ (2M, 0.5 mL). The mixture was heated to 70° C. and stirred overnight. The reaction system was cooled to rt; LiOH.H₂O (55 mg, 1.3 mmol) was added and the resultant mixture was stirred for 30 min. The reaction mixture was quenched with water (10 mL), acidified to pH~4-5 with aqueous HCl (1M) and extracted with EtOAc (5 mL*3). The combined organic phase was washed with brine (10 mL), dried over Na₂SO₄, concentrated in vacuo and purified by Prep-HPLC (MeCN/H₂O) to afford Compound 13 (25 mg, 13% yield) as a white solid.

TLC: MeOH/DCM=1/10 (v/v), Rf=0.3

LCMS: RT=4.358 min; [M−1]=442.9

¹H NMR: (400 MHz, DMSO-d₆) δ 13.11 (s, 1H), 9.36 (s, 1H), 7.34-7.25 (m, 3H), 7.15 (d, J=6.8 Hz, 1H), 7.12 (s, 2H), 7.03 (d, J=2.2 Hz, 1H), 6.89 (dd, J=8.4, 2.4 Hz, 1H), 6.82 (d, J=8.4 Hz, 1H), 4.76 (s, 2H), 4.11 (s, 2H), 2.90 (p, J=6.8 Hz, 1H), 1.22 (d, J=6.8 Hz, 6H).

Example 14

Synthesis of 2-(3,5-dichloro-4-((6-hydroxy-3'-(methylsulfonyl)-[1,1'-biphenyl]-3-yl)methyl)phenoxy)acetic Acid (Compound 14)

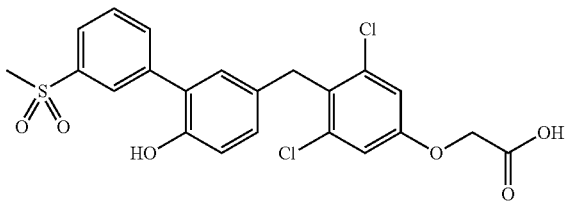 [SMILES: CS(=O)(=O)c1cccc(-c2cc(Cc3c(Cl)cc(OCC(=O)O)cc3Cl)ccc2O)c1]

To a solution of Intermediate A7 (200 mg, 0.40 mmol), 3-methylsulfonyl-phenylboronic acid (128 mg, 0.60 mmol) and NaHCO₃ (2M, 0.5 mL) in 1,4-dioxane (3 mL) at rt was added Pd(dppf)Cl₂ (31 mg, 0.04 mmol) under nitrogen atmosphere; the resultant mixture was heated at 70° C. overnight. The reaction mixture was cooled to rt, LiOH.H₂O (84 mg, 2.0 mmol) was added and the resultant mixture was stirred at rt for 30 min. The reaction was quenched with water (10 mL), the pH was adjusted to pH~4-5 with 1N HCl, and the mixture was extracted with EtOAc (10 mL*2). The combined organic phase was washed with brine (10 mL*2), dried over Na₂SO₄, and concentrated in vacuo. The crude product was purified by Prep-TLC (methanol/DCM=1/10) to afford 87 mg of crude product. Further purification with Prep-HPLC (ACN/water range from 20/80 to 90/10 for 25 min) afforded Compound 14 (21 mg, 10% yield) as an off-white solid.

TLC: MeOH/DCM=1/10 (v/v), Rf=0.21

LCMS: RT=3.39 min; [M−1]=478.8

¹H NMR: (400 MHz, DMSO) δ 13.11 (s, 1H), 9.69 (s, 1H), 8.06 (t, J=2.0 Hz, 1H), 7.85-7.80 (m, 2H), 7.67 (t, J=7.6 Hz, 1H), 7.17 (d, J=2.0 Hz, 1H), 7.12 (s, 2H), 6.93 (dd, J=8.4, 2.4 Hz, 1H), 6.88 (d, J=8.4 Hz, 1H), 4.78 (s, 2H), 4.14 (s, 2H), 3.23 (s, 3H).

Example 15

Synthesis of 2-(3,5-dichloro-4-((6-hydroxy-3'-(methoxymethyl)-[1,1'-biphenyl]-3-yl)methyl)phenoxy)acetic Acid (Compound 15)

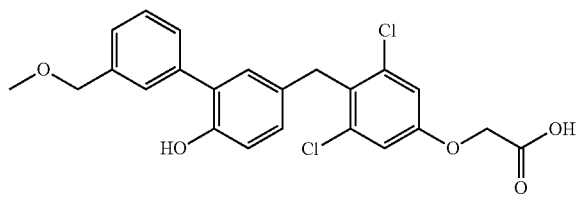 [SMILES: COCc1cccc(-c2cc(Cc3c(Cl)cc(OCC(=O)O)cc3Cl)ccc2O)c1]

A solution of Intermediate A7 (200 mg, 0.43 mmol), NaHCO₃ (1.29 mmol, 0.6 mL), Pd(dppf)Cl₂ (30 mg, 0.04 mmol), and 3-methoxymethyl-phenylboronic acid (106 mg, 0.64 mmol) in 1,4-dioxane (10 mL) and H₂O (2 mL), was refluxed overnight. The mixture was cooled to rt; LiOH.H₂O (54 mg, 1.29 mmol) was added, and the resultant mixture was stirred at rt for 30 min. Water (10 mL) was added, and the mixture was extracted with ether (10 mL*2). The aqueous phase was adjusted to pH~3 with HCl (1N), then re-extracted with EtOAc (10 mL*2). The combined EtOAc phase was washed with brine (5 mL), dried over Na₂SO₄, concentrated in vacuo and purified by Prep-TLC (DCM/MeOH=10/1) and Prep-HPLC (MeCN/H₂O) to afford Compound 15 (10 mg, 5% yield) as a white solid.

TLC: Pet. ether/EtOAc=5/1 (v/v), Rf=0.1

LCMS: RT=3.77 min; [M−1]=444.8

¹H NMR: (400 MHz, DMSO-d₆) δ 13.11 (s, 1H), 9.40 (s, 1H), 7.42 (s, 1H), 7.36 (dd, J=4.8, 2.1 Hz, 2H), 7.24-7.20 (m, 1H), 7.12 (s, 2H), 7.04 (d, J=2.2 Hz, 1H), 6.89 (dd, J=8.4, 2.2 Hz, 1H), 6.83 (d, J=8.4 Hz, 1H), 4.77 (s, 2H), 4.43 (s, 2H), 4.11 (s, 2H), 3.30 (s, 3H).

Example 16

Synthesis of 2-(3,5-dichloro-4-((6-hydroxy-3'-propyl-[1,1'-biphenyl]-3-yl)methyl)phenoxy)acetic Acid (Compound 16)

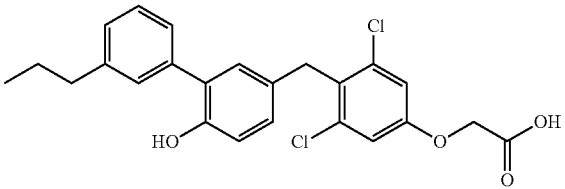 [SMILES: CCCc1cccc(-c2cc(Cc3c(Cl)cc(OCC(=O)O)cc3Cl)ccc2O)c1]

To a mixture of Intermediate A7 (200 mg, 428 umol), 3-n-propylphenylboronic acid (105 mg, 642 umol) and Pd(dppf)Cl₂·CH₂Cl₂ (39 mg, 54 umol) in 1,4-dioxane (5.0 mL) at rt was added aqueous NaHCO₃ (2M, 0.5 mL). The mixture was heated to 70° C. and stirred overnight. The reaction was cooled to rt; LiOH.H₂O (55 mg, 1.3 mmol) was added and the resultant mixture was stirred for 30 min. The reaction was quenched with water (10 mL), acidified to pH~4-5 with aqueous HCl (1 M) and extracted with EtOAc (5 mL*3). The combined organic phase was washed with brine (10 mL), dried over Na₂SO₄, concentrated in vacuo and purified by Prep-HPLC (MeCN/H₂O) to afford Compound 16 (35 mg, 18% yield) as a white solid.

TLC: MeOH/DCM=1/10 (v/v), Rf=0.25

LCMS: RT=4.361 min; [M−1]=442.9

¹H NMR: (400 MHz, DMSO-d₆) δ 13.11 (s, 1H), 9.34 (s, 1H), 7.29-7.22 (m, 3H), 7.10 (s, 2H), 7.08 (dd, J=4.0, 1.2 Hz, 1H), 7.02 (d, J=2.0 Hz, 1H), 6.87 (dd, J=8.4, 2.4 Hz, 1H), 6.81 (d, J=8.0 Hz, 1H), 4.75 (s, 2H), 4.09 (s, 2H), 2.55 (d, J=7.6 Hz, 2H), 1.63-1.54 (m, 2H), 0.90 (t, J=7.2 Hz, 3H).

Example 17

Synthesis of 2-(3,5-dichloro-4-((6-hydroxy-3'-methyl-[1,1'-biphenyl]-3-yl)methyl)phenoxy)acetic Acid (Compound 17)

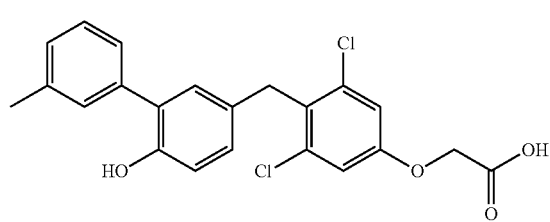

To a solution of Intermediate A7 (200 mg, 428 umol) in 1,4-dioxane (4 mL) at rt were added Pd(dppf)Cl$_2$ (34.97 mg, 42.82 umol), NaHCO$_3$ (2N, 1 mL) and toluene-3-boronic acid (87.3 mg, 642 umol). The mixture was heated to 70° C. overnight, then cooled to rt. LiOH.H$_2$O (135 mg, 7.5 mmol) was added; the mixture was stirred at rt for 30 min, diluted with water (5 mL), acidified with 1N HCl to pH~4-5 and extracted with DCM (5 mL*3). The combined organic phase was washed with brine (5 mL), dried over Na$_2$SO$_4$ and concentrated in vacuo. The crude product was purified by Prep-HPLC (ACN/water range from 30/70 to 85/15) to afford Compound 17 (30 mg, 16% yield) as an off-white solid.

TLC: DCM/MeOH=10/1 (v/v), Rf=0.33
LCMS: RT=2.441 min; [M−1]=414.8.
$^1$H NMR: (400 MHz, DMSO-d$_6$) δ 13.11 (s, 1H), 9.35 (s, 1H), 7.29-7.20 (m, 3H), 7.11 (s, 2H), 7.09 (d, J=7.0 Hz, 1H), 7.02 (d, J=2.2 Hz, 1H), 6.88 (dd, J=8.3, 2.3 Hz, 1H), 6.82 (d, J=8.3 Hz, 1H), 4.77 (s, 2H), 4.10 (s, 2H), 2.32 (s, 3H).

Example 18

Synthesis of methyl 2-(3,5-dichloro-4-((3'-cyano-6-hydroxy-[1,1'-biphenyl]-3-yl)methyl)phenoxy)acetate (Compound 18)

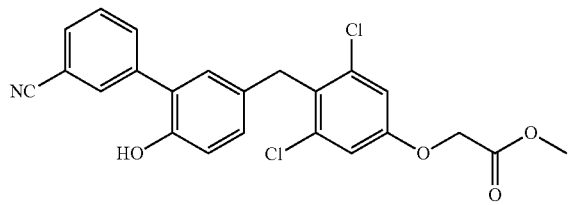

A mixture of 3-cyanophenylboronic acid (77 mg, 0.48 mmol), Intermediate A7 (150 mg, 0.32 mmol), 2N NaHCO$_3$ (0.48 mL, 0.96 mmol) and Pd(dppf)Cl$_2$ (11 mg, 0.02 mmol) in 1,4-dioxane (2 mL) was stirred at 85° C. for 16 h under N$_2$ atmosphere. The resultant solution of Compound 18 was used for the next step without further purification.

TLC: EtOAc/pet. ether=1/5 (v/v), Rf=0.44
LCMS: RT=2.48 min; [M−1]=440.0.

Example 19

Synthesis of 2-(3,5-dichloro-4-((3'-cyano-6-hydroxy-[1,1'-biphenyl]-3-yl)methyl)phenoxy)acetic Acid (Compound 19)

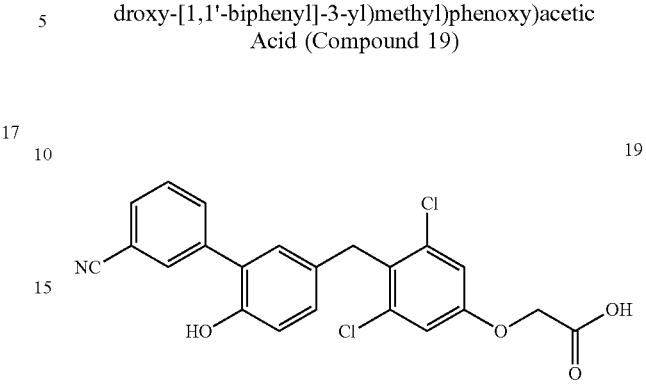

To a solution of Compound 18 (141 mg, 0.32 mmol) dissolved in THF (1 mL)/water (5 mL) at rt was added LiOH (39 mg, 0.96 mmol); the resulting mixture was stirred at rt for 1 h. The reaction was acidified to pH~6-7 with 2N HCl, concentrated in vacuo and purified by Prep-HPLC to afford Compound 19 (10 mg, 10% yield) as a light yellow solid.

TLC: EtOAc/pet. ether=1/5 (v/v), Rf=0
$^1$H NMR: (400 MHz, DMSO) δ 13.07 (s, 1H), 9.68 (s, 1H), 7.92 (s, 1H), 7.80 (m, 1H), 7.75 (m, 1H), 7.60 (t, J=7.8 Hz, 1H), 7.17-7.07 (m, 3H), 6.91 (m, 2H), 4.75 (s, 2H), 4.12 (s, 2H).
LCMS: RT=3.64 Min; [M−1]=427.

Example 20

Synthesis of methyl 2-(3,5-dichloro-4-((6-hydroxy-3'-vinyl-[1,1'-biphenyl]-3-yl)methyl)phenoxy)acetate (Compound 20)

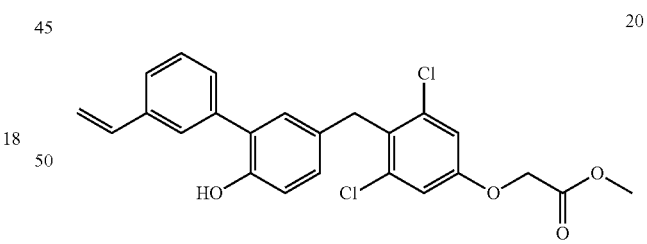

To a solution of Intermediate A7 (100 mg, 0.21 mmol) and styrene-2-boronic acid (48 mg, 0.32 mmol) in 1,4-dioxane (3 mL) at rt were added Pd(PPh$_3$)$_2$Cl$_2$ (15 mg, 0.21 mmol) and K$_3$PO$_4$ (91 mg, 0.43 mmol) under nitrogen atmosphere. The mixture was heated to 70° C. overnight. The reaction mixture was diluted with EtOAc (10 mL), washed with brine (10 mL), dried over Na$_2$SO$_4$, and concentrated in vacuo. The crude product was purified by Prep-TLC (EtOAc/pet. ether-1/10) to afford Compound 20 (20 mg, 21% yield) as a light yellow solid.

TLC: MeOH/DCM=1/10 (v/v), Rf=0.41
LCMS: RT=2.97 min; [M−1]=441.0.

Example 21

Synthesis of 2-(3,5-dichloro-4-((6-hydroxy-3'-vinyl-[1,1'-biphenyl]-3-yl)methyl)phenoxy)acetic Acid (Compound 21)

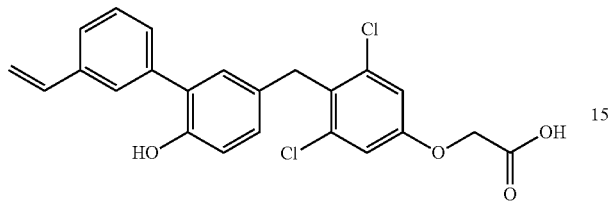

21

To a solution of Compound 20 (20 mg, 0.04 mmol) in water (0.5 mL)/THF (2 mL) at rt was added LiOH.H$_2$O (4 mg, 0.08 mmol); the resultant mixture was stirred overnight. The reaction was diluted with water (10 mL), acidified to pH~5 with HCl (2N), and extracted with EtOAc (5 mL*2). The combined extracts were dried over Na$_2$SO$_4$ and concentrated in vacuo. The crude product was purified by Prep-TLC (Methanol/DCM=1/10) to afford Compound 21 (12 mg, 61% yield) as a white solid.

TLC: Methanol/DCM=1/10 (v/v), Rf=0.23

LCMS: RT=3.99 min; [M−1]=427.0

$^1$H NMR: (400 MHz, DMSO) δ 9.53 (s, 1H), 7.53 (s, 1H), 7.45-7.31 (m, 3H), 7.06 (s, 1H), 6.95 (s, 2H), 6.88 (s, 2H), 6.76 (dd, J=17.6, 10.8 Hz, 1H), 5.82 (d, J=17.6 Hz, 1H), 5.26 (d, J=10.8 Hz, 1H), 4.24 (s, 2H), 4.09 (s, 2H).

Example 22

Synthesis of 2-(3,5-dichloro-4-((6-hydroxy-3'-(prop-1-en-2-yl)-[1,1'-biphenyl]-3-yl)methyl)phenoxy) acetic Acid (Compound 22)

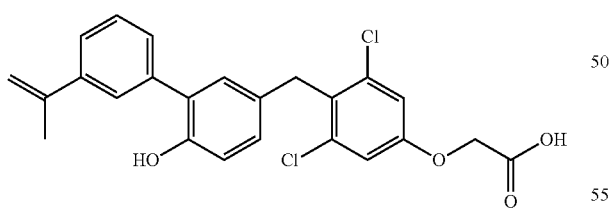

22

A mixture of Intermediate B2 (118 mg, 482 umol), Intermediate A7 (150 mg, 321 umol), NaHCO$_3$ (2 M, 0.48 mL) and Pd(dppf)Cl$_2$ (24 mg, 32.1 umol) in 1,4-dioxane (2 mL) was stirred at 100° C. overnight. The mixture was cooled to rt; LiOH.H$_2$O (40 mg, 963 umol) was added and the mixture was stirred for 1 h. The mixture was acidified to pH~5-6 with 1N HCl; water (30 mL) was added, and the mixture was extracted with EtOAc (25 mL*2). The combined organic layer was washed with water (25 mL), then brine (50 mL), dried over Na$_2$SO$_4$, and purified by Prep-HPLC to afford Compound 22 (20 mg, 14% yield) as a white solid.

TLC: EtOAc/pet. ether=1/5 (v/v), Rf=0

LCMS: RT=4.151 min; [M−1]=441.0/443.0

$^1$H NMR: (400 MHz, DMSO-d$_6$) δ 13.08 (s, 1H), 9.39 (s, 1H), 7.57 (d, J=2.1 Hz, 1H), 7.44-7.31 (m, 3H), 7.11 (s, 2H), 7.06 (d, J=2.2 Hz, 1H), 6.91 (dd, J=8.3, 2.3 Hz, 1H), 6.84 (d, J=8.3 Hz, 1H), 5.41 (s, 1H), 5.11 (t, J=1.6 Hz, 1H), 4.77 (s, 2H), 4.12 (s, 2H), 2.12 (s, 3H).

Example 23

Synthesis of methyl 2-(3,5-dichloro-4-((3'-formyl-6-hydroxy-[1,1'-biphenyl]-3-yl)methyl)phenoxy)acetate (Compound 23)

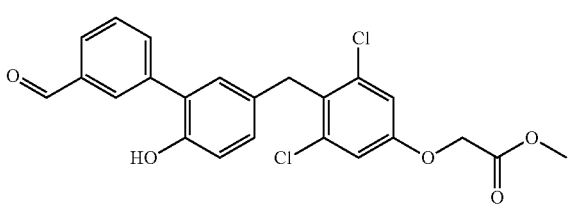

23

To a mixture of Intermediate A7 (500 mg, 1.0 mmol), 2-formylphenylboronic acid (225 mg, 1.5 mmol) and Pd(dppf)Cl$_2$·CH$_2$Cl$_2$ (82 mg, 100 umol) in 1,4-dioxane (5.0 mL) at rt was added aqueous NaHCO$_3$ (2M, 1.5 mL). The mixture was heated to 70° C. overnight. The reaction mixture was cooled to rt, quenched with water (10 mL), acidified to pH~4-5 with aqueous HCl (1M) and extracted with EtOAc (5 mL*3). The combined organic phase was washed with brine (10 mL), dried over Na$_2$SO$_4$, concentrated in vacuo and purified by Prep-TLC (pet. ether/EtOAc=5/1) to afford Compound 23 (130 mg, 27% yield) as a white solid.

TLC: EtOAc/pet. ether=1/5 (v/v), Rf=0.3

LCMS: RT=2.018 min; [M−1]=457.1

$^1$H NMR: (400 MHz, DMSO-d$_6$) δ 10.05 (s, 1H), 9.60 (s, 1H), 8.03 (s, 1H), 7.86-7.75 (m, 2H), 7.63 (t, J=7.6 Hz, 1H), 7.15 (s, 2H), 7.13 (s, 1H), 6.92 (s, 1H), 6.89 (s, 1H), 4.88 (s, 2H), 4.21-4.15 (m, 2H), 4.14 (s, 2H), 1.19 (t, J=7.2 Hz, 3H).

Example 24

Synthesis of methyl 2-(3,5-dichloro-4-((3'-ethynyl-6-hydroxy-[1,1'-biphenyl]-3-yl)methyl)phenoxy) acetate (Compound 24)

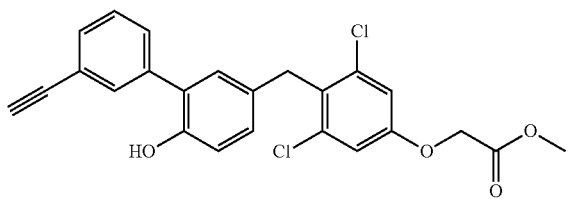

24

To a mixture of Compound 23 (120 mg, 261 umol) and K$_2$CO$_3$ (72 mg, 523 umol) in MeOH (1 mL) and THF (1 mL)

was added 1-dimethylphosphonyl-1-diazo-acetone (60 mg, 314 umol). The mixture was stirred at rt overnight. Water (10 mL) was added and the resultant mixture was extracted with EtOAc (5 mL*3). The combined organic phase was washed with brine (10 mL), dried over $Na_2SO_4$ and concentrated in vacuo. The crude product was purified by Prep-TLC (EtOAc/pet. ether=⅓) to afford Compound 24 (50 mg, 42% yield) as a light yellow oil.

TLC: EtOAc/Pet. ether-⅕ (v/v), Rf=0.35

Example 25

Synthesis of 2-(3,5-dichloro-4-((3'-ethynyl-6-hydroxy-[1,1'-biphenyl]-3-yl)methyl)phenoxy)acetic Acid (Compound 25)

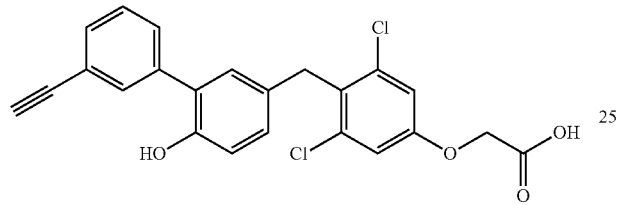

25

To a solution of Compound 24 (50 mg, 110 umol) in THF/$H_2O$ (1 mL/0.5 mL) at rt was added LiOH.$H_2O$ (14 mg, 330 umol). The mixture was stirred at rt for 1 h. The mixture was diluted with water (5 mL), acidified with 1N HCl to pH~4-5 and extracted with EtOAc (3 mL*3). The combined organic phase was washed with brine (5 mL), dried over $Na_2SO_4$ and concentrated in vacuo. The crude product was purified by Prep-HPLC (MeCN/$H_2$) to afford Compound 25 (10 mg, 21% yield) as a white solid.

TLC: MeOH/DCM=1/10 (v/v), Rf=0.30

LCMS: RT=1.691 min; [M−1]=425.0

$^1$H NMR: (400 MHz, DMSO-$d_6$) δ 9.52 (s, 1H), 7.58 (d, J=1.6 Hz, 1H), 7.49 (dt, J=6.4, 2.4 Hz, 1H), 7.43-7.38 (m, 2H), 7.12 (s, 2H), 7.07 (d, J=2.4 Hz, 1H), 6.91 (dd, J=8.4, 2.4 Hz, 1H), 6.85 (d, J=8.4 Hz, 1H), 4.77 (s, 2H), 4.17 (s, 1H), 4.12 (s, 2H).

Example 26

Synthesis of 2-(3,5-dichloro-4-((6-hydroxy-3'-(2,2,2-trifluoroethyl)-[1,1'-biphenyl]-3-yl)methyl)phenoxy)acetic Acid (Compound 26)

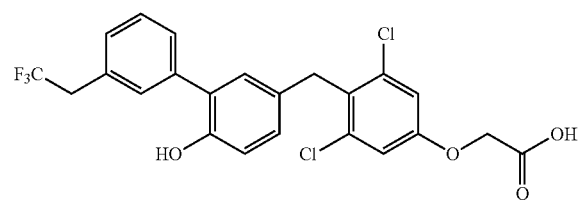

26

A mixture of Intermediate B3 (138 mg, 482 umol), Intermediate A7 (150 mg, 321 umol), $NaHCO_3$ (2M, 0.48 mL) and Pd(dppf)$Cl_2$ (24 mg, 32.1 umol) in 1,4-dioxane (2 mL) was stirred at 100° C. overnight. The mixture was cooled to rt; LiOH.$H_2O$ (40 mg, 963 umol) was added and the resultant mixture was stirred for 1 h. The mixture was acidified to pH~5-6 with 1N HCl; water (30 mL) was added, the mixture was extracted with EtOAc (25 mL*2). The combined organic layer was washed with water (25 mL), then brine (50 mL), dried over $Na_2SO_4$, and purified by Prep-HPLC to afford Compound 26 (20 mg, 13% yield) as a white solid.

TLC: EtOAc/pet. ether=⅕ (v/v), Rf=0

LCMS: RT=3.884 min; [M−1]=483.0/484.9

$^1$H NMR: (400 MHz, DMSO-$d_6$) δ 13.04 (s, 1H), 9.45 (s, 1H), 7.45 (d, J=10.6 Hz, 2H), 7.38 (t, J=7.6 Hz, 1H), 7.27 (d, J=7.5 Hz, 1H), 7.11 (s, 2H), 7.05 (d, J=2.1 Hz, 1H), 6.90 (dd, J=8.2, 2.2 Hz, 1H), 6.84 (d, J=8.3 Hz, 1H), 4.77 (s, 2H), 4.11 (s, 2H), 3.67 (q, J=11.6 Hz, 2H).

Example 27

Synthesis of methyl 2-(3,5-dichloro-4-((6-hydroxy-3'-(perfluoroethyl)-[1,1'-biphenyl]-3-yl)methyl)phenoxy)acetate (Compound 27)

27

To a solution of Intermediate A7 (300 mg, 0.64 mmol), Intermediate B4 (310 mg, 0.96 mmol) and $NaHCO_3$ (2M, 1 mL) in 1, 4-dioxane (10 mL) at rt was added Pd(dppf)$Cl_2$ (66 mg, 0.09 mmol). The mixture was refluxed overnight. The mixture was cooled to rt, poured into water (10 mL) and extracted with EtOAc (10 mL*2). The combined organic phase was washed with brine (10 mL), dried over $Na_2SO_4$, concentrated in vacuo and purified by Prep-HPLC (MeCN/$H_2O$) to afford Compound 27 (30 mg, 16% yield) as a white solid.

TLC: Pet. ether/EtOAc=5/1 (v/v), Rf=0.4

$^1$H NMR: (400 MHz, DMSO-$d_6$) δ 9.68 (s, 1H), 7.80 (d, J=7.2 Hz, 2H), 7.67 (t, J=7.8 Hz, 1H), 7.61 (d, J=7.8 Hz, 1H), 7.16 (s, 2H), 7.12 (d, J=2.2 Hz, 1H), 6.95 (dd, J=8.4, 2.4 Hz, 1H), 6.87 (d, J=8.4 Hz, 1H), 4.89 (s, 2H), 4.13 (s, 2H), 3.70 (s, 3H).

Example 28

Synthesis of 2-(3,5-dichloro-4-((6-hydroxy-3'-(perfluoroethyl)-[1,1'-biphenyl]-3-yl)methyl)phenoxy) acetic Acid (Compound 28)

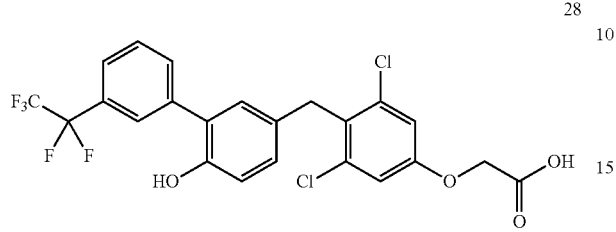

To a solution of Compound 27 (30 mg, 0.05 mmol) in THF (5 mL), LiOH.H₂O (13 mg, 0.30 mmol) in water (0.2 mL) was added; the mixture was stirred at rt for 2 h. Water (5 mL) was added, the reaction was acidified to pH~6-7 with 2N HCl, and was extracted with EtOAc (10 mL*2). The combined organic phase was washed with brine (20 mL), dried over Na₂SO₄, concentrated in vacuo and purified by Prep-HPLC (MeCN/H₂O) to afford Compound 28 (25 mg, 85% yield) as a white solid.

TLC: Pet. ether/EtOAc=1/1 (v/v), Rf=0.1
LCMS: RT=4.253 min; [M−1]=519
¹H NMR: (400 MHz, DMSO-d₆) δ 13.08 (s, 1H), 9.66 (s, 1H), 7.82-7.76 (m, 2H), 7.69-7.59 (m, 2H), 7.13 (d, J=2.4 Hz, 1H), 7.12 (s, 2H), 6.95 (dd, J=8.4, 2.3 Hz, 1H), 6.88 (d, J=8.4 Hz, 1H), 4.77 (s, 2H), 4.13 (s, 2H).

Example 29

Synthesis of 2-(3,5-dichloro-4-((3'-chloro-6-hydroxy-[1,1'-biphenyl]-3-yl)methyl)phenoxy)acetic Acid (Compound 29)

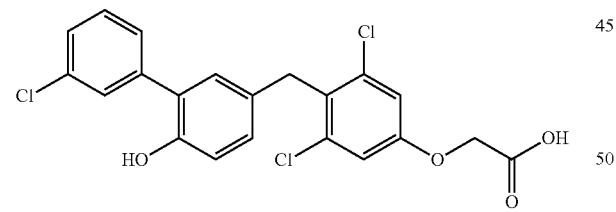

To a solution of Intermediate A7 (150 mg, 321 umol) in 1,4-dioxane (3 mL) at rt were added Pd(dppf)Cl₂ (27 mg, 32 umol), NaHCO₃ (2N, 1 mL) and 3-chlorophenylboronic acid (76 mg, 482 umol). The mixture was heated to 70° C. overnight. The mixture was cooled to rt, LiOH.H₂O (67 mg, 1.6 mmol), was added and the resultant mixture was stirred at rt for 1 h. The reaction was diluted with water (5 mL), acidified with 1N HCl to pH~3, and extracted with DCM (5 mL*3). The combined organic phase was washed with brine (10 mL), dried over Na₂SO₄, and concentrated in vacuo. The crude product was purified by Prep-HPLC to afford Compound 29 (40 mg, 28% yield) as an off-white solid.

TLC: DCM/MeOH=10/1 (v/v), Rf=0.33
LCMS: RT=2.319 min; [M−1]=435.

¹H NMR: (400 MHz, DMSO-d₆) δ 9.61 (s, 1H), 7.53 (q, J=1.3 Hz, 1H), 7.44-7.39 (m, 2H), 7.35 (dt, J=6.5, 2.4 Hz, 1H), 7.12 (s, 2H), 7.09 (d, J=2.2 Hz, 1H), 6.92 (dd, J=8.3, 2.2 Hz, 1H), 6.86 (d, J=8.3 Hz, 1H), 4.78 (s, 2H), 4.11 (s, 2H).

Example 30

Synthesis of methyl 2-(3,5-dichloro-4-((3'-chloro-6-hydroxy-[1,1'-biphenyl]-3-yl)methyl)phenoxy)acetate (Compound 30)

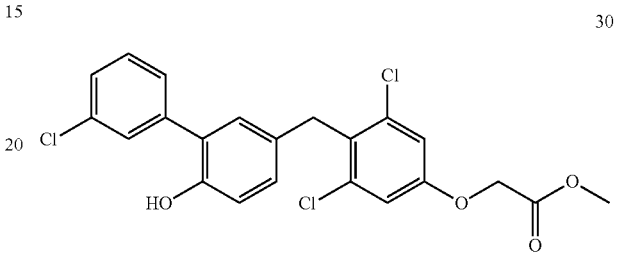

To a solution of Intermediate A7 (500 mg, 1.07 mmol) in 1,4-dioxane (5 mL) at rt was added Pd(dppf)Cl₂ (88 mg, 107 umol), NaHCO₃ (2N, 1 mL) and 3-chlorophenylboronic acid (251 mg, 1.61 mmol). The mixture was heated to 70° C. overnight. The mixture was diluted with water (5 mL), acidified with 1N HCl to pH<7, and extracted with DCM (5 mL*3). The combined organic phase was washed with brine (10 mL), dried over Na₂SO₄, and concentrated in vacuo. The crude product was purified by Prep-HPLC to afford Compound 30 (200 mg, 41% yield) as an off-white solid.

TLC: Pet. ether/EtOAc=5/1 (v/v), Rf=0.44
¹H NMR: (400 MHz, DMSO-d₆) δ 9.58 (s, 1H), 7.54-7.52 (m, 1H), 7.41 (dd, J=5.0, 1.9 Hz, 2H), 7.37-7.32 (m, 1H), 7.16 (s, 2H), 7.08 (d, J=2.0 Hz, 1H), 6.92 (dd, J=8.3, 2.2 Hz, 1H), 6.86 (d, J=8.3 Hz, 1H), 4.89 (s, 2H), 4.12 (s, 2H), 3.70 (s, 3H).

Example 31

Synthesis of 2-(3,5-dichloro-4-((3'-chloro-6-hydroxy-[1,1'-biphenyl]-3-yl)methyl) phenoxy)-N-methylacetamide (Compound 31)

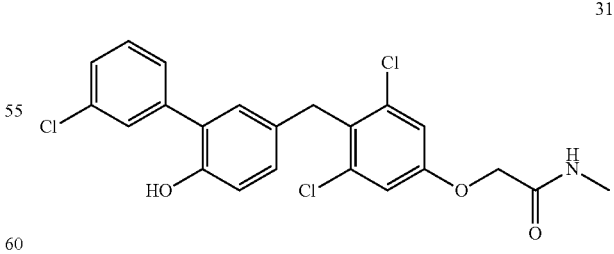

To a solution of Compound 30 (100 mg, 221 umol) in THF (0.5 mL) at rt was added aqueous methylamine (40% wt/wt, 1.5 mL). The mixture was heated to 70° C. in a sealed tube overnight, then cooled to rt, diluted with water (10 mL), and extracted with EtOAc (5 mL*3). The combined organic phase was washed with brine (20 mL), dried over Na₂SO₄, and concentrated in vacuo. The crude product was purified by Prep-TLC (MeOH/DCM=1/30) to afford Compound 31 (20 mg, 20% yield) as a brown solid.

TLC: DCM/MeOH=5/1 (v/v), Rf=0.44
LCMS: RT=4.059; [M−1]=448.
¹H NMR: (400 MHz, DMSO-d₆) δ 9.57 (s, 1H), 8.05 (s, 1H), 7.55-7.51 (m, 1H), 7.44-7.39 (m, 2H), 7.35 (dt, J=6.4, 2.4 Hz, 1H), 7.15 (s, 2H), 7.08 (d, J=2.2 Hz, 1H), 6.96-6.89 (m, 1H), 6.86 (d, J=8.3 Hz, 1H), 4.54 (s, 2H), 4.12 (s, 2H), 2.65 (d, J=4.6 Hz, 3H).

Example 32

Synthesis of 2-(3,5-dichloro-4-((3'-chloro-6-hydroxy-[1,1'-biphenyl]-3-yl)methyl) phenoxy)-N,N-dimethylacetamide (Compound 32)

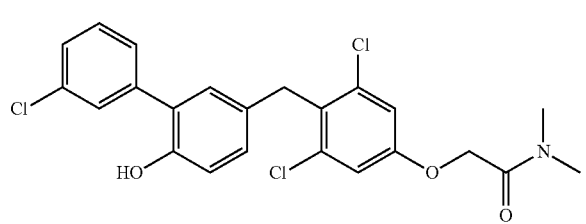

To a solution of Compound 29 (80 mg, 183 umol) in DCM (2 mL), cooled with an ice-bath was added DMF (one drop) and oxalyl chloride (46 mg, 366 umol). The mixture was stirred at rt for 2 h and concentrated in vacuo. The crude product (80 mg, 175 umol) in DCM (1 mL) was added to a solution of methylamine (2 mL, 34 mmol) in DCM (3 mL) stirring in an ice bath. The mixture was warmed to rt and stirred for 2 h, then concentrated in vacuo. The crude product was purified by Prep-TLC (MeOH/DCM=1/30) to afford Compound 32 (50 mg, 61% yield) as an off-white solid.

TLC: DCM/MeOH=30/1 (v/v), Rf=0.34
LCMS: RT=4.109; [M−1]=462.
¹H NMR: (400 MHz, DMSO-d₆) δ 9.57 (s, 1H), 7.56-7.50 (m, 1H), 7.39-7.45 (m, 2H), 7.32-7.36 (m, 1H), 7.10 (s, 2H), 7.09 (d, J=2.2 Hz, 1H), 6.92 (dd, J=8.4, 2.3 Hz, 1H), 6.86 (d, J=8.3 Hz, 1H), 4.90 (s, 2H), 4.11 (s, 2H), 2.96 (s, 3H), 2.84 (s, 3H).

Example 33

Synthesis of methyl 2-(3,5-dichloro-4-(4-hydroxy-3-(thiophen-2-yl)benzyl)phenoxy) acetate (Compound 33)

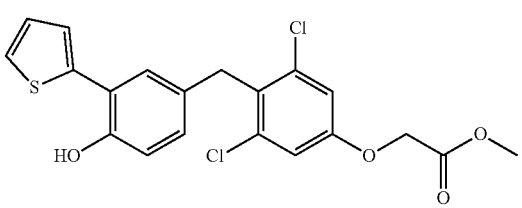

To a solution of Intermediate A7 (200 mg, 0.43 mmol) in 1,4-dioxane (3 mL) at rt were added thiophene-2-boronic acid (82 mg, 0.64 mmol), Pd(dppf)Cl₂ (32 mg, 0.04 mmol) and NaHCO₃ (2N) (1.29 mmol, 0.6 mL). The mixture was stirred at 85° C. overnight. The mixture was diluted with EtOAc (20 mL) and filtered. The filtrate was washed with brine (30 mL), dried over Na₂SO₄ and concentrated in vacuo to afford Compound 33 (100 mg, 55% yield) which was used without further purification.

TLC: Pet. ether/EtOAc=5/1 (v/v), Rf=0.4
LCMS: RT=4.333 min; [M−1]=421.0

Example 34

Synthesis of 2-(3,5-dichloro-4-(4-hydroxy-3-(thiophen-2-yl)benzyl)phenoxy)acetic acid (Compound 34)

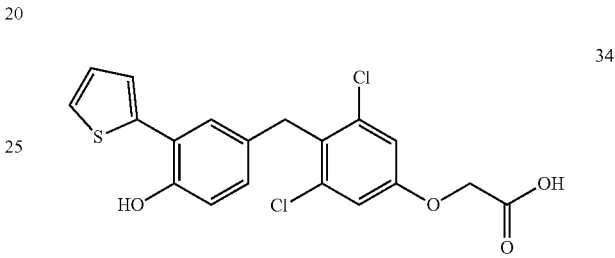

To a solution of Compound 33 (100 mg, 0.35 mmol) in THF (3 mL) and H₂O (2 mL) was added LiOH.H₂O (44 mg, 1.05 mmol). The mixture was stirred at rt for 2 h; the pH was adjusted to ~4 with 1 N HCl. The aqueous layer was extracted with EtOAc (20 mL*2). The combined organic layer was washed with brine (20 mL), dried over Na₂SO₄ and concentrated in vacuo. The residue was purified by Prep-HPLC to afford Compound 34 (40 mg, 28% yield) as a white solid.

TLC: DCM/MeOH=10/1 (v/v), Rf=0.2
LCMS: RT=3.857 min; [M−1]=407.0
¹H NMR: (400 MHz, DMSO-d₆) δ 12.99 (s, 1H), 10.01 (s, 1H), 7.47 (d, J=3.6 Hz, 1H), 7.45 (s, 1H), 7.40 (s, 1H), 7.13 (s, 2H), 7.07 (t, J=4.8 Hz, 1H), 6.85 (s, 2H), 4.78 (s, 2H), 4.11 (s, 2H).

Example 35

Synthesis of methyl 2-(3,5-dichloro-4-(3-(4-chlorothiophen-2-yl)-4-hydroxybenzyl) phenoxy)acetate (Compound 35)

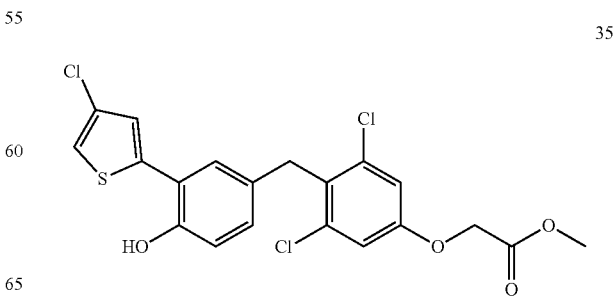

To a solution of Intermediate A7 (150 mg, 0.31 mmol) and Intermediate B5 (152 mg, 0.62 mmol) in water (1 mL) and 1,4-dioxane (6 mL) at rt were added NaHCO₃ (52 mg, 0.62 mmol) and Pd(dppf)Cl₂ (11 mg, 15.6 umol). The reaction was stirred at 75° C. overnight. The mixture was concentrated in vacuo. The residue was purified by Prep-HPLC to afford Compound 35 (30 mg, 20% yield) as a light yellow solid.

TLC: EtOAc/pet. ether=⅕, Rf=0.52

Example 36

Synthesis of 2-(3,5-dichloro-4-(3-(4-chlorothiophen-2-yl)-4-hydroxybenzyl)phenoxy) acetic Acid (Compound 36)

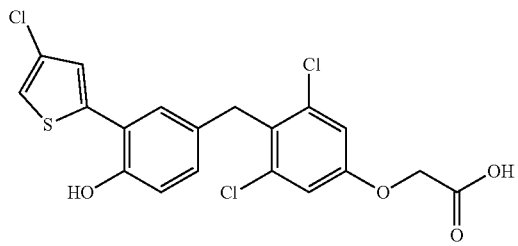

To a solution of Compound 35 (100 mg, 0.21 mmol) in water (2 mL)/THF (4 mL) at rt was added NaOH (34 mg, 0.84 mmol); the resultant mixture was stirred at rt overnight. The reaction mixture was acidified to pH~3 with HCl (1N) and extracted with EtOAc (10 mL*3); the combined organic phase was dried over Na₂SO₄ and concentrated in vacuo. The crude product was purified by Prep-TLC (methanol/DCM=¹/₁₀) to afford Compound 36 (25 mg, 26% yield) as a white solid.

TLC: EtOAc/pet. ether=⅕, Rf=0.21
LCMS: RT=3.92 min; [M−1]:=440.9
¹H NMR: (400 MHz, DMSO-d₆) δ 10.66 (brs, 1H), 7.51-7.43 (m, 3H), 6.95 (s, 2H), 6.91 (d, J=8.4 Hz, 1H), 6.83 (dd, J=8.4, 2.4 Hz, 1H), 4.22 (s, 2H), 4.08 (s, 2H).

Example 37

Synthesis of 2-(3,5-dichloro-4-(4-hydroxy-3-(5-(trifluoromethylthiophen-2-ylbenzyl) phenoxy)acetic Acid (Compound 37)

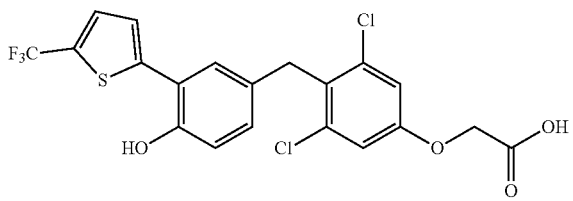

A mixture of [5-(trifluoromethyl)thienyl]boron pinacolate (58 mg, 0.21 mmol), Intermediate A7 (100 mg, 0.21 mmol), Cs₂CO₃ (135 mg, 0.42 mmol) and Pd(dppf)Cl₂ (16 mg, 0.02 mmol) in 1,4-dioxane (3 mL)/water (1 mL) was stirred at 85° C. for 16 h under N₂ atmosphere. The reaction was acidified to pH~6-7 with 2N HCl, concentrated in vacuo and purified by Prep-HPLC to afford Compound 37 (7 mg, 5% yield) as a light yellow solid.

TLC: EtOAc/pet. ether=⅕ (v/v), Rf=0
¹H NMR: (400 MHz, DMSO) δ 10.62 (s, 1H), 7.65 (d, J=4.0 Hz, 1H), 7.60 (s, 1H), 7.56 (d, J=4.1 Hz, 1H), 7.14 (s, 2H), 6.91 (d, J=2.0 Hz, 2H), 4.79 (s, 2H), 4.14 (s, 2H).
LCMS: RT=4.07 min; [M−1]=477.

Example 38

Synthesis of 2-(3,5-dichloro-4-(3-(furan-2-yl)-4-hydroxybenzyl)phenoxy)acetic acid (Compound 38)

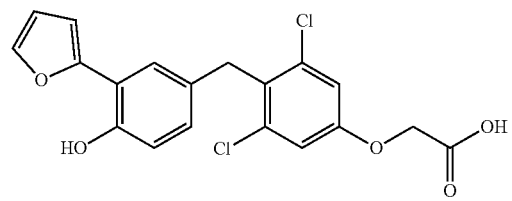

To a solution of Intermediate A7 (150 mg, 321 umol) in 1,4-dioxane (4 mL) at rt were added Pd(dppf)Cl₂ (27 mg, 32 umol), NaHCO₃ (2M, 0.5 mL) and furan-2-boronic acid (54 mg, 482 umol). The mixture was heated to 70° C. overnight. The mixture was cooled to rt, LiOH.H₂O (67 mg, 1.6 mmol) was added, and the mixture was stirred at rt for 30 min. The reaction was quenched with water (5 mL), acidified with 1N HCl to pH~4-5, and extracted with DCM (5 mL*3). The combined organic phase was washed with brine (10 mL), dried over Na₂SO₄, and concentrated in vacuo. The crude product was purified by Prep-HPLC (ACN/water range from 30/70 to 85/15) to afford Compound 38 (40 mg, 31% yield) as an off-white solid.

TLC: DCM/MeOH=10/1 (v/v), Rf=0.33
LCMS: RT=3.494 min; [M−1]=391
¹H NMR: (400 MHz, DMSO-d₆) δ 9.97 (s, 1H), 7.67 (dd, J=1.8, 0.8 Hz, 1H), 7.43 (d, J=2.1 Hz, 1H), 7.13 (s, 2H), 6.91 (dd, J=3.3, 0.8 Hz, 1H), 6.87 (d, J=2.2 Hz, 1H), 6.84 (d, J=8.3 Hz, 1H), 6.54 (dd, J=3.3, 1.8 Hz, 1H), 4.78 (s, 2H), 4.11 (s, 2H).

Example 39

Synthesis of methyl 2-(3,5-dichloro-4-(3-(furan-3-yl)-4-hydroxybenzyl)phenoxy) acetate (Compound 39)

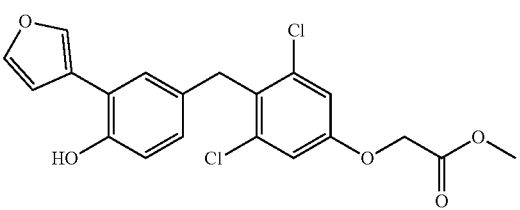

To a solution of Intermediate A7 (200 mg, 0.43 mmol), furan-3-boronic acid (72 mg, 0.64 mmol) and NaHCO$_3$ (2M, 0.6 mL) in 1,4-dioxane (10 mL) at rt was added Pd(dppf)Cl$_2$ (31 mg, 0.04 mmol). The mixture was refluxed overnight. The mixture was cooled to rt, water (10 mL) was added, and the mixture was extracted with EtOAc (10 mL*2). The combined organic phase was washed with brine (10 mL), dried over Na$_2$SO$_4$, concentrated in vacuo and purified by Prep-HPLC (MeCN/H$_2$O) to afford Compound 39 (100 mg, 57% yield) as a yellow liquid.

TLC: Pet. ether/EtOAc=5/1 (v/v), Rf=0.4

Example 40

Synthesis of 2-(3,5-dichloro-4-(3-(furan-3-yl)-4-hydroxybenzyl)phenoxy)acetic acid (Compound 40)

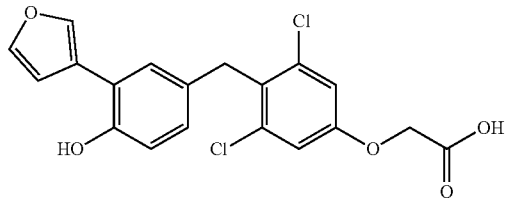

To a solution of Compound 39 (100 mg, 0.24 mmol) in THF (5 mL)/water (0.2 mL) at rt was added LiOH.H$_2$O (30 mg, 0.72 mmol); the resulting mixture was stirred at rt for 1 h. The reaction was acidified to pH~6-7 with 2N HCl and extracted with EtOAc (3*10 mL). The combined organic layer was washed with brine (5 mL), dried over Na$_2$SO$_4$, and concentrated in vacuo. The crude product was purified by Prep-HPLC to afford Compound 40 (50 mg, 52% yield) as a white solid.

TLC: Pet. ether/EtOAc=1/1 (v/v), Rf=0.1
LCMS: RT=3.579 min; [M−1]=391
$^1$H NMR: (400 MHz, DMSO-d$_6$) δ 13.10 (s, 1H), 9.80 (s, 1H), 8.08 (d, J=1.8 Hz, 1H), 7.68 (t, J=1.7 Hz, 1H), 7.35 (d, J=2.2 Hz, 1H), 7.12 (s, 2H), 6.85-6.78 (m, 2H), 6.74 (dd, J=8.4, 2.2 Hz, 1H), 4.78 (s, 2H), 4.11 (s, 2H).

Example 41

Synthesis of methyl 2-(3,5-dichloro-4-(4-hydroxy-3-(thiophen-3-yl)benzyl)phenoxy) acetate (Compound 41)

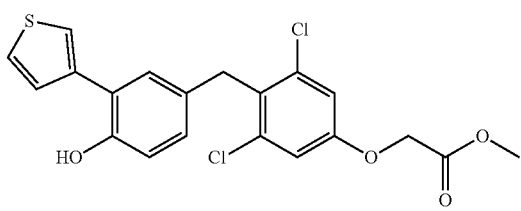

A solution of thiophene-3-boronic acid (82 mg, 642 umol), Intermediate A7 (150 mg, 321 umol), Pd(dppf)Cl$_2$ (24 mg, 32.1 umol) and NaHCO$_3$ (2M, 0.48 mL) in 1,4-dioxane (5 mL) was stirred at 85° C. overnight. The mixture was concentrated to dryness. Water (30 mL) was added, and the mixture was extracted with EtOAc (25 mL*2). The combined organic layer was washed with brine (50 mL), dried over Na$_2$SO$_4$, and purified by Prep-TLC (pet. ether/EtOAc=5/1) to afford Compound 41 (80 mg, 29% yield, 50% purity) as a yellow solid.

TLC: EtOAc/pet. ether=1/5 (v/v), Rf=0.42

Example 42

Synthesis of 2-(3,5-dichloro-4-(4-hydroxy-3-(thiophen-3-yl)benzyl)phenoxy)acetic acid (Compound 42)

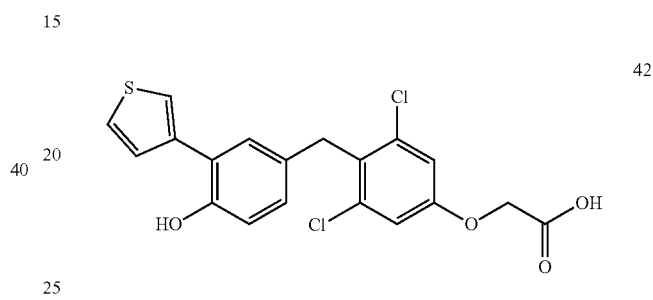

To a solution of Compound 41 (80 mg, 50% purity, 94.4 umol) in water (1 mL) and MeOH (2 mL) was added LiOH.H$_2$O (12 mg, 283 umol). The mixture was stirred at room temperature for 1 h. The mixture was acidified to pH~5-6 with 1N HCl and extracted with DCM (5 mL). The organic layer was concentrated to dryness and purified by Prep-HPLC to afford Compound 42 (15 mg, 38% yield) as a white solid.

TLC: EtOAc/pet. ether=1/5 (v/v), Rf=0
LCMS: RT=1.728 min; [M−1]=407.0/409.0
$^1$H NMR: (400 MHz, DMSO-d$_6$) δ 13.10 (s, 1H), 9.62 (s, 1H), 7.73 (dd, J=3.0, 1.3 Hz, 1H), 7.53 (dd, J=5.0, 3.0 Hz, 1H), 7.42 (dd, J=5.0, 1.3 Hz, 1H), 7.30 (s, 1H), 7.12 (s, 2H), 6.83 (d, J=1.3 Hz, 2H), 4.77 (s, 2H), 4.11 (s, 2H).

Example 43

Synthesis of 2-(3,5-dichloro-4-(3-(5-chlorothiophen-3-yl)-4-hydroxybenzyl)phenoxy) acetic Acid (Compound 43)

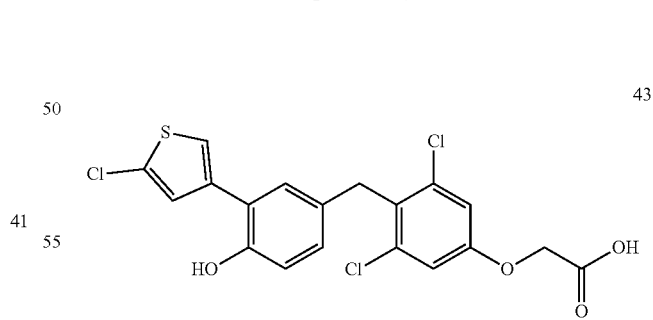

A mixture of 2-chlorothiophene-4-boron pinacolate (50 mg, 240 umol), Intermediate A7 (98 mg, 240 umol), NaHCO$_3$ (2 M, 0.36 mL) and Pd(dppf)Cl$_2$ (15 mg, 24.5 umol) in 1,4-dioxane (2 mL) was stirred at 100° C. overnight. The mixture was cooled to rt, LiOH.H$_2$O (25 mg, 613 umol) was added and the resultant mixture stirred for 1 h. The mixture was acidified to pH~5-6 with 1N HCl, water (30 mL) was added and the resultant mixture was extracted with EtOAc (25 mL*2). The combined organic layer was washed with water (25 mL*2) then brine (50 mL), dried over Na₂SO₄, concentrated in vacuo and purified by Prep-HPLC to afford Compound 43 (35 mg, 39% yield) as a white solid.

TLC: EtOAc/pet. ether=⅕ (v/v), Rf=0

LCMS: RT=2.419 min; [M−1]=440.9/442.9

¹H NMR: (400 MHz, DMSO-d₆) δ 13.11 (s, 1H), 9.77 (s, 1H), 7.62 (d, J=1.8 Hz, 1H), 7.43 (d, J=1.8 Hz, 1H), 7.30 (d, J=1.7 Hz, 1H), 7.12 (s, 2H), 6.85-6.80 (m, 2H), 4.78 (s, 2H), 4.10 (s, 2H).

Example 44

Synthesis of 2-(3,5-dichloro-4-(4-hydroxy-3-(3-methylfuran-2-yl)benzyl)phenoxy)acetic Acid (Compound 44)

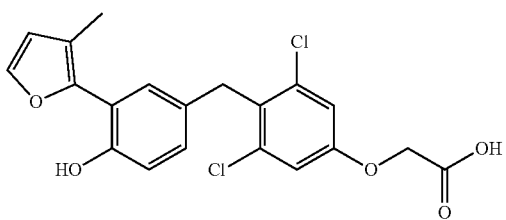

To a solution of Intermediate A7 (200 mg, 0.43 mmol) and Intermediate B6 (179 mg, 0.86 mmol) in 1,4-dioxane/H₂O (5/2 mL) were added Pd(dppf)Cl₂ (16 mg, 0.022 mmol), and NaHCO₃ (109 mg, 1.29 mmol). The reaction was heated to 80° C. overnight. The reaction mixture was cooled to rt; LiOH.H₂O (90 mg, 2.15 mmol) was added, and the resultant mixture was stirred at rt for 30 min. Water (10 mL) was added, the pH was adjusted to pH~3-4 with 1N HCl, and the mixture was extracted with EtOAc (10 mL*3). The combined organic phase was washed with brine (20 mL), dried over Na₂SO₄, and concentrated in vacuo; the residue was purified by Prep-HPLC to afford Compound 44 (10 mg) as a light yellow solid, the minor of two similar products.

LCMS: RT=3.795 min; [M−1]=405.1/406.9

¹H NMR: (400 MHz, DMSO-d₆) δ 12.96 (s, 1H), 9.51 (s, 1H), 7.56 (d, J=1.7 Hz, 1H), 7.11 (s, 2H), 7.03-6.91 (m, 2H), 6.84 (d, J=8.3 Hz, 1H), 6.36 (d, J=1.4 Hz, 1H), 4.77 (s, 2H), 4.09 (s, 2H), 1.94 (s, 3H)

Example 45

Synthesis of 2-(3,5-dichloro-4-((2'-fluoro-6-hydroxy-5'-(trifluoromethyl)-[1,1'-biphenyl]-3-yl)methyl)phenoxy)acetic Acid (Compound 45)

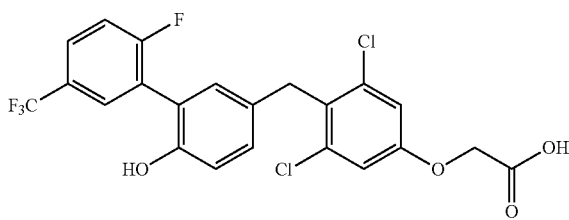

To a solution of Intermediate A7 (150 mg, 321 umol) in 1,4-dioxane (3 mL) at rt were added Pd(dppf)Cl₂ (27 mg, 32 umol), NaHCO₃ (2M, 0.5 mL) and 2-fluoro-5-trifluoromethyl-phenylboronic acid (100 mg, 482 umol). The mixture was heated to 70° C. overnight. The mixture was cooled to rt, LiOH.H₂O (67 mg, 1.6 mmol) was added, and the resultant mixture was stirred at rt for 30 min. The reaction was quenched with water (5 mL), acidified with 1N HCl to pH~4-5, and extracted with DCM (5 mL*3). The combined organic phase was washed with brine (10 mL), dried over Na₂SO₄, and concentrated in vacuo. The crude product was purified by Prep-HPLC (ACN/water range from 30/70 to 85/15) to afford Compound 45 (10 mg, 6% yield) as an off-white solid.

TLC: DCM/MeOH=10/1 (v/v), Rf=0.33

LCMS: RT=2.291 min; [M−1]=487.

¹H NMR: (400 MHz, DMSO-d₆) δ 13.09 (s, 1H), 9.66 (s, 1H), 7.77 (dt, J=7.8, 3.1 Hz, 1H), 7.72-7.66 (m, 1H), 7.48 (t, J=9.1 Hz, 1H), 7.12 (s, 2H), 7.05 (s, 1H), 6.98 (dd, J=8.4, 2.1 Hz, 1H), 6.87 (d, J=8.4 Hz, 1H), 4.77 (s, 2H), 4.11 (s, 2H).

Example 46

Synthesis of 2-(3,5-dichloro-4-((2'-fluoro-6-hydroxy-5'-(trifluoromethyl)-[1,1'-biphenyl]-3-yl)methyl)phenoxy)-N-methylacetamide (Compound 46)

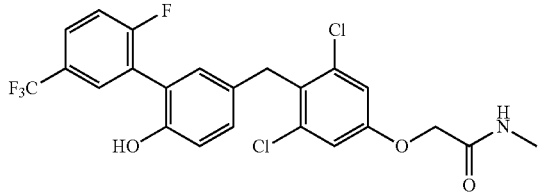

To Compound 45 (100 mg, 0.2 mmol) in DCM (2 mL) was added a catalytic amount of DMF (1 drop). The mixture was cooled to 0° C. and oxalyl chloride (51 mg, 0.4 mmol) was added. The mixture was stirred at rt for 30 min. The mixture was concentrated in vacuo to afford 2-(3,5-dichloro-4-((2'-fluoro-6-hydroxy-5'-(trifluoromethyl)-[1,1'-biphenyl]-3-yl)methyl)phenoxy)acetyl chloride (100 mg, 99% yield) as alight yellow solid. TLC: MeOH/DCM=1/10 (v/v), Rf=0.90 To 2-(3,5-dichloro-4-((2'-fluoro-6-hydroxy-5'-(trifluoromethyl)-[1,1'-biphenyl]-3-yl)methyl)phenoxy)acetyl chloride (50 mg, 0.1 mmol) in DCM (2 mL) at 0° C. was added dropwise MeNH₂ (40% w/w in H₂O, 2 mL). The reaction was stirred at rt for 30 min. Water (10 mL) was added and the mixture was extracted with DCM (5 mL*3). The combined organic phase was washed with brine (15 mL), dried over Na₂SO₄, concentrated in vacuo and purified by Prep-HPLC to afford Compound 46 (12 mg, 24% yield) as a white solid.

TLC: MeOH/DCM=1/10 (v/v), Rf=0.60

LCMS: RT=3.004 min; [M−1]=502.1

¹H NMR: (400 MHz, DMSO) δ 9.66 (s, 1H), 8.05 (s, 1H), 7.77 (s, 1H), 7.70 (d, J=6.8 Hz, 1H), 7.49 (t, J=9.2, 19.2 Hz, 1H), 7.15 (s, 1H), 7.05 (s, 1H), 6.99 (d, J=7.2 Hz, 1H), 6.87

(d, J=8.0 Hz, 1H), 4.54 (s, 1H), 4.12 (s, 1H), 2.65 (d, J=4.8 Hz, 1H).
$^{19}$F NMR: (376 MHz, DMSO) δ −60.31 (s), −108.13 (s).

Example 47

Synthesis of 2-(3,5-dichloro-4-((2'-fluoro-6-hydroxy-5'-(trifluoromethyl)-[1,1'-biphenyl]-3-yl)methyl)phenoxy)-N,N-dimethylacetamide (Compound 47)

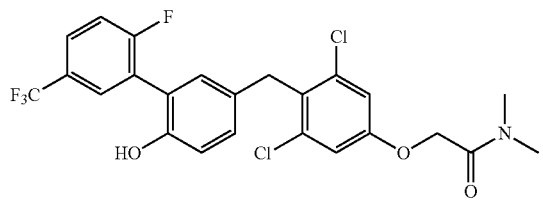

47

To Compound 45 (100 mg, 0.2 mmol) in DCM (2 mL) was added a catalytic amount of DMF (1 drop). The mixture was cooled to 0° C. and oxalyl chloride (51 mg, 0.4 mmol) was added. The mixture was stirred at rt for 30 min. The mixture was concentrated in vacuo to afford 2-(3,5-dichloro-4-((2'-fluoro-6-hydroxy-5'-(trifluoromethyl)-[1,1'-biphenyl]-3-yl)methyl)phenoxy)acetyl chloride (100 mg, 99% yield) as a light yellow solid. TLC: MeOH/DCM=1/10 (v/v), $R_f$=0.90

To 2-(3,5-dichloro-4-((2'-fluoro-6-hydroxy-5'-(trifluoromethyl)-[1,1'-biphenyl]-3-yl)methyl)phenoxy)acetyl chloride (50 mg, 0.1 mmol) in DCM (2 mL) at 0° C. was added dropwise dimethylamine (2M in THF, 0.15 mL). The mixture was stirred at rt for 30 min. Water (10 mL) was added and the mixture was extracted with DCM (5 mL*3). The combined organic phase was washed with brine (15 mL), dried over Na$_2$SO$_4$, concentrated in vacuo and purified by Prep-HPLC to afford Compound 47 (20 mg, 39% yield) as a white solid.

TLC: MeOH/DCM=1/10 (v/v), $R_f$=0.60
LCMS: T=3.004 min; [M−1]=502.1
$^1$H NMR: (400 MHz, DMSO) δ 9.64 (s, 1H), 7.76 (d, J=3.0 Hz, 1H), 7.70 (dd, J=6.4, 2.0 Hz, 1H), 7.49 (t, J=8.8 Hz, 1H), 7.10 (s, 1H), 7.05 (s, 1H), 6.98 (dd, J=8.0, 2.4 Hz, 1H), 6.88 (d, J=8.4 Hz, 1H), 4.90 (s, 1H), 4.11 (s, 1H), 2.96 (s, 1H), 2.84 (s, 1H).
$^{19}$F NMR: (376 MHz, DMSO) δ −60.31 (s), −108.11 (s).

Example 48

Synthesis of 2-(3,5-dichloro-4-((4'-fluoro-6-hydroxy-3'-(trifluoromethyl)-[1,1'-biphenyl]-3-yl)methyl)phenoxy)acetic acid (Compound 48)

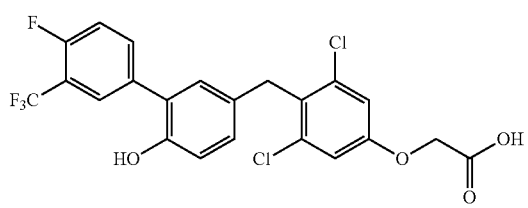

48

A solution of [3-(trifluoromethyl)-4-fluorophenyl]boron pinacolate (140 mg, 482 umol), Intermediate A7 (150 mg, 321 umol), Pd(dppf)Cl$_2$ (24 mg, 32 umol) and NaHCO$_3$ (aq) (2 M, 0.48 mL) in 1,4-dioxane (5 mL) was stirred at 85° C. overnight. The mixture was cooled to rt, LiOH.H$_2$O (23 mg, 963 umol) was added, and the resultant mixture stirred for 20 min. The mixture was acidified to pH~5-6 with 1M HCl. Water (30 mL) was added; the mixture was extracted with EtOAc (25 mL*2). The combined organic layer was washed with brine (20 mL), dried over Na$_2$SO$_4$, concentrated in vacuo, and purified by Prep-TLC (DCM/MeOH=10/1) to afford Compound 48 (10 mg, 6% yield) as a brown solid.

TLC: DCM/MeOH=10/1 (v/v), Rf=0.32
LCMS: T=2.427 min; [M−1]:486.8/488.8
$^1$H NMR: (400 MHz, DMSO-d$_6$) δ 13.19 (s, 1H), 9.72 (s, 1H), 7.88-7.85 (m, 1H), 7.84-7.77 (m, 1H), 7.56-7.51 (m, 1H), 7.15 (d, J=2.0 Hz, 1H), 7.10 (s, 2H), 6.95-6.85 (m, 2H), 4.73 (s, 2H), 4.12 (s, 2H).

Example 49

Synthesis of 2-(3,5-dichloro-4-((2'-fluoro-6-hydroxy-3'-(trifluoromethyl)-[1,1'-biphenyl]-3-yl)methyl)phenoxy)acetic Acid (Compound 49)

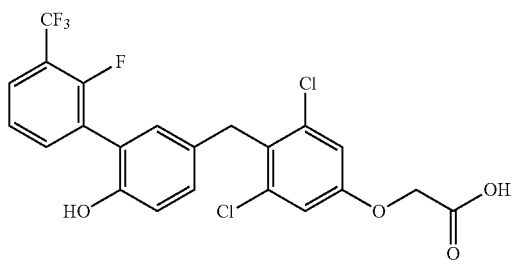

49

To a mixture of Intermediate A7 (150 mg, 321 umol), [3-(trifluoromethyl)-2-fluorophenyl]boronic acid (100 mg, 482 umol) and Pd(dppf)Cl$_2$·CH$_2$Cl$_2$ (26 mg, 32 umol) in 1,4-dioxane (5.0 mL) at rt was added aqueous NaHCO$_3$ (2M, 0.5 mL). The mixture was heated to 70° C. and stirred overnight. The reaction mixture was cooled to rt; LiOH.H$_2$O (55 mg, 1.3 mmol) was added and the resultant mixture was stirred for 30 min. The reaction was quenched with water (10 mL), acidified to pH~4-5 with aqueous HCl (1N), and extracted with EtOAc (5 mL*3). The combined organic phase was washed with brine (10 mL), dried over Na$_2$SO$_4$, concentrated in vacuo and purified by Prep-HPLC (MeCN/H$_2$O) to afford Compound 49 (10 mg, 6% yield) as a white solid.

TLC: MeOH/DCM=1/10 (v/v), Rf=0.3
LCMS: RT=4.534 min; [M−1]=487.8
$^1$H NMR: (400 MHz, DMSO-d$_6$) δ 9.66 (s, 1H), 7.74 (t, J=6.8 Hz, 1H), 7.65 (t, J=6.4 Hz, 1H), 7.43 (t, J=8.0 Hz, 1H), 7.10 (s, 2H), 7.04-6.95 (m, 2H), 6.87 (d, J=8.0 Hz, 1H), 4.72 (s, 2H), 4.11 (s, 2H).
$^{19}$F NMR: (376 MHz, DMSO-d$_6$) δ −59.85, −59.89, −116.66, −116.70, −116.73, −116.76.

Example 50

Synthesis of 2-(3,5-dichloro-4-((3'-fluoro-6-hydroxy-5'-(trifluoromethyl)-[1,1'-biphenyl]-3-yl)methyl)phenoxy)acetic Acid (Compound 50)

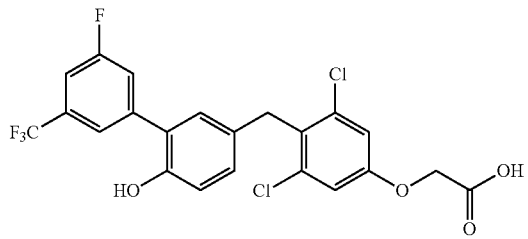

To a solution of 3-fluoro-5-trifluoromethylphenyl boronic acid (100 mg, 0.48 mmol), Intermediate A7 (150 mg, 0.32 mmol) and NaHCO$_3$ (0.7 mL, 1.44 mmol) in 1,4-dioxane (5 mL) at rt was added Pd(dppf)Cl$_2$ (16 mg, 0.03 mmol); the mixture was refluxed overnight. The reaction was cooled to rt; LiOH.H$_2$O (61 mg, 1.44 mmol) was added, and the resultant mixture was stirred at rt for 30 min. Water (10 mL) was added, and the mixture was extracted with ether (10 mL*2). The aqueous phase was adjusted pH to ~3 with HCl (2N), then re-extracted with EtOAc (10 mL*2). The combined EtOAc extracts were washed with brine (10 mL), dried over Na$_2$SO$_4$, concentrated in vacuo and purified by Prep-HPLC (MeCN/H$_2$O) to afford Compound 50 (4 mg, 4% yield) as a white solid.

TLC: Pet. ether/EtOAc=1/5 (v/v), Rf=0.1

LCMS: RT=4.156 min; [M−1]=487

$^1$H NMR: (400 MHz, DMSO-d$_6$) δ 13.10 (s, 1H), 9.81 (s, 1H), 7.70 (s, 1H), 7.65 (d, J=9.8 Hz, 1H), 7.60 (d, J=8.8 Hz, 1H), 7.24 (d, J=2.0 Hz, 1H), 7.12 (s, 2H), 6.94-6.87 (m, 2H), 4.77 (s, 2H), 4.13 (s, 2H).

Example 51

Synthesis of 2-(3,5-dichloro-4-((5'-ethyl-2'-fluoro-6-hydroxy-[1,1'-biphenyl]-3-yl)methyl)phenoxy)acetic Acid (Compound 51)

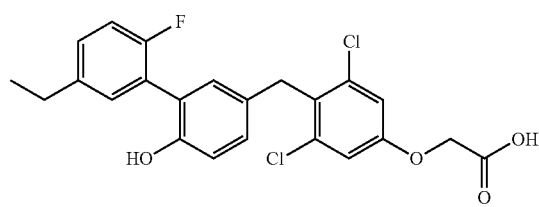

To a solution of Intermediate A7 (100 mg, 0.21 mmol), 2-fluoro-5-ethylphenyl boronic acid (80 mg, 0.32 mmol) and NaHCO$_3$ (0.3 mL, 0.63 mmol) in 1,4-dioxane (5 mL) was added Pd(dppf)Cl$_2$ (16 mg, 0.02 mmol); the mixture was refluxed overnight. The reaction was cooled to rt; LiOH.H$_2$O (27 mg, 0.63 mmol) was added, and the resultant mixture was stirred for 30 min. Water (10 mL) was added, and the mixture was extracted with ether (10 mL*2). The aqueous phase was adjusted to pH ~3 with HCl (2N), then re-extracted with EtOAc (10 mL*2). The combined EtOAc extracts were washed with brine (10 mL), dried over Na$_2$SO$_4$, concentrated in vacuo and purified by Prep-HPLC (MeCN/H$_2$O) to afford Compound 51 (4 mg, 4% yield) as a white solid.

TLC: Pet. ether/EtOAc=1/5 (v/v), Rf=0.1

LCMS: RT=4.011 min; [M−1]=417

$^1$H NMR: (400 MHz, DMSO-d$_6$) δ 13.11 (s, 1H), 9.40 (s, 1H), 7.17 (dd, J=8.4, 4.8 Hz, 1H), 7.11 (s, 3H), 7.08 (d, J=8.6 Hz, 1H), 6.93 (d, J=10.0 Hz, 2H), 6.82 (d, J=8.2 Hz, 1H), 4.77 (s, 2H), 4.10 (s, 2H), 2.60 (q, J=7.6 Hz, 2H), 1.17 (t, J=7.6 Hz, 3H).

Example 52

Synthesis of 2-(3,5-dichloro-4-((5'-(difluoromethoxy)-2'-fluoro-6-hydroxy-[1,1'-biphenyl]-3-yl)methyl)phenoxy)acetic Acid (Compound 52)

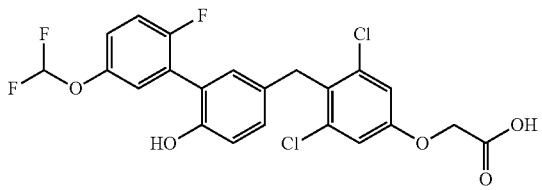

To a mixture of Intermediate B8 (470 mg, 1.6 mmol), Intermediate A7 (150 mg, 0.32 mmol) and Pd(dppf)Cl$_2$·CH$_2$Cl$_2$ (13 mg, 0.016 mmol) in 1,4-dioxane (5 mL) and H$_2$O (0.5 mL) at rt was added NaHCO$_3$ (0.96 mmol, 0.48 mL). The reaction was heated to 80° C. under N$_2$ (g) overnight. The reaction mixture was cooled to rt. LiOH.H$_2$O (25 mg, 0.6 mmol) was added and the resultant mixture was stirred for 30 min. Water (20 mL) was added and the mixture was extracted with EtOAc (10 mL*3), the combined organic phase was washed with brine (20 mL), dried over Na$_2$SO$_4$ and concentrated in vacuo. The crude product was purified by Prep-HPLC to afford Compound 52 (20 mg, 12% yield) as a white solid.

TLC: DCM/MeOH=10/1 (v/v), Rf=0.2

LCMS: RT=3.779 min; [M−1]=485.0

$^1$H NMR: (400 MHz, DMSO-d$_6$) δ 13.09 (s, 1H), 9.58 (s, 1H), 7.29 (t, J=9.2 Hz, 1H), 7.16 (ddd, J=11.6, 6.0, 3.6 Hz, 2H), 6.98 (dd, J=12.0, 3.6 Hz, 2H), 6.86 (d, J=8.2 Hz, 1H), 4.76 (s, 2H), 4.11 (s, 2H).

$^{19}$F NMR: (376 MHz, DMSO-d$_6$) δ −81.96, −118.49.

Example 53

Synthesis of methyl 2-(3,5-dichloro-4-((3'-(difluoromethoxy)-5'-fluoro-6-hydroxy-[1,1'-biphenyl]-3-yl)methyl)phenoxy)acetate (Compound 53)

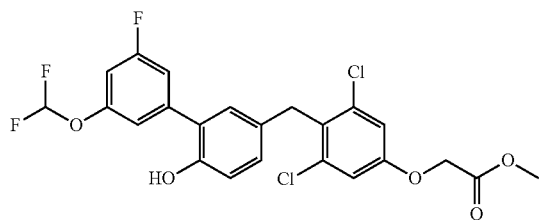

A mixture of Intermediate B9 (144 mg, 0.50 mmol), Intermediate A7 (155 mg, 0.33 mmol), 2N NaHCO$_3$ (0.5 mL, 1.0 mmol) and Pd(dppf)Cl$_2$ (17 mg, 0.02 mmol) in 1,4-dioxane (5 mL) was stirred at 85° C. for 16 h under N$_2$ atmosphere. The reaction mixture was concentrated in vacuo and Compound 53 was used for the next step without further purification.

TLC: pet. ether/EtOAc=5/1 (v/v), Rf=0.4

LCMS: RT=2.87 min; [M−1]=499.0.

Example 54

Synthesis of 2-(3,5-dichloro-4-((3'-(difluoromethoxy)-5'-fluoro-6-hydroxy-[1,1'-biphenyl]-3-yl)methyl)phenoxy)acetic Acid (Compound 54)

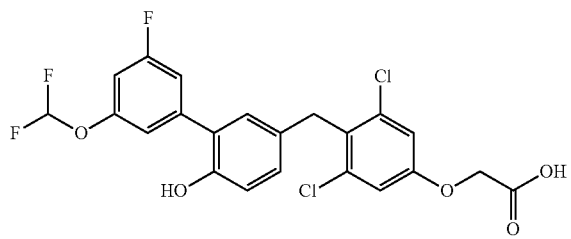

To a solution of Compound 53 (165 mg, 0.33 mmol) in THF (1 mL)/water (5 mL) at rt was added LiOH (155 mg, 1.0 mmol); the resulting mixture was stirred at 50° C. for 1 h. The reaction was acidified to pH~6-7 with 2N HCl, concentrated in vacuo and purified by Prep-HPLC to afford Compound 54 (45 mg, 57% yield).

TLC: pet. ether/EtOAc=5/1 (v/v), Rf=0.4

LCMS: RT=2.09 min; [M−1]=485.

$^1$H NMR: (400 MHz, DMSO) δ 13.10 (s, 1H), 9.71 (s, 1H), 7.50 (s, 0.24H), 7.32 (s, 0.52H), 7.22 (M, 1H), 7.16 (t, J=2.2 Hz, 2H), 7.14 (s, 0.33H), 7.12 (s, 2H), 7.06 (m, 1H), 6.92 (m, 1H), 6.86 (d, J=8.4 Hz, 1H), 4.77 (s, 2H), 4.12 (s, 2H).

Example 55

Synthesis of 2-(3,5-dichloro-4-((3'-(difluoromethoxy)-4'-fluoro-6-hydroxy-[1,1'-biphenyl]-3-yl)methyl)phenoxy)acetic Acid (Compound 55)

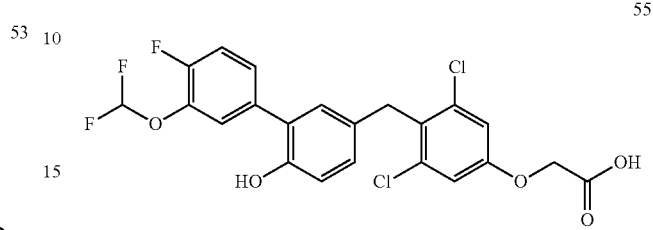

A mixture of compound A7 (138 mg, 0.48 mmol), Intermediate B10 (150 mg, 0.32 mmol), Pd(dppf)Cl$_2$ (22 mg, 0.03 mmol) and NaHCO$_3$ (2 N) (0.96 mmol, 0.48 mL) in 1,4-dioxane (4 mL) was stirred at 85° C. under N$_2$ overnight. The mixture was cooled to rt, LiOH.H$_2$O (67 mg, 1.6 mmol) was added, and the resultant mixture was stirred at rt for 30 min. The mixture was adjusted to pH ~4 with 1N HCl. The aqueous layer was extracted with EtOAc (20 mL*2). The combined organic layer was washed with brine (20 mL), dried over Na$_2$SO$_4$ and concentrated in vacuo. The residue was purified by Prep-HPLC to afford Compound 55 (8 mg, 5% yield) as a white solid.

TLC: DCM/MeOH=10/1 (v/v), Rf=0.2

LCMS: RT=3.885 min; [M−1]=485.0

$^1$H NMR: (400 MHz, DMSO-d$_6$) δ 13.08 (s, 1H), 9.62 (s, 1H), 7.51-7.49 (dd, J$_1$=8.0 Hz, J$_2$=7.2 Hz, 1H), 7.45-7.42 (dd, J=8.0 Hz, J$_2$=12 Hz, 1H), 7.40-7.38 (dd, J$_1$=3.2 Hz, J$_2$=5.2 Hz, 1H), 7.27 (t, J=73.6 Hz, 1H), 7.27 (s, 1H), 7.13 (s, 2H), 7.10 (d, J=2.0 Hz, 1H), 6.93-6.91 (dd, J$_1$=8.0 Hz, J$_2$=8.4 Hz, 1H), 6.86 (d, J=8.4 Hz, 1H), 4.78 (s, 2H), 4.12 (s, 2H).

Example 56

Synthesis of 2-(3,5-dichloro-4-((3'-(difluoromethoxy)-2'-fluoro-6-hydroxy-[1,1'-biphenyl]-3-yl)methyl)phenoxy)acetic Acid (Compound 56)

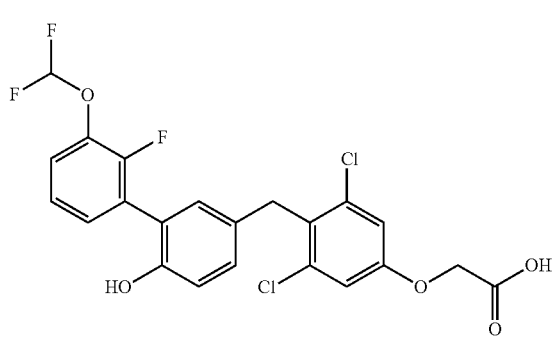

To a mixture of Intermediate B12 (470 mg, 1.6 mmol), Intermediate A7 and Pd(dppf)Cl$_2$·CH$_2$Cl$_2$ (150 mg, 321.14 umol) in 1,4-dioxane (5 mL) and H$_2$O (0.5 mL) at rt was added aqueous NaHCO$_3$ (2M, 0.48 mL). The reaction was heated to 80° C. under N₂(g) overnight. The reaction mixture was cooled to rt. LiOH.H₂O (55 mg, 1.3 mmol) was added and the resultant mixture was stirred for 30 min. The mixture was adjusted to pH ~4 with 1N HCl, and the resultant mixture was extracted with EtOAc (10 mL*3). The combined organic phase was washed with brine (20 mL), dried over Na₂SO₄ and concentrated in vacuo. The crude product was purified by Prep-HPLC to afford Compound 56 (30 mg, 19% yield) as a white solid.

TLC: DCM/MeOH=10/1 (v/v), Rf=0.2

LCMS: RT=3.835 min; [M−1]=485.0

¹H NMR: (400 MHz, DMSO-d₆) δ 13.09 (s, 1H), 9.55 (s, 1H), 7.31 (t, J=8.0 Hz, 1H), 7.25 (t, J=73.2 Hz, 1H), 7.25-7.16 (m, 2H), 7.11 (s, 2H), 6.99 (m, 2H), 6.86 (d, J=8.2 Hz, 1H), 4.77 (s, 2H), 4.11 (s, 2H).

¹⁹F NMR: (376 MHz, DMSO-d₆) δ −81.95, −132.15.

Example 57

Synthesis of methyl 2-(3,5-dichloro-4-((3'-(difluoromethoxy)-6-hydroxy-[1,1'-biphenyl]-3-yl)methyl)phenoxy)acetate (Compound 57)

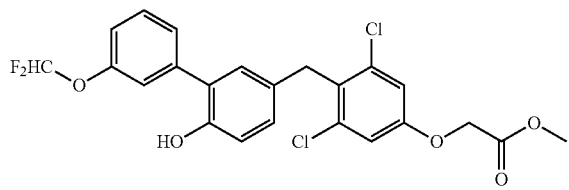

A solution of Intermediate C1 (750 mg, 3.17 mmol), Intermediate A10 (300 mg, 1.06 mmol) and ZnCl₂ (2.65 mmol, 2.6 mL) in DCE (10 mL) was stirred at 85° C. overnight. The mixture was concentrated to dryness and purified by silica gel column chromatography (pet. ether/EtOAc=20/1 to 5/1, v/v) to afford Compound 57 (180 mg, 35% yield) as a white solid.

TLC: EtOAc/pet. ether=⅕ (v/v), Rf=0.45

Example 58

Synthesis of 2-(3,5-dichloro-4-((3'-(difluoromethoxy)-6-hydroxy-[1,1'-biphenyl]-3-yl) methyl)phenoxy)-N-methylacetamide (Compound 58)

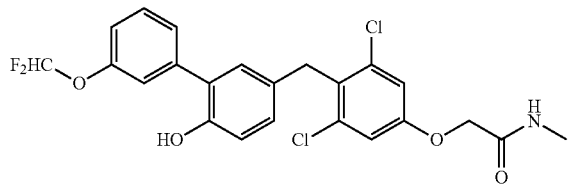

A solution of Compound 57 (200 mg, 414 umol) and methylamine (321 mg, 4.14 mmol, 40% in water) in THF (2 mL) was stirred at 70° C. in a tube overnight. The mixture was concentrated and purified by Prep-HPLC to afford Compound 58 (50 mg, 25% yield) as a white solid.

TLC: EtOAc/pet. ether=⅕ (v/v), Rf=0.35

LCMS: RT=3.894 min; [M−1]=479.8/481.9

¹H NMR: (400 MHz, DMSO-d₆) δ 9.09 (s, 1H), 7.28 (d, J=2.8 Hz, 1H), 7.17 (d, J=2.4 Hz, 1H), 6.96 (s, 1H), 6.68-6.61 (m, 2H), 4.88 (s, 2H), 4.17 (q, J=7.2 Hz, 2H), 4.08 (s, 2H), 3.16-3.09 (m, 1H), 1.20 (t, J=7.2 Hz, 3H), 1.10 (d, J=6.8 Hz, 6H).

Example 59

Synthesis of methyl 2-(3-chloro-4-((3'-ethyl-6-hydroxy-[1,1'-biphenyl]-3-yl)methyl)-5-methylphenoxy)acetate (Compound 59)

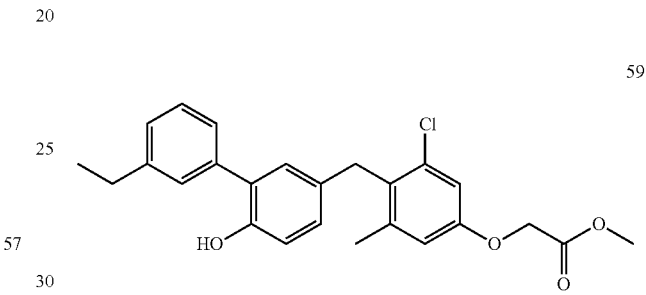

To a solution of Intermediate A15 (135 mg, 0.69 mmol) in DCE (5 mL) at RT were added Intermediate C2 (60 mg, 0.23 mmol) and ZnCl₂/THF (1M) (0.57 mL, 0.58 mmol). The resulting mixture was stirred at 80° C. overnight. The mixture was concentrated and purified by silica gel column chromatography (pet. ether/EtOAc=5/1, v/v) to give Compound 59 (80 mg, 83% yield) as a yellow oil.

TLC: EtOAc/pet.ether=⅕ (v/v), Rf=0.4

¹H NMR: (400 MHz, DMSO) δ 9.29 (s, 1H), 7.27 (m, 3H), 7.11 (d, J=6.9 Hz, 1H), 6.94 (m, 2H), 6.81 (m, 3H), 4.81 (s, 2H), 4.00 (s, 2H), 3.69 (s, 3H), 2.61 (m, 2H), 2.23 (s, 3H), 1.16 (m, 3H).

Example 60

Synthesis of 2-(3-chloro-4-((3'-ethyl-6-hydroxy-[1,1'-biphenyl]-3-yl)methyl)-5-methylphenoxy)acetic Acid (Compound 60)

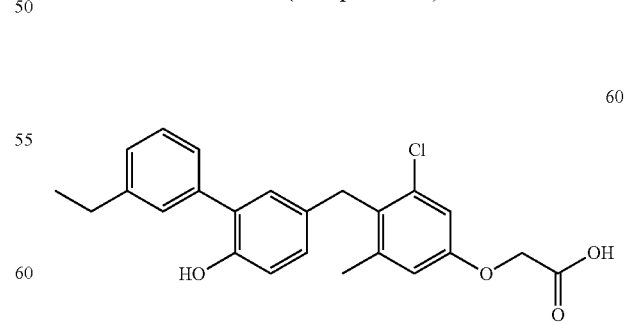

To a solution of Compound 59 (80 mg, 0.19 mmol) in water (5 mL)/THF (1 mL) at rt was added LiOH (23 mg, 0.57 mmol); the resultant mixture was stirred at rt for 1 h. The reaction was acidified to pH~6-7 with 2N HCl, then extracted with DCM (30 mL*3). The combined organic phase was washed with brine (50 mL), dried over Na₂SO₄, concentrated in vacuo and purified by Prep-HPLC to afford Compound 60 (20 mg, 25% yield) as a light yellow solid.

TLC: Pet. ether/EtOAc=⅕ (v/v), Rf=0.0

LCMS: RT=4.09 min; [M+1]=410.13.

¹H NMR: (400 MHz, DMSO) δ 13.02 (s, 1H), 9.29 (s, 1H), 7.31-7.22 (m, 3H), 7.11 (m, 1H), 6.95 (d, J=2.1 Hz, 1H), 6.89 (m, 1H), 6.84-6.76 (m, 3H), 4.67 (s, 2H), 4.00 (s, 2H), 2.62 (m, 2H), 2.22 (s, 3H), 1.19 (t, J=7.6 Hz, 3H).

Example 61

Synthesis of methyl 2-(3-chloro-4-((3'-(difluoromethoxy)-6-hydroxy-[1,1'-biphenyl]-3-yl)methyl)-5-methylphenoxy)acetate (Compound 61)

61

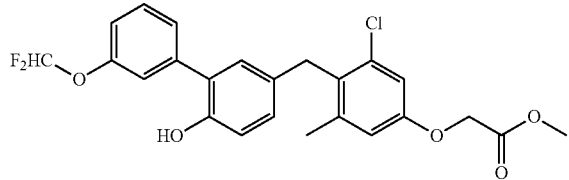

A solution of Intermediate C1 (162 mg, 0.68 mmol), Intermediate A15 (60 mg, 0.23 mmol) and ZnCl₂ (1 M, 0.57 mL) in DCE (2 mL) was stirred at 85° C. overnight. The mixture was concentrated to dryness and purified by silica gel column chromatography (pet. ether/EtOAc=5/1, v/v) to afford Compound 61 (50 mg, 47% yield) as a white solid.

TLC: EtOAc/pet. ether=⅕ (v/v), Rf=0.39

Example 62

Synthesis of 2-(3-chloro-4-((3'-(difluoromethoxy)-6-hydroxy-[1,1'-biphenyl]-3-yl)methyl)-5-methylphenoxy)acetic Acid (Compound 62)

62

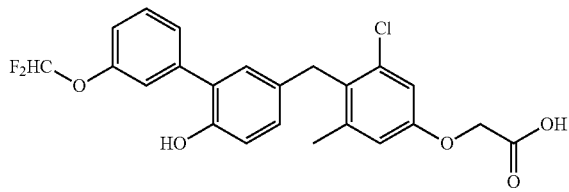

To a solution of Compound 61 (40 mg, 86.4 umol) in water (1 mL) and MeOH (2 mL) was added LiOH.H₂O (6 mg, 0.26 mmol). The mixture was stirred at room temperature for 1 h. The mixture was adjusted to pH~5-6 with 1N HCl (20 mL) and extracted with DCM (20 mL). The organic phase was concentrated to dryness, purified by Prep-HPLC and Prep-TLC (DCM/MeOH=5/1) to afford Compound 62 (5 mg, 12% yield) as a white solid.

TLC: EtOAc/pet. ether=⅕ (v/v), Rf=0

LCMS: RT=3.829 min; [M−1]=446.9

¹H NMR: (400 MHz, DMSO-d₆) δ 13.19 (s, 1H), 9.57 (s, 1H), 7.43 (t, J=8.0 Hz, 1H), 7.34-7.27 (m, 2H), 7.24 (t, J=74.4 Hz, 1H), 7.10-7.05 (m, 1H), 7.01 (d, J=2.0 Hz, 1H), 6.89-6.75 (m, 4H), 4.60 (s, 2H), 4.00 (s, 2H), 2.22 (s, 3H).

Example 63

Synthesis of methyl 2-(3-chloro-4-((6-hydroxy-3'-(trifluoromethyl)-[1,1'-biphenyl]-3-yl)methyl)-5-methylphenoxy)acetate (Compound 63)

63

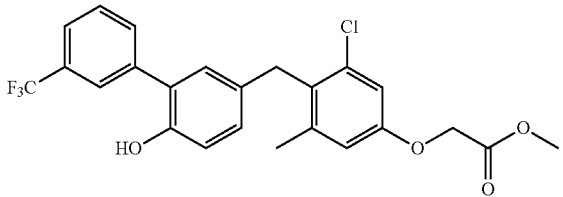

A solution of Intermediate A15 (70 mg, 266 umol), Intermediate C3 (190 mg, 800 umol) and ZnCl₂ (1M, 0.65 mL) in DCE (2 mL) was stirred at 85° C. overnight. The mixture was concentrated to dryness, then purified by silica column chromatography (pet. ether/EtOAc=5/1, v/v) to afford Intermediate 63 (50 mg, 40% yield) as a white solid.

TLC: EtOAc/pet. ether=⅕ (v/v), Rf=0.4

¹H NMR: (400 MHz, DMSO-d₆) δ 9.61 (s, 1H), 7.82 (s, 1H), 7.75 (s, 1H), 7.64 (d, J=1.2 Hz, 2H), 7.06 (d, J=2.0 Hz, 1H), 6.94 (d, J=2.4 Hz, 1H), 6.86-6.82 (m, 3H), 4.81 (s, 2H), 4.03 (s, 2H), 3.70 (s, 3H), 2.23 (s, 3H).

Example 64

Synthesis of 2-(3-chloro-4-((6-hydroxy-3'-(trifluoromethyl)-[1,1'-biphenyl]-3-yl)methyl)-5-methylphenoxy)acetic Acid (Compound 64)

64

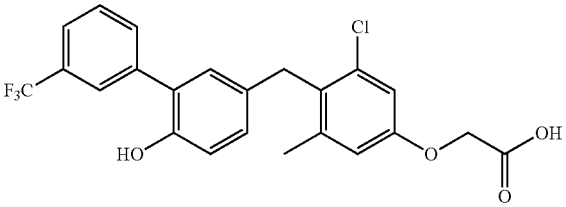

To a solution of Compound 63 (50 mg, 107 umol) in H₂O (1 mL) and MeOH (2 mL) was added NaOH (13 mg, 323 umol). The mixture was stirred at room temperature for 1 h. The mixture was adjusted to pH~5-6 with 1N HCl (20 mL) and extracted with DCM (20 mL). The organic layer was concentrated to dryness, then purified by Prep-HPLC to afford Compound 64 (15 mg, 31% yield) as a white solid.

TLC: EtOAc/pet. ether=⅕ (v/v), Rf=0

LCMS: RT=4.053 min; [M−1]=448.9

¹H NMR: (400 MHz, DMSO-d₆) δ 13.04 (s, 1H), 9.60 (s, 1H), 7.83 (s, 1H), 7.78-7.71 (m, 1H), 7.67-7.57 (m, 2H), 7.07 (d, J=2.0 Hz, 1H), 6.93-6.76 (m, 4H), 4.68 (s, 2H), 4.02 (s, 2H), 2.23 (s, 3H).

Example 65

Synthesis of ethyl 2-(3-bromo-4-((3'-(difluoromethoxy)-6-hydroxy-[1,1'-biphenyl]-3-yl) methyl)-5-methylphenoxy)acetate (Compound 65)

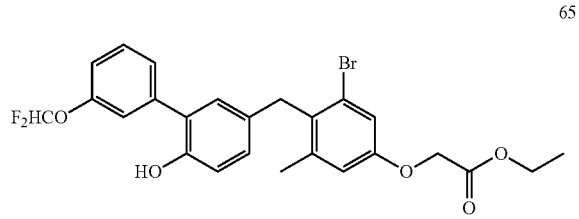

To a solution of Intermediate C1 (1.7 g, 7.47 mmol) in DCE (5 mL) at rt were added Intermediate A18 (800 mg, 2.49 mmol) and 1M ZnCl$_2$ (6.22 mL, 6.22 mmol). The resulting mixture was stirred at 85° C. overnight. The mixture was poured into water (20 mL), and extracted with DCM (30 mL*3). The combined organic phase was dried over Na$_2$SO$_4$ and concentrated. The residue was purified by silica gel column chromatography (pet. ether/EtOAc=10/1, v/v) to afford Compound 65 (1.1 g, 84% yield) as a yellow oil.

TLC: EtOAc/pet. ether=⅕ (v/v), Rf=0.4

$^1$H NMR: (400 MHz, DMSO-d$_6$) δ 9.51 (s, 1H), 7.46-7.38 (m, 1.44H), 7.36-7.27 (m, 2H), 7.24 (s, 0.54H), 7.12-7.04 (m, 3H), 6.99 (m, 1H), 6.88-6.80 (m, 4H), 4.79 (s, 2H), 4.16 (m, 2H), 4.05 (m, 2H), 2.23 (s, 3H), 1.19-1.15 (m, 3H).

Example 66

Synthesis of 2-(3-bromo-4-((3'-(difluoromethoxy)-6-hydroxy-[1,1'-biphenyl]-3-yl) methyl)-5-methylphenoxy)acetic Acid (Compound 66)

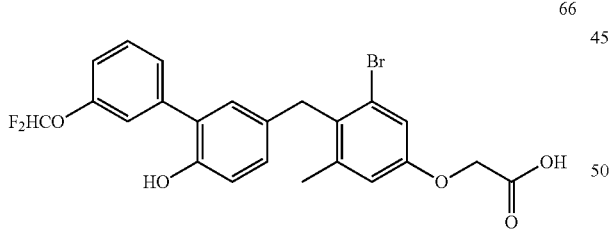

To a solution of Compound 65 (1.2 g, 2.30 mmol) in water (10 mL)/THF (5 mL) at rt was added LiOH.H$_2$O (278 mg, 6.90 mmol); the resulting mixture was stirred at rt for 1 h. The reaction was acidified to pH~3-4 with 2N HCl, concentrated in vacuo, and purified by reversed-phase column chromatography to afford Compound 66 (731 mg, 67% yield).

TLC: Pet. ether/EtOAc=⅕ (v/v), Rf=0

LCMS: RT: 3.91 min; [M−1]=491.0

$^1$H NMR: (400 MHz, DMSO-d$_6$) δ 9.51 (s, 1H), 7.45-7.39 (m, 1.25H), 7.36-7.28 (m, 2H), 7.23 (s, 0.48H), 7.10 (m, 1H), 7.06-7.03 (m, 1H), 7.01 (m, 1H), 6.83 (m, 3H), 4.68 (s, 2H), 4.05 (s, 2H), 2.23 (s, 3H).

Example 67

Synthesis of 2-(3-bromo-4-((3'-(difluoromethoxy)-6-hydroxy-[1,1'-biphenyl]-3-yl) methyl)-5-methylphenoxy)-N-methylacetamide (Compound 67)

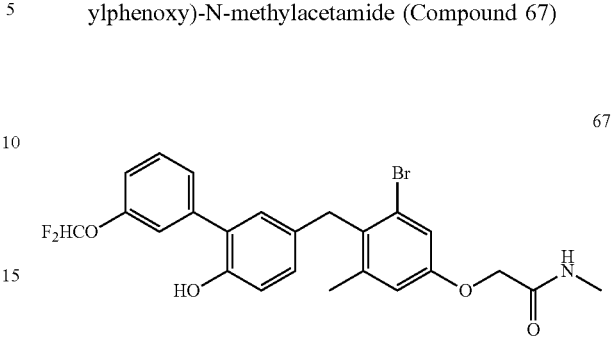

To a solution of Compound 66 (80 mg, 0.16 mmol) in DCM (15 mL) were added oxalyl chloride (62 mg, 0.48 mmol) and DMF (cat.). After stirring at rt for 1 h, the reaction mixture was concentrated in vacuo. The residue was dissolved in DCM (5 mL), and methylamine/THF (1M, 1.6 mL) was added. After stirring at room temperature for 2 h, the mixture was poured into water (20 mL) and was extracted with DCM (30 mL*3). The combined organic phase was washed with brine (30 mL), dried over Na$_2$SO$_4$, concentrated in vacuo and purified by Prep-TLC to afford Compound 67 (53 mg, 64% yield) as a white solid.

TLC: EtOAc/pet.ether=1/1 (v/v), Rf=0.3

LCMS: RT=3.86 min; [M−1]=504.0

$^1$H NMR: (400 MHz, DMSO) δ 9.51 (s, 1H), 8.02 (d, J=5.1 Hz, 1H), 7.43 (m, 1H), 7.35-7.27 (m, 2H), 7.24 (s, 0.54H), 7.13-7.04 (m, 2.47H), 7.02-6.98 (m, 1H), 6.86 (m, 3H), 4.46 (s, 2H), 4.05 (s, 2H), 2.65 (d, J=4.6 Hz, 3H), 2.23 (s, 3H).

Example 68

Synthesis of 2-(3-bromo-4-((3'-(difluoromethoxy)-6-hydroxy-[1,1'-biphenyl]-3-yl) methyl)-5-methylphenoxy)-1-(pyrrolidin-1-yl)ethan-1-one (Compound 68)

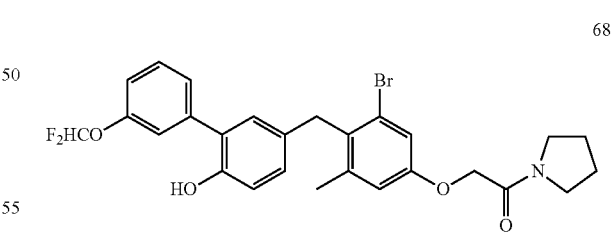

To a solution of Compound 66 (80 mg, 0.16 mmol) in DCM (10 mL) were added oxalyl chloride (62 mg, 0.48 mmol) and DMF (cat.). After stirring at rt for 1 h, the reaction mixture was concentrated in vacuo. The residue was dissolved in DCM (5 mL) and the solution was added dropwise to a mixture of Na$_2$CO$_3$ (52 mg, 0.48 mmol) and pyrrolidine (11 mg, 0.16 mmol) in DCM (10 mL). The reaction was stirred at rt for 1 h, then poured into water (20 mL) and extracted with DCM (10 mL*3). The combined organic phase was washed with brine (20 mL), dried over Na$_2$SO$_4$, concentrated in vacuo and purified by Prep-TLC (pet. ether/EtOAc=1:1) to afford Compound 68 (60 mg, 67% yield) as a white solid.

TLC: EtOAc/pet. ether=1/1 (v/v), Rf=0.2

LCMS: RT=4.08 min; [M−1]=544.1

$^1$H NMR: (400 MHz, DMSO) δ 9.51 (s, 1H), 7.42 (m, 1.34H), 7.36-7.27 (m, 2.27H), 7.24 (s, 0.24H), 7.11-7.04 (m, 2H), 7.00 (s, 1H), 6.83 (s, 3H), 4.72 (s, 2H), 4.04 (s, 2H), 3.48-3.40 (m, 2H), 3.29 (s, 1H), 2.22 (s, 3H), 1.94-1.83 (m, 2H), 1.81-1.72 (m, 2H).

Example 69

Synthesis of methyl 2-(3,5-dichloro-4-(3-(4-fluorobenzyl)-4-hydroxybenzyl)phenoxy) acetate (Compound 69)

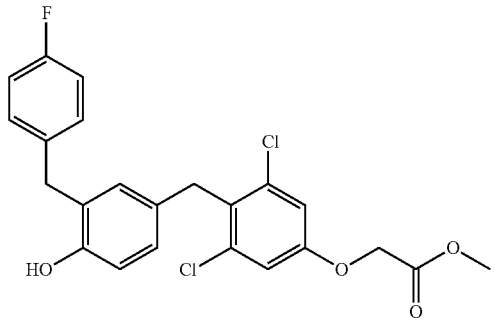

To a solution of Intermediate A6 (300 mg, 0.88 mmol) in 1,2-dichloroethane (5 mL) at rt were added ZnCl$_2$ (1N/hexane)(1.76 mmol, 1.8 mL) and 4-fluorobenzyl chloride (166 mg, 0.88 mmol). The reaction was heated to 90° C. overnight. The reaction mixture was cooled to rt, quenched with water (20 mL), and extracted with DCM (20 mL*2). The combined organic phase was washed with water (2*10 mL), and brine (2*10 mL), dried over Na$_2$SO$_4$ and concentrated in vacuo. The crude product was purified by prep-TLC (pet. ether/EtOAc=3/1) to afford Compound 69 (60 mg, 0.15 mmol, 43% yield) as a brown liquid.

TLC: Pet. ether/EtOAc=⅓ (v/v), Rf=0.5

Example 70

Synthesis of 2-(3,5-dichloro-4-(3-(4-fluorobenzyl)-4-hydroxybenzyl)phenoxy)acetic Acid (Compound 70)

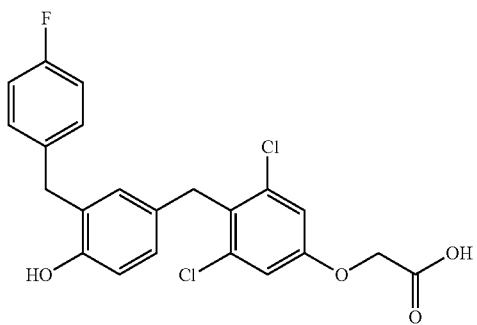

To a solution of Compound 69 (100 mg, 0.22 mmol) in THF (5 mL) was added LiOH.H$_2$O (46 mg, 1.1 mmol) in water (1 mL). The reaction was stirred at rt for 1 h. Water (10 mL) was added, and the pH was adjusted to pH~6 with HCl (1N). The mixture was extracted with EtOAc (10 mL*2); the combined organic phase was washed with brine (10 mL), dried over Na$_2$SO$_4$ and concentrated in vacuo. The crude product was purified through prep-HPLC (ACN/water range from 15/85 to 75/25) to afford Compound 70 (25 mg, 0.057 mmol, 26% yield) as a gray solid.

TLC: Pet. ether/EtOAc=1/1 (v/v), Rf=0.1

$^1$H NMR: (400 MHz, DMSO-d$_6$) δ 9.36 (s, 1H), 7.18 (dd, J=8.5, 5.6 Hz, 2H), 7.05 (t, J=8.9 Hz, 2H), 7.00 (s, 2H), 6.85 (s, 1H), 6.72 (s, 2H), 4.51 (s, 2H), 3.98 (s, 2H), 3.78 (s, 2H).

Example 71

Synthesis of 2-(3,5-dichloro-4-(3-(4-fluorobenzyl)-4-hydroxybenzyl)phenoxy)-N-methylacetamide (Compound 71)

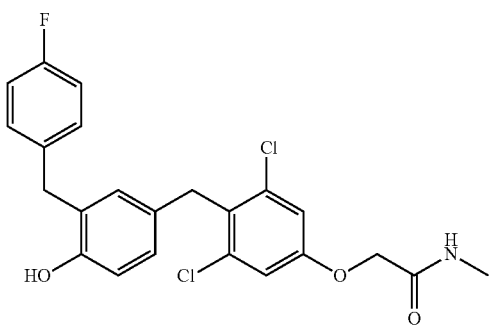

To a solution of Compound 69 (100 mg, 223 umol) in THF (5 mL) at rt was added methylamine (40% in H$_2$O) (8 mL). The mixture was stirred in a sealed tube at 65° C. overnight. The mixture was diluted with water (10 mL) and extracted with EtOAc (5 mL*3). The combined organic phase was washed with brine (10 mL), dried over Na$_2$SO$_4$, and concentrated in vacuo. The crude product was purified by Prep-TLC (pet. ether/EtOAc=1/1) to afford Compound 71 (80 mg, 80% yield) as an off-white solid.

TLC: EtOAc/pet. ether=1/1 (v/v), R$_f$=0.39

LCMS: RT=2.039 min; [M−1]=446.

$^1$H NMR: (400 MHz, DMSO-d$_6$) δ 9.27 (s, 1H), 8.06 (d, J=5.3 Hz, 1H), 7.21-7.15 (m, 2H), 7.11 (s, 2H), 7.05 (m, 2H), 6.85 (d, J=2.1 Hz, 1H), 6.73 (dd, J=8.3, 2.2 Hz, 1H), 6.68 (d, J=8.2 Hz, 1H), 4.53 (s, 2H), 4.00 (s, 2H), 3.78 (s, 2H), 2.65 (d, J=4.6 Hz, 3H).

Example 72

Synthesis of methyl 2-(3,5-dichloro-4-(3-(1-(4-fluorophenyl)ethyl)-4-hydroxybenzyl)phenoxy)acetate (Compound 72)

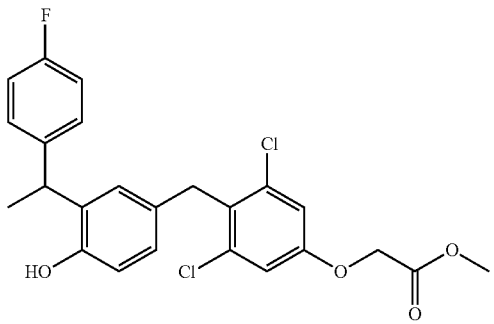

To a solution of Intermediate D1 (2.6 g, 7.62 mmol) in DCE (50 mL) at rt were added Intermediate A6 (806 mg, 5.08 mmol) and ZnCl₂ (10 mL, 10.2 mmol). The reaction was heated to 85° C. and stirred overnight. The reaction mixture was cooled to rt, diluted with DCM (20 mL), washed with brine (2*10 mL), dried over Na₂SO₄, and concentrated in vacuo. The crude product was purified by silica gel column chromatography (EtOAc/pet. ether=1/10) to afford Compound 72 (1.2 g, 50% yield) as a colorless oil.

TLC: Pet. ether/EtOAc=5/1 (v/v), Rf=0.55

LCMS: RT=4.47 min; [M−1]=462.1

¹H NMR: (400 MHz, DMSO-d₆) δ 9.24 (s, 1H), 7.21-7.19 (m, 2H), 7.12 (s, 2H), 7.05 (t, J=8.8 Hz, 2H), 6.96 (d, J=2.2 Hz, 1H), 6.70 (dd, J=2.4, 8.4 Hz, 1H), 6.65 (d, J=8.2 Hz, 1H), 4.89 (s, 2H), 4.37-4.39 (m, 1H), 4.02 (d, J=3.2 Hz, 2H), 3.70 (s, 3H), 1.44 (d, J=7.2 Hz, 3H).

Example 73

Synthesis of 2-(3,5-dichloro-4-(3-(1-(4-fluorophenyl)ethyl)-4-hydroxybenzyl)phenoxy) acetic Acid (Compound 73)

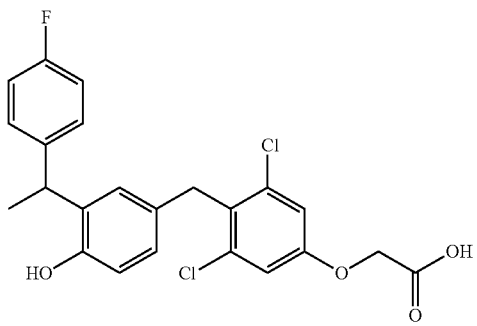

To a solution of Compound 72 (100 mg, 0.22 mmol) in THF/H₂O (4/1 mL) at rt was added NaOH (17.2 mg, 432 umol). The mixture was stirred for 4 h, then diluted with water (15 mL). 1N HCl was added to adjust to pH~3-4. The mixture was extracted with EtOAc (10 mL*3). The combined organic phase was washed with brine (20 mL), dried over Na₂SO₄ and concentrated in vacuo to afford Compound 73 (20 mg, 45 umol, 20.6% yield) as a white solid.

TLC: DCM/MeOH=10/1 (v/v), Rf=0.21

¹H NMR: (400 MHz, DMSO-d₆) δ 13.10 (s, 1H), 9.21 (s, 1H), 7.21-7.19 (m, 2H), 7.08 (s, 2H), 7.07-7.02 (m, 2H), 6.96 (d, J=2.2 Hz, 1H), 6.70 (dd, J=2.2, 8.2 Hz, 1H), 6.64 (d, J=8.2 Hz, 1H), 4.76 (s, 2H), 4.37-4.39 (m, 1H), 4.01 (d, J=3.4 Hz, 2H), 1.44 (d, J=7.2 Hz, 3H).

Example 74

Synthesis of (S)-2-(3,5-dichloro-4-(3-(1-(4-fluorophenyl)ethyl)-4-hydroxybenzyl) phenoxy)acetic Acid (Compound 74)

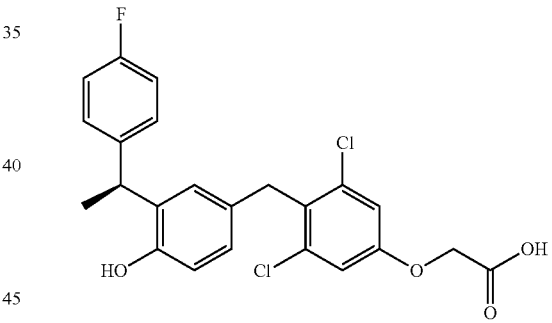

To a solution of Compound 72 (1.2 g, 2.58 mmol) in TH (3 mL)/Water (20 mL) at rt was added LiOH.H₂O (326 mg, 7.74 mmol). The mixture was stirred at rt for 1 h. The reaction was acidified to pH~3-4 with 2N HCl, and concentrated in vacuo to give crude Compound 73. Compound 73 was purified by chiral HPLC (chiral HPLC preparative conditions: column: Superchiral S-AD (Chiralway Biotech) 21×250 mm, 5 μm, temperature: 35° C., wave length: 220 nm, mobile phase: isocratic hexane/EtOH/fomic acid=70:30:0.05, flow rate: 15 ml/min; chiral HPLC analytical conditions: Superchiral S-AD (Chiralway Biotech) 4.6×150 mm, 5 μm, temperature: 35° C., wave length: 220 nm, mobile phase: isocratic hexane/EtOH/formic acid=70:30:0.05, flow rate: 0.9 ml/min) to afford Compound 74 (380 mg, 32% yield) as the early-eluting peak (analytical chiral HPLC peak 1 ret. time: 3.4 min, >98% ee).

Example 75

Synthesis of (R)-2-(3,5-dichloro-4-(3-(1-(4-fluorophenyl)ethyl)-4-hydroxybenzyl) phenoxy)acetic Acid (Compound 75)

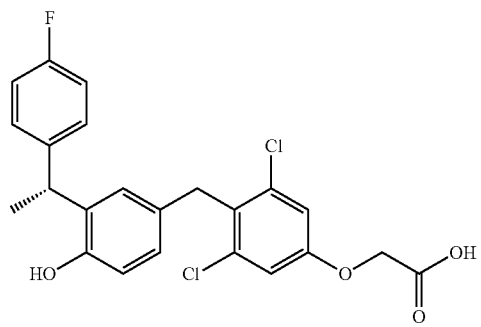

Compound 75 (380 mg, 32% yield) was isolated from the above chiral hplc purification of Compound 73 as the late-eluting peak (analytical chiral HPLC peak 2 ret. time: 5.2 min, >98% ee).

Example 76

Synthesis of methyl (R)-2-(3,5-dichloro-4-(3-(1-(4-fluorophenyl)ethyl)-4-hydroxybenzyl)phenoxy)acetate (Compound 76)

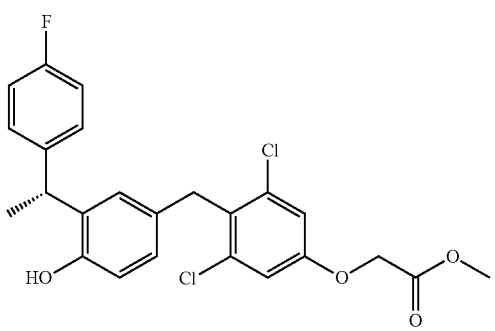

To a solution of Compound 75 (100 mg, 0.22 mmol) in MeOH (5 mL) at rt was added thionyl chloride (52 mg, 0.44 mmol); the mixture was stirred at 80° C. for 1 h. The reaction was concentrated in vacuo to afford Compound 76 (101 mg, 100% yield).

TLC: Pet. ether/EtOAc=1/1 (v/v), Rf=0.1
LCMS: RT=3.01 min; [M−1]=461.0

Example 77

Synthesis of (R)-2-(3,5-dichloro-4-(3-(1-(4-fluorophenyl)ethyl)-4-hydroxybenzyl) phenoxy)-N-methylacetamide (Compound 77)

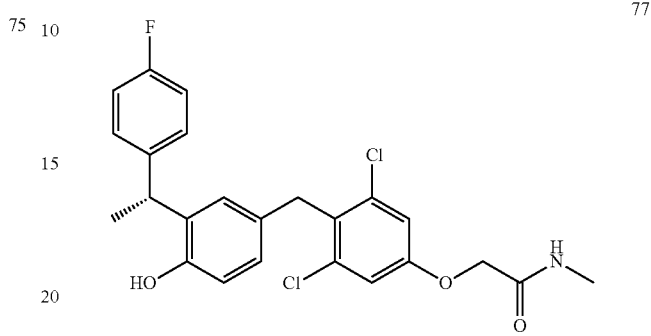

To a solution of Compound 76 (103 mg, 0.23 mmol) in THF (1 mL) at rt was added aqueous methylamine (1M, 4.45 mL). The resultant mixture was stirred at 75° C. for 16 h. The reaction was concentrated and purified by silica gel column chromatography (pet. ether/EtOAc=2/1) to afford Compound 77 (60 mg, 57% yield).

TLC: Pet. ether/EtOAc=1/1 (v/v), Rf=0.2
LCMS: (RT=2.23 min; [M−1]=459.9)
$^1$H NMR: (400 MHz, DMSO) δ 9.22 (s, 1H), 8.05 (d, J=5.1 Hz, 1H), 7.22-7.16 (m, 2H), 7.12 (s, 2H), 7.09-7.02 (m, 2H), 6.96 (d, J=2.2 Hz, 1H), 6.71 (m, 1H), 6.64 (d, J=8.2 Hz, 1H), 4.53 (s, 2H), 4.38 (m, 1H), 4.07-3.96 (m, 2H), 2.65 (d, J=4.7 Hz, 3H), 1.45 (d, J=7.3 Hz, 3H).

Example 78

Synthesis of (R)-2-(3,5-dichloro-4-(3-(1-(4-fluorophenyl)ethyl)-4-hydroxybenzyl) phenoxy)-N,N-dimethylacetamide (Compound 78)

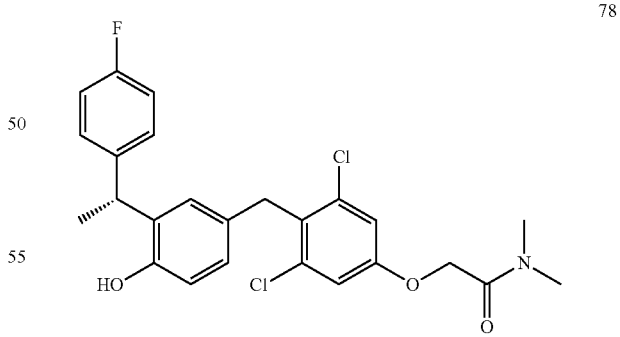

To a solution of Compound 76 (103 mg, 0.23 mmol) in THF (5 mL) at rt was added dimethylamine/THF (1M, 3.58 mL). The resultant mixture was stirred at 75° C. for 16 h. The reaction was concentrated and purified by Prep-TLC (pet. ether/EtOAc=1/1) to afford Compound 78 (4 mg, 4% yield).

TLC: Pet. ether/EtOAc=1/1 (v/v), Rf=0.2
LCMS: RT=2.45 min; [M−1]=474.0)

$^1$H NMR: (400 MHz, DMSO) δ 9.21 (s, 1H), 7.23-7.15 (m, 2H), 7.05 (m, 4H), 6.97 (d, J=2.2 Hz, 1H), 6.71 (m, 1H), 6.64 (d, J=8.2 Hz, 1H), 4.90 (s, 2H), 4.38 (d, J=7.2 Hz, 1H), 4.01 (d, J=3.8 Hz, 2H), 2.97 (s, 3H), 2.84 (s, 3H), 1.45 (d, J=7.3 Hz, 3H).

Example 79

Synthesis of methyl 2-(3,5-dichloro-4-(3-(4-cyanobenzyl)-4-hydroxybenzyl)phenoxy) acetate (Compound 79)

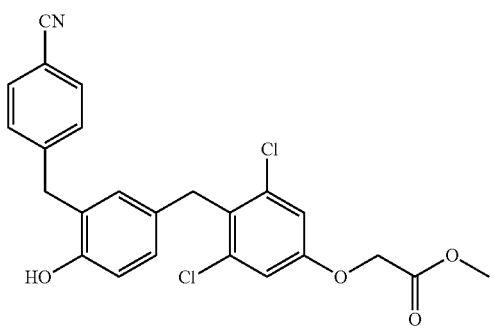

To a solution of Intermediate C5 (443 mg, 2.2 mmol) and Intermediate A6 (200 mg, 0.71 mmol) in DCE (6 mL) was added ZnCl$_2$ (1M in THF) (1.8 mmol). The mixture was stirred at 85° C. for 3 h. Water (5 mL) was added, and the resultant mixture was extracted with DCM (3 mL*3). The combined organic phase was washed with brine, dried over Na$_2$SO$_4$, concentrated in vacuo and purified by Prep-TLC (pet. ether/EtOAc=3/1). The product was washed with MeOH to afford Compound 79 (70 mg, 22% yield) as a white solid.

TLC: EtOAc/pet. ether=⅕ (v/v), R$_f$=0.2
$^1$H NMR: (400 MHz, DMSO-d$_6$) δ 9.35 (s, 1H), 7.71 (d, J=8.0 Hz, 2H), 7.35 (d, J=8.0 Hz, 2H), 7.13 (s, 2H), 6.89 (s, 1H), 6.76 (dd, J=8.4, 2.0 Hz, 1H), 6.70 (d, J=8.3 Hz, 1H), 4.89 (s, 2H), 4.01 (s, 2H), 3.89 (s, 2H), 3.70 (s, 3H).

Example 80

Synthesis of 2-(3,5-dichloro-4-(3-(4-cyanobenzyl)-4-hydroxybenzyl)phenoxy)acetic Acid (Compound 80)

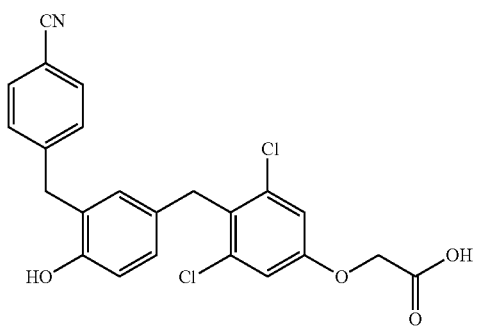

To a solution of Compound 79 (70 mg, 153 umol) in THF/H$_2$O (2 mL/0.5 mL) at rt was added LiOH (20 mg, 461 umol). The mixture was stirred at rt for 2 h. The mixture was diluted with water (5 mL), acidified with 1N HCl to pH~5-6 and extracted with EtOAc (3 mL*3). The combined organic phase was washed with brine (5 mL), dried over Na$_2$SO$_4$, and concentrated in vacuo. The crude product was purified by Prep-TLC (DCM/MeOH=10/1) to afford Compound 80 (60 mg, 89% yield) as a white solid.

TLC: MeOH/DCM=1/10 (v/v), Rf=0.25
LCMS: RT=3.86 min; [M−1]=439.8
$^1$H NMR: (400 MHz, DMSO) δ 9.36 (s, 1H), 7.71 (d, J=8.2 Hz, 1H), 7.35 (d, J=8.0 Hz, 1H), 7.06 (s, 1H), 6.90 (s, 1H), 6.79-6.74 (m, 1H), 6.70 (d, J=8.2 Hz, 1H), 4.70 (s, 1H), 4.01 (s, 1H), 3.89 (s, 1H).

Example 81

Synthesis of methyl 2-(3,5-dichloro-4-(4-hydroxy-3-(pyridin-4-ylmethyl)benzyl) phenoxy)acetate (Compound 81)

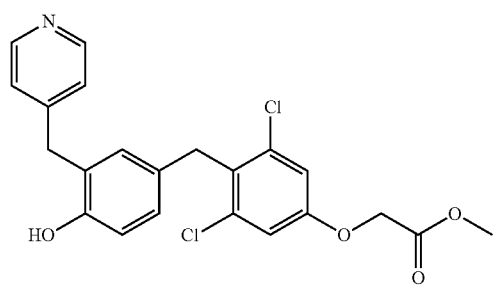

To a solution of Intermediate C7 (200 mg, 0.74 mmol) and Intermediate A10 (411 mg, 2.22 mmol) in DCE (8 mL) at rt was added ZnCl$_2$ (1.9 mL, 1.85 mmol). The mixture was heated to 85° C. overnight. The reaction mixture was cooled to rt and DCM (10 mL) was added. The mixture was washed with water (2*10 mL), and brine (2*10 mL), dried over Na$_2$SO$_4$ and concentrated in vacuo. The residue was washed with MeOH to afford Compound 81 (40 mg, 12% yield) as a white solid.

TLC: MeOH/DCM=1/15 (v/v), Rf=0.6
$^1$H NMR: (400 MHz, DMSO-d$_6$) δ 9.34 (s, 1H), 8.40 (d, J=5.4 Hz, 2H), 7.15 (d, J=5.4 Hz, 2H), 7.13 (s, 2H), 6.90 (d, J=2.2 Hz, 1H), 6.77 (d, J=8.4 Hz, 1H), 6.71 (d, J=8.2 Hz, 1H), 4.89 (s, 2H), 4.02 (s, 2H), 3.82 (s, 2H), 3.70 (s, 3H).

Example 82

Synthesis of 2-(3,5-dichloro-4-(4-hydroxy-3-(pyridin-4-ylmethyl)benzyl)phenoxy) acetic Acid (Compound 82)

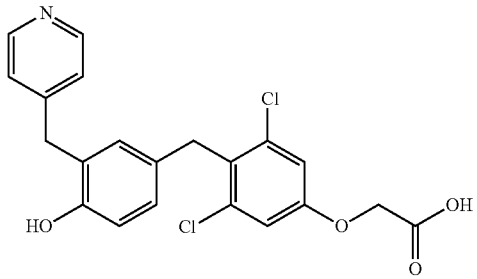

To a solution of Compound 81 (40 mg, 0.09 mmol) in THF (5 mL) and H$_2$O (0.5 mL) was added LiOH.H$_2$O (12 mg, 0.27 mmol). The mixture was stirred at rt for 1 h; water (5 mL) was added, the mixture was adjusted to pH~5-6 with HCl (1N) and extracted with EtOAc (10 mL*2). The combined organic phase was washed with brine (20 mL), dried over Na$_2$SO$_4$, and concentrated in vacuo to afford Compound 82 (30 mg, 77% yield) as a white solid.

TLC: MeOH/DCM=1/15 (v/v), Rf=0.1

LCMS: RT=2.518 min; [M−1]=416

$^1$H NMR: (400 MHz, DMSO-d$_6$) δ 9.40 (s, 1H), 8.46 (d, J=5.0 Hz, 2H), 7.24 (s, 2H), 7.09 (s, 2H), 6.92 (s, 1H), 6.79-6.70 (m, 2H), 4.77 (s, 2H), 4.02 (s, 2H), 3.86 (s, 2H).

Example 83

Synthesis of methyl 2-(3,5-dichloro-4-(3-(2-fluorobenzyl)-4-hydroxybenzyl)phenoxy) acetate (Compound 83)

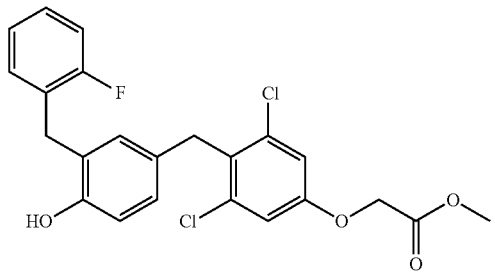

A mixture of Intermediate A6 (100 mg, 0.3 mmol), 2-fluorobenzyl chloride (52 mg, 0.36 mmol) and ZnCl$_2$ (1M in THF, 0.6 mL, 0.6 mmol) in DCE (3 mL) was stirred at 95° C. overnight. The mixture was diluted with DCM (10 mL), washed with water (10 mL) and brine (10 mL). The organic layer was dried over Na$_2$SO$_4$ and concentrated in vacuo. The residue was purified by Prep-HPLC to afford Intermediate 83 (30 mg, 22% yield) as a white solid.

TLC: Pet. ether/EtOAc=5/1 (v/v), Rf=0.4

LCMS: RT=2.998 min; [M−1]=447.7

Example 84

Synthesis of 2-(3,5-dichloro-4-(3-(2-fluorobenzyl)-4-hydroxybenzyl)phenoxy)acetic Acid (Compound 84)

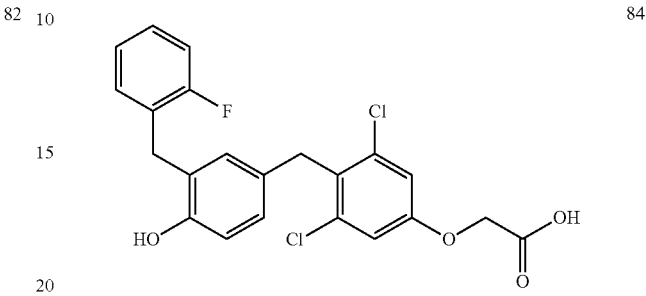

To a mixture of Intermediate 83 (30 mg, 0.07 mmol) in THF (2 mL) and water (1 mL) was added LiOH.H$_2$O (9 mg, 0.21 mmol). The mixture was stirred at rt for 2 h. The pH was adjusted to pH~4 with 1N HCl; the aqueous layer was extracted with EtOAc (20 mL*2). The combined organic layer was washed with brine (20 mL), dried over Na$_2$SO$_4$ and concentrated in vacuo. The residue was purified by Prep-HPLC to afford Compound 84 (14 mg, 47% yield) as a white solid.

TLC: DCM/MeOH=10/1 (v/v), Rf=0.1

LCMS: RT=3.974 min; [M−1]=432.8

$^1$H NMR: (400 MHz, DMSO-d$_6$) δ 9.37 (s, 1H), 7.22 (d, J=10.2 Hz, 1H), 7.13 (d, J=7.0 Hz, 2H), 7.08 (d, J=7.8 Hz, 1H), 6.99 (s, 2H), 6.77 (d, J=16.8 Hz, 2H), 6.70 (d, J=7.8 Hz, 1H), 4.54 (s, 2H), 3.97 (s, 2H), 3.80 (s, 2H).

Example 85

Synthesis of methyl 2-(3,5-dichloro-4-(3-(3-fluorobenzyl)-4-hydroxybenzyl)phenoxy) acetate (Compound 85)

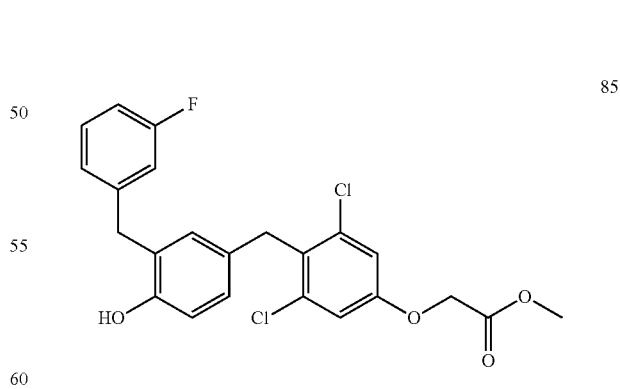

To a solution of 3-fluorobenzyl chloride (42 mg, 293 umol) in DCE (6 mL) at rt were added ZnCl$_2$ in THF (1 M, 6 mL) and Intermediate A6 (200 mg, 586 umol). The mixture was heated to reflux overnight. The mixture was diluted with DCM (5 mL), washed with brine (5 mL), dried over Na$_2$SO$_4$, and concentrated in vacuo. The crude product was purified by Prep-TLC (pet. ether/EtOAc=5/1) to afford Compound 85 (23 mg, 17% yield) as a colorless oil.

TLC: EtOAc/pet. ether=1/5 (v/v), Rf=0.36

$^1$H NMR: (400 MHz, DMSO-d$_6$) δ 9.30 (s, 1H), 7.28 (q, J=7.3 Hz, 1H), 7.12 (s, 2H), 7.01 (d, J=7.7 Hz, 1H), 6.96 (t, J=8.9 Hz, 2H), 6.89 (d, J=2.0 Hz, 1H), 6.77-6.73 (dd, J=8.4 Hz, 1.6 Hz, 1H), 6.70 (d, J=8.2 Hz, 1H), 4.88 (s, 2H), 4.01 (s, 2H), 3.82 (s, 2H), 3.70 (s, 3H).

Example 86

Synthesis of 2-(3,5-dichloro-4-(3-(3-fluorobenzyl)-4-hydroxybenzyl)phenoxy)acetic Acid (Compound 86)

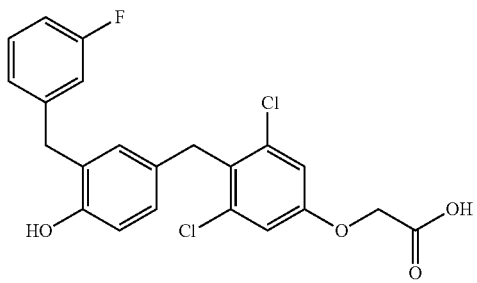

To a solution of Compound 85 (23 mg, 51.19 umol) in THF (3 mL) and water (1 mL) at rt was added LiOH (2 mg, 76.79 umol). The mixture was stirred at rt for 2 h. The mixture was diluted with water (3 mL), acidified with 1N HCl to pH~6-7, and extracted with EtOAc (3 mL*3). The combined organic phase was washed with brine (5 mL), dried over Na$_2$SO$_4$, and concentrated in vacuo to afford Compound 86 (15 mg, 68% yield) as a grey solid.

TLC: MeOH/DCM=1/10 (v/v), R$_f$=0.25

LCMS: RT=2.067 min; [M−1]=433.

$^1$H NMR: (400 MHz, DMSO-d$_6$) δ 9.38 (s, 1H), 7.28 (q, J=7.7 Hz, 1H), 7.01 (d, J=7.6 Hz, 1H), 6.99-6.92 (m, 2H), 6.89 (d, J=5.5 Hz, 3H), 6.72 (q, J=8.2 Hz, 2H), 4.19 (s, 2H), 3.98 (s, 2H), 3.82 (s, 2H).

Example 87

Synthesis of methyl 2-(3,5-dichloro-4-(3-(2,4-difluorobenzyl)-4-hydroxybenzyl) phenoxy)acetate (Compound 87)

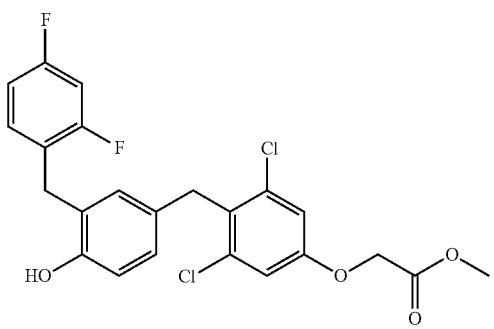

A mixture of 2,4-difluorobenzyl chloride (96 mg, 0.6 mmol), Intermediate A6 (200 mg, 0.6 mmol) and ZnCl$_2$ (1 M in THF) in DCE (5 mL) was stirred at 95° C. overnight. The mixture was cooled to rt, diluted with DCM (10 mL) and washed with water (10 mL). The combined organic layer was washed with brine (20 mL), dried over Na$_2$SO$_4$ and concentrated in vacuo. The residue was purified by Prep-HPLC to afford Compound 87 (20 mg, 7% yield) as a white solid.

TLC: Pet. ether/EtOAc=5/1 (v/v), Rf=0.4

LCMS: RT=3.360 min; [M−1]=464.8

Example 88

Synthesis of 2-(3,5-dichloro-4-(3-(2,4-difluorobenzyl)-4-hydroxybenzyl)phenoxy)acetic Acid (Compound 88)

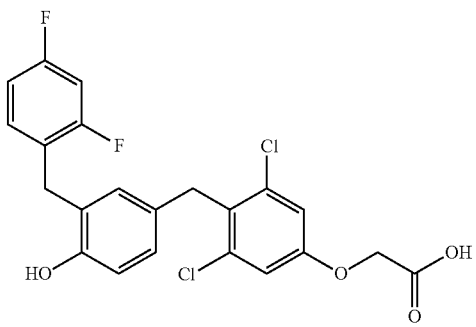

To a solution of Compound 87 (20 mg, 0.04 mmol) in THF (2 mL) and water (1 mL) was added LiOH.H$_2$O (5 mg, 0.12 mmol). The mixture was stirred at rt for 2 h, then adjusted to pH~4 with 1N HCl and extracted with EtOAc (20 mL*2). The combined organic layer was washed with brine (20 mL), dried over Na$_2$SO$_4$ and concentrated in vacuo. The residue was purified by Prep-HPLC to afford Compound 88 (5 mg, 28% yield) as a white solid.

TLC: DCM/MeOH=10/1 (v/v), Rf=0.1

LCMS: RT=3.992 min; [M−1]=450.8

$^1$H NMR: (400 MHz, DMSO-d$_6$) δ 9.35 (s, 1H), 7.20-7.13 (dd, J$_1$=16.4 Hz, J$_2$=19.2 Hz, 2H), 7.06 (s, 2H), 6.97 (t, J=7.6 Hz, 1H), 6.77 (d, J=8.0 Hz, 2H), 6.70 (d, J=7.6 Hz, 1H), 4.74 (s, 2H), 3.98 (s, 2H), 3.77 (s, 2H).

Example 89

Synthesis of methyl 2-(3,5-dichloro-4-(3-(4-chlorobenzyl)-4-hydroxybenzyl)phenoxy) acetate (Compound 89)

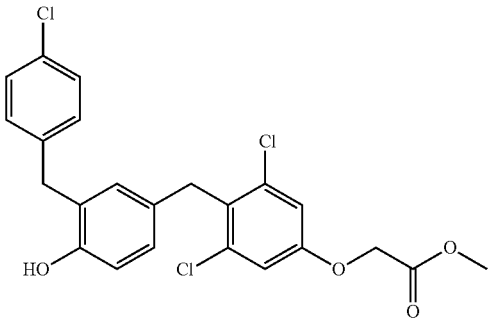

89

To a solution of 4-chlorobenzyl chloride (95 mg, 586 umol) in DCE (5 mL) at rt were added ZnCl$_2$ in THF (1M, 1.17 mL) and Intermediate A6 (200 mg, 586 umol). The mixture was heated to reflux overnight. The mixture was diluted with DCM (5 mL). The combined organic phase was washed with brine (5 mL), dried over Na$_2$SO$_4$, and concentrated in vacuo. The crude product was purified by Prep-TLC (pet. ether/EtOAc=5/1) to afford Compound 89 (30 mg, 11% yield) as a white solid.

TLC: EtOAc/pet. ether=⅕ (v/v), Rf=0.36

$^1$H NMR: (400 MHz, DMSO-d$_6$) δ 9.28 (s, 1H), 7.29 (d, J=8.3 Hz, 2H), 7.18 (d, J=8.4 Hz, 2H), 7.12 (s, 2H), 6.87-6.85 (m, 1H), 6.74 (dd, J=8.3, 1.9 Hz, 1H), 6.69 (d, J=8.2 Hz, 1H), 4.89 (s, 2H), 4.01 (s, 2H), 3.79 (s, 2H), 3.70 (s, 3H).

Example 90

Synthesis of 2-(3,5-dichloro-4-(3-(4-chlorobenzyl)-4-hydroxybenzyl)phenoxy)acetic Acid (Compound 90)

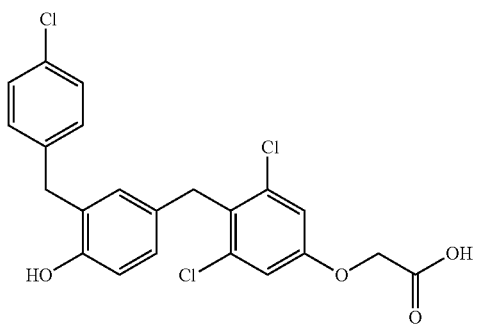

90

To a solution of Compound 89 (30 mg, 64 umol) in THF (2 mL) and water (1 mL) at rt was added LiOH (3 mg, 97 umol). The mixture was stirred at rt for 2 h, diluted with water (5 mL), acidified with 1N HCl to pH~6-7, then extracted with EtOAc (5 mL*2). The combined organic phase was washed with brine (5 mL), dried over Na$_2$SO$_4$, and concentrated in vacuo to afford Compound 90 (20 mg, 69% yield) as a white solid.

TLC: MeOH/DCM=1/10 (v/v), Rf=0.25

LCMS: RT=2.515 min; [M−1]=449.

$^1$H NMR: (400 MHz, DMSO-d$_6$) δ 9.43 (s, 1H), 7.32-7.25 (m, 2H), 7.22-7.15 (m, 2H), 6.88 (m, 3H), 6.75-6.67 (m, 2H), 4.20 (s, 2H), 3.97 (s, 2H), 3.78 (s, 2H).

Example 91

Synthesis of methyl 2-(3,5-dichloro-4-(4-hydroxy-3-(4-methylbenzyl)benzyl)phenoxy) acetate (Compound 91)

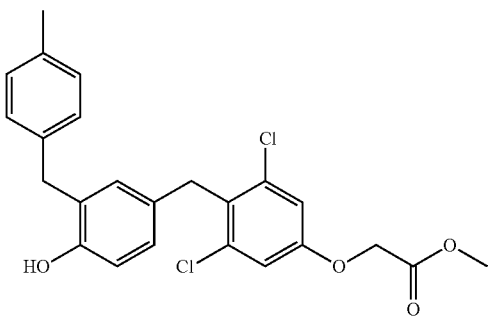

91

To a solution of 4-methylbenzyl chloride (83 mg, 586 umol) in DCE (5 mL) at rt were added ZnCl$_2$ in THF (1 M, 1.17 mL) and Intermediate A6 (200 mg, 586 umol). The mixture was heated to reflux overnight. The mixture was diluted with DCM (5 mL). The combined organic phase was washed with brine (5 mL), dried over Na$_2$SO$_4$, and concentrated in vacuo. The crude product was purified by Prep-TLC (pet. ether/EtOAc=5/1) to afford Compound 91 (40 mg, 16% yield) as a colorless oil.

TLC: EtOAc/pet. ether=⅕ (v/v), Rf=0.31

$^1$H NMR: (400 MHz, DMSO-d$_6$) δ 9.19 (s, 1H), 7.12 (s, 2H), 7.04 (s, 4H), 6.84 (s, 1H), 6.73-6.69 (m, 1H), 6.67 (d, J=8.3 Hz, 1H), 4.89 (s, 2H), 3.99 (s, 2H), 3.74 (s, 2H), 3.70 (s, 3H), 2.23 (s, 3H).

Example 92

Synthesis of 2-(3,5-dichloro-4-(4-hydroxy-3-(4-methylbenzyl)benzyl)phenoxy)acetic Acid (Compound 92)

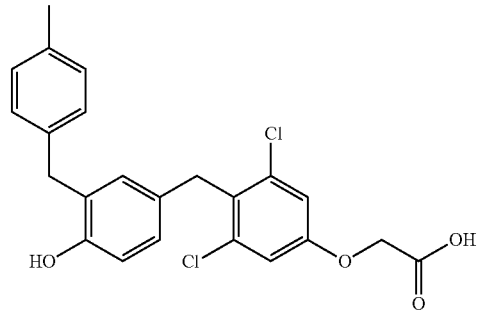

92

To a solution of Compound 91 (17 mg, 38 umol) in THF (3 mL) and water (1 mL) at rt was added LiOH (1.4 mg, 57 umol). The mixture was stirred at rt for 2 h. The mixture was diluted with water (3 mL), acidified with 1N HCl to pH~6-7, and extracted with EtOAc (3 mL*3). The combined organic phase was washed with brine (5 mL), dried over $Na_2SO_4$, and concentrated in vacuo to afford Compound 92 (15 mg, 91% yield) as a grey solid.

TLC: MeOH/DCM=1/10 (v/v), $R_f$=0.25
LCMS: RT=2.296 min; [M−1]=429.
$^1$H NMR: (400 MHz, DMSO-$d_6$) δ 9.33 (s, 1H), 7.04 (d, J=1.4 Hz, 4H), 6.89-6.83 (m, 3H), 6.68 (d, J=1.7 Hz, 2H), 4.16 (s, 2H), 3.96 (s, 2H), 3.74 (s, 2H), 2.23 (s, 3H).

Example 93

Synthesis of methyl 2-(3,5-dichloro-4-(4-hydroxy-3-(pyrimidin-5-ylmethyl)benzyl) phenoxy)acetate (Compound 93)

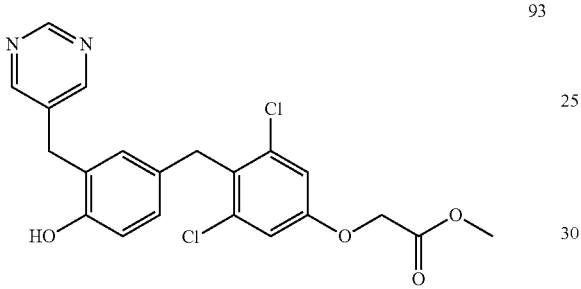

To a solution of Intermediate C10 (197 mg, 1.05 mmol) in DCE (10 mL) at rt were added Intermediate A6 (100 mg, 0.35 mmol) and $ZnCl_2$/THF (1M, 0.87 mL). The reaction was heated to 100° C. for 2 days. The mixture was cooled to rt and diluted with DCM (20 mL); the resultant mixture was washed with brine (2*10 mL). The organic phase was dried over $Na_2SO_4$ and concentrated in vacuo. The crude product was purified by Prep-TLC (EtOAc/pet. ether-1/3) to afford Compound 93 (150 mg, 20% purity) as a light yellow oil.

TLC: Pet. ether/EtOAc=1/5 (v/v), Rf=0.4
LCMS: RT=3.53 min; [M−1]=432.0

Example 94

Synthesis of 2-(3,5-dichloro-4-(4-hydroxy-3-(pyrimidin-5-ylmethyl)benzyl)phenoxy) acetic Acid (Compound 94)

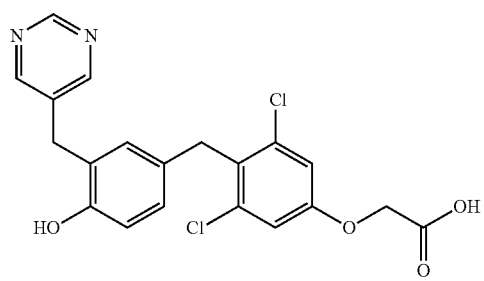

To a solution of Compound 93 (150 mg, 0.35 umol) in THF/water (2/1 mL) at rt was added $LiOH.H_2O$ (30 mg, 0.70 mmol). The mixture was stirred at rt for 1 h. The reaction mixture was acidified to pH~3-4 with 2N HCl, concentrated in vacuo and purified by Prep-HPLC to afford Compound 94 (13 mg, 2.9% yield over 2 steps).

TLC: Pet. ether/EtOAc=1/5 (v/v), Rf=0
LCMS: RT=3.00 min; [M−1]=418.9
$^1$H NMR: (400 MHz, DMSO) δ 13.11 (s, 1H), 9.45 (s, 1H), 8.99 (s, 1H), 8.61 (s, 2H), 7.09 (s, 2H), 6.98 (d, J=2.2 Hz, 1H), 6.77 (m, 1H), 6.70 (d, J=8.2 Hz, 1H), 4.77 (s, 2H), 4.03 (s, 2H), 3.83 (s, 2H).

Example 95

Synthesis of methyl 2-(3,5-dichloro-4-(4-hydroxy-3-(4-(2,2,2-trifluoroethyl)benzyl) benzyl)phenoxy) acetate (Compound 95)

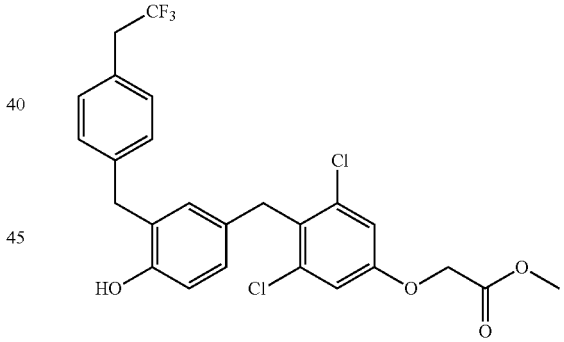

To a solution of Intermediate C13 (100 mg, 479 umol) and Intermediate A6 (327 mg, 958 umol) in chlorobenzene (5 mL) was added $ZnCl_2$ (1.2 mmol, 1.20 mL). The mixture was stirred at 120° C. overnight. The mixture was concentrated to dryness, water (20 mL) was added and the resultant mixture was extracted with DCM (20 mL*2). The organic layer was dried over $Na_2SO_4$ and concentrated in vacuo to afford Compound 95 (200 mg, 16% yield, 20% purity), which was used without further purification.

TLC: EtOAc/pet. ether=1/5 (v/v), Rf=0.38

Example 96

Synthesis of 2-(3,5-dichloro-4-(4-hydroxy-3-(4-(2,2,2-trifluoroethyl)benzyl)benzyl) phenoxy)acetic Acid (Compound 96)

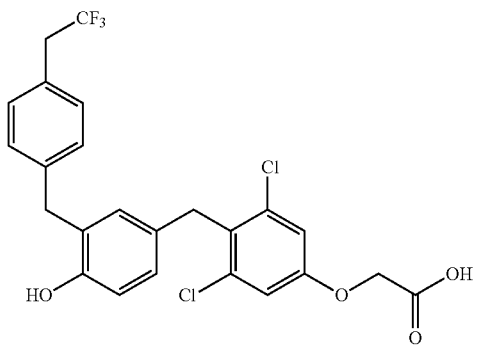

To a solution of Compound 95 (200 mg, 77.9 umol, 20% purity) in MeOH (3 mL) and Water (1 mL) was added LiOH.H$_2$O (16 mg, 389.6 umol). The mixture was stirred at rt for 2 h. Water (10 mL) was added and the mixture was acidified to pH~4-5 with 1N HCl. The mixture was extracted with DCM (10 mL*2). The organic layer was concentrated to dryness, then purified by Prep-TLC (DCM/MeOH=10/1) and Prep-HPLC to afford Compound 96 (30 mg, 77% yield) as a white solid.

TLC: EtOAc/pet. ether=1/5 (v/v), Rf=0

LCMS: RT=3.994 min; [M−1]=496.8/498.8

$^1$H NMR: (400 MHz, DMSO-d$_6$) δ 13.12 (s, 1H), 9.27 (s, 1H), 7.22 (d, J=7.9 Hz, 2H), 7.17 (d, J=8.0 Hz, 2H), 7.08 (s, 2H), 6.88 (d, J=2.1 Hz, 1H), 6.74 (dd, J=8.3, 2.2 Hz, 1H), 6.69 (d, J=8.2 Hz, 1H), 4.77 (s, 2H), 4.00 (s, 2H), 3.80 (s, 2H), 3.56 (q, J=11.6 Hz, 2H).

Example 97

Synthesis of methyl 2-(3,5-dichloro-4-(3-(1-(4-fluorophenyl)propyl)-4-hydroxybenzyl) phenoxy)acetate (Compound 97)

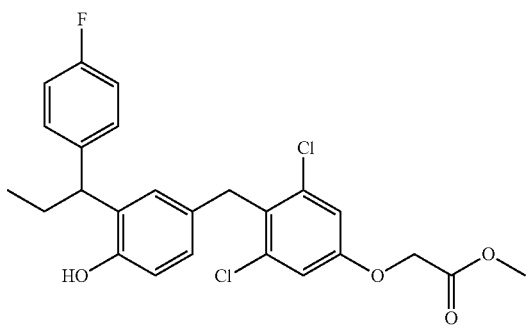

To a solution of Intermediate C15 (244 mg, 1.06 mmol) in DCE (2 mL) at rt were added Intermediate A10 (100 mg, 0.36 mmol) and ZnCl$_2$ (1.0 M in THF) (1.0 M, 0.9 mL). The mixture was heated to reflux overnight. The mixture was cooled to rt and diluted with DCM (5 mL); the organic phase was washed with brine (5 mL), dried over Na$_2$SO$_4$, and concentrated in vacuo. The crude product was purified by Prep-TLC (pet. ether/EtOAc=5/1) to afford compound 97 (52 mg, 30% yield) as a colorless oil.

TLC: EtOAc/pet. ether=1/5 (v/v), R$_f$=0.36

$^1$H NMR: (400 MHz, DMSO-d$_6$) δ 9.19 (s, 1H), 7.20 (ddd, J=8.2, 5.2, 2.3 Hz, 2H), 7.14 (s, 2H), 7.08-7.01 (m, 3H), 6.71 (dd, J=8.3, 2.2 Hz, 1H), 6.63 (d, J=8.3 Hz, 1H), 4.89 (s, 2H), 4.10 (t, J=7.9 Hz, 1H), 4.03 (s, 2H), 3.70 (s, 3H), 1.89 (td, J=7.5, 3.3 Hz, 2H), 0.78 (t, J=7.2 Hz, 3H).

Example 98

Synthesis of 2-(3,5-dichloro-4-(3-(1-(4-fluorophenyl)propyl)-4-hydroxybenzyl) phenoxy)acetic Acid (Compound 98)

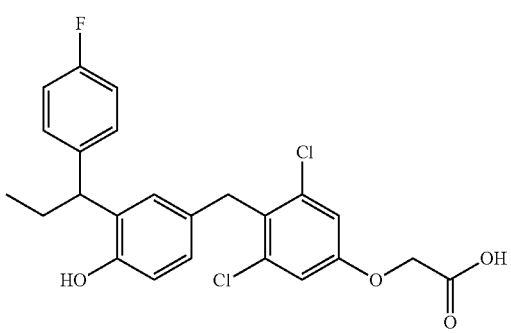

To a solution of Compound 97 (43 mg, 90 umol) in THF (2 mL) at rt was added LiOH.H$_2$O (7.5 mg, 180 umol) in water (1 mL). The mixture was stirred at rt for 2 h, diluted with water (10 mL), acidified with HCl (1N) to pH~3, and extracted with EtOAc (5 mL*3). The combined organic phase was washed with brine (10 mL), dried over Na$_2$SO$_4$, and concentrated in vacuo. The crude product was purified by Prep-HPLC to afford Compound 98 (10 mg, 23% yield) as an off-white solid.

TLC: DCM/MeOH=10/1 (v/v), R$_f$=0.39

LCMS: RT=2.543 min; [M−1]=461.

$^1$H NMR: (400 MHz, DMSO-d$_6$) δ 13.15 (s, 1H), 9.18 (s, 1H), 7.21 (t, J=7.1 Hz, 2H), 7.05 (dd, J=16.7, 7.2 Hz, 5H), 6.70 (d, J=8.1 Hz, 1H), 6.63 (d, J=8.3 Hz, 1H), 4.74 (s, 2H), 4.09 (d, J=8.7 Hz, 1H), 4.03 (s, 2H), 1.89 (s, 2H), 0.78 (t, J=7.2 Hz, 3H).

Example 99

Synthesis of 2-(3,5-dichloro-4-(3-(1-(4-fluorophenyl)propyl)-4-hydroxybenzyl) phenoxy)-N-methylacetamide (Compound 99)

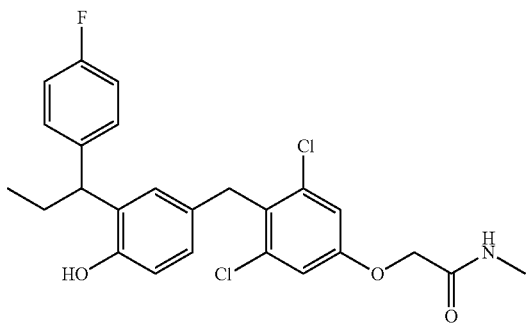

A solution of Compound 97 (150 mg, 305 umol) and aqueous methylamine (1 mL of 40%) in THF (5 mL) was stirred in sealed tube at 70° C. overnight. Water (30 mL) was added, and the mixture was extracted with EtOAc (25 mL*2). The combined organic layer was washed with water (20 mL*2), and brine (20 mL), dried over $Na_2SO_4$, concentrated in vacuo and purified by Prep-TLC (DCM/MeOH=20/1) to afford Compound 99 (50 mg, 34% yield) as a white solid.

TLC: EtOAc/pet. ether=⅕ (v/v), Rf=0.17

LCMS: RT=4.134 min; [M−1]=476.1

$^1$H NMR: (400 MHz, DMSO-$d_6$) δ 9.17 (s, 1H), 8.05 (d, J=6.4 Hz, 1H), 7.24-7.18 (m, 2H), 7.12 (s, 2H), 7.08-7.00 (m, 3H), 6.71 (dd, J=8.4, 2.4 Hz, 1H), 6.63 (d, J=8.4 Hz, 1H), 4.53 (s, 2H), 4.10 (t, J=7.9 Hz, 1H), 4.04 (s, 2H), 2.65 (d, J=4.8 Hz, 3H), 1.92-1.87 (m, 2H), 0.78 (t, J=7.2 Hz, 3H).

Example 100

Synthesis of 2-(3,5-dichloro-4-(3-(1-(4-fluorophenyl)propyl)-4-hydroxybenzyl) phenoxy)-N,N-dimethylacetamide (Compound 100)

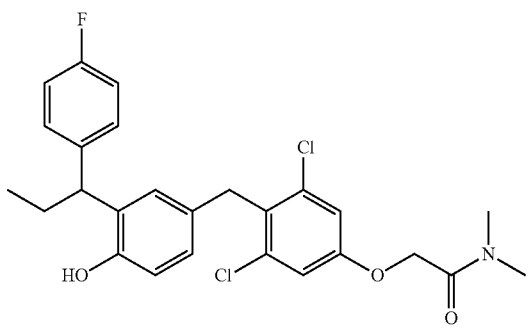

To a mixture of Compound 98 (130 mg, 281 umol) in DCM (5 mL) was added oxalyl chloride (107 mg, 842 umol). The mixture was stirred at rt for 2 h. The mixture was concentrated to dryness to afford the crude acid chloride (130 mg, 96% yield), which was combined with 2 mL of dimethylamine solution (2M in THF) and stirred at rt for 5 min. The mixture was concentrated to dryness. Water (30 mL) was added and the resultant mixture was extracted with EtOAc (15 mL*2). The combined organic layer was washed with brine (20 mL), dried over $Na_2SO_4$, concentrated in vacuo and purified by Prep-TLC (DCM/MeOH=20/1) and Prep-HPLC to afford Compound 100 (80 mg, 60% yield) as a white solid.

TLC: DCM/MeOH=20/1 (v/v), Rf=0.4

LCMS: RT=4.261 min; [M−1]=488.1

$^1$H NMR: (400 MHz, DMSO-$d_6$) δ 9.16 (s, 1H), 7.24-7.18 (m, 2H), 7.10-7.01 (m, 5H), 6.74-6.69 (m, 1H), 6.64 (d, J=8.4 Hz, 1H), 4.90 (s, 2H), 4.11 (t, J=8.0 Hz, 1H), 4.03 (s, 2H), 2.96 (s, 3H), 2.84 (s, 3H), 1.92-1.87 (m, 2H), 0.78 (t, J=7.2 Hz, 3H).

Example 101

Synthesis of methyl 2-(3,5-dichloro-4-(3-(1-(4-fluorophenyl)butyl)-4-hydroxybenzyl) phenoxy)acetate (Compound 101)

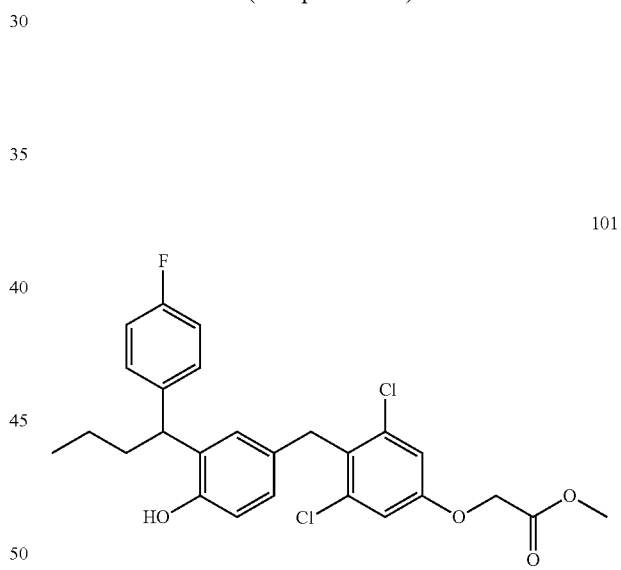

To a solution of Intermediate C17 (338 mg, 1.6 mmol) and Intermediate A10 (150 mg, 0.5 mmol) in DCE (5 mL) was added $ZnCl_2$ (1M, in THF) (1.3 mmol, 1.3 mL) The mixture was stirred at 85° C. overnight. Water (5 mL) was added and the mixture was extracted with DCM (3 mL*3). The combined organic phase was washed with brine, dried over $Na_2SO_4$, concentrated in vacuo and purified by Prep-TLC (EtOAc/pet. ether=1/10) to afford Compound 101 (55 mg, 22% yield) as a white solid.

TLC: EtOAc/pet. ether=⅕ (v/v), $R_f$=0.2

Example 102

Synthesis of 2-(3,5-dichloro-4-(3-(1-(4-fluorophenyl)butyl)-4-hydroxybenzyl)phenoxy) acetic Acid (Compound 102)

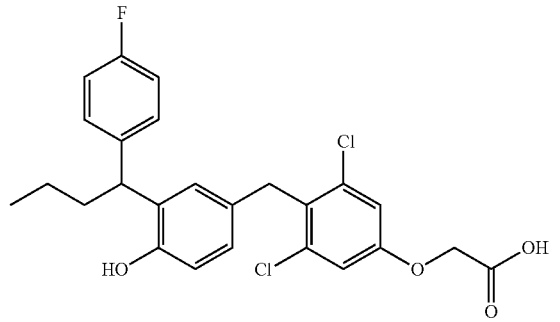

102

To a solution of Compound 101 (55 mg, 112 umol) in THF/H₂O (2 mL/0.5 mL) at rt was added LiOH (14 mg, 336 umol). The mixture was stirred at rt for 2 h; the mixture was quenched with water (5 mL), acidified with 1N HCl to pH~5-6 and extracted with EtOAc (3 mL*3). The combined organic phase was washed with brine (5 mL), dried over Na₂SO₄ and concentrated in vacuo. The crude product was purified by Prep-HPLC (MeCN/H₂O/TFA) to afford Compound 102 (45 mg, 85% yield) as a white solid.

TLC: MeOH/DCM=1/10 (v/v), Rf=0.30
LCMS: RT=4.338 min; [M-1]=474.9
¹H NMR: (400 MHz, DMSO) δ 9.24 (s, 1H), 7.21 (dd, J=6.0, 2.8 Hz, 2H), 7.05 (dd, J=4.8, 2.4 Hz, 2H), 7.03 (s, 2H), 7.02 (s, 1H), 6.70 (dd, J=8.4, 2.0 Hz, 1H), 6.64 (d, J=8.0 Hz, 1H), 4.60 (s, 2H), 4.23 (t, J=8.0 Hz, 1H), 4.02 (s, 2H), 1.92-1.78 (m, 2H), 1.15 (m, 2H), 0.84 (t, J=7.2 Hz, 3H).

Example 103

Synthesis of ethyl 2-(3,5-dichloro-4-(3-(1-(4-fluorophenyl)-2-methylpropyl)-4-hydroxybenzyl)phenoxy)acetate (Compound 103)

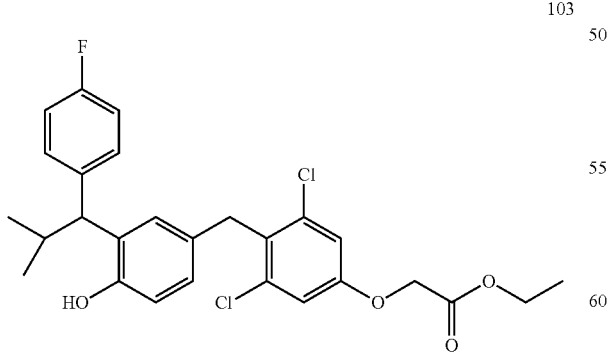

103

To a solution of Intermediate C19 (382 mg, 1.56 mmol) and Intermediate A12 (155 mg, 521 umol) in DCE (10 mL) was added ZnCl₂ (1.3 mmol, 1.30 mL of 1M in THF). The mixture was stirred at 90° C. overnight. The mixture was cooled to rt and concentrated to dryness, water (20 mL) was added, and the resultant mixture was extracted with DCM (20 mL*2). The organic layer was dried over Na₂SO₄, concentrated in vacuo, and purified by Prep-TLC (pet. ether/EtOAc=5/1) to afford Compound 103 (140 mg, 32% yield, 60% purity) as a white solid.

TLC: EtOAc/pet. ether=⅕ (v/v), Rf=0.38

Example 104

Synthesis of 2-(3,5-dichloro-4-(3-(1-(4-fluorophenyl)-2-methylpropyl)-4-hydroxybenzyl)phenoxy) acetic Acid (Compound 104)

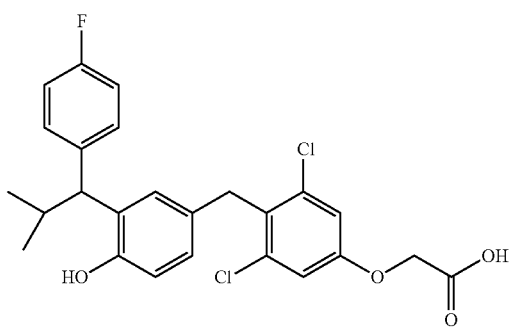

104

To a solution of Compound 103 (140 mg, 166 umol, 60% purity) in MeOH (3 mL) and water (1 mL) was added LiOH (21 mg, 499 umol). The mixture was stirred at rt for 1 h. Water (10 mL) was added, the mixture was acidified to pH~4-5 with 1N HCl and extracted with DCM (10 mL). The organic layer was dried over Na₂SO₄, concentrated in vacuo, and purified by Prep-HPLC to afford Compound 104 (40 mg, 50% yield) as a white solid.

TLC: EtOAc/pet. ether=⅕ (v/v), Rf=0
LCMS: RT=4.181 min; [M-1]=475.1/477.1
¹H NMR: (400 MHz, DMSO-d₆) δ 13.10 (s, 1H), 9.14 (s, 1H), 7.30-7.22 (m, 2H), 7.18 (d, J=2.2 Hz, 1H), 7.10 (s, 2H), 7.07-6.98 (m, 2H), 6.68 (dd, J=8.3, 2.2 Hz, 1H), 6.61 (d, J=8.3 Hz, 1H), 4.77 (s, 2H), 4.04 (s, 2H), 3.82 (d, J=11.3 Hz, 1H), 2.45-2.36 (m, 1H), 0.77 (dd, J=14.4, 6.4 Hz, 6H).

Example 105

Synthesis of 2-(3,5-dichloro-4-(3-(2-(4-fluorophenyl)propan-2-yl)-4-hydroxybenzyl) phenoxy)acetic Acid (Compound 105)

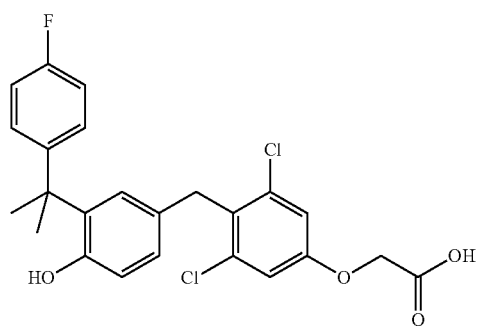

105

To a solution of Intermediate D2 (200 mg, 1.16 mmol), Intermediate A6 (395 mg, 1.16 mmol) in DCE (5 mL) was added ZnCl$_2$ (1M, 2.32 mL). The mixture was stirred at 85° C. overnight. The mixture was cooled to rt and concentrated to dryness; THF/H$_2$O (5/2 mL) and LiOH.H$_2$O (146 mg, 3.48 mmol) were added, and the resultant mixture was stirred at rt for 30 min. Water (10 mL) was added, the mixture was acidified to pH~4-5 with 1N HCl and extracted with DCM (10 mL*2). The organic layer was concentrated in vacuo, then purified by Prep-TLC (DCM/MeOH=5/1) and Prep-HPLC to afford Compound 105 (10 mg, 2% yield) as a white solid.

TLC: EtOAc/pet. ether=⅕ (v/v), Rf=0

$^1$H NMR: (400 MHz, DMSO-d$_6$) δ 8.83 (s, 1H), 7.21 (d, J=2.1 Hz, 1H), 7.11-7.08 (m, 2H), 7.04-6.91 (m, 4H), 6.80-6.75 (m, 1H), 6.55 (d, J=8.2 Hz, 1H), 4.35 (s, 2H), 4.07 (s, 2H), 1.57 (s, 6H).

Example 106

Synthesis of methyl 2-(3,5-dichloro-4-(3-(cyclopropyl(4-fluorophenyl)methyl)-4-hydroxybenzyl)phenoxy)acetate (Compound 106)

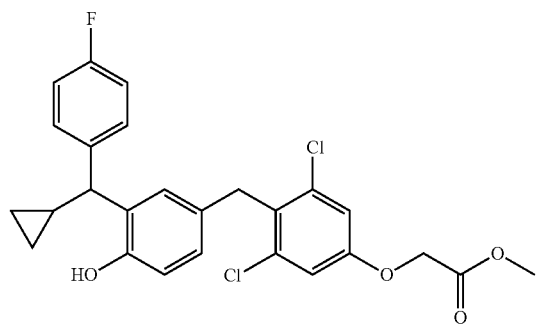

106

To a solution of Intermediate C21 (100 mg, 0.39 mmol) in DCE (10 mL) at rt were added Intermediate A10 (40 mg, 0.13 mmol) and ZnCl$_2$/THF (1 M, 0.32 mL). The reaction was heated to 95° C. for 2 days. The reaction mixture was cooled to rt and diluted with DCM (20 mL); the resultant mixture was washed with brine (2*10 mL), dried over Na$_2$SO$_4$, and concentrated in vacuo. The crude product was purified by Prep-TLC (EtOAc/pet. ether=⅕) to afford Compound 106 (20 mg, 28% yield,) as a light-yellow oil.

TLC: Pet. ether/EtOAc=⅕ (v/v), Rf=0.4

$^1$H NMR: (400 MHz, DMSO) δ 9.10 (s, 1H), 7.21 (m, 3H), 7.14 (m, 3H), 7.08-7.01 (m, 2H), 6.77-6.71 (m, 1H), 6.61 (m, 1H), 4.89 (s, 2H), 4.08-4.04 (m, 2H), 3.70 (s, 3H), 3.50-3.41 (m, 3H), 1.41-1.29 (m, 1H), 1.09 (m, 2H), 0.58 (m, 2H), 0.23 (m, 1H), 0.08 (m, 1H).

Example 107

Synthesis of 2-(3,5-dichloro-4-(3-(cyclopropyl(4-fluorophenyl)methyl)-4-hydroxybenzyl)phenoxy)acetic Acid (Compound 107)

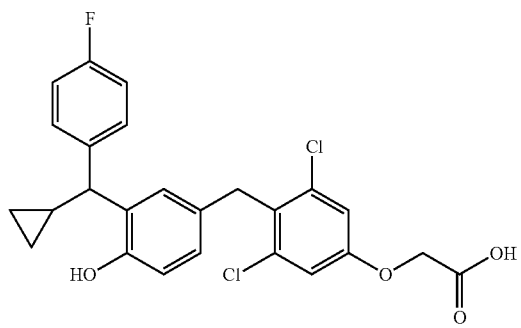

107

To a solution of Compound 106 (20 mg, 0.04 mmol) in THF/water (2/1 mL) at rt was added LiOH.H$_2$O (5 mg, 0.12 mmol); the resultant mixture was stirred at rt for 1 h. The reaction mixture was acidified to pH~3-4 with 2N HCl, concentrated in vacuo and purified by Prep-HPLC to afford Compound 107 (4 mg, 21% yield).

TLC: Pet. ether/EtOAc=⅕ (v/v), Rf=0

LCMS: RT: 2.41 min; [M+1]=472.9

$^1$H NMR (400 MHz, DMSO) δ 9.02 (s, 1H), 7.12 (s, 3H), 6.96 (m, 4H), 6.64 (d, J=7.1 Hz, 1H), 6.53 (d, J=8.0 Hz, 1H), 4.65 (s, 2H), 3.96 (s, 2H), 3.40 (s, 1H), 1.26 (s, 1H), 0.41 (d, J=28.8 Hz, 2H), 0.13 (s, 1H), 0.00 (s, 1H).

Example 108

Synthesis of methyl 2-(3,5-dichloro-4-(3-(cyclobutyl(4-fluorophenyl)methyl)-4-hydroxybenzyl)phenoxy)acetate (Compound 108)

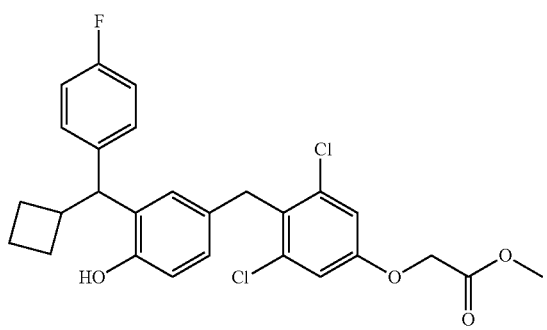

108

To a solution of Intermediate C25 (287.11 mg, 1.1 mmol) in DCE (4 mL) at rt were added Intermediate A10 (100 mg, 0.4, mmol) and ZnCl$_2$ (1 M, in THF) (0.8 mL). The reaction was heated to 85° C. and stirred overnight. The reaction mixture was diluted with DCM (10 mL), washed with brine (5 mL*3), dried over Na$_2$SO$_4$ and concentrated in vacuo. The crude product was purified by silica gel column chromatography (EtOAc/pet. ether=1/30 to 1/10) to afford Compound 108 (90 mg, 50% yield) as a colorless oil.

TLC: EtOAc/pet. ether=1/5 (v/v), R$_f$=0.2

$^1$H NMR (400 MHz, DMSO-d$_6$) δ 9.13 (s, 1H), 7.16 (dd, J=8.4, 6.4 Hz, 2H), 7.10 (s, 2H), 7.05-6.98 (m, 3H), 6.72 (dd, J=8.0, 1.6 Hz, 1H), 6.61 (d, J=8.2 Hz, 1H), 4.76 (s, 2H), 4.16 (d, J=11.2 Hz, 1H), 4.04 (s, 2H), 2.96 (q, J=9.4, 8.6 Hz, 1H), 1.92-1.61 (m, 6H).

Example 109

Synthesis of 2-(3,5-dichloro-4-(3-(cyclobutyl(4-fluorophenyl)methyl)-4-hydroxybenzyl)phenoxy) acetic Acid (Compound 109)

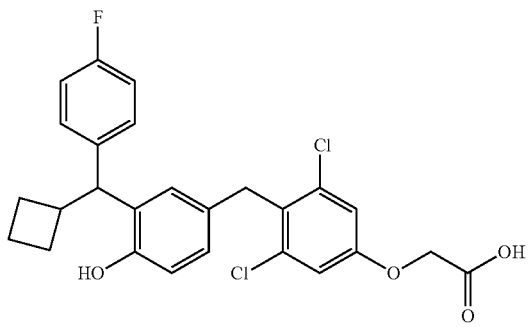

To a mixture of Compound 108 (90 mg, 185 umol) in THF/H$_2$O (2 mL/0.5 mL) was added LiOH.H$_2$O (13.3 mg, 556 umol). The mixture was stirred at rt for 2 h. Water (2 mL) was added and the pH was adjusted to pH~3-4 with 1N HCl. The resultant mixture was extracted with EtOAc (5 mL*3); the combined organic phase was washed with brine (15 mL), dried over Na$_2$SO$_4$, concentrated in vacuo and purified by Prep-TLC (DCM/MeOH=10/1) to afford Compound 109 (30 mg, 34% yield) as a white solid.

TLC: MeOH/DCM=1/10 (v/v), Rf=0.25

LCMS: RT=4.394 min; [M−1]=487.0

$^1$H NMR (400 MHz, DMSO-d$_6$) δ 13.19 (s, 1H), 9.13 (s, 1H), 7.20-7.13 (m, 2H), 7.10 (s, 2H), 7.06-6.97 (m, 3H), 6.72 (d, J=7.2 Hz, 1H), 6.62 (d, J=8.2 Hz, 1H), 4.77 (s, 2H), 4.16 (d, J=11.2 Hz, 1H), 4.04 (s, 2H), 3.02-2.93 (m, 1H), 1.90-1.65 (m, 5H), 1.55-1.45 (m, 1H).

Example 110

Synthesis of methyl 2-(3,5-dichloro-4-(3-(6-fluoro-1,2,3,4-tetrahydronaphthalen-1-yl)-4-hydroxybenzyl)phenoxy)acetate (Compound 110)

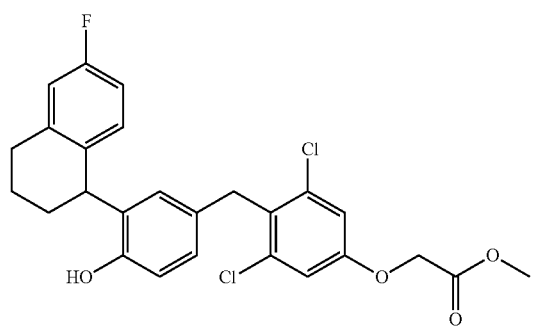

To a solution of Intermediate C27 (110 mg, 454 umol) and Intermediate A10 (65 mg, 227 umol) in DCE (5 mL) was added ZnCl$_2$ (1 M/THF) (567 umol, 0.6 mL). The mixture was stirred at 85° C. overnight. Water (10 mL) was added and the mixture was extracted with DCM (5 mL*3). The combined organic phase was washed with brine, dried over Na$_2$SO$_4$, concentrated in vacuo and purified by Prep-TLC (EtOAc/pet. ether-1/5) to afford Compound 110 (35 mg, 31% yield) as a colorless oil.

TLC: EtOAc/pet. ether=1/5 (v/v), R$_f$=0.2

LCMS: RT=3.298 min; [M−1]=486.9

Example 111

Synthesis of 2-(3,5-dichloro-4-(3-(6-fluoro-1,2,3,4-tetrahydronaphthalen-1-yl)-4-hydroxybenzyl)phenoxy)acetic Acid (Compound 111)

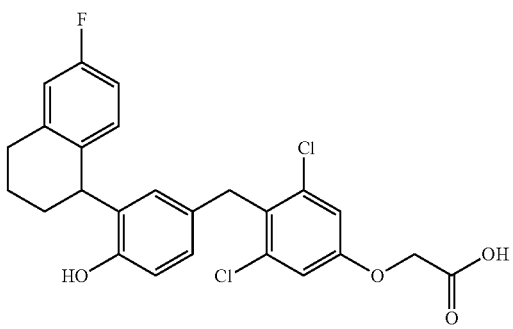

To a solution of Compound 110 (35 mg, 74 umol) in THF/H$_2$O (2 mL/0.5 mL) at rt was added LiOH.H$_2$O (5 mg, 221 umol). The mixture was stirred at rt for 2 h. The mixture was diluted with water (10 mL), acidified with 1N HCl to pH~3-4 and extracted with EtOAc (5 mL*3). The combined organic phase was washed with brine (10 mL), dried over Na$_2$SO$_4$ and concentrated in vacuo. The crude product was purified by Prep-HPLC to afford Compound 111 (15 mg, 44% yield) as a white solid.

TLC: MeOH/DCM=1/10 (v/v), Rf=0.30

LCMS: RT=4.170 min; [M−1]=473.0

$^1$H NMR (400 MHz, DMSO-d$_6$) δ 13.12 (s, 1H), 9.30 (s, 1H), 7.03 (s, 2H), 6.92 (dd, J=10.0, 2.8 Hz, 1H), 6.81 (td, J=8.4, 2.8 Hz, 1H), 6.77-6.69 (m, 3H), 6.37 (s, 1H), 4.75 (s, 2H), 4.33 (t, J=5.6 Hz, 1H), 3.89 (s, 2H), 3.34 (s, 2H), 2.77 (m, 2H), 1.85 (m, 2H), 1.63 (m, 2H).

$^{19}$F NMR (376 MHz, DMSO) δ −117.90 (s).

Example 112

Synthesis of methyl 2-(3,5-dichloro-4-(3-(5-fluoro-2,3-dihydro-1H-inden-1-yl)-4-hydroxybenzyl)phenoxy)acetate (Compound 112)

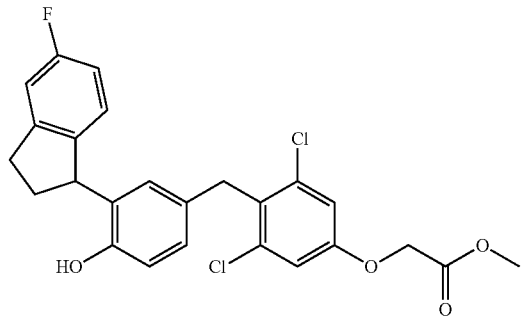

112

To a solution of Intermediate C29 (110 mg, 454 umol) and Intermediate A10 (65 mg, 227 umol) in DCE (5 mL) was added ZnCl$_2$ (1M/THF) (567 umol, 0.6 mL). The mixture was stirred at 85° C. overnight. Water (10 mL) was added and the resultant mixture was extracted with DCM (5 mL*3). The combined organic phase was washed with brine, dried over Na$_2$SO$_4$, concentrated in vacuo and purified by silica gel column chromatography (EtOAc/pet. ether=1/30 to 1/10) to afford Compound 112 (30 mg, 33% yield) as a colorless oil.

TLC: EtOAc/pet. ether=1/5 (v/v), R$_f$=0.1

LCMS: RT=4.534 min; [M−1]=472.9

Example 113

Synthesis of 2-(3,5-dichloro-4-(3-(5-fluoro-2,3-dihydro-1H-inden-1-yl)-4-hydroxybenzyl)phenoxy)acetic Acid (Compound 113)

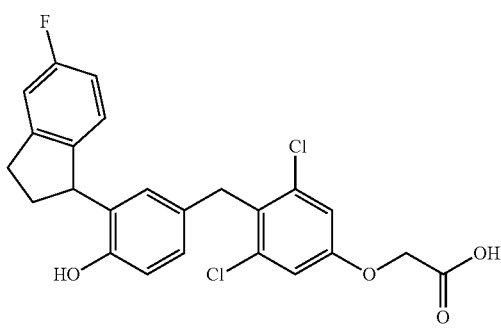

113

To a solution of Compound 112 (30 mg, 74 umol) in THF/H$_2$O (1 mL/0.3 mL) at rt was added LiOH.H$_2$O (5 mg, 221 umol). The mixture was stirred at rt for 1 h. The mixture was diluted with water (5 mL), acidified with 1N HCl to pH~3-4 and extracted with EtOAc (3 mL*3). The combined organic phase was washed with brine (5 mL), dried over Na$_2$SO$_4$ and concentrated in vacuo. The crude product was purified by Prep-HPLC (MeCN/H$_2$O/TFA) to afford Compound 113 (5 mg, 17% yield) as a white solid.

TLC: MeOH/DCM=1/10 (v/v), Rf=0.30

LCMS: T=4.115 min; [M−1]=458.8

$^1$H NMR (400 MHz, DMSO-d$_6$) δ 13.18 (s, 1H), 9.33 (s, 1H), 7.08 (d, J=9.0 Hz, 1H), 7.04 (s, 2H), 6.93-6.85 (m, 2H), 6.79-6.71 (m, 2H), 6.66-6.62 (m, 1H), 4.72 (s, 2H), 4.54 (t, J=8.0 Hz, 1H), 3.94 (s, 2H), 2.87 (dt, J=17.6, 9.6 Hz, 2H), 2.47-2.42 (m, 1H), 1.91 (dd, J=12.4, 8.0 Hz, 1H).

$^{19}$F NMR (376 MHz, DMSO) δ −117.58 (s).

Example 114

Synthesis of methyl 2-(3-chloro-4-(3-(4-fluorobenzyl)-4-hydroxybenzyl)-5-methylphenoxy)acetate (Compound 114)

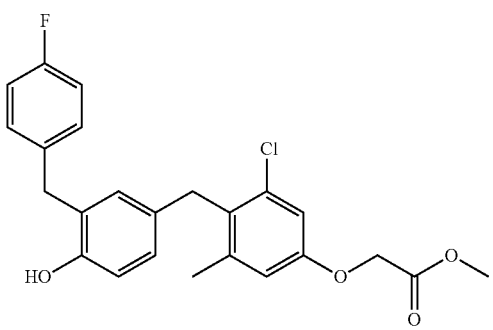

114

To a solution of Intermediate C31 (138 mg, 0.69 mmol) in DCE (5 mL) at RT were added Intermediate A15 (60 mg, 0.23 mmol) and ZnCl$_2$/THF (1M) (0.57 mL, 0.58 mmol). The resulting mixture was stirred overnight at 80° C. The mixture was concentrated in vacuo and purified by silica gel column chromatography (pet. ether/EtOAc=5/1, v/v) to give Compound 114 (60 mg, 61% yield) as a yellow oil.

TLC: Pet. ether/EtOAc=1/5 (v/v), Rf=0.4

$^1$H NMR: (400 MHz, DMSO) δ 9.23 (s, 1H), 7.24-7.13 (m, 2H), 7.05 (m, 2H), 6.90 (d, J=2.7 Hz, 1H), 6.79 (d, J=2.5 Hz, 2H), 6.72-6.58 (m, 2H), 4.81 (s, 2H), 3.90 (s, 2H), 3.77 (s, 2H), 3.70 (s, 3H), 2.16 (s, 3H).

Example 115

Synthesis of 2-(3-chloro-4-(3-(4-fluorobenzyl)-4-hydroxybenzyl)-5-methylphenoxy) acetic Acid (Compound 115)

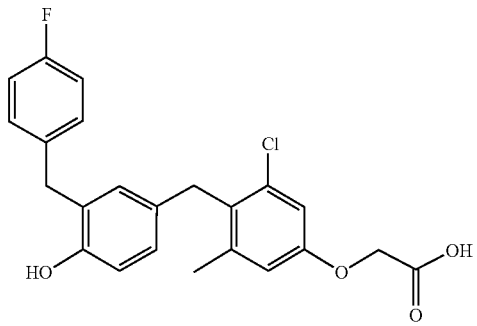

To a solution of compound 114 (60 mg, 0.14 mmol) in THF/water (5 mL/1 mL) at rt was added LiOH.H$_2$O (17 mg, 0.52 mmol); the resulting mixture was stirred at rt for 1 h. The mixture was adjusted to pH~6-7 with HCl (1N) and the solid was collected by filtration, washed with water and dried to afford Compound 115 (26 mg, 45% yield).

TLC: pet. ether/EtOAc=5/1 (v/v), Rf=0

$^1$H NMR: (400 MHz, DMSO) δ 9.27 (s, 1H), 7.22-7.14 (m, 2H), 7.05 (m, 2H), 6.80 (m, 2H), 6.72 (d, J=2.6 Hz, 1H), 6.68 (d, J=8.2 Hz, 1H), 6.63 (m, 1H), 4.52 (s, 2H), 3.88 (s, 2H), 3.77 (s, 2H), 2.14 (s, 3H).

LCMS: RT=3.81 min; [M−1]=413.

Example 116

Synthesis of 2-(3-chloro-4-(3-(4-fluorobenzyl)-4-hydroxybenzyl)-5-methylphenoxy)-N-methylacetamide (Compound 116)

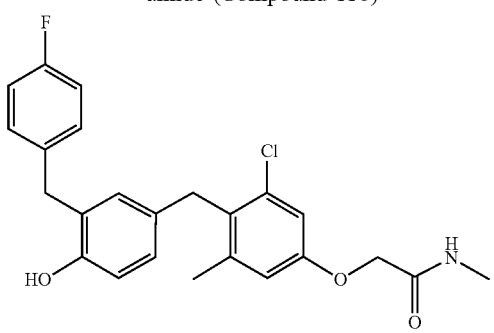

A solution of Compound 114 (45 mg, 104.92 umol) and methylamine (2M/THF, 1 mL) in THF (3 mL) was stirred in a sealed tube at 70° C. overnight. Water (30 mL) was added, and the mixture was extracted with EtOAc (25 mL*2). The combined organic layer was washed with water (20 mL*2) then brine (20 mL), dried over Na$_2$SO$_4$, and purified by Prep-TLC (DCM/MeOH=20/1) to afford Compound 116 (35 mg, 78% yield) as a white solid.

TLC: EtOAc/pet. ether=⅕ (v/v), Rf=0.25

LCMS: RT=3.754 min; [M−1]=426.1

$^1$H NMR: (400 MHz, DMSO-d$_6$) δ 9.21 (s, 1H), 8.01 (d, J=5.6 Hz, 1H), 7.21-7.14 (m, 2H), 7.08-7.02 (m, 2H), 6.92 (d, J=2.6 Hz, 1H), 6.81-6.78 (m, 2H), 6.69-6.62 (m, 2H), 4.45 (s, 2H), 3.90 (s, 2H), 3.78 (s, 2H), 2.65 (d, J=4.8 Hz, 3H), 2.16 (s, 3H).

Example 117

Synthesis of 2-(3-chloro-4-(3-(4-fluorobenzyl)-4-hydroxybenzyl)-5-methylphenoxy)-N,N-dimethylacetamide (Compound 117)

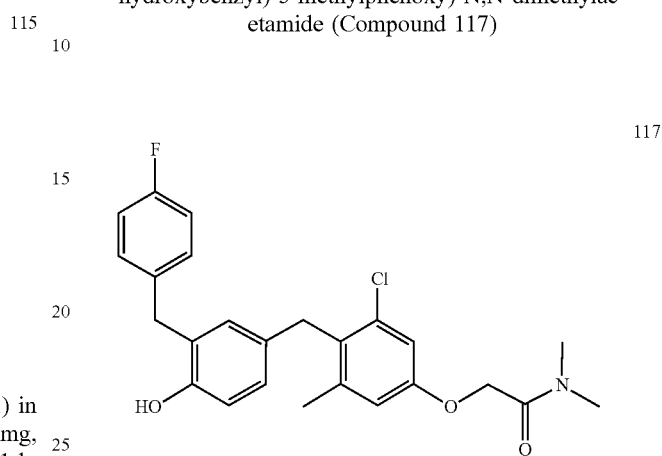

To a mixture of Compound 115 (230 mg, 554 umol) in DCM (5 mL) was added oxalyl chloride (211 mg, 1.66 mmol). The mixture was stirred at RT for 2 h. The mixture was concentrated to dryness to afford the crude acid chloride (230 mg, 96% yield), which was added to a dimethylamine solution (2M/THF, 2 mL) and stirred at RT for 5 min. The mixture was concentrated in vacuo; water (30 mL) was added, and the resultant mixture was extracted with EtOAc (15 mL*2). The combined organic layer was washed with brine (20 mL), dried over Na$_2$SO$_4$, and purified by Prep-TLC (DCM/MeOH=20/1) to afford Compound 117 (150 mg, 64% yield) as a white solid.

TLC: DCM/MeOH=20/1 (v/v), Rf=0.4

LCMS: RT=3.794 min; [M−1]=440.1

$^1$H NMR: (400 MHz, DMSO-d$_6$) δ 9.21 (s, 1H), 7.19-7.16 (m, 2H), 7.06 (t, J=8.8 Hz, 2H), 6.87 (d, J=2.8 Hz, 1H), 6.80-6.75 (m, 2H), 6.69-6.63 (m, 2H), 4.80 (s, 2H), 3.89 (s, 2H), 3.78 (s, 2H), 2.98 (s, 3H), 2.84 (s, 3H), 2.15 (s, 3H).

Example 118

Synthesis of methyl 2-(3,5-dichloro-4-(3-(furan-3-ylmethyl)-4-hydroxybenzyl) phenoxy)acetate (Compound 118)

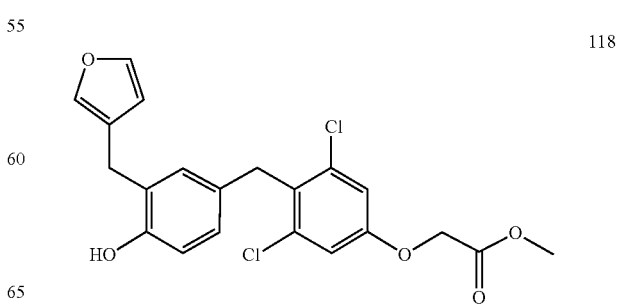

A mixture of Intermediate D4 (120 mg, 1.03 mmol), Intermediate A6 (703 mg, 2.06 mmol) and ZnCl$_2$ (2.57 mmol, 2.57 mL of 1N/THF) in DCE (5 mL) was stirred at 90° C. overnight. The mixture was concentrated in vacuo and purified by Prep-TLC to afford Compound 118 (40 mg, 9% yield) as a colorless oil.

TLC: EtOAc/pet. ether=⅕ (v/v), Rf=0.38

Example 119

Synthesis of 2-(3,5-dichloro-4-(3-(furan-3-ylmethyl)-4-hydroxybenzyl)phenoxy)acetic Acid (Compound 119)

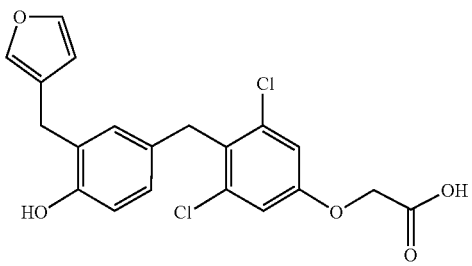

119

To a solution of Compound 118 (35 mg, 83 umol) in MeOH (3 mL) and water (1 mL) was added LiOH.H$_2$O (10 mg, 249 umol). The mixture was stirred at rt for 2 h. The mixture was acidified to pH~4-5 with 1N HCl. Water (10 mL) was added, and the mixture was extracted with DCM (10 mL). The organic layer was concentrated in vacuo and purified by Prep-HPLC to afford Compound 119 (14 mg, 41% yield) as a white solid.

TLC: EtOAc/pet. ether=⅕ (v/v), Rf=0
LCMS: RT=1.609 min; [M−1]=405.0/406.9
HNMR $^1$H NMR: (400 MHz, DMSO-d$_6$) δ 9.26 (s, 1H), 7.52 (t, J=1.7 Hz, 1H), 7.36 (t, J=1.2 Hz, 1H), 7.09 (s, 2H), 6.86 (d, J=2.2 Hz, 1H), 6.73 (dd, J=8.2, 2.2 Hz, 1H), 6.68 (d, J=8.3 Hz, 1H), 6.28 (d, J=1.8 Hz, 1H), 4.77 (s, 2H), 4.00 (s, 2H), 3.57 (s, 2H).

Example 120

Synthesis of ethyl 2-(3,5-dichloro-4-(4-hydroxy-3-(thiophen-3-ylmethyl)benzyl) phenoxy)acetate (Compound 120)

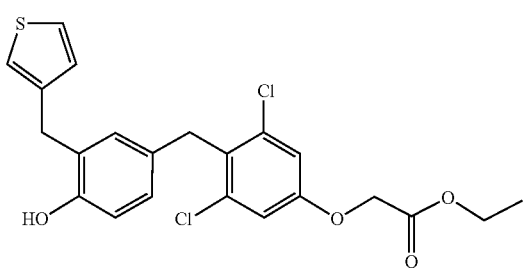

120

To a solution of Intermediate C33 (150 mg, 0.50 mmol) in DCE (10 mL) at rt were added Intermediate A12 (287 mg, 1.51 mmol) and ZnCl$_2$ (206 mg, 1.51 mmol). The reaction was heated to 90° C. and stirred for 3 h. The reaction mixture was cooled to rt and diluted with DCM (20 mL); the resultant mixture was washed with brine (10 mL*2), dried over Na$_2$SO$_4$, and concentrated in vacuo. The crude product was purified by Prep-TLC (pet. ether/EtOAc=5/1) to afford Compound 120 (50 mg, 21% yield) as a colorless oil.

TLC: Pet. ether/EtOAc=5/1 (v/v), Rf=0.21
LCMS: RT=4.284 min; [M−1]=449.0
$^1$H NMR: (400 MHz, DMSO-d$_6$) δ 9.27 (s, 1H), 7.40 (dd, J=4.8, 2.8 Hz, 1H), 7.12 (s, 2H), 7.06-7.04 (m, 1H), 6.91 (dd, J=4.8, 1.6 Hz, 1H), 6.85 (d, J=2.4 Hz, 1H), 6.73 (dd, J=8.0, 2.0 Hz, 1H), 6.69 (d, J=8.4 Hz, 1H), 4.87 (s, 2H), 4.17 (q, J=7.2 Hz, 2H), 4.08-3.96 (m, 3H), 3.78 (s, 2H), 1.21-1.16 (m, 3H)

Example 121

Synthesis of 2-(3,5-dichloro-4-(4-hydroxy-3-(thiophen-3-ylmethyl)benzyl)phenoxy) acetic Acid (Compound 121)

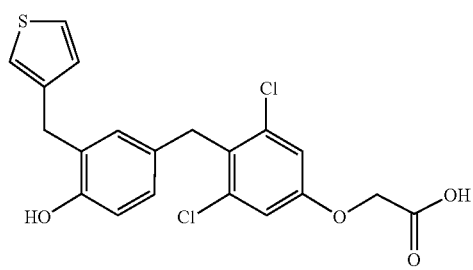

121

To a solution of Compound 120 (50 mg, 0.11 mmol) in water (1 mL) and THF (10 mL) was added LiOH.H$_2$O (14 mg, 0.33 mmol). The mixture was stirred at rt for 2 h. Water (10 mL) was added, the mixture was adjusted to pH~3-4 with 1N HCl and extracted with EtOAc (5 mL*2). The combined organic phase was washed with brine (10 mL), dried over Na$_2$SO$_4$, and concentrated in vacuo to afford Compound 121 (30 mg, 63% yield) as a white solid.

TLC: DCM/MeOH=15/1 (v/v), Rf=0.23
LCMS: RT=3.757 min; [M−1]=421.0
$^1$H NMR: (400 MHz, DMSO-d$_6$) δ 9.27 (s, 1H), 7.39 (dd, J=4.8, 2.8 Hz, 1H), 7.09-7.03 (m, 3H), 6.91 (dd, J=5.2, 1.2 Hz, 1H), 6.86 (d, J=2.0 Hz, 1H), 6.75-6.65 (m, 2H), 4.73 (s, 2H), 3.99 (s, 2H), 3.78 (s, 2H).

Example 122

Synthesis of ethyl 2-(3,5-dichloro-4-(4-hydroxy-3-(thiophen-2-ylmethyl)benzyl) phenoxy)acetate (Compound 122)

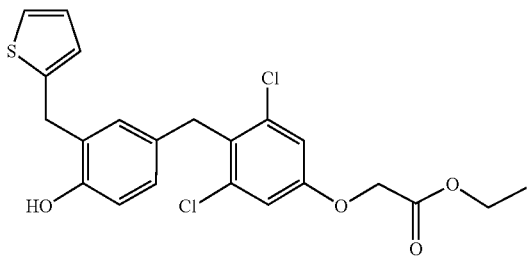

To a solution of Intermediate C35 (200 mg, 0.67 mmol) in DCE (10 mL) at rt were added Intermediate A12 (384 mg, 2.02 mmol) and $ZnCl_2$ (275 mg, 2.02 mmol). The reaction was heated to 90° C. overnight. The reaction was cooled to rt and diluted with DCM (20 mL); the mixture was washed with brine (10 mL*2), dried over $Na_2SO_4$, and concentrated in vacuo. The crude product was purified by Prep-TLC (EtOAc/pet. ether=⅕) and Prep-HPLC to afford Compound 122 (50 mg, 16% yield) as a colorless oil.

TLC: EtOAc/pet. ether=⅕ (v/v), Rf=0.45

$^1$H NMR: (400 MHz, DMSO-$d_6$) δ 9.37 (s, 1H), 7.26 (dd, J=5.2, 1.2 Hz, 1H), 7.12 (s, 2H), 6.92-6.87 (m, 2H), 6.79 (dd, J=3.6, 1.2 Hz, 1H), 6.74 (d, J=2.4 Hz, 1H), 6.69 (d, J=8.4 Hz, 1H), 4.87 (s, 2H), 4.17 (q, J=7.2 Hz, 2H), 4.02 (d, J=2.0 Hz, 2H), 3.97 (s, 2H), 1.20-1.17 (m, 3H).

Example 123

Synthesis of 2-(3,5-dichloro-4-(4-hydroxy-3-(thiophen-2-ylmethyl)benzyl)phenoxy) acetic Acid (Compound 123)

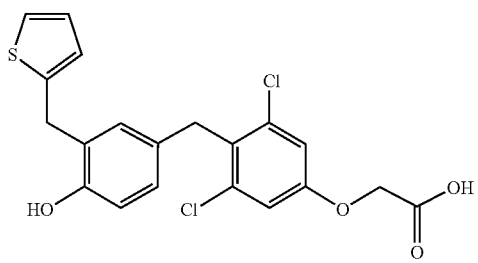

To a solution of Compound 122 (40 mg, 88.6 umol) in water (1 mL)/THF (10 mL) at rt was added LiOH.H$_2$O (11 mg, 266 umol); the mixture was stirred for 2 h at rt. The reaction mixture was acidified to pH~4-5 with 2N HCl and extracted with EtOAc (5 mL*2); the combined organic phase was washed with brine (5 mL*2), dried over $Na_2SO_4$, concentrated in vacuo and purified by Prep-HPLC to afford Compound 123 (25 mg, 66% yield) as a white solid.

TLC: Pet. ether/EtOAc=1/1 (v/v), Rf=0.1

LCMS: RT=3.80 min; [M−1]=421.0

$^1$H NMR: (400 MHz, DMSO-$d_6$) δ 9.35 (s, 1H), 7.26 (dd, J=5.2, 1.2 Hz, 1H), 7.09 (s, 2H), 6.93-6.87 (m, 2H), 6.81-6.78 (m, 1H), 6.76 (dd, J=8.4, 2.4 Hz, 1H), 6.69 (d, J=8.4 Hz, 1H), 4.77 (s, 2H), 4.01 (s, 2H), 3.97 (s, 2H).

Example 124

Synthesis of ethyl 2-(3,5-dichloro-4-(4-hydroxy-3-(2,2,2-trifluoro-1-(4-fluorophenyl) ethyl)benzyl) phenoxy)acetate (Compound 124)

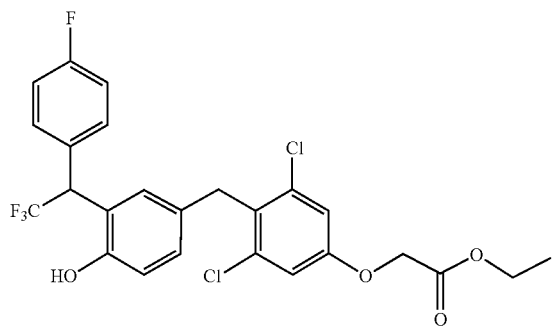

To a solution of Intermediate C37 (300 mg, 1.11 mmol) and Intermediate A12 (165 mg, 555 umol) in DCE (5 mL) was added $ZnCl_2$ (1M, 1.39 mL). The mixture was microwaved at 150° C. for 2 h. The mixture was cooled to rt and concentrated to dryness; water (20 mL) was added, and the resultant mixture was extracted with DCM (20 mL). The organic layer was dried over $Na_2SO_4$, concentrated in vacuo, and purified by Prep-TLC (pet. ether/EtOAc=5/1) to afford Compound 124 (100 mg, 34% yield) as a colorless oil.

TLC: EtOAc/pet. ether=⅕ (v/v), Rf=0.38

$^1$H NMR: (400 MHz, DMSO-$d_6$) δ 9.77 (s, 1H), 7.36 (dd, J=8.5, 5.4 Hz, 2H), 7.27 (d, J=2.1 Hz, 1H), 7.22-7.17 (m, 2H), 7.15 (s, 2H), 6.93 (dd, J=8.4, 2.2 Hz, 1H), 6.76 (d, J=8.3 Hz, 1H), 5.27 (q, J=10.7 Hz, 1H), 4.88 (s, 2H), 4.35 (t, J=5.1 Hz, 2H), 4.09 (s, 2H), 1.16 (t, J=6.8 Hz, 3H).

Example 125

Synthesis of 2-(3,5-dichloro-4-(4-hydroxy-3-(2,2,2-trifluoro-1-(4-fluorophenylethyl) benzyl)phenoxy) acetic Acid (Compound 125)

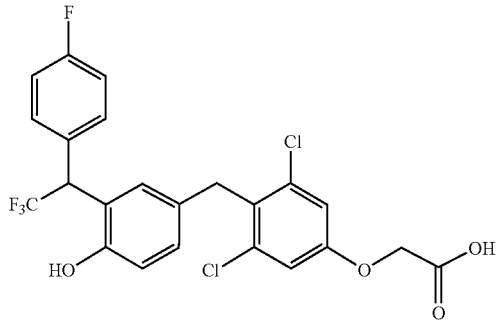

To a solution of Compound 124 (100 mg, 188 umol) in MeOH (3 mL) and water (1 mL) was added NaOH (23 mg, 565 umol). The mixture was stirred at rt for 1 h. The mixture was acidified to pH~4-5 with 1N HCl, water (10 mL) was added and the resultant mixture was extracted with DCM (10 mL). The organic layer was dried over $Na_2SO_4$, concentrated in vacuo, and purified by Prep-HPLC to afford Compound 125 (30 mg, 32% yield) as a white solid.

TLC: EtOAc/pet. ether=1/5 (v/v), Rf=0

LCMS: RT=4.034 min; [M−1]=501.0/502.9

$^1$H NMR: (400 MHz, DMSO-d$_6$) δ 9.78 (s, 1H), 7.38-7.35 (m, 2H), 7.28 (s, 1H), 7.18 (t, J=8.8 Hz, 2H), 7.12 (s, 2H), 6.93 (dd, J=8.3, 2.2 Hz, 1H), 6.76 (d, J=8.3 Hz, 1H), 5.27 (q, J=10.8 Hz, 1H), 4.78 (s, 2H), 4.08 (s, 2H).

Example 126

Synthesis of methyl 2-(3,5-dichloro-4-(4-hydroxy-3-(3,3,3-trifluoro-1-(4-fluorophenyl) propyl)benzyl) phenoxy)acetate (Compound 126)

126

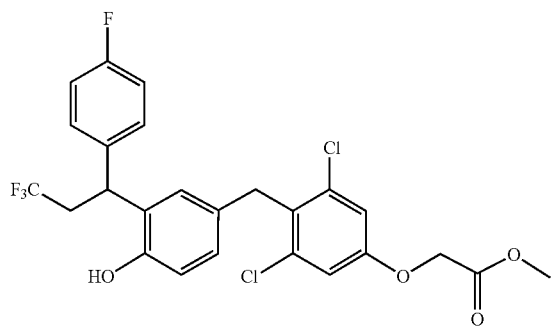

To a solution of Intermediate C38 (360 mg, 1.3 mmol) and Intermediate A10 (180 mg, 650 umol) in DCE (5 mL) was added $ZnCl_2$ (1M/in THF) (1.6 mmol, 1.6 mL). The mixture was stirred at 85° C. overnight. Water (10 mL) was added and the resultant mixture was extracted with DCM (5 mL*3). The combined organic phase was washed with brine (20 mL), dried over $Na_2SO_4$, concentrated in vacuo and purified by silica gel column chromatography (EtOAc/pet. ether=1/30 to 1/10) to afford Compound 126 (120 mg, 34% yield) as a colorless oil.

TLC: EtOAc/pet. ether=1/5 (v/v), R$_f$=0.2

LCMS: RT=2.196 min; [M−1]=529.0

Example 127

Synthesis of 2-(3,5-dichloro-4-(4-hydroxy-3-(3,3,3-trifluoro-1-(4-fluorophenyl)propyl) benzyl)phenoxy) acetic Acid (Compound 127)

127

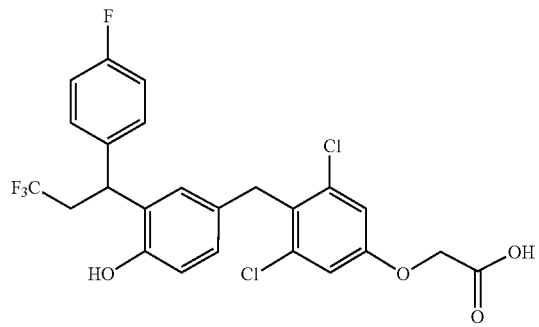

To a mixture of Compound 126 (120 mg, 220 umol) in THF/H$_2$O (3 mL/0.5 mL) at rt was added LiOH.H$_2$O (28 mg, 660 umol). The reaction was stirred at rt for 5 min. The mixture was diluted with water (5 mL), acidified to pH~4-5 with 1N HCl and extracted with EtOAc (5 mL*3). The combined organic phase was washed with brine (5 mL), dried over $Na_2SO_4$ and concentrated in vacuo. The crude product was purified by Prep-HPLC (MeCN/H$_2$O) to afford Compound 127 (25 mg, 22% yield) as a white solid.

TLC: MeOH/DCM=1/10 (v/v), Rf=0.30

LCMS: RT=1.691 min; [M−1]=425.0

$^1$H NMR: (400 MHz, DMSO-d$_6$) δ 9.48 (s, 1H), 7.40-7.34 (m, 2H), 7.17-7.02 (m, 5H), 6.71-6.64 (m, 2H), 4.76 (s, 2H), 4.57 (m, 1H), 4.02 (d, J=2.8 Hz, 2H), 3.09-2.96 (m, 2H).

$^{19}$F NMR: (376 MHz, DMSO-d$_6$) δ −62.37, −116.81.

Example 128

Synthesis of ethyl 2-(3,5-dichloro-4-(3-(1-(4-fluorophenyl)-2-methoxyethyl)-4-hydroxybenzyl)phenoxy) acetate (Compound 128)

128

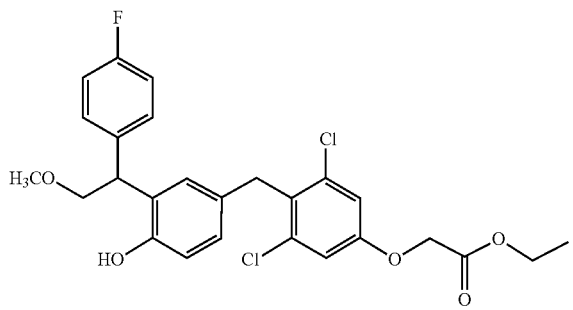

To a solution of Intermediate C41 (36 mg, 0.12 mmol) in DCE (5 mL) at rt were added Intermediate A12 (90 mg, 0.36 mmol) and ZnCl$_2$ (50 mg, 0.36 mmol). The reaction was heated to 90° C. and stirred for 2d. The reaction mixture was cooled to rt and diluted with DCM (20 mL); the resultant mixture was washed with brine (10 mL*2), dried over Na₂SO₄, and concentrated in vacuo. The crude product was purified by Prep-TLC (pet. ether/EtOAc=5/1) to afford Compound 128 (30 mg, 48% yield) as a white solid.

TLC: pet. ether/EtOAc=5/1 (v/v), $R_f$=0.21

LCMS: RT=2.13; [M−1]=505.1.

Example 129

Synthesis of 2-(3,5-dichloro-4-(3-(1-(4-fluorophenyl)-2-methoxyethyl)-4-hydroxybenzyl)phenoxy) acetic Acid (Compound 129)

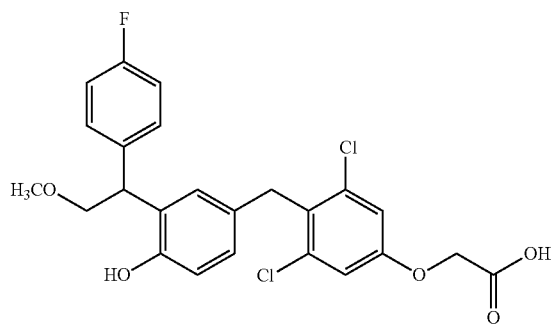

To a solution of Compound 128 (30 mg, 59.1 umol) in THF (5 mL)/water (1 mL) at rt was added LiOH.H₂O (8 mg, 177 umol); the mixture was stirred at rt for 1 h. Water (10 mL) was added; the mixture was acidified to pH~4-5 with 2N HCl and extracted with EtOAc (5 mL*2). The combined organic phase washed with brine (5 mL), dried over Na₂SO₄, concentrated in vacuo and purified by Prep-HPLC to afford Compound 129 (8 mg, 28% yield) as a white solid.

TLC: MeOH/DCM=1/10 (v/v), Rf=0.26.

LCMS: RT=3.84; [M−1]=447.0.

¹H NMR: (400 MHz, DMSO-d₆) δ 12.99 (s, 1H), 9.28 (s, 1H), 7.24-7.18 (m, 2H), 7.11-7.02 (m, 3H), 6.96 (d, J=2.4 Hz, 1H), 6.75 (dd, J=8.4, 2.4 Hz, 1H), 6.66 (d, J=8.4 Hz, 1H), 4.77 (s, 2H), 4.48 (s, 1H), 4.07-3.95 (m, 2H), 3.74 (qd, J=9.6, 7.2 Hz, 2H), 3.20 (s, 3H).

¹⁹F NMR: (376 MHz, DMSO-d₆) δ −117.31.

Example 130

Synthesis of ethyl 2-(3-bromo-4-(3-(1-(4-fluorophenyl)ethyl)-4-hydroxybenzyl)-5-methylphenoxy)acetate (Compound 130)

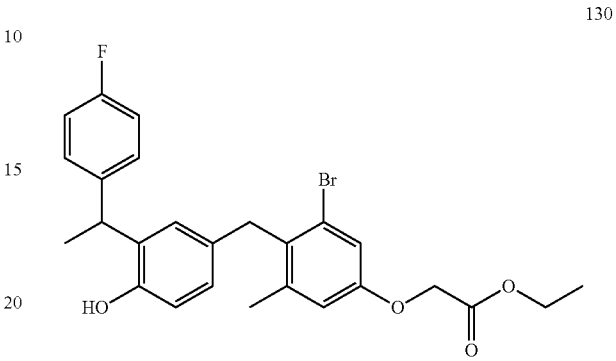

To a solution of Intermediate C43 (1.0 g, 4.65 mmol) in DCE (5 mL) at RT was added Intermediate A18 (500 mg, 1.55 mmol) and ZnCl₂ (3.8 mL, 3.80 mmol). The mixture was stirred at 85° C. overnight. The reaction mixture was poured into water (20 mL) and extracted with DCM (30 mL*3). The combined organic phase was washed with brine (100 mL), dried over Na₂SO₄, concentrated in vacuo and purified by silica gel column chromatography (pet. ether/EtOAc=10/1, v/v) to afford Compound 130 (410 mg, 52% yield) as a yellow oil.

TLC: EtOAc/pet. ether=1/5 (v/v), Rf=0.4

¹H NMR: (400 MHz, DMSO) δ 9.17 (s, 1H), 7.18 (m, 2H), 7.10-6.99 (m, 3H), 6.88 (d, J=2.1 Hz, 1H), 6.82 (d, J=2.7 Hz, 1H), 6.62 (m, 2H), 4.78 (s, 2H), 4.37 (d, J=7.3 Hz, 1H), 4.17 (d, J=7.1 Hz, 2H), 3.95 (s, 2H), 2.16 (s, 3H), 1.43 (d, J=7.3 Hz, 3H), 1.17 (m, 3H).

Example 131

Synthesis of 2-(3-bromo-4-(3-(1-(4-fluorophenyl)ethyl)-4-hydroxybenzyl)-5-methylphenoxy)acetic Acid (Compound 131)

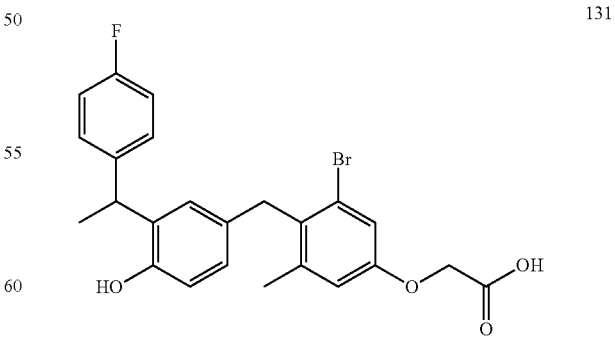

To a solution of Compound 130 (410 mg, 0.82 mmol) in water (10 mL)/THF (5 mL) at rt was added LiOH.H₂O (103 mg, 2.46 mmol). The mixture was stirred at rt for 1 h. The reaction was acidified to pH~3-4 with 2N HCl, concentrated in vacuo and purified by reversed-phase column chromatography to afford Compound 131 (260 mg, 67% yield) as a light yellow solid.

TLC: Pet. ether/EtOAc=⅕ (v/v), Rf=0

LCMS: RT=4.04 min; [M−1]=471.0

$^1$H NMR: (400 MHz, DMSO) δ 9.19 (s, 1H), 7.24-7.13 (m, 2H), 7.05 (m, 2H), 6.96 (d, J=2.7 Hz, 1H), 6.90 (d, J=2.1 Hz, 1H), 6.75 (d, J=2.6 Hz, 1H), 6.68-6.55 (m, 2H), 4.49 (s, 2H), 4.37 (m, 1H), 3.94 (s, 2H), 2.15 (s, 3H), 1.44 (d, J=7.3 Hz, 3H).

Example 132

Synthesis of 2-(3-bromo-4-(3-(1-(4-fluorophenyl)ethyl)-4-hydroxybenzyl)-5-methylphenoxy)-N-methylacetamide (Compound 132)

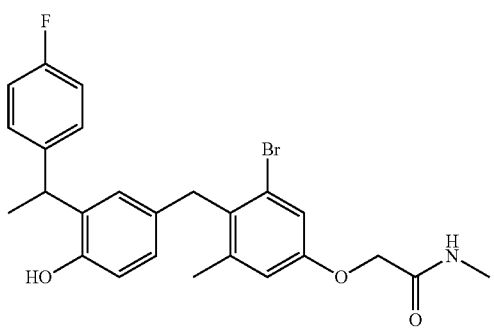

To a solution of Compound 131 (80 mg, 0.16 mmol) in DCM (15 mL) were added oxalyl chloride (62 mg, 0.48 mmol) and DMF (cat.). After stirring at RT for 1 h, the reaction mixture was concentrated in vacuo. The residue was dissolved in DCM (15 mL) and methylamine/THF (1M, 1.6 mL) was added. After stirring at room temperature for 2 h, the mixture was poured into water (20 mL) and was extracted with DCM (30 mL*3). The combined organic phase was washed with brine (30 mL), dried over Na$_2$SO$_4$, concentrated in vacuo and purified by Prep-TLC to give Compound 132 (40 mg, 50% yield) as a white solid.

TLC: EtOAc/pet. ether=1/1 (v/v), Rf=0.3

LCMS: RT=4.0 min; [M−1]=484.1

$^1$H NMR: (400 MHz, DMSO) δ 9.17 (s, 1H), 8.02 (d, J=5.2 Hz, 1H), 7.18 (m, 2H), 7.10-7.02 (m, 3H), 6.89 (d, J=2.0 Hz, 1H), 6.85 (d, J=2.6 Hz, 1H), 6.61 (m, 2H), 4.46 (d, J=6.1 Hz, 2H), 4.41-4.34 (m, 1H), 3.96 (s, 2H), 2.65 (d, J=4.5 Hz, 3H), 2.16 (s, 3H), 1.44 (d, J=7.2 Hz, 2H).

Example 133

Synthesis of 2-(4-(3-(4-fluorobenzyl)-4-hydroxybenzyl)-3,5-dimethylphenoxy)acetic Acid (Compound 133)

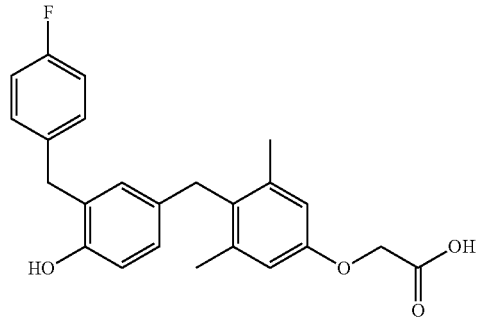

A solution of Intermediate C31 (213 mg, 1.05 mmol), Intermediate A21 (100 mg, 0.35 mmol) and ZnCl$_2$ (1 M, 0.88 mL) in DCE (4 mL) was stirred at 85° C. overnight. The mixture was cooled to rt, water (30 mL) was added, and the mixture was extracted with EtOAc (25 mL*2). The combined organic layer was washed with brine (20 mL), dried over Na$_2$SO$_4$, and purified by Prep-TLC (DCM/MeOH=5/1) to afford Compound 133 (30 mg, 19% yield) as a white solid.

TLC: DCM/MeOH=5/1 (v/v), Rf=0.39

LCMS: RT=3.705 min; [M−1]=392.9

$^1$H NMR: (400 MHz, DMSO-d$_6$) δ 12.90 (s, 1H), 9.17 (s, 1H), 7.19-7.15 (m, 2H), 7.09-7.01 (m, 2H), 6.73 (d, J=2.4 Hz, 1H), 6.66 (d, J=8.0 Hz, 1H), 6.59-6.52 (m, 3H), 4.58 (s, 2H), 3.76 (d, J=8.8 Hz, 4H), 2.11 (s, 6H).

Example 134

Synthesis of methyl 2-(3,5-dichloro-4-(3-(4-fluorophenethyl)-4-hydroxybenzyl) phenoxy)acetate (Compound 134)

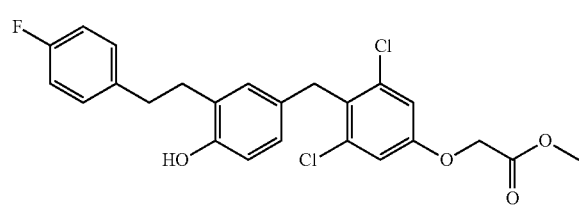

To a solution of Intermediate C45 (120 mg, 555 umol) and Intermediate A10 (52 mg, 185 umol) in DCE (2 mL) was added ZnCl$_2$ (1M, in THF) (463 umol, 0.46 mL). The mixture was stirred at 85° C. overnight. Water (5 mL) was added and the resultant mixture was extracted with DCM (3 mL*3). The combined organic phase was washed with brine (10 mL), dried over Na$_2$SO$_4$, concentrated in vacuo and purified by Prep-TLC (EtOAc/pet. ether=1/5) to afford Compound 134 (40 mg, 51% yield) as a white solid.

TLC: EtOAc/pet. ether=1/5 (v/v), Rf=0.2

$^1$H NMR: (400 MHz, DMSO) δ 9.19 (s, 1H), 7.19-7.15 (m, 1H), 7.14 (s, 1H), 7.13 (d, J=4.0 Hz, 1H), 7.04 (dt, J=4.8, 2.0 Hz, 1H), 6.76 (s, 1H), 6.74-6.70 (m, 1H), 6.68 (d, J=8.0 Hz, 1H), 4.90 (s, 1H), 4.00 (s, 1H), 3.71 (s, 1H), 2.74 (dt, J=11.6, 6.0 Hz, 1H).

Example 135

Synthesis of 2-(3,5-dichloro-4-(3-(4-fluorophenethyl)-4-hydroxybenzyl)phenoxy)acetic Acid (Compound 135)

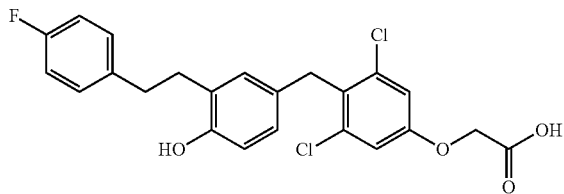

To a mixture of Compound 134 (90 mg, 185 umol) in THF/H$_2$O (2/0.5 mL) was added LiOH.H$_2$O (13.3 mg, 556 umol). The mixture was stirred at rt for 2 h. Water (5 mL) was added and the pH was adjusted to pH~3-4 with 1N HCl. The resultant mixture was extracted with EtOAc (3 mL*3); the combined organic phase was washed with brine (10 mL), dried over Na$_2$SO$_4$, concentrated in vacuo and purified by Prep-TLC (DCM/MeOH=10/1) to afford Compound 135 (25 mg, 65% yield) as a white solid.

TLC: MeOH/DCM=1/10 (v/v), Rf=0.25

LCMS: T=4.058 min; [M−1]=447.0

$^1$H NMR: (400 MHz, DMSO) δ 9.18 (s, 1H), 7.16 (dd, J=8.4, 6.4 Hz, 1H), 7.07 (d, J=8.8 Hz, 1H), 7.03 (t, J=8.8 Hz, 1H), 6.76 (s, 1H), 6.73-6.66 (m, 1H), 4.77 (s, 1H), 3.99 (s, 1H), 2.73 (dt, J=12.4, 6.0 Hz, 1H).

$^{19}$F NMR: (376 MHz, DMSO) δ −117.77 (s).

Example 136

Synthesis of 2-(3,5-dichloro-4-(3-(4-fluorobenzoyl)-4-hydroxybenzyl)phenoxy)acetic Acid (Compound 136)

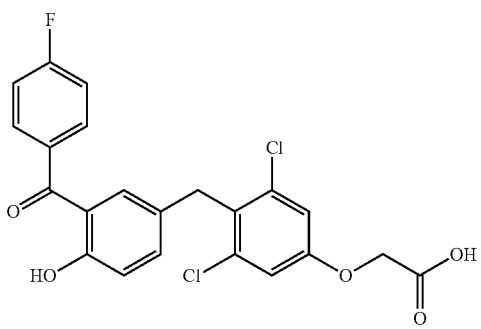

To a solution of Intermediate A6 (500 mg, 1.5 mmol) and TEA (296 mg, 3.0 mmol) in DCM (20 mL) at rt was added 4-fluorobenzoyl chloride (243 mg, 1.5 mmol). The mixture was stirred at rt for 16 h. The mixture was diluted with DCM (20 mL), washed with water (10 mL), then brine (10 mL), dried over Na$_2$SO$_4$, and concentrated in vacuo. The crude product was purified by Prep-TLC (EtOAc/pet. ether=1/5) to afford 4-(2,6-dichloro-4-(2-methoxy-2-oxoethoxy)benzyl)phenyl 4-fluorobenzoate (Intermediate 136-1) (460 mg, 68% yield) as a white solid.

TLC: MeOH/DCM=1/20 (v/v), Rf=0.67

$^1$H NMR: (400 MHz, DMSO-d$_6$) δ 8.18 (dd, J=8.8, 5.6 Hz, 2H), 7.43 (t, J=8.8 Hz, 2H), 7.19 (s, 5H), 4.91 (s, 2H), 4.22 (s, 2H), 3.71 (s, 3H).

To a solution of Intermediate 136-1 (150 mg, 0.3 mmol) in DCE (5.0 mL) was added AlCl$_3$ (86 mg, 0.6 mmol). The mixture was heated to 120° C. for 12 h. The reaction mixture was cooled to rt, and reaction was quenched by the addition of water (10 mL). The mixture was extracted with DCM (10 mL*3); the combined organic phase was dried over Na$_2$SO$_4$ and concentrated in vacuo. The crude product was purified by Prep-TLC (Methanol/DCM=1/10) to afford Compound 136 (11 mg, 8% yield) as a brown solid.

TLC: MeOH/DCM=1/20 (v/v), Rf=0.2

LCMS: RT=3.07 min; [M−1]=447.

$^1$H NMR: (400 MHz, DMSO-d$_6$) δ 13.12 (s, 1H), 10.23 (s, 1H), 7.77-7.71 (m, 2H), 7.37-7.30 (m, 3H), 7.21 (dd, J=8.4, 2.4 Hz, 1H), 7.12 (s, 2H), 7.09 (d, J=2.4 Hz, 1H), 6.91 (d, J=8.4 Hz, 1H), 4.78 (s, 2H), 4.11 (s, 2H).

Example 137

Synthesis of 2-(3,5-dichloro-4-(3-((4-fluorophenyl)(hydroxy)methyl)-4-hydroxybenzyl) phenoxy)acetic Acid (Compound 137)

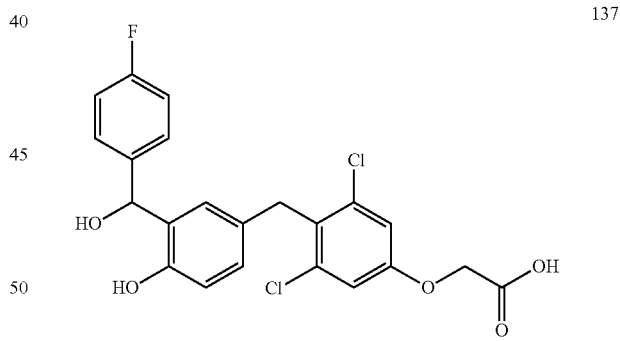

To a solution of Compound 136 (11 mg, 24.5 umol) in THF (3 mL) at 10° C. was added NaBH$_4$ (1.1 mg, 29.4 umol). The mixture was warmed to rt and stirred for 16 h. The reaction was quenched with water (5 mL), acidified to pH~4-5 with aqueous HCl (1N), and extracted with EtOAc (5*2 mL). The combined organic phase was dried over Na$_2$SO$_4$, and concentrated in vacuo. The crude product was purified by Prep-TLC (Methanol/DCM=1/10) to afford Compound 137 (9 mg, 81% yield) as a brown solid.

TLC: MeOH/DCM=1/10 (v/v), Rf=0.12

LCMS: RT=2.54 min; [M−1]=449.

$^1$H NMR: (400 MHz, DMSO-d$_6$) δ 13.20 (s, 1H), 9.28 (s, 1H), 7.35-7.29 (m, 2H), 7.26 (d, J=2.4 Hz, 1H), 7.10-7.04 (m, 3H), 6.74 (dd, J=8.4, 2.4 Hz, 1H), 6.64 (d, J=8.4 Hz,

1H), 5.89 (d, J=4.0 Hz, 1H), 5.68 (d, J=4.4 Hz, 1H), 5.32 (t, J=5.2 Hz, 1H), 4.68 (s, 2H), 4.10-3.97 (m, 2H).

Example 138

Synthesis of 1-(aziridin-1-yl)-2-(3,5-dichloro-4-((3'-(difluoromethoxy)-6-hydroxy-[1,1'-biphenyl]-3-yl)methyl)phenoxy)ethan-1-one (Compound 138)

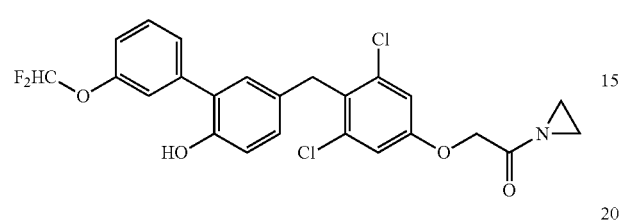

Compound 138 is prepared according to the procedures described in Example 4, substituting Compound 3 with Compound 5 and aqueous methylamine with aqueous aziridine.

Example 139

Synthesis of 1-(azetidin-1-yl)-2-(3,5-dichloro-4-((3'-(difluoromethoxy)-6-hydroxy-[1,1'-biphenyl]-3-yl)methyl)phenoxy)ethan-1-one (Compound 139)

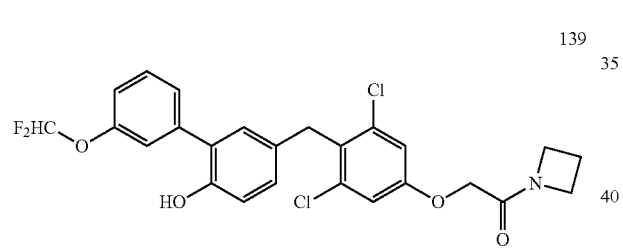

Compound 139 is prepared according to the procedures described in Example 4, substituting Compound 3 with Compound 5 and aqueous methylamine with aqueous azetidine.

Example 140

Synthesis of 2-(3,5-dichloro-4-((3'-(difluoromethoxy)-6-hydroxy-[1,1'-biphenyl]-3-yl)methyl)phenoxy)-1-(pyrrolidin-1-yl)ethan-1-one (Compound 140)

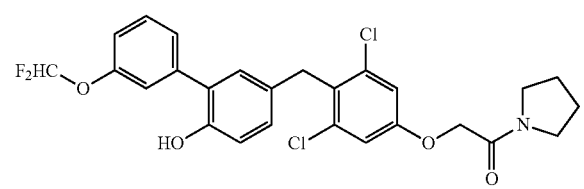

Compound 140 is prepared according to the procedures described in Example 4, substituting Compound 3 with Compound 5 and aqueous methylamine with aqueous pyrrolidine.

Example 141

Synthesis of 2-(3,5-dichloro-4-((3'-(difluoromethoxy)-6-hydroxy-[1,1'-biphenyl]-3-yl)methyl)phenoxy)-1-(piperidin-1-yl)ethan-1-one (Compound 141)

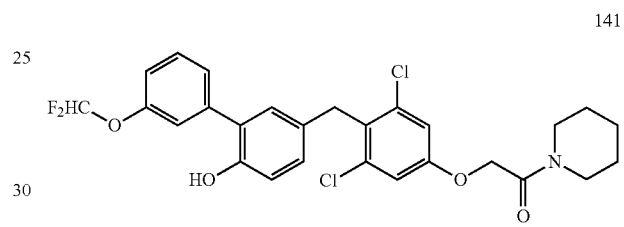

Compound 141 is prepared according to the procedures described in Example 4, substituting Compound 3 with Compound 5 and aqueous methylamine with aqueous piperidine.

Example 142

Synthesis of 2-(3,5-dichloro-4-((6-hydroxy-[1,1'-biphenyl]-3-yl) methyl)phenoxy)-acetic Acid (Compound 142)

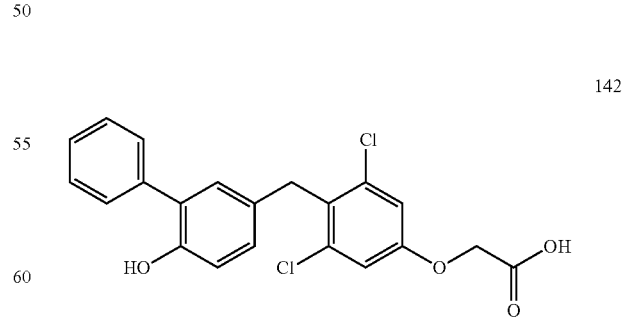

Compound 142 was prepared according to the procedures described in Example 1, substituting 3-trifluoromethyl-phenylboronic acid for potassium phenyltrifluoroborate and Pd(dppf)Cl$_2$ for Pd(OAc)$_2$. MS (ES-API) m/z 400.9/402.9.

Example 143

Synthesis of 2-(3,5-dichloro-4-((3'-cyclopropyl-6-hydroxy-[1,1'-biphenyl]-3-yl)methyl)phenoxy)acetic Acid (Compound 143)

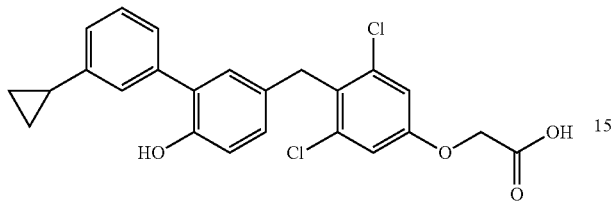

143

Compound 143 was prepared according to the procedures described in Example 1, substituting (3-cyclopropylphenyl)boronic acid for 3-trifluoromethyl-phenylboronic acid. MS (ES-API) m/z 440.7/442.8.

Example 144

Synthesis of 1-(aziridin-1-yl)-2-(3,5-dichloro-4-((6-hydroxy-3'-propyl-[1,1'-biphenyl]-3-yl)methyl)phenoxy)ethan-1-one (Compound 144)

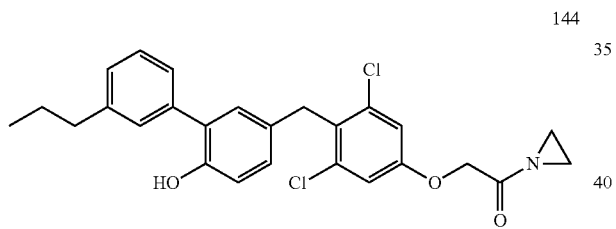

144

Compound 144 is prepared according to the procedures described in Example 4, substituting Compound 3 with Compound 16 and aqueous methylamine with aqueous aziridine.

Example 145

Synthesis of 1-(azetidin-1-yl)-2-(3,5-dichloro-4-((6-hydroxy-3'-propyl-[1,1'-biphenyl]-3-yl)methyl)phenoxy)ethan-1-one (Compound 145)

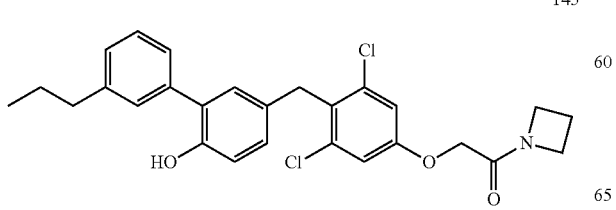

145

Compound 145 is prepared according to the procedures described in Example 4, substituting Compound 3 with Compound 16 and aqueous methylamine with aqueous azetidine.

Example 146

Synthesis of 2-(3,5-dichloro-4-((6-hydroxy-3'-propyl-[1,1'-biphenyl]-3-yl)methyl)phenoxy)-1-(pyrrolidin-1-yl)ethan-1-one (Compound 146)

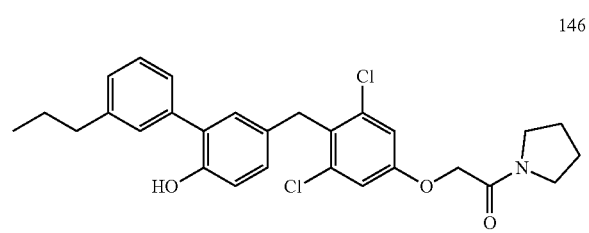

146

Compound 146 is prepared according to the procedures described in Example 4, substituting Compound 3 with Compound 16 and aqueous methylamine with aqueous pyrrolidine.

Example 147

Synthesis of 2-(3,5-dichloro-4-((6-hydroxy-3'-propyl-[1,1'-biphenyl]-3-yl)methyl)phenoxy)-1-(piperidin-1-yl)ethan-1-one (Compound 147)

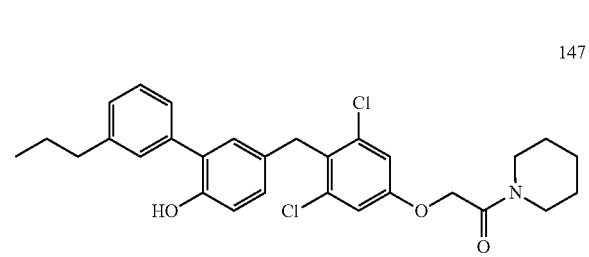

147

Compound 147 is prepared according to the procedures described in Example 4, substituting Compound 3 with Compound 16 and aqueous methylamine with aqueous piperidine.

Example 148

Synthesis of 1-(aziridin-1-yl)-2-(3-chloro-4-((3'-ethyl-6-hydroxy-[1,1'-biphenyl]-3-yl)methyl)-5-methylphenoxy)ethan-1-one (Compound 148)

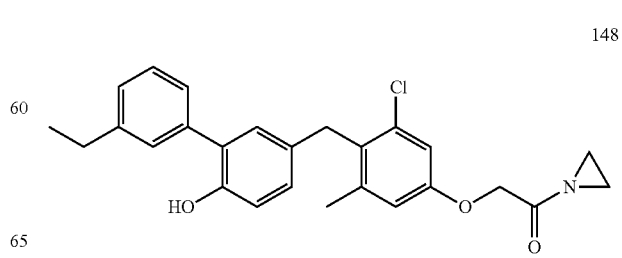

148

Compound 148 is prepared according to the procedures described in Example 4, substituting Compound 3 with Compound 60 and aqueous methylamine with aqueous aziridine.

Example 149

Synthesis of 1-(azetidin-1-yl)-2-(3-chloro-4-((3'-ethyl-6-hydroxy-[1,1'-biphenyl]-3-yl)methyl)-5-methylphenoxy)ethan-1-one (Compound 149)

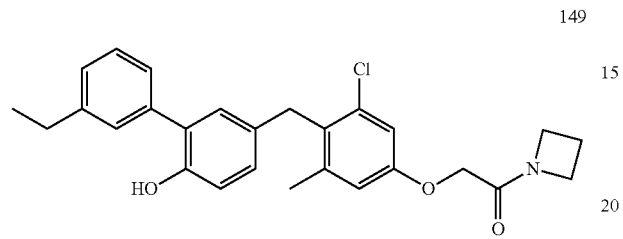

149

Compound 149 is prepared according to the procedures described in Example 4, substituting Compound 3 with Compound 60 and aqueous methylamine with aqueous azetidine.

Example 150

Synthesis of 2-(3-chloro-4-((3'-ethyl-6-hydroxy-[1,1'-biphenyl]-3-yl)methyl)-5-methylphenoxy)-1-(pyrrolidin-1-yl)ethan-1-one (Compound 150)

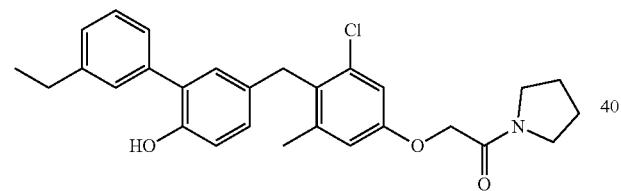

150

Compound 150 is prepared according to the procedures described in Example 4, substituting Compound 3 with Compound 60 and aqueous methylamine with aqueous pyrrolidine.

Example 151

Synthesis of 2 2-(3-chloro-4-((3'-ethyl-6-hydroxy-[1,1'-biphenyl]-3-yl)methyl)-5-methylphenoxy)-1-(piperidin-1-yl)ethan-1-one (Compound 151)

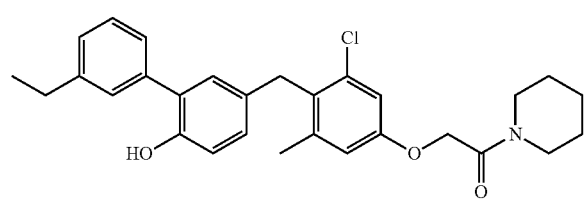

151

Compound 151 is prepared according to the procedures described in Example 4, substituting Compound 3 with Compound 60 and aqueous methylamine with aqueous piperidine.

Example 152

Synthesis of 1-(aziridin-1-yl)-2-(3,5-dichloro-4-(3-(1-(4-fluorophenyl)ethyl)-4-hydroxybenzyl)phenoxy)ethan-1-one (Compound 152)

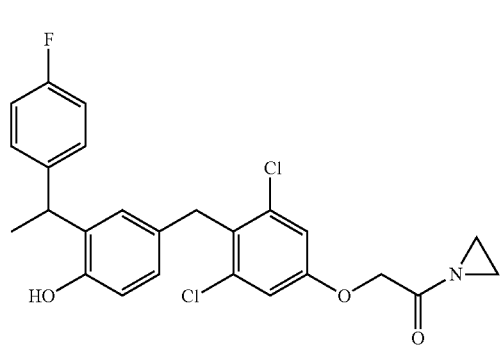

152

Compound 152 is prepared according to the procedures described in Example 71, substituting Compound 69 with Compound 72 and aqueous methylamine with aqueous aziridine.

Example 153

Synthesis of 1-(azetidin-1-yl)-2-(3,5-dichloro-4-(3-(1-(4-fluorophenyl)ethyl)-4-hydroxybenzyl)phenoxy)ethan-1-one (Compound 153)

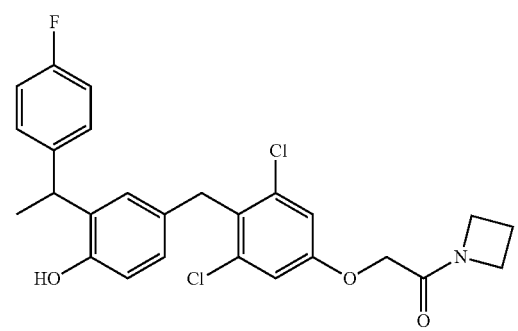

153

Compound 153 is prepared according to the procedures described in Example 71, substituting Compound 69 with Compound 72 and aqueous methylamine with aqueous azetidine.

Example 154

Synthesis of 2-(3,5-dichloro-4-(3-(1-(4-fluorophenyl)ethyl)-4-hydroxybenzyl)phenoxy)-1-(pyrrolidin-1-yl)ethan-1-one (Compound 154)

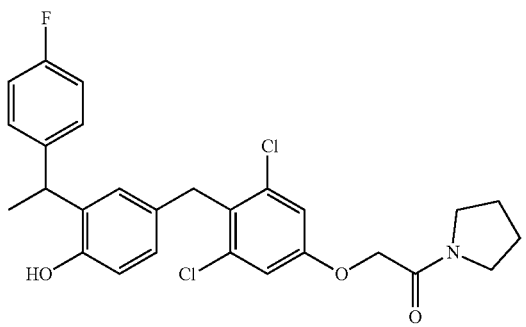

154

Compound 154 is prepared according to the procedures described in Example 71, substituting Compound 69 with Compound 72 and aqueous methylamine with aqueous pyrrolidine.

Example 155

Synthesis of 2-(3,5-dichloro-4-(3-(1-(4-fluorophenyl)ethyl)-4-hydroxybenzyl)phenoxy)-1-(piperidin-1-yl)ethan-1-one (Compound 155)

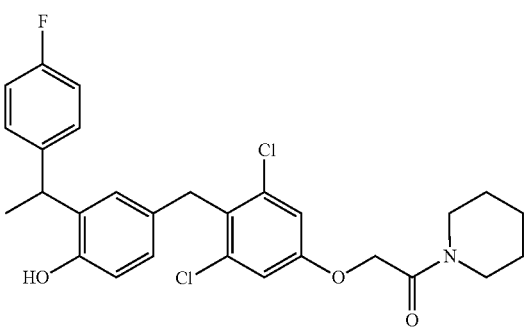

155

Compound 155 is prepared according to the procedures described in Example 71, substituting Compound 69 with Compound 72 and aqueous methylamine with aqueous piperidine.

Example 156

Synthesis of 2-(4-(3-(bis(4-fluorophenyl)methyl)-4-hydroxybenzyl)-3,5-dichlorophenoxy)acetic Acid (Compound 156)

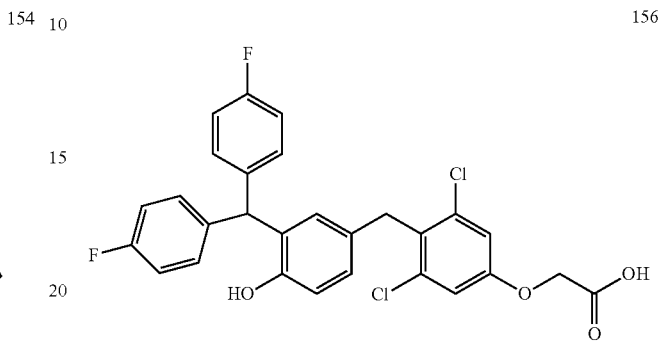

156

Compound 156 was prepared according to the procedures described in Examples 70 and 71, substituting 4-fluorobenzyl chloride with 4,4'-(chloromethylene)bis(fluorobenzene) in Example 70. MS (ES-API) m/z 526.8/528.8.

Example 157

Synthesis of 1-(aziridin-1-yl)-2-(3-chloro-4-(3-(4-fluorobenzyl)-4-hydroxybenzyl)-5-methylphenoxy)ethan-1-one (Compound 157)

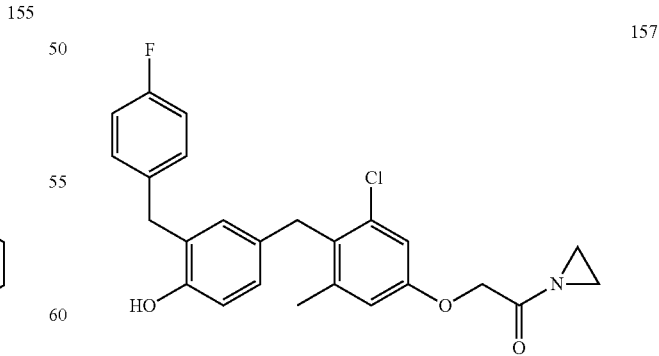

157

Compound 157 is prepared according to the procedures described in Example 71, substituting Compound 69 with Compound 114 and aqueous methylamine with aqueous aziridine.

Example 158

Synthesis of 1-(azetidin-1-yl)-2-(3-chloro-4-(3-(4-fluorobenzyl)-4-hydroxybenzyl)-5-methylphenoxy)ethan-1-one (Compound 158)

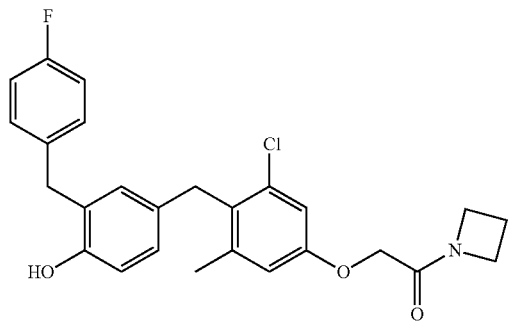

Compound 158 is prepared according to the procedures described in Example 71, substituting Compound 69 with Compound 114 and aqueous methylamine with aqueous azetidine.

Example 159

Synthesis of 2-(3-chloro-4-(3-(4-fluorobenzyl)-4-hydroxybenzyl)-5-methylphenoxy)-1-(pyrrolidin-1-yl)ethan-1-one (Compound 159)

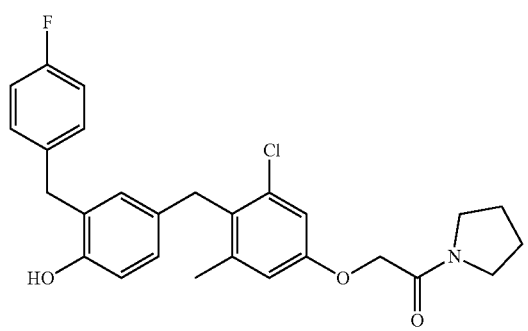

Compound 159 is prepared according to the procedures described in Example 71, substituting Compound 69 with Compound 114 and aqueous methylamine with aqueous pyrrolidine.

Example 160

Synthesis of 2-(3-chloro-4-(3-(4-fluorobenzyl)-4-hydroxybenzyl)-5-methylphenoxy)-1-(piperidin-1-yl)ethan-1-one (Compound 160)

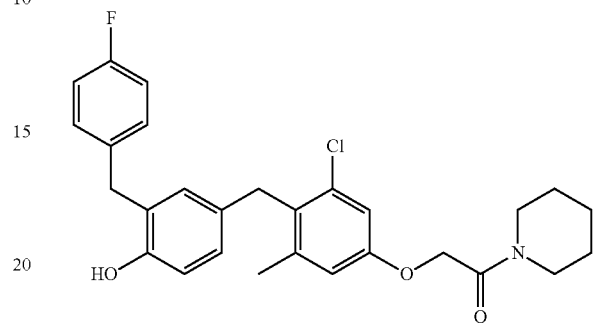

Compound 160 is prepared according to the procedures described in Example 71, substituting Compound 69 with Compound 114 and aqueous methylamine with aqueous piperadine.

Example 161

Synthesis of 2-(4-(3-benzyl-4-hydroxybenzyl)-3,5-dichlorophenoxy)acetic acid (Compound 161)

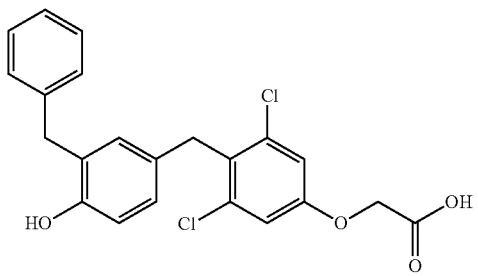

Compound 161 was prepared according to the procedures described in Examples 114 and 115, substituting Intermediate A15 with Intermediate A10 and 2-(4-fluorobenzyl)phenol with 2-benzylphenol in Example 114. MS (ES-API) m/z 414.9/416.9.

Example 162

Synthesis of 1-(aziridin-1-yl)-2-(3,5-dichloro-4-(3-(1-(4-fluorophenyl)propyl)-4-hydroxybenzyl)phenoxy)ethan-1-one (Compound 162)

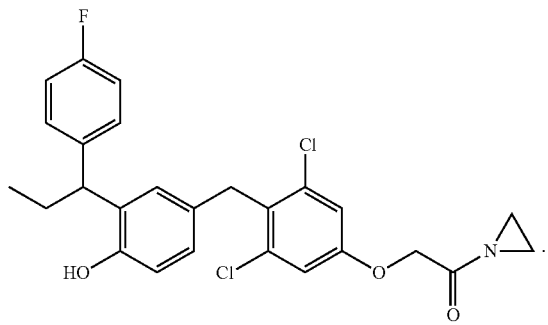

Compound 162 is prepared according to the procedures described in Example 4, substituting Compound 3 with Compound 98 and aqueous methylamine with aqueous aziridine.

Example 163

Synthesis of 1-(azetidin-1-yl)-2-(3,5-dichloro-4-(3-(1-(4-fluorophenyl)propyl)-4-hydroxybenzyl)phenoxy)ethan-1-one (Compound 163)

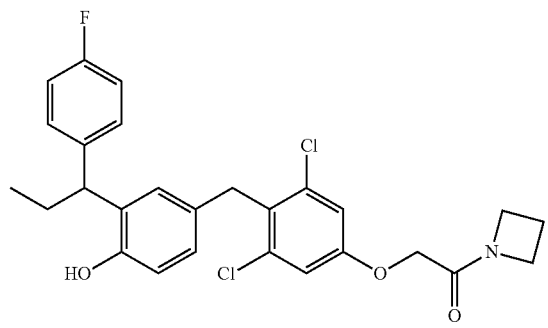

Compound 163 is prepared according to the procedures described in Example 4, substituting Compound 3 with Compound 98 and aqueous methylamine with aqueous azetidine.

Example 164

Synthesis of 2-(3,5-dichloro-4-(3-(1-(4-fluorophenyl)propyl)-4-hydroxybenzyl)phenoxy)-1-(pyrrolidin-1-yl)ethan-1-one (Compound 164)

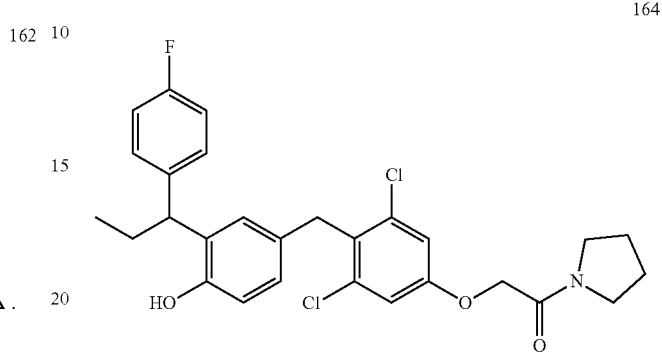

Compound 164 is prepared according to the procedures described in Example 4, substituting Compound 3 with Compound 98 and aqueous methylamine with aqueous pyrrolidine.

Example 165

Synthesis of 2-(3,5-dichloro-4-(3-(1-(4-fluorophenyl)propyl)-4-hydroxybenzyl)phenoxy)-1-(piperidin-1-yl)ethan-1-one (Compound 165)

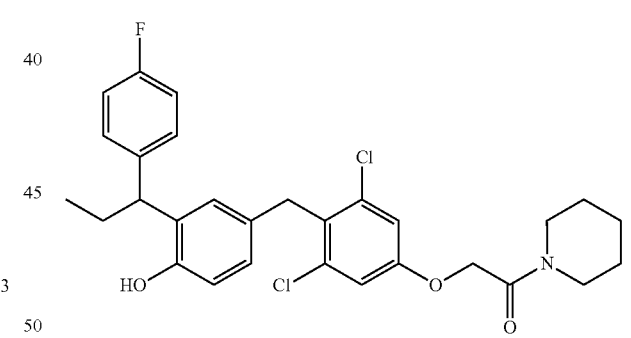

Compound 165 is prepared according to the procedures described in Example 4, substituting Compound 3 with Compound 98 and aqueous methylamine with aqueous piperidine.

Example 166

Thyroid-Hormone Reporter-Gene Assays

Compounds were tested for thyroid-hormone receptor activity using TR reporter-gene assays. Reporter cells used in the assays express a TR-receptor hybrid (either TRα or TRβ) in which the native N-terminal DNA binding domain (DBD) has been replaced with that of the yeast Gal4 DBD. The reporter gene, firefly luciferase, is functionally linked to the Gal4 upstream activation sequence (UAS). Both cell lines were derived from human embryonic kidney (HEK293).

Step 1:

A suspension of reporter cells was prepared in cell recovery medium containing 10% charcoal-stripped FBS, and dispensed into assay plates. The plates were pre-incubated for 6 hours in a cell culture incubator (37° C./5% $CO_2$/85% humidity).

Step 2:

Test compound master stocks and triiodothyronine were diluted in DMSO to generate solutions at "1,000×-concentration" relative to each final treatment concentration. These intermediate stocks were subsequently diluted directly into compound screening medium containing 10% charcoal-stripped FBS to generate "2×-concentration" treatment media (containing 0.2, 0.4 or 0.8% DMSO).

Step 3:

At the end of the pre-incubation period, culture media were discarded from the assay plates, and all wells received 100 µl of compound screening medium. 100 µl of each of the previously prepared "2×-concentration" treatment media were dispensed into duplicate assay wells, thereby achieving the desired final treatment concentrations. The final concentration of DMSO in all assay wells was 0.1, 0.2 or 0.4%. Assay plates were incubated for 24 hr in a cell culture incubator (37° C./5% $CO_2$/85% humidity).

Step 4:

At the 24 h assay endpoint, treatment media were discarded and 100/well of luciferase detection reagent was added. Relative luminometer units (RLUs) were quantified from each assay well. The performance of the TRα and TRβ assays was validated using the reference agonist triiodothyronine (T3).

The results of these assays are presented in Table 2 below, wherein data are reported as $EC_{50}$ values determined for TRα and TRβ receptors, and the selectivity index (SI) is calculated as $EC_{50}$ (TRα)/$EC_{50}$ (TRβ). To this end, $EC_{50}$ and SI values are expressed as follows:

TABLE 2

Activity Data

| Cpd. No. | TRα | TRβ | T3-SI |
|---|---|---|---|
| T3 | ++++ | +++ | + |
| 1 | ++ | ++ | ++ |
| 3 | + | ++ | +++ |
| 5 | + | ++ | +++ |
| 6 | ND | + | ND |
| 7 | + | + | ++ |
| 8 | ND | + | ND |
| 9 | ND | + | ND |
| 11 | + | + | ND |
| 12 | + | ++ | +++ |
| 13 | + | ++ | +++ |
| 14 | ND | + | ND |
| 15 | ND | + | ND |
| 16 | + | ++ | +++ |
| 17 | + | ++ | ++ |
| 19 | ++ | +++ | ++ |
| 21 | + | ++ | ++ |
| 22 | + | + | ND |
| 25 | | | |
| 26 | + | ++ | +++ |
| 28 | ND | + | ND |
| 29 | ++ | +++ | ++ |
| 34 | + | ++ | ++ |
| 36 | + | + | ++ |
| 37 | ND | + | ND |
| 38 | + | + | ++ |

TABLE 2-continued

Activity Data

| Cpd. No. | TRα | TRβ | T3-SI |
|---|---|---|---|
| 40 | + | + | ++ |
| 42 | + | ++ | ++ |
| 43 | + | ++ | ++ |
| 44 | ND | + | ND |
| 45 | ++ | +++ | ++ |
| 48 | ND | + | ND |
| 49 | + | ++ | ++ |
| 50 | ND | ++ | ND |
| 51 | + | + | ++ |
| 52 | ++ | +++ | ++ |
| 54 | + | ++ | ++ |
| 55 | ND | + | ND |
| 56 | + | ++ | ++ |
| 60 | + | ++ | +++ |
| 62 | + | ++ | ++ |
| 64 | ++ | ++ | ++ |
| 66 | ++ | +++ | ++ |
| 70 | + | ++ | +++ |
| 73 | +++ | +++ | ++ |
| 74 | + | ++ | ++ |
| 75 | +++ | ++++ | ++ |
| 80 | ND | + | ND |
| 82 | + | + | ++ |
| 84 | + | + | ++ |
| 86 | + | + | ++ |
| 88 | ++ | ++ | ++ |
| 90 | + | + | ++ |
| 92 | ND | + | ND |
| 94 | ND | + | ND |
| 96 | ND | + | ND |
| 98 | ++ | +++ | ++ |
| 102 | + | ++ | +++ |
| 104 | ++ | +++ | ++ |
| 105 | ++ | +++ | ++ |
| 107 | ++ | +++ | ++ |
| 109 | + | ++ | +++ |
| 111 | ++ | ++ | ++ |
| 113 | + | + | ++ |
| 115 | ++ | +++ | ++ |
| 119 | + | ++ | ++ |
| 121 | + | ++ | ++ |
| 123 | + | ++ | ++ |
| 125 | ++ | +++ | ++ |
| 127 | ++ | +++ | ++ |
| 129 | + | ++ | +++ |
| 131 | +++ | ++++ | ++ |
| 133 | ++ | +++ | ++ |
| 135 | + | + | ++ |
| 138 | + | ++ | ++ |

| Potency: | + | $EC_{50}$ > 1,000 nM |
|---|---|---|
| | ++ | 100 nM < $EC_{50}$ ≤ 1,000 nM |
| | +++ | 10 nM < $EC_{50}$ ≤ 100 nM |
| | ++++ | $EC_{50}$ ≤ 10 Nm |
| | ND | Not determined |
| Selectivity: | + | T3-SI ≤ 3X |
| | ++ | 3X < T3-SI ≤ 30X |
| | +++ | T3-SI > 30X |
| | ND | Not determined |

As indicated by the above experiments, compounds of the present invention show improved TRβ selectivity when compared to the natural agonist T3.

Example 167

In Vivo Activity

Animal Studies

Compounds of the current invention may be tested for thyroid-hormone receptor agonist activity in an in vivo model according to the following protocol.

Male Sprague-Dawley rats (~6 weeks old) are placed on a high cholesterol chow (HC Chow; 1.5% Cholesterol, 0.5% choline) for at least 10 days. Animals are weighed on Day −1. Test compounds are formulated in 1% NMP/1% solutol and dosed orally (PO), subcutaneously (SC) or intraperitoneally (IP) for 7 days, with each daily dose based on the body weight on that day. On Day 1 and Day 7, approximately 24 hrs after the first and last dose, respectively, blood samples are obtained via the saphenous vein, processed for serum and frozen at −80° C. Serum samples are analyzed for total cholesterol, LDL cholesterol and/or triglycerides using a clinical chemistry analyzer. If desired, test compound levels may be determined in these same samples by LCMS, comparing peak area to authentic standards. The rats are then anesthetized with isoflurane and an additional blood sample collected from the inferior vena cava or via cardiac puncture. Samples were again processed for serum, then analyzed for T3/T4/TSH levels by ELISA. Rats are terminated by exsanguination or pneumothorax; organs are harvested and weighed. Organ weight data are reported both as absolute values and as a percent of final body weight.

Compounds of the current invention may be tested for thyroid-hormone mediated remyelination according to the following protocol.

Eight week old, male and female iCKO-Myrf mice are treated with 100 μL (20 mg/mL) tamoxifen i.p. daily for 5 days to induce oligodendrocyte depletion through deletion of Myrf from the mature oligodendrocytes (Koenning et al. 2012 J. Neuroscience). Test compounds are formulated into the food or formulated in 1% NMP/1% solutol and dosed PO, SC or IP starting at week 2, 5 or 12 after tamoxifen induction. Dosing frequency may be daily (QD), every other day (Q2D), three times a week (QIW) or weekly (QW). The functional impact of central demyelination is measured by subjecting the mice to an accelerating rotorod technique where the time at which the mice fall off of a rotating rod is indicative of their neuromuscular function. Mice are subjected to the rotorod protocol weekly, every other week or at specific times during the study. Loss of myelination is associated with decreased time such that a nadir in ability occurs around 12 weeks after tamoxifen treatment. Partial recovery occurs from 12-24 weeks. Mice are sacrificed at 24 weeks after tamoxifen induction and brain and spinal cord tissues examined for remyelination using histologic analysis.

Compounds of the current invention may be tested for thyroid-hormone mediated inhibition of fibrosis according to the following protocol.

Adult male, C57Bl/6 mice are induced with pulmonary fibrosis through a single oropharangeal (OP) administration of 1.5-2 U/kg of bleomycin. Test compounds are formulated in 1% NMP/1% solutol and dosed PO, SC or IP, QD starting at day −1 (prophylactic) or Day 7 (therapeutic) after bleomycin administration. On Day 21, mice are anesthetized and blood drawn via cardiac puncture. Lungs are excised and weighed, subjected broncheoalveolar lavage, inflated and fixed for histologic analysis. Lung samples are embedded in paraffin and stained with hematoxylin and eosin and Masson's trichrome stain. A pathologist evaluates degree of fibrosis using the Ashcroft's score to quantify fibrosis. A minimum of 10 sites per lung are assessed and an average score reported for each lung.

Tissue Distribution Studies

For tissue concentration studies in male C57Bl/6 mice, test compounds are formulated as NMP/solutol/PBS solution, at a concentration of 0.05 mg/mL and dosed at 2 mL/kg with the targeted dose of 0.100 mg/kg via SC injection or oral dosing. Plasma, brain, liver, lung, kidney, heart and other selected tissue samples are collected at 0.5, 2, 8 and 24 hr (for AUC determination) or 1 hr (single time point) post-dose with three animals per time point. Tissue homogenates and plasma concentrations of test compounds are determined using LC-MS/MS with lower limits of quantitation of 0.0200 ng/mL or 0.100 ng/g. The pharmacokinetic parameters are determined by non-compartmental methods using WinNonlin.

Gene Activation

Adult male Sprague-Dawley rats or C57BL/6 mice are dosed orally with test compounds at up to 3 dose levels (e.g. 1×, 3× and 0x higher than the $ED_{50}$ values obtained in the cholesterol lowering studies described above). At predefined times, 4, 8 or 24 hrs after test compound administration, rodents are anesthetized and blood drawn for plasma samples to measure drug concentrations. Samples of multiple organs including, but not limited to, liver, brain, kidney, heart, lung, skeletal muscle, pituitary and testes, are harvested and processed for RNA analysis. Samples are analyzed either by RNA-Seq after RNA isolation or by targeted gene analysis using an appropriate platform such as Quantigene™ which does not require RNA isolation. Multiple genes are used to represent a T3-mediated gene signature in each tissue; different genes are used for each tissue and all are normalized to multiple housekeeping genes that account for any variability in overall RNA quality.

Conversion Studies

Amides of Formula II may be converted to active agonist acids of Formula IV through the action of amidases such as FAAH. Similarly, esters of Formula III may be converted to active agonist acids of Formula IV through the action of various esterases. This in vivo conversion can be demonstrated through pharmacokinetics studies which measure the level of test compounds as described below:

The pharmacokinetics of test compounds are evaluated following IV, PO or SC administration to fasted male Sprague-Dawley rats (N=3/route/dose). Test compounds are dosed as clear solutions in NMP/solutol/PBS, at a concentration of 0.1 mg/mL as a single dose via IV injection (0.1 mg/kg) or orally (1 mg/kg) or subcutaneous injection (SC, 0.1 mg/kg). Blood samples are collected into $K_2$EDTA tubes at pre-dose, 0.083, 0.25, 0.5, 1, 2, 4, 8 and 24 hours post-dose administration. Plasma concentrations of test compounds are determined using LC-MS/MS with a lower limit of quantitation of 0.0200 ng/mL. The pharmacokinetic parameters are determined by non-compartmental methods using WinNonlin.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. In addition, the terms used in the following claims should not be construed as limited to the specific embodiments disclosed in the specification, but should be construed to include all possible embodiments along with the full scope of equivalents to which such claims are entitled.

This application claims the benefit of priority to U.S. Provisional Application No. 62/812,890, filed Mar. 1, 2019, and U.S. Provisional Application No. 62/953,100, filed Dec. 23, 2019, which applications are hereby incorporated by reference in their entirety.

The invention claimed is:
1. A compound having the structure of Formula (I):

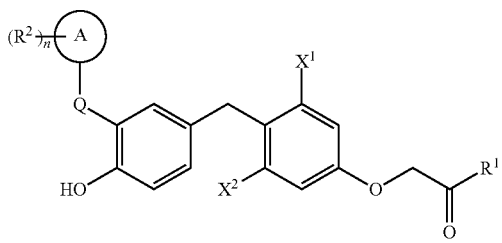

(I)

or a pharmaceutically acceptable isomer, racemate, hydrate, solvate, isotope, or salt thereof, wherein:
$X^1$ is lower alkyl, lower haloalkyl, or halo;
$X^2$ is lower alkyl, lower haloalkyl, or halo;
$R^1$ is —$NR^{1a}R^{1b}$ or —$OR^{1c}$;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl;
Q is a bond;
A is aryl or heteroaryl;
each $R^2$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
n is 1-5; and
$R^a$ and $R^b$ are each, independently, H, lower alkyl, or lower haloalkyl;
wherein $R^{1a}$, $R^{1b}$, $R^{1c}$, $R^2$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

2. The compound of claim 1 having the structure of Formula (III):

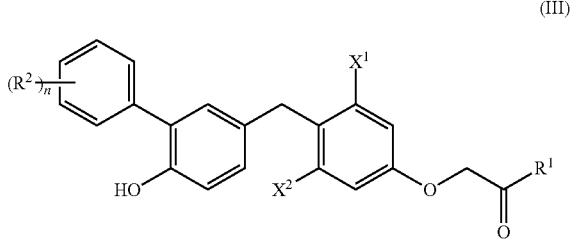

(III)

or a pharmaceutically acceptable isomer, racemate, hydrate, solvate, isotope, or salt thereof, wherein:
$X^1$ is lower alkyl, lower haloalkyl, or halo;
$X^2$ is lower alkyl, lower haloalkyl, or halo;
$R^1$ is $NR^{1a}R^{1b}$ or —$OR^{1c}$;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1c}$ is H, lower alkyl, carbocycle, heterocycle, carbocyclealkyl, or heterocyclealkyl;
A is aryl or heteroaryl;
each $R^2$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
n is 1-5; and
$R^a$ and $R^b$ are each, independently, H, lower alkyl, or lower haloalkyl;
wherein $R^{1a}$, $R^{1b}$, $R^{1c}$, $R^2$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

3. The compound of claim 1 having the structure of Formula (IV):

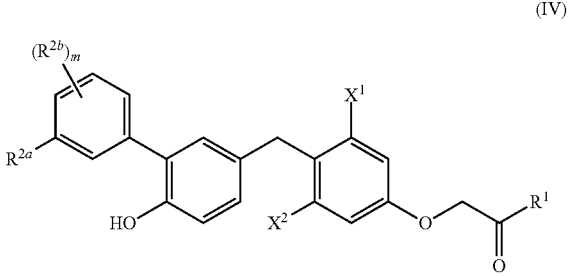

(IV)

or a pharmaceutically acceptable isomer, racemate, hydrate, solvate, isotope, or salt thereof, wherein:
$X^1$ is lower alkyl, lower haloalkyl, or halo;
$X^2$ is lower alkyl, lower haloalkyl, or halo;
$R^1$ is —$NR^{1a}R^{1b}$ or —$OR^{1c}$;
$R^{1a}$ and $R^{1b}$ are each, independently, H, lower alkyl, lower alkenyl, lower alkynyl, —$OR^a$, —$NR^aR^b$, carbocycle, carbocyclealkyl, heterocycle, or heterocyclealkyl, or $R^{1a}$ and $R^{1b}$ taken together with the nitrogen atom to which they are attached form heterocycle;
$R^{1C}$ is H, lower alkyl, carbocycle, heterocycle, carbocyclealkyl, or heterocyclealkyl;
$R^{2a}$ is halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
each $R^{2b}$ is, independently, halo, cyano, lower alkyl, lower alkenyl, lower alkynyl, lower haloalkyl, carbocycle, heterocycle, carbocyclealkyl, heterocyclealkyl, —$OR^a$, —$NR^aR^b$, —$C(O)R^a$, —$C(O)OR^a$, —$C(O)NR^aR^b$, —$NR^aC(O)R^b$, —$S(O)_2R^a$, or —$S(O)_2OR^a$;
m is 0-4; and
$R^a$ and $R^b$ are each, independently, H, lower alkyl, or lower haloalkyl;
wherein $R^{1a}$, $R^{1b}$, $R^{1c}$, $R^{2a}$, $R^{2b}$, $R^a$, and $R^b$ are each, independently, optionally substituted with one or more halo, cyano, —OR', —NR'R", —$S(O)_2R'$ or —$S(O)_2OR'$, wherein R' and R" are each, independently, H, lower alkyl, or lower haloalkyl.

4. The compound of claim 1, or a pharmaceutically acceptable isomer, racemate, hydrate, solvate, isotope, or salt thereof, wherein $R^{1a}$ is lower alkyl.

5. The compound of claim 4, or a pharmaceutically acceptable isomer, racemate, hydrate, solvate, isotope, or salt thereof, wherein $R^{1a}$ is methyl.

6. The compound of claim 1, or a pharmaceutically acceptable isomer, racemate, hydrate, solvate, isotope, or salt thereof, wherein $R^{1b}$ is H.

7. The compound of claim 1, or a pharmaceutically acceptable isomer, racemate, hydrate, solvate, isotope, or salt thereof, wherein $R^{1c}$ is H or lower alkyl.

8. The compound of claim 7, or a pharmaceutically acceptable isomer, racemate, hydrate, solvate, isotope, or salt thereof, wherein $R^{1c}$ is methyl.

9. The compound of claim 1, or a pharmaceutically acceptable isomer, racemate, hydrate, solvate, isotope, or salt thereof, wherein $X^1$ is methyl.

10. The compound of claim 1, or a pharmaceutically acceptable isomer, racemate, hydrate, solvate, isotope, or salt thereof, wherein $X^1$ is Cl or Br.

11. The compound of claim 1, or a pharmaceutically acceptable isomer, racemate, hydrate, solvate, isotope, or salt thereof, wherein $X^1$ is —$CF_3$.

12. The compound of claim 1, or a pharmaceutically acceptable isomer, racemate, hydrate, solvate, isotope, or salt thereof, wherein $X^2$ is methyl.

13. The compound of claim 1, or a pharmaceutically acceptable isomer, racemate, hydrate, solvate, isotope, or salt thereof, wherein $X^2$ is Cl or Br.

14. The compound of claim 1, or a pharmaceutically acceptable isomer, racemate, hydrate, solvate, isotope, or salt thereof, wherein $X^2$ is —$CF_3$.

15. The compound of claim 1, or a pharmaceutically acceptable isomer, racemate, hydrate, solvate, isotope, or salt thereof, wherein at least one $R^2$ is lower alkyl.

16. The compound of claim 1, or a pharmaceutically acceptable isomer, racemate, hydrate, solvate, isotope, or salt thereof, wherein at least one $R^2$ is lower alkyl substituted with —OR', wherein R' is H or lower alkyl.

17. The compound of claim 1, or a pharmaceutically acceptable isomer, racemate, hydrate, solvate, isotope, or salt thereof, wherein at least one $R^2$ is lower haloalkyl.

18. The compound of claim 1, or a pharmaceutically acceptable isomer, racemate, hydrate, solvate, isotope, or salt thereof, wherein at least one $R^2$ is —$OR^a$.

19. The compound of claim 1, or a pharmaceutically acceptable isomer, racemate, hydrate, solvate, isotope, or salt thereof, wherein at least one $R^2$ is —$C(O)R^a$.

20. The compound of claim 1, or a pharmaceutically acceptable isomer, racemate, hydrate, solvate, isotope, or salt thereof, wherein at least one $R^2$ is —$NR^aC(O)R^b$.

21. The compound of claim 20, or a pharmaceutically acceptable isomer, racemate, hydrate, solvate, isotope, or salt thereof, wherein $R^a$ is H and $R^b$ is lower alkyl.

22. The compound of claim 1, or a pharmaceutically acceptable isomer, racemate, hydrate, solvate, isotope, or salt thereof, wherein at least one $R^2$ is —$C(O)OR^a$.

23. The compound of claim 1, or a pharmaceutically acceptable isomer, racemate, hydrate, solvate, isotope, or salt thereof, wherein at least one $R^2$ is —$S(O)_2R^a$.

24. The compound of claim 1, or a pharmaceutically acceptable isomer, racemate, hydrate, solvate, isotope, or salt thereof, wherein at least one $R^2$ is halo.

25. The compound of claim 24, or a pharmaceutically acceptable isomer, racemate, hydrate, solvate, isotope, or salt thereof, wherein at least one $R^2$ is F.

26. The compound of claim 1, or a pharmaceutically acceptable isomer, racemate, hydrate, solvate, isotope, or salt thereof, wherein at least one $R^2$ is cyano.

27. The compound of claim 1, or a pharmaceutically acceptable isomer, racemate, hydrate, solvate, isotope, or salt thereof, having the structure of any one of the following compounds:

| Compound Number | Structure |
|---|---|
| 1 | 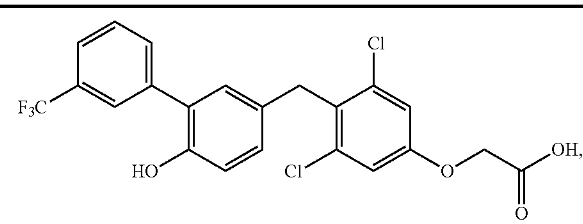 |
| 2 | 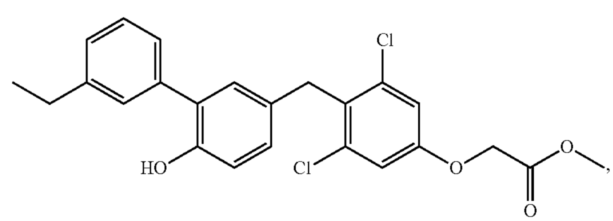 |
| 3 | 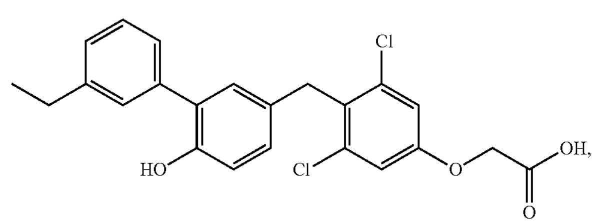 |

-continued

| Compound Number | Structure |
|---|---|
| 4 | (structure: 3'-ethyl-biphenyl with 2-OH, linked via CH₂ to 3,5-dichloro-4-(OCH₂C(O)NHCH₃)phenyl) |
| 5 | (structure: 3'-(OCHF₂)-biphenyl with 2-OH, linked via CH₂ to 3,5-dichloro-4-(OCH₂COOH)phenyl) |
| 6 | (structure: 3'-(ethoxycarbonyl)-biphenyl with 2-OH, linked via CH₂ to 3,5-dichloro-4-(OCH₂COOH)phenyl) |
| 7 | (structure: 3'-methoxy-biphenyl with 2-OH, linked via CH₂ to 3,5-dichloro-4-(OCH₂COOH)phenyl) |
| 8 | (structure: 3'-(hydroxymethyl)-biphenyl with 2-OH, linked via CH₂ to 3,5-dichloro-4-(OCH₂COOH)phenyl) |
| 9 | (structure: 3'-acetamido-biphenyl with 2-OH, linked via CH₂ to 3,5-dichloro-4-(OCH₂COOH)phenyl) |
| 10 | (structure: 3'-acetyl-biphenyl with 2-OH, linked via CH₂ to 3,5-dichloro-4-(OCH₂C(O)OCH₃)phenyl) |

-continued
| Compound Number | Structure |
|---|---|
| 11 | 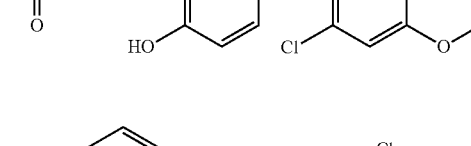 |
| 12 | 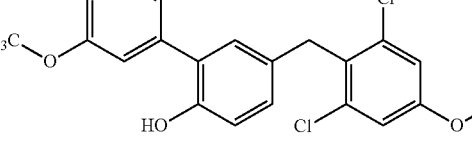 |
| 13 | 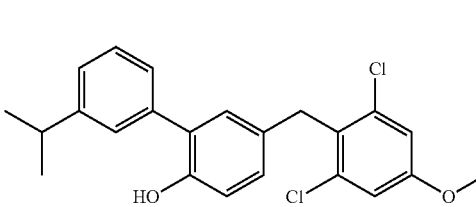 |
| 14 | 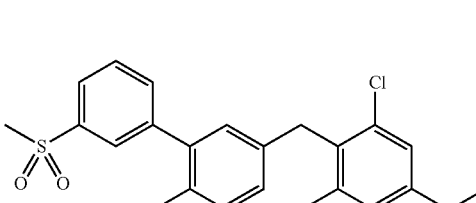 |
| 15 | 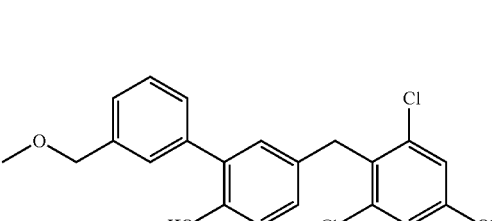 |
| 16 | 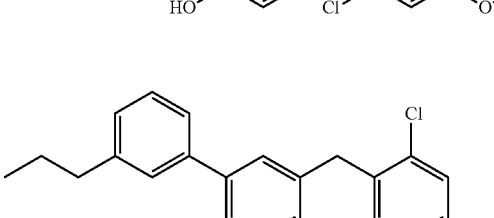 |
| 17 | 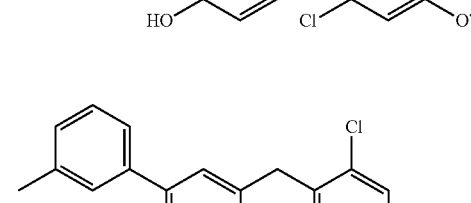 |

-continued
| Compound Number | Structure |
|---|---|
| 18 | 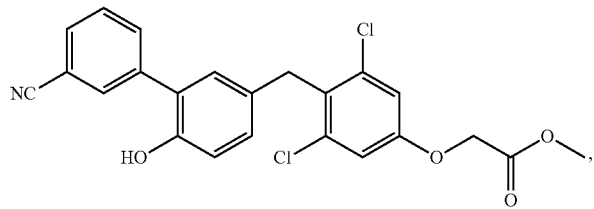 [SMILES: COC(=O)COc1cc(Cl)c(Cc2ccc(O)c(-c3cccc(C#N)c3)c2)c(Cl)c1] |
| 19 | 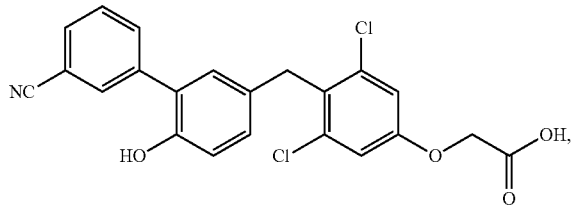 [SMILES: N#Cc1cccc(-c2cc(Cc3c(Cl)cc(OCC(=O)O)cc3Cl)ccc2O)c1] |
| 20 | 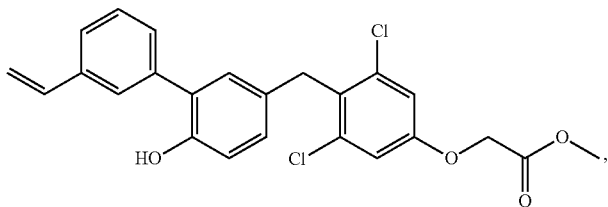 [SMILES: C=Cc1cccc(-c2cc(Cc3c(Cl)cc(OCC(=O)OC)cc3Cl)ccc2O)c1] |
| 21 | 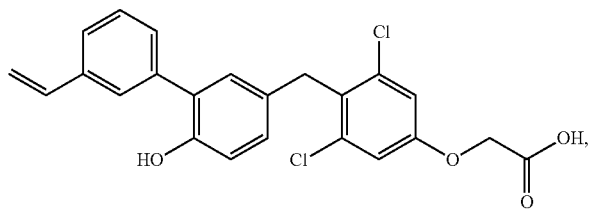 [SMILES: C=Cc1cccc(-c2cc(Cc3c(Cl)cc(OCC(=O)O)cc3Cl)ccc2O)c1] |
| 22 | 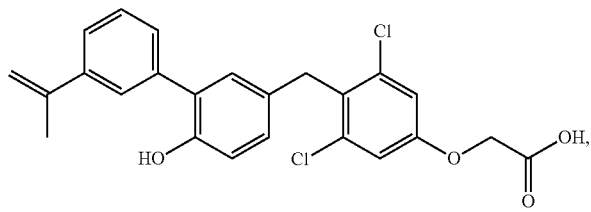 [SMILES: C=C(C)c1cccc(-c2cc(Cc3c(Cl)cc(OCC(=O)O)cc3Cl)ccc2O)c1] |
| 23 | 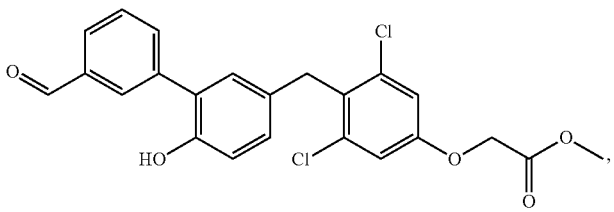 [SMILES: COC(=O)COc1cc(Cl)c(Cc2ccc(O)c(-c3cccc(C=O)c3)c2)c(Cl)c1] |
| 24 | 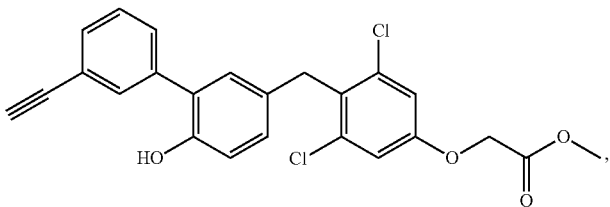 [SMILES: C#Cc1cccc(-c2cc(Cc3c(Cl)cc(OCC(=O)OC)cc3Cl)ccc2O)c1] |

| Compound Number | Structure |
|---|---|
| 25 | 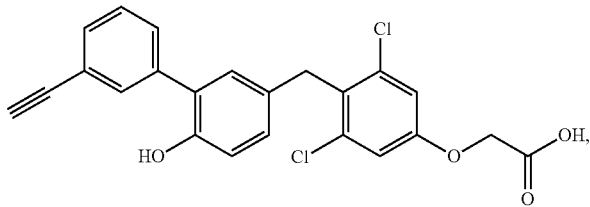 [SMILES: C#Cc1cccc(-c2cc(Cc3c(Cl)cc(OCC(=O)O)cc3Cl)ccc2O)c1] |
| 26 | 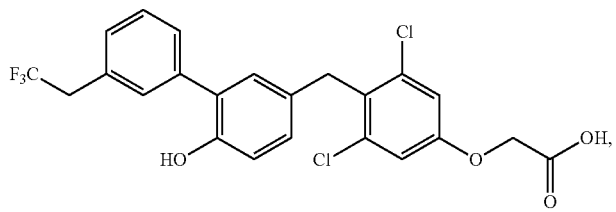 [SMILES: O=C(O)COc1cc(Cl)c(Cc2ccc(O)c(-c3cccc(CC(F)(F)F)c3)c2)c(Cl)c1] |
| 27 | 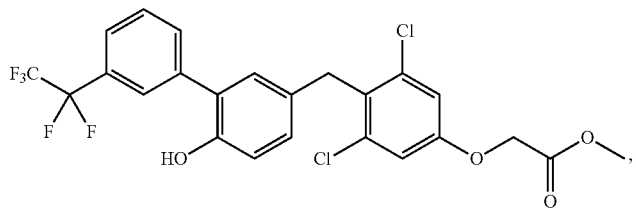 [SMILES: COC(=O)COc1cc(Cl)c(Cc2ccc(O)c(-c3cccc(C(F)(F)C(F)(F)F)c3)c2)c(Cl)c1] |
| 28 | 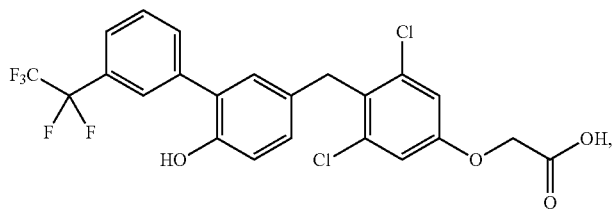 [SMILES: O=C(O)COc1cc(Cl)c(Cc2ccc(O)c(-c3cccc(C(F)(F)C(F)(F)F)c3)c2)c(Cl)c1] |
| 29 | 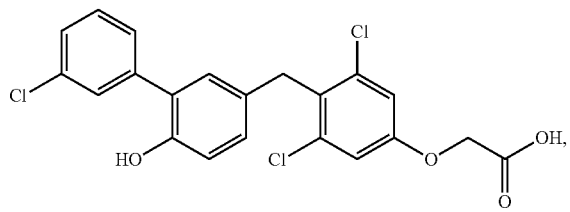 [SMILES: O=C(O)COc1cc(Cl)c(Cc2ccc(O)c(-c3cccc(Cl)c3)c2)c(Cl)c1] |
| 30 | 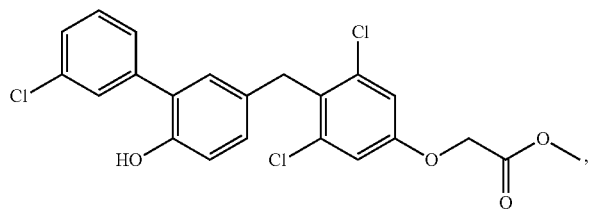 [SMILES: COC(=O)COc1cc(Cl)c(Cc2ccc(O)c(-c3cccc(Cl)c3)c2)c(Cl)c1] |
| 31 | 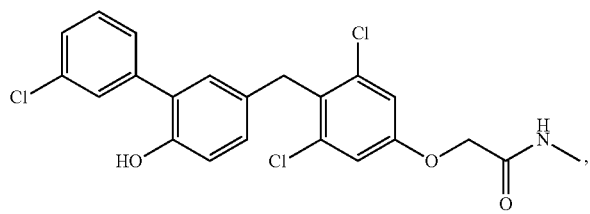 [SMILES: CNC(=O)COc1cc(Cl)c(Cc2ccc(O)c(-c3cccc(Cl)c3)c2)c(Cl)c1] |

-continued
| Compound Number | Structure |
|---|---|
| 32 | 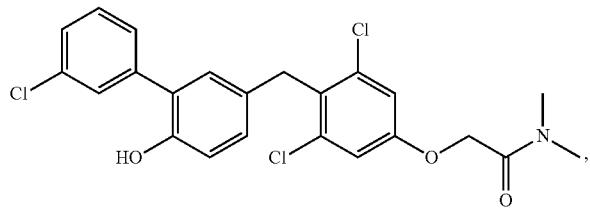 [SMILES: CN(C)C(=O)COc1cc(Cl)c(Cc2ccc(O)c(-c3cccc(Cl)c3)c2)c(Cl)c1] |
| 33 | 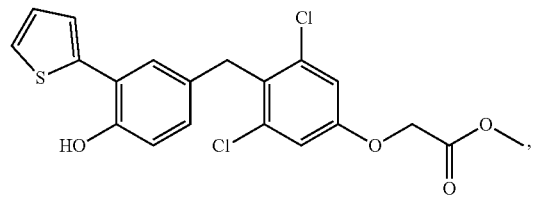 [SMILES: COC(=O)COc1cc(Cl)c(Cc2ccc(O)c(-c3cccs3)c2)c(Cl)c1] |
| 34 | 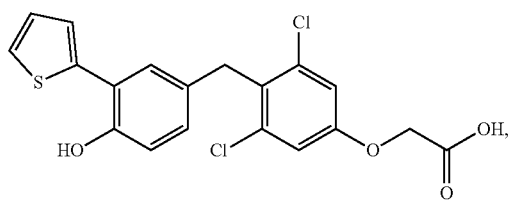 [SMILES: O=C(O)COc1cc(Cl)c(Cc2ccc(O)c(-c3cccs3)c2)c(Cl)c1] |
| 35 | 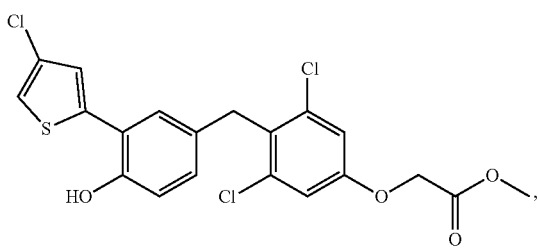 [SMILES: COC(=O)COc1cc(Cl)c(Cc2ccc(O)c(-c3cc(Cl)cs3)c2)c(Cl)c1] |
| 36 | 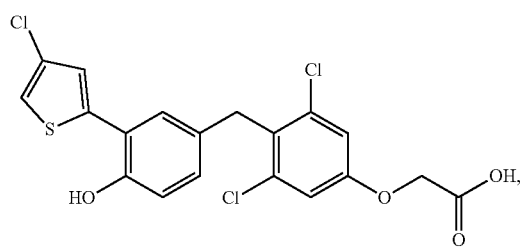 [SMILES: O=C(O)COc1cc(Cl)c(Cc2ccc(O)c(-c3cc(Cl)cs3)c2)c(Cl)c1] |
| 37 | 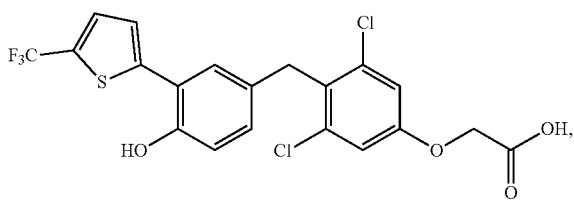 [SMILES: O=C(O)COc1cc(Cl)c(Cc2ccc(O)c(-c3ccc(C(F)(F)F)s3)c2)c(Cl)c1] |
| 38 | 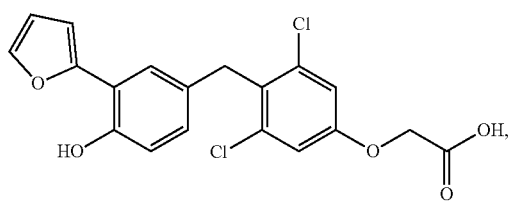 [SMILES: O=C(O)COc1cc(Cl)c(Cc2ccc(O)c(-c3ccco3)c2)c(Cl)c1] |

-continued
| Compound Number | Structure |
|---|---|
| 39 | 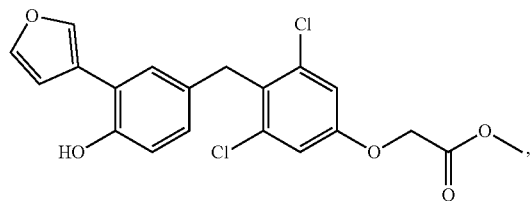 [SMILES: COC(=O)COc1cc(Cl)c(Cc2ccc(O)c(-c3ccoc3)c2)c(Cl)c1] |
| 40 | 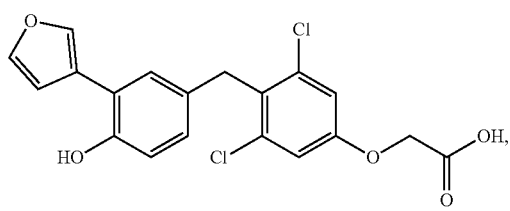 [SMILES: O=C(O)COc1cc(Cl)c(Cc2ccc(O)c(-c3ccoc3)c2)c(Cl)c1] |
| 41 | 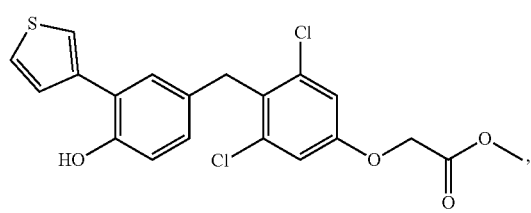 [SMILES: COC(=O)COc1cc(Cl)c(Cc2ccc(O)c(-c3ccsc3)c2)c(Cl)c1] |
| 42 | 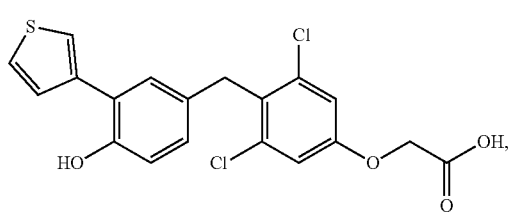 [SMILES: O=C(O)COc1cc(Cl)c(Cc2ccc(O)c(-c3ccsc3)c2)c(Cl)c1] |
| 43 | 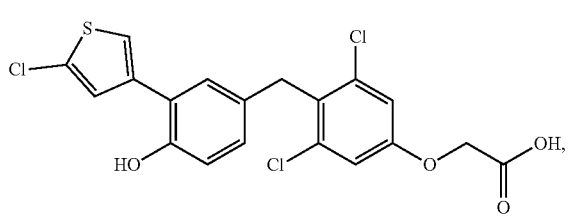 [SMILES: O=C(O)COc1cc(Cl)c(Cc2ccc(O)c(-c3csc(Cl)c3)c2)c(Cl)c1] |
| 44 | 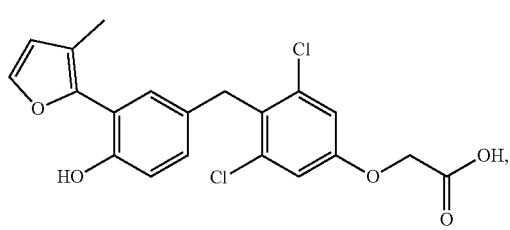 [SMILES: Cc1ccoc1-c1cc(Cc2c(Cl)cc(OCC(=O)O)cc2Cl)ccc1O] |
| 45 | 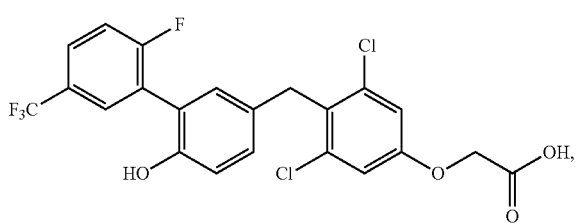 |

| Compound Number | Structure |
|---|---|
| 46 | 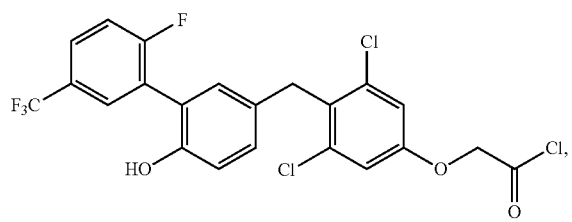 [SMILES: O=C(Cl)COc1cc(Cl)c(Cc2ccc(O)c(-c3cc(C(F)(F)F)ccc3F)c2)c(Cl)c1] |
| 46 | 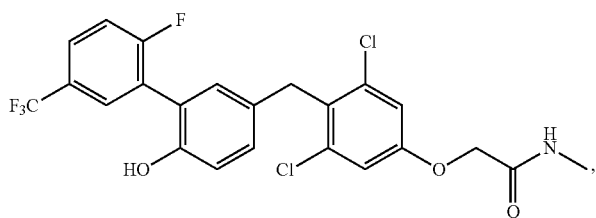 [SMILES: CNC(=O)COc1cc(Cl)c(Cc2ccc(O)c(-c3cc(C(F)(F)F)ccc3F)c2)c(Cl)c1] |
| 47 | 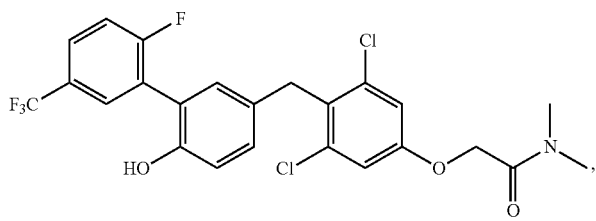 [SMILES: CN(C)C(=O)COc1cc(Cl)c(Cc2ccc(O)c(-c3cc(C(F)(F)F)ccc3F)c2)c(Cl)c1] |
| 48 | 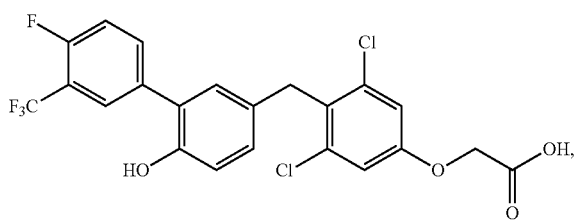 |
| 49 | 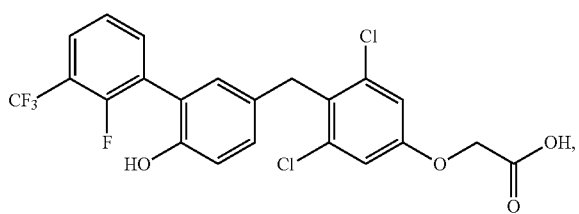 [SMILES: O=C(O)COc1cc(Cl)c(Cc2ccc(O)c(-c3cccc(C(F)(F)F)c3F)c2)c(Cl)c1] |
| 50 | 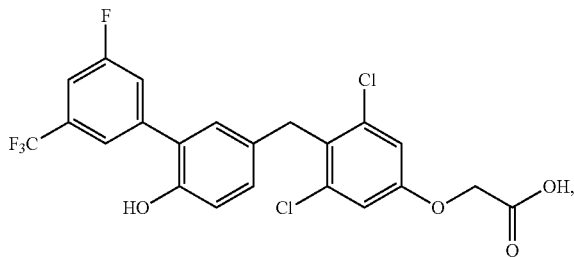 |

-continued
| Compound Number | Structure |
|---|---|
| 51 | 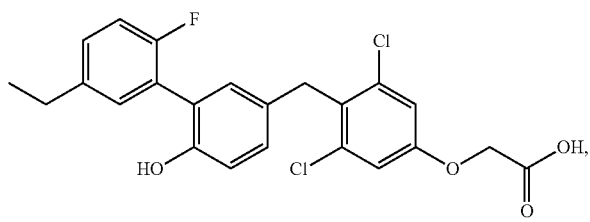 [SMILES: CCc1ccc(F)c(-c2cc(Cc3c(Cl)cc(OCC(=O)O)cc3Cl)ccc2O)c1] |
| 52 | 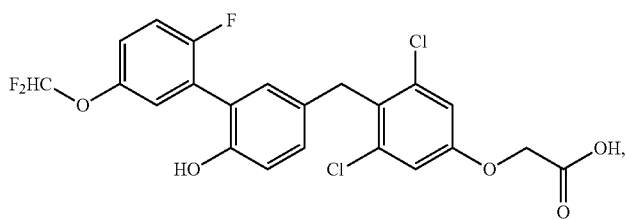 [SMILES: O=C(O)COc1cc(Cl)c(Cc2ccc(O)c(-c3cc(OC(F)F)ccc3F)c2)c(Cl)c1] |
| 53 | 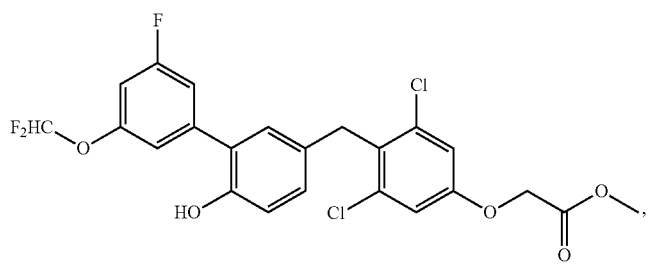 [SMILES: COC(=O)COc1cc(Cl)c(Cc2ccc(O)c(-c3cc(F)cc(OC(F)F)c3)c2)c(Cl)c1] |
| 54 | 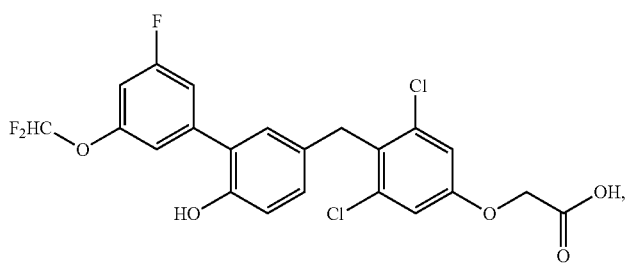 [SMILES: O=C(O)COc1cc(Cl)c(Cc2ccc(O)c(-c3cc(F)cc(OC(F)F)c3)c2)c(Cl)c1] |
| 55 | 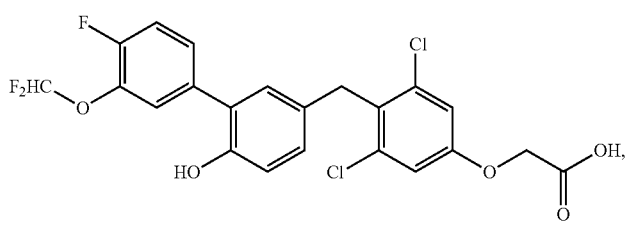 [SMILES: O=C(O)COc1cc(Cl)c(Cc2ccc(O)c(-c3ccc(F)c(OC(F)F)c3)c2)c(Cl)c1] |
| 56 | 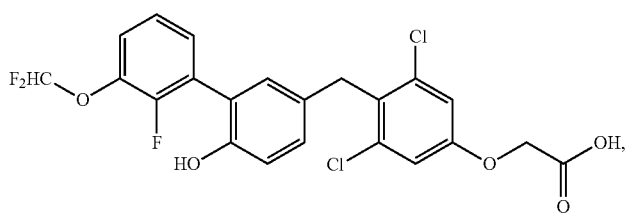 [SMILES: O=C(O)COc1cc(Cl)c(Cc2ccc(O)c(-c3cccc(OC(F)F)c3F)c2)c(Cl)c1] |

-continued
| Compound Number | Structure |
|---|---|
| 57 | 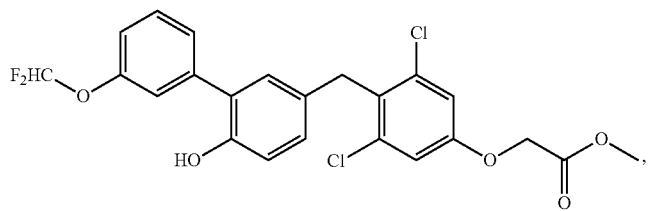 [SMILES: COC(=O)COc1cc(Cl)c(Cc2ccc(O)c(-c3cccc(OC(F)F)c3)c2)c(Cl)c1] |
| 58 | 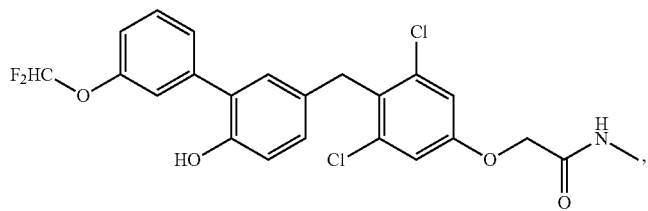 [SMILES: CNC(=O)COc1cc(Cl)c(Cc2ccc(O)c(-c3cccc(OC(F)F)c3)c2)c(Cl)c1] |
| 59 | 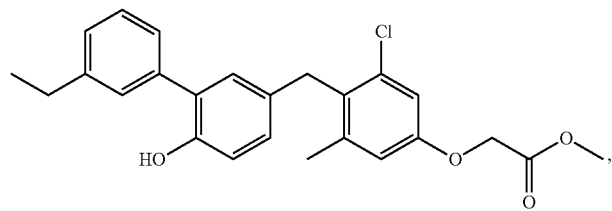 [SMILES: CCc1cccc(-c2cc(Cc3c(C)cc(OCC(=O)OC)cc3Cl)ccc2O)c1] |
| 60 | 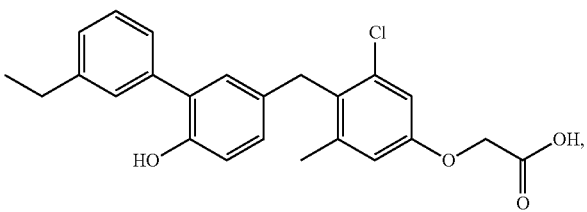 [SMILES: CCc1cccc(-c2cc(Cc3c(C)cc(OCC(=O)O)cc3Cl)ccc2O)c1] |
| 61 | 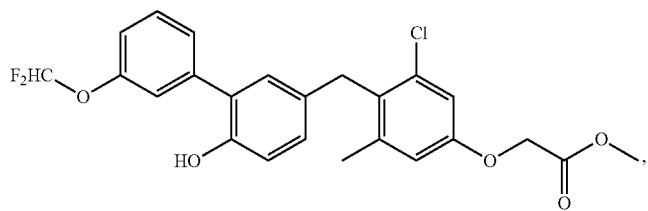 [SMILES: COC(=O)COc1cc(C)c(Cc2ccc(O)c(-c3cccc(OC(F)F)c3)c2)c(Cl)c1] |
| 62 | 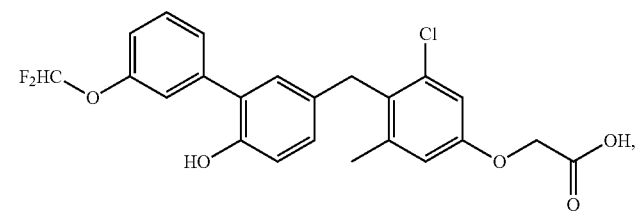 [SMILES: Cc1cc(OCC(=O)O)cc(Cl)c1Cc1ccc(O)c(-c2cccc(OC(F)F)c2)c1] |
| 63 | 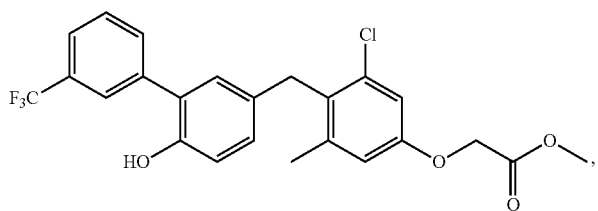 |

-continued
| Compound Number | Structure |
|---|---|
| 64 | 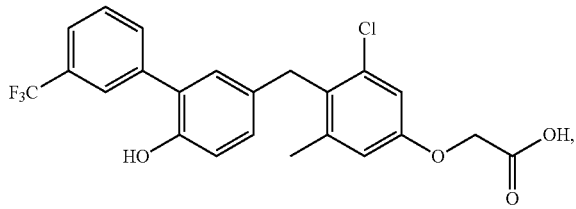 |
| 65 | 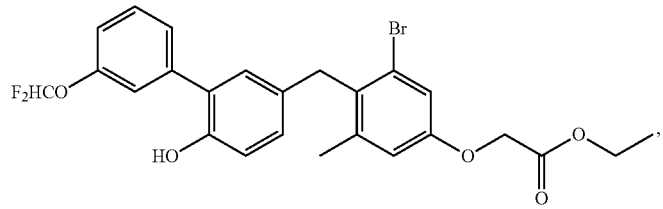 [SMILES: CCOC(=O)COc1cc(C)c(Cc2ccc(O)c(-c3cccc(OC(F)F)c3)c2)c(Br)c1] |
| 66 | 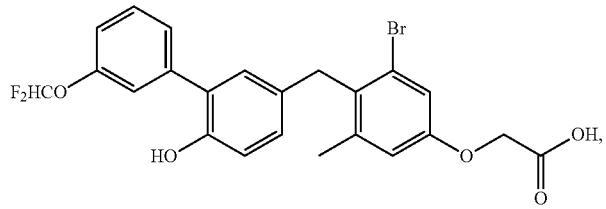 [SMILES: Cc1cc(OCC(=O)O)cc(Br)c1Cc1ccc(O)c(-c2cccc(OC(F)F)c2)c1] |
| 67 | 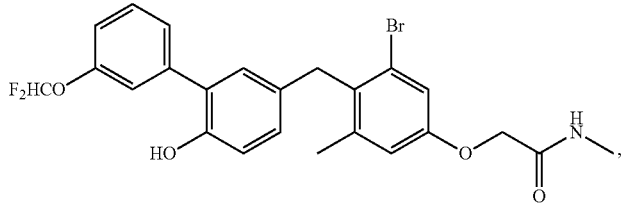 [SMILES: CNC(=O)COc1cc(C)c(Cc2ccc(O)c(-c3cccc(OC(F)F)c3)c2)c(Br)c1] |
| 68 | 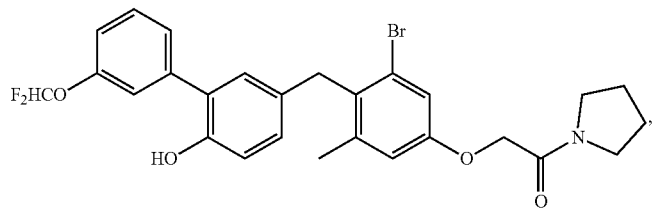 [SMILES: Cc1cc(OCC(=O)N2CCCC2)cc(Br)c1Cc1ccc(O)c(-c2cccc(OC(F)F)c2)c1] |
| 69 | 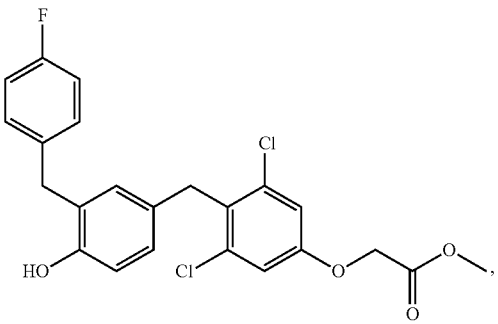 [SMILES: COC(=O)COc1cc(Cl)c(Cc2ccc(O)c(Cc3ccc(F)cc3)c2)c(Cl)c1] |

| Compound Number | Structure |
|---|---|
| 70 | 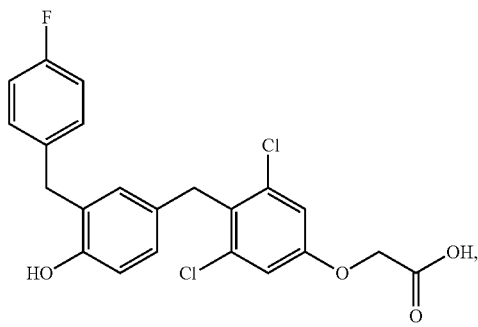 [SMILES: O=C(O)COc1cc(Cl)c(Cc2ccc(O)c(Cc3ccc(F)cc3)c2)c(Cl)c1] |
| 71 | 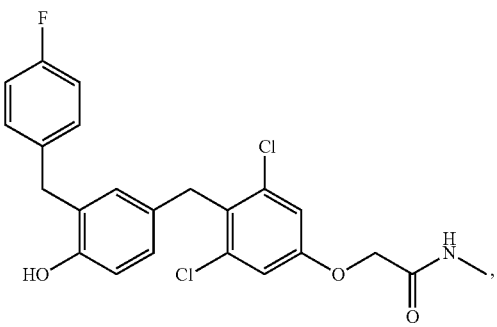 [SMILES: CNC(=O)COc1cc(Cl)c(Cc2ccc(O)c(Cc3ccc(F)cc3)c2)c(Cl)c1] |
| 72 | 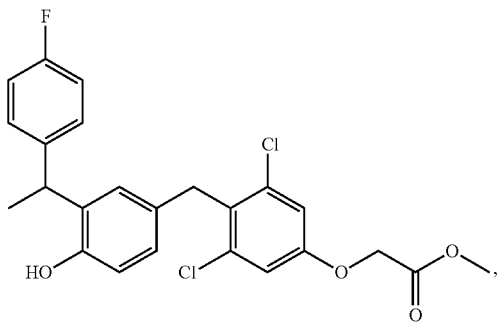 [SMILES: COC(=O)COc1cc(Cl)c(Cc2ccc(O)c(C(C)c3ccc(F)cc3)c2)c(Cl)c1] |
| 73 | 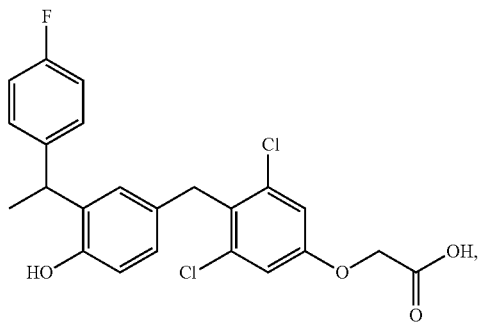 [SMILES: CC(c1ccc(F)cc1)c1cc(Cc2c(Cl)cc(OCC(=O)O)cc2Cl)ccc1O] |

-continued
| Compound Number | Structure |
|---|---|
| 74 | 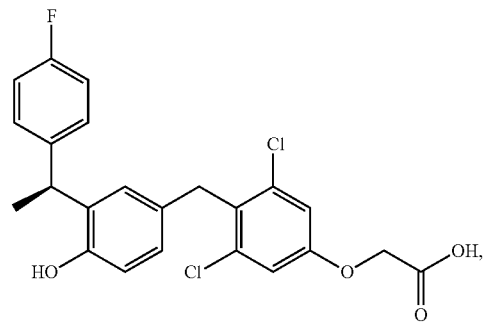 [SMILES: C[C@@H](c1ccc(F)cc1)c1cc(Cc2c(Cl)cc(OCC(=O)O)cc2Cl)ccc1O] |
| 75 | 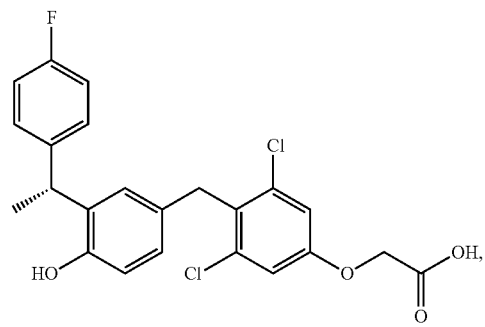 [SMILES: C[C@H](c1ccc(F)cc1)c1cc(Cc2c(Cl)cc(OCC(=O)O)cc2Cl)ccc1O] |
| 76 | 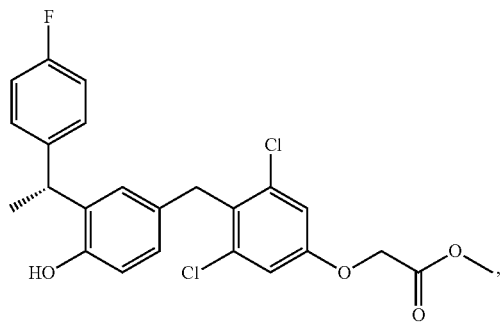 [SMILES: COC(=O)COc1cc(Cl)c(Cc2ccc(O)c([C@H](C)c3ccc(F)cc3)c2)c(Cl)c1] |
| 77 | 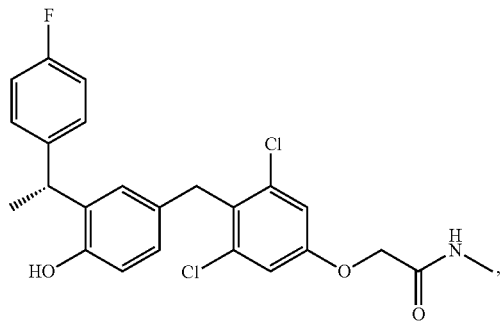 [SMILES: CNC(=O)COc1cc(Cl)c(Cc2ccc(O)c([C@H](C)c3ccc(F)cc3)c2)c(Cl)c1] |

| Compound Number | Structure |
|---|---|
| 78 | 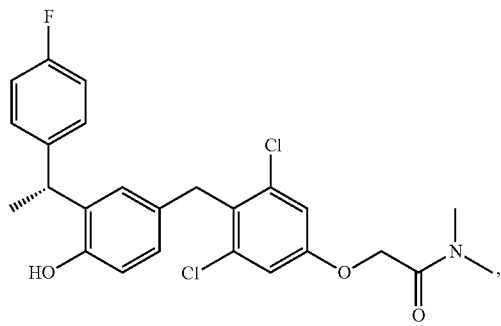 [SMILES: C[C@H](c1ccc(F)cc1)c1cc(Cc2c(Cl)cc(OCC(=O)N(C)C)cc2Cl)ccc1O] |
| 79 | 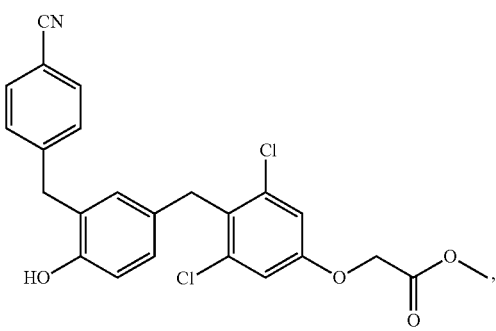 |
| 80 | 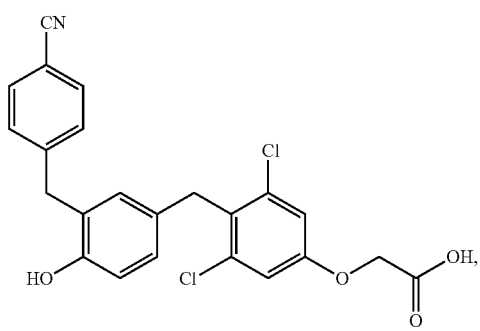 [SMILES: N#Cc1ccc(Cc2cc(Cc3c(Cl)cc(OCC(=O)O)cc3Cl)ccc2O)cc1] |
| 81 | 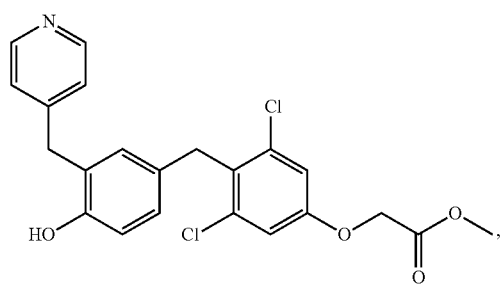 [SMILES: COC(=O)COc1cc(Cl)c(Cc2ccc(O)c(Cc3ccncc3)c2)c(Cl)c1] |
| 82 | 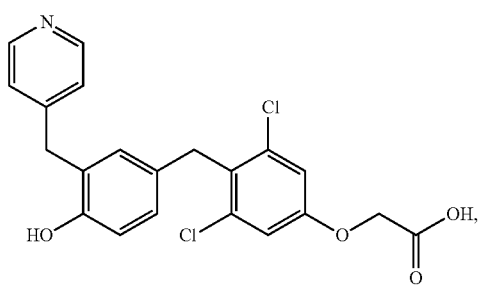 [SMILES: O=C(O)COc1cc(Cl)c(Cc2ccc(O)c(Cc3ccncc3)c2)c(Cl)c1] |

-continued
| Compound Number | Structure |
|---|---|
| 83 | 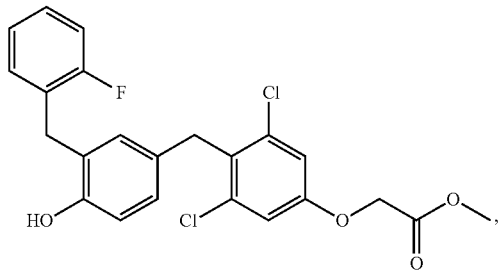 [SMILES: COC(=O)COc1cc(Cl)c(Cc2ccc(O)c(Cc3ccccc3F)c2)c(Cl)c1] |
| 84 | 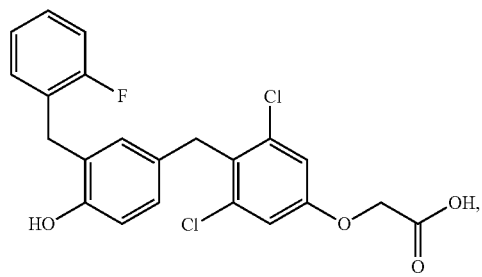 [SMILES: O=C(O)COc1cc(Cl)c(Cc2ccc(O)c(Cc3ccccc3F)c2)c(Cl)c1] |
| 85 | 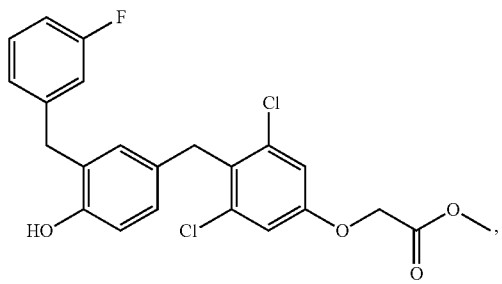 [SMILES: COC(=O)COc1cc(Cl)c(Cc2ccc(O)c(Cc3cccc(F)c3)c2)c(Cl)c1] |
| 86 | 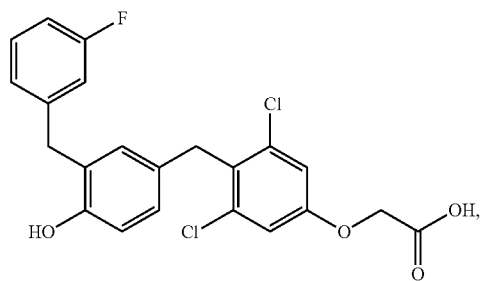 [SMILES: O=C(O)COc1cc(Cl)c(Cc2ccc(O)c(Cc3cccc(F)c3)c2)c(Cl)c1] |
| 87 | 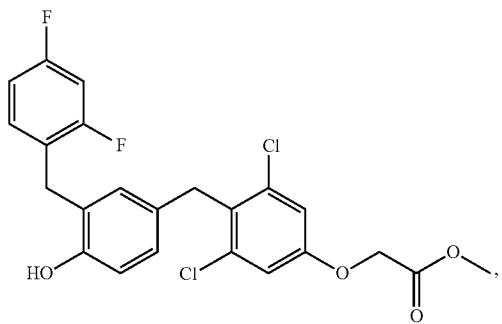 [SMILES: COC(=O)COc1cc(Cl)c(Cc2ccc(O)c(Cc3ccc(F)cc3F)c2)c(Cl)c1] |

| Compound Number | Structure |
|---|---|
| 88 | 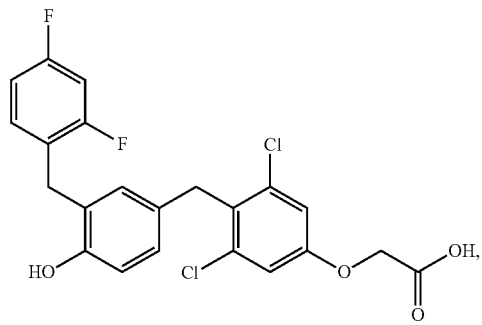 [SMILES: O=C(O)COc1cc(Cl)c(Cc2ccc(O)c(Cc3ccc(F)cc3F)c2)c(Cl)c1] |
| 89 | 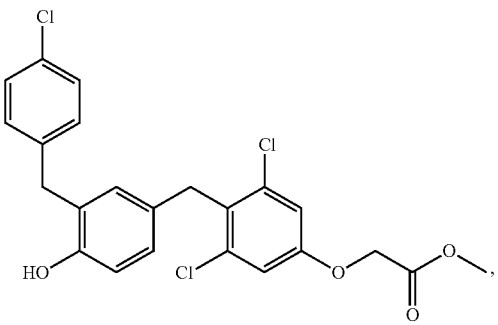 |
| 90 | 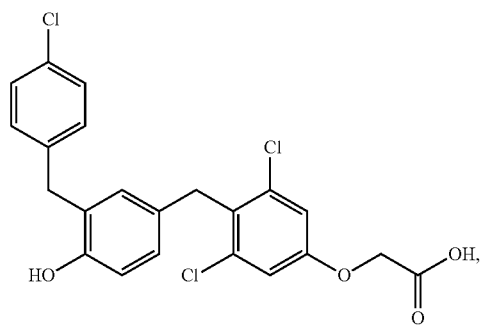 [SMILES: O=C(O)COc1cc(Cl)c(Cc2ccc(O)c(Cc3ccc(Cl)cc3)c2)c(Cl)c1] |
| 91 | 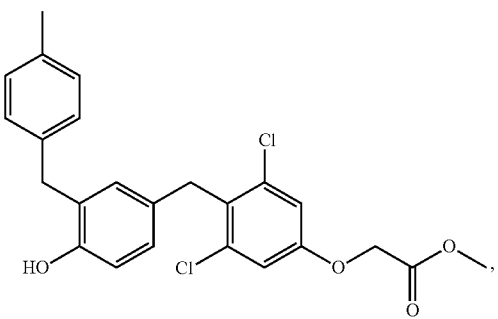 [SMILES: COC(=O)COc1cc(Cl)c(Cc2ccc(O)c(Cc3ccc(C)cc3)c2)c(Cl)c1] |

-continued

| Compound Number | Structure |
|---|---|
| 92 | ![Structure 92] 4-methylbenzyl-(hydroxyphenyl)methyl-(3,5-dichloro-phenoxy)acetic acid |
| 93 | ![Structure 93] pyrimidin-5-ylmethyl-(hydroxyphenyl)methyl-(3,5-dichloro-phenoxy)acetic acid methyl ester |
| 94 | ![Structure 94] pyrimidin-5-ylmethyl-(hydroxyphenyl)methyl-(3,5-dichloro-phenoxy)acetic acid |
| 95 | ![Structure 95] 4-(2,2,2-trifluoroethyl)benzyl-(hydroxyphenyl)methyl-(3,5-dichloro-phenoxy)acetic acid methyl ester |
| 96 | ![Structure 96] 4-(2,2,2-trifluoroethyl)benzyl-(hydroxyphenyl)methyl-(3,5-dichloro-phenoxy)acetic acid |

| Compound Number | Structure |
|---|---|
| 97 | 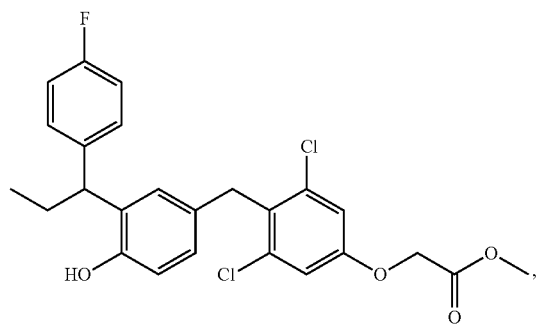 [SMILES: CCC(c1ccc(F)cc1)c1cc(Cc2c(Cl)cc(OCC(=O)OC)cc2Cl)ccc1O] |
| 98 | 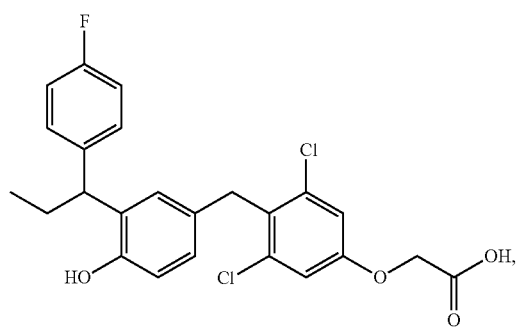 [SMILES: CCC(c1ccc(F)cc1)c1cc(Cc2c(Cl)cc(OCC(=O)O)cc2Cl)ccc1O] |
| 99 | 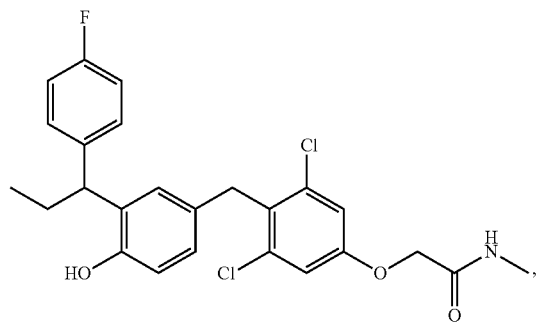 [SMILES: CCC(c1ccc(F)cc1)c1cc(Cc2c(Cl)cc(OCC(=O)NC)cc2Cl)ccc1O] |
| 100 | 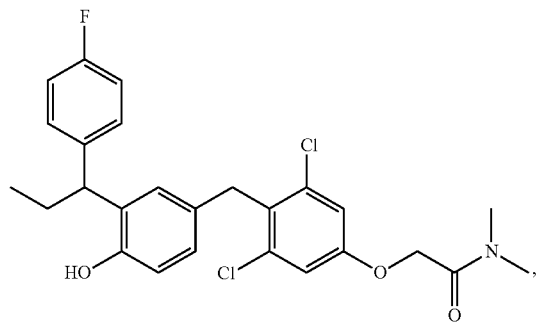 [SMILES: CCC(c1ccc(F)cc1)c1cc(Cc2c(Cl)cc(OCC(=O)N(C)C)cc2Cl)ccc1O] |

-continued
| Compound Number | Structure |
|---|---|
| 101 | 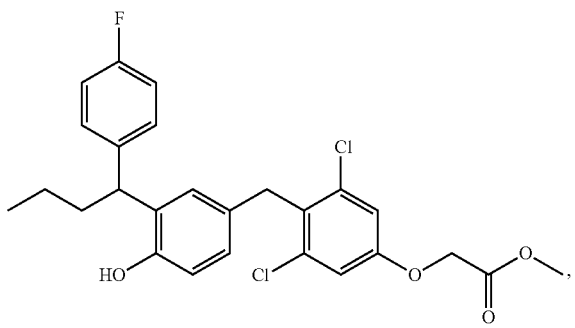 [SMILES: CCCC(c1ccc(F)cc1)c1cc(Cc2c(Cl)cc(OCC(=O)OC)cc2Cl)ccc1O] |
| 102 | 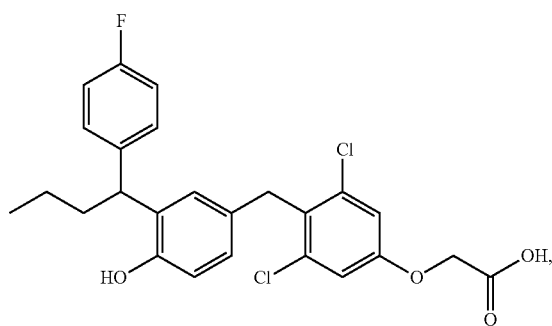 [SMILES: CCCC(c1ccc(F)cc1)c1cc(Cc2c(Cl)cc(OCC(=O)O)cc2Cl)ccc1O] |
| 103 | 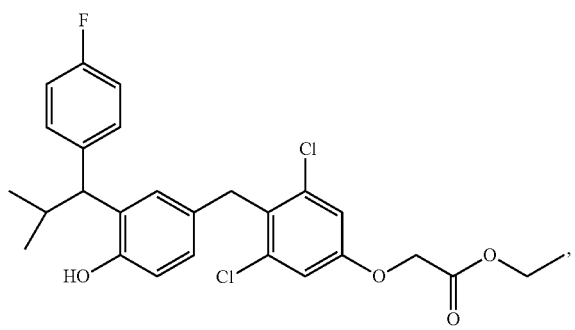 [SMILES: CCOC(=O)COc1cc(Cl)c(Cc2ccc(O)c(C(c3ccc(F)cc3)C(C)C)c2)c(Cl)c1] |
| 104 | 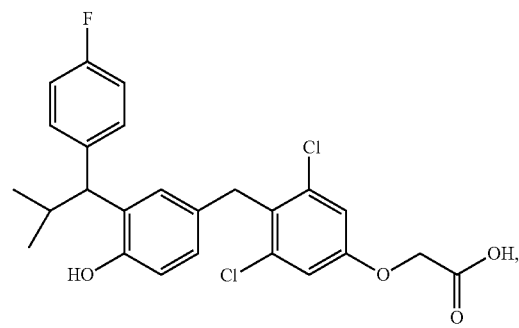 [SMILES: CC(C)C(c1ccc(F)cc1)c1cc(Cc2c(Cl)cc(OCC(=O)O)cc2Cl)ccc1O] |

-continued
| Compound Number | Structure |
|---|---|
| 105 | 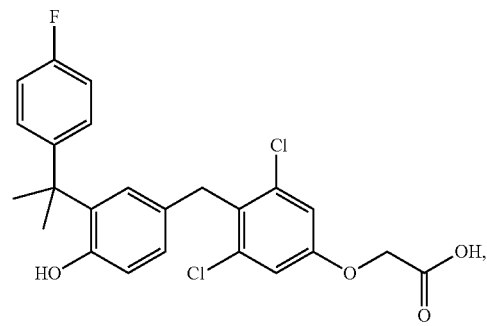 [SMILES: CC(C)(c1ccc(F)cc1)c1cc(Cc2c(Cl)cc(OCC(=O)O)cc2Cl)ccc1O] |
| 106 | 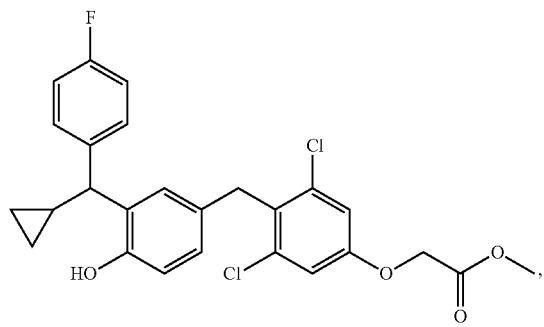 [SMILES: COC(=O)COc1cc(Cl)c(Cc2ccc(O)c(C(c3ccc(F)cc3)C3CC3)c2)c(Cl)c1] |
| 107 | 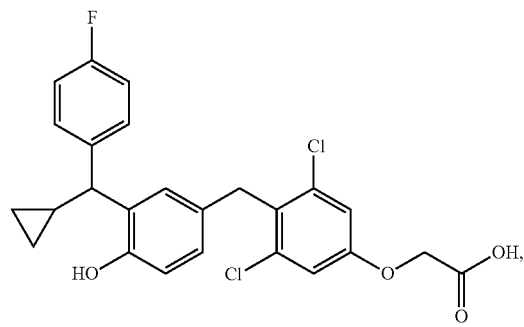 [SMILES: O=C(O)COc1cc(Cl)c(Cc2ccc(O)c(C(c3ccc(F)cc3)C3CC3)c2)c(Cl)c1] |
| 108 | 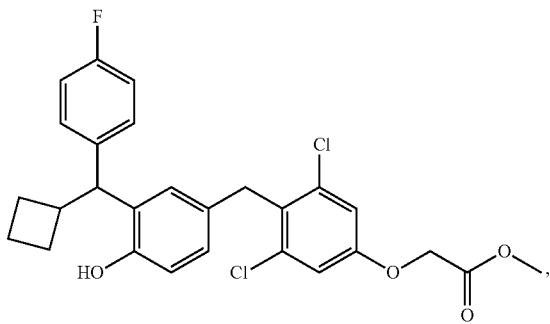 [SMILES: COC(=O)COc1cc(Cl)c(Cc2ccc(O)c(C(c3ccc(F)cc3)C3CCC3)c2)c(Cl)c1] |

| Compound Number | Structure |
|---|---|
| 109 | 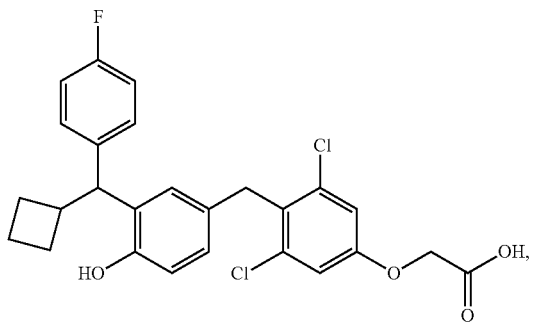 [SMILES: O=C(O)COc1cc(Cl)c(Cc2ccc(O)c(C(c3ccc(F)cc3)C3CCC3)c2)c(Cl)c1] |
| 110 | 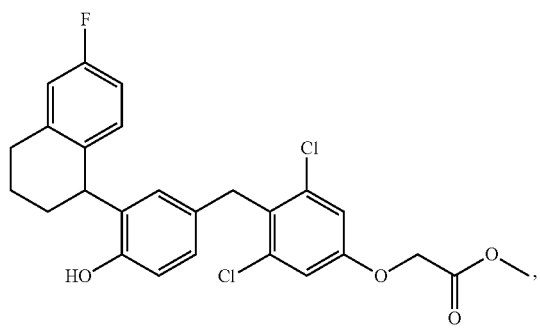 [SMILES: COC(=O)COc1cc(Cl)c(Cc2ccc(O)c(C3CCCc4cc(F)ccc43)c2)c(Cl)c1] |
| 111 | 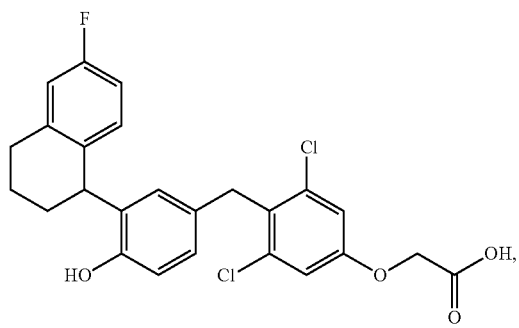 [SMILES: O=C(O)COc1cc(Cl)c(Cc2ccc(O)c(C3CCCc4cc(F)ccc43)c2)c(Cl)c1] |
| 112 | 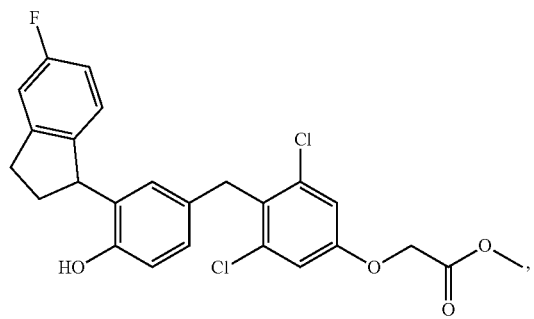 [SMILES: COC(=O)COc1cc(Cl)c(Cc2ccc(O)c(C3CCc4cc(F)ccc43)c2)c(Cl)c1] |

| Compound Number | Structure |
|---|---|
| 113 | 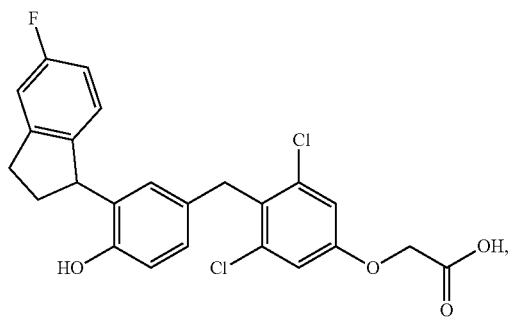 [SMILES: O=C(O)COc1cc(Cl)c(Cc2ccc(O)c(C3CCc4cc(F)ccc43)c2)c(Cl)c1] |
| 114 | 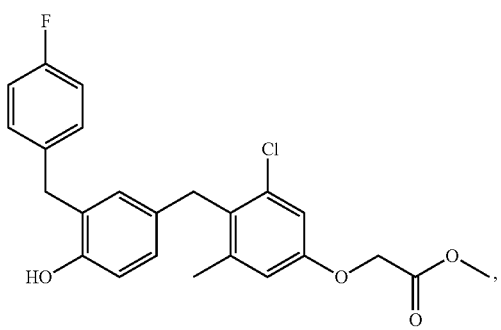 [SMILES: COC(=O)COc1cc(C)c(Cc2ccc(O)c(Cc3ccc(F)cc3)c2)c(Cl)c1] |
| 115 | 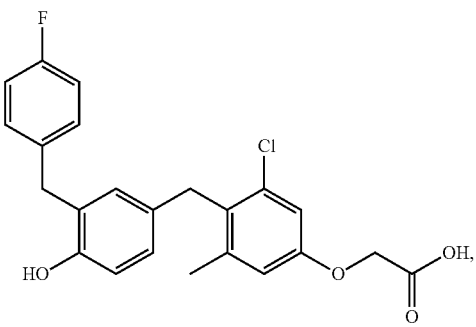 |
| 116 | 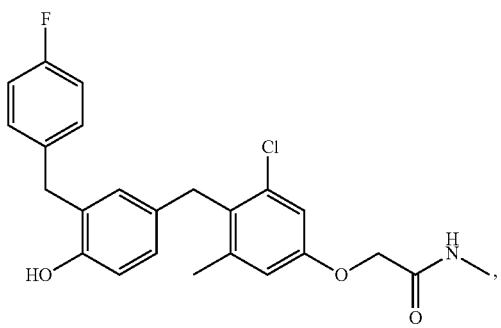 [SMILES: CNC(=O)COc1cc(C)c(Cc2ccc(O)c(Cc3ccc(F)cc3)c2)c(Cl)c1] |

-continued
| Compound Number | Structure |
| --- | --- |
| 117 | 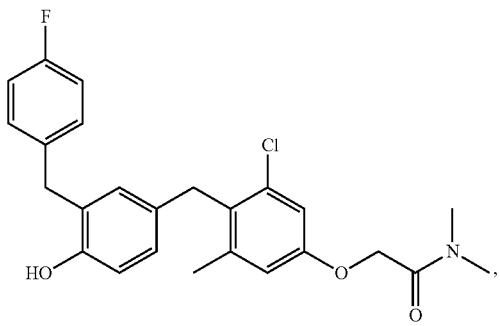 [SMILES: Cc1cc(OCC(=O)N(C)C)cc(Cl)c1Cc1ccc(O)c(Cc2ccc(F)cc2)c1] |
| 118 | 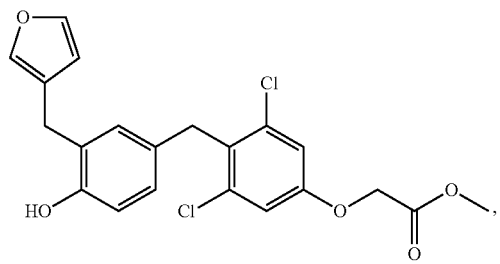 [SMILES: COC(=O)COc1cc(Cl)c(Cc2ccc(O)c(Cc3ccoc3)c2)c(Cl)c1] |
| 119 | 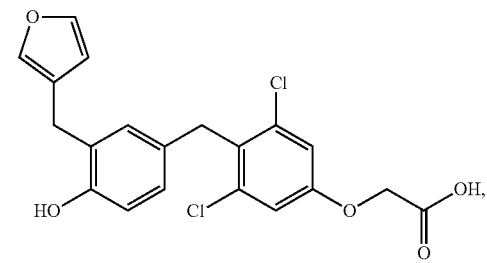 [SMILES: O=C(O)COc1cc(Cl)c(Cc2ccc(O)c(Cc3ccoc3)c2)c(Cl)c1] |
| 120 | 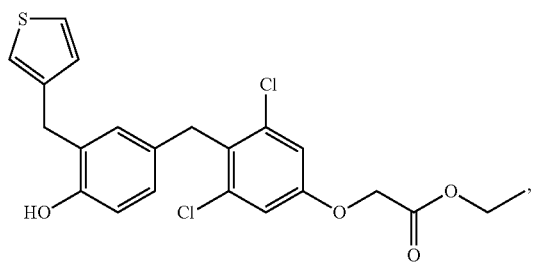 [SMILES: CCOC(=O)COc1cc(Cl)c(Cc2ccc(O)c(Cc3ccsc3)c2)c(Cl)c1] |
| 121 | 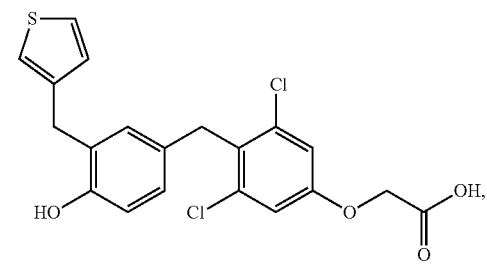 [SMILES: O=C(O)COc1cc(Cl)c(Cc2ccc(O)c(Cc3ccsc3)c2)c(Cl)c1] |

| Compound Number | Structure |
|---|---|
| 122 | (structure) |
| 123 | (structure) |
| 124 | (structure) |
| 125 | (structure) |
| 126 | (structure) |

-continued
| Compound Number | Structure |
|---|---|
| 127 | 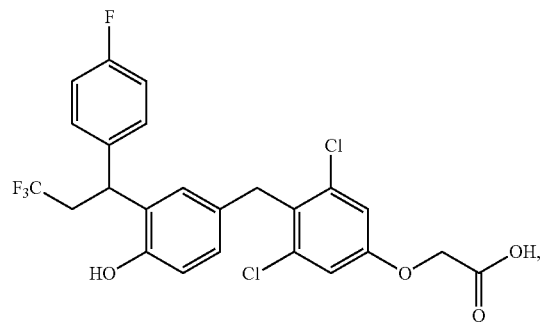 [SMILES: O=C(O)COc1cc(Cl)c(Cc2ccc(O)c(C(CC(F)(F)F)c3ccc(F)cc3)c2)c(Cl)c1] |
| 128 | 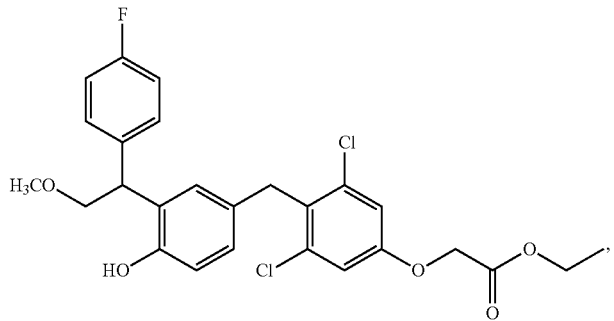 [SMILES: CCOC(=O)COc1cc(Cl)c(Cc2ccc(O)c(C(COC)c3ccc(F)cc3)c2)c(Cl)c1] |
| 129 | 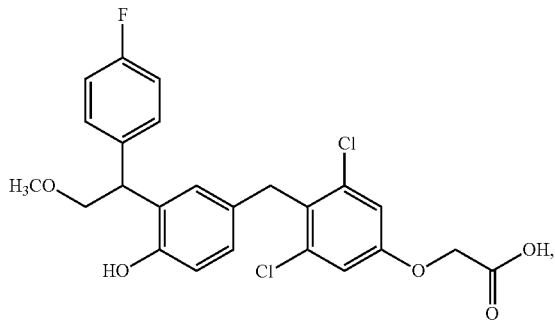 [SMILES: COCC(c1ccc(F)cc1)c1cc(Cc2c(Cl)cc(OCC(=O)O)cc2Cl)ccc1O] |
| 130 | 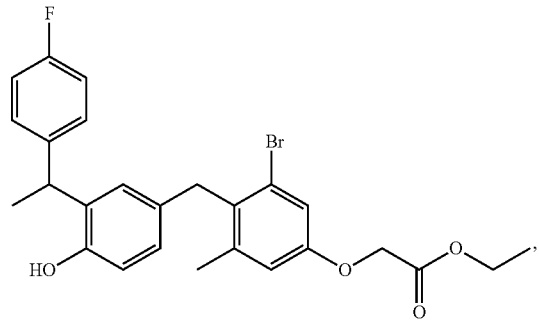 [SMILES: CCOC(=O)COc1cc(C)c(Cc2ccc(O)c(C(C)c3ccc(F)cc3)c2)c(Br)c1] |

-continued
| Compound Number | Structure |
|---|---|
| 131 | 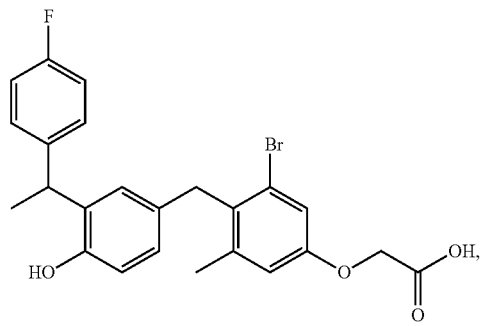 [SMILES: Cc1cc(OCC(=O)O)cc(Br)c1Cc1ccc(O)c(C(C)c2ccc(F)cc2)c1] |
| 132 | 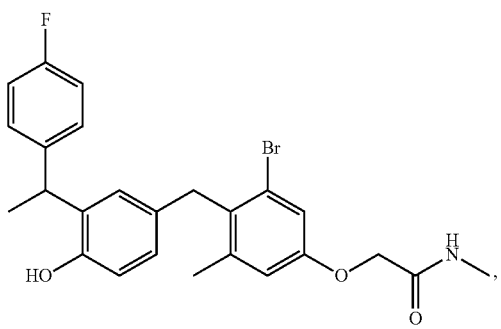 [SMILES: CNC(=O)COc1cc(C)c(Cc2ccc(O)c(C(C)c3ccc(F)cc3)c2)c(Br)c1] |
| 133 | 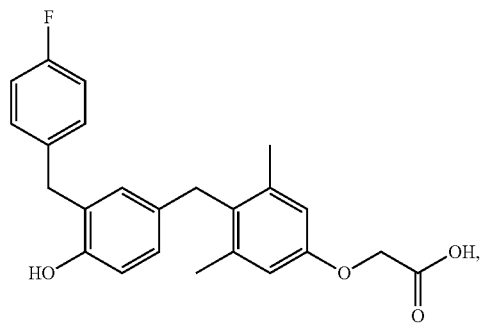 [SMILES: Cc1cc(OCC(=O)O)cc(C)c1Cc1ccc(O)c(Cc2ccc(F)cc2)c1] |
| 134 | 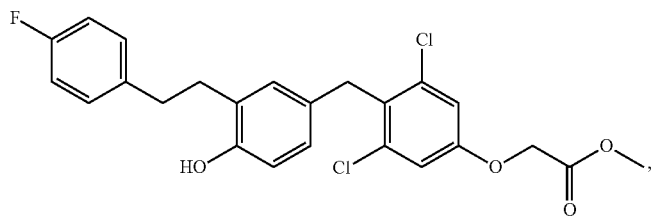 [SMILES: COC(=O)COc1cc(Cl)c(Cc2ccc(O)c(CCc3ccc(F)cc3)c2)c(Cl)c1] |
| 135 | 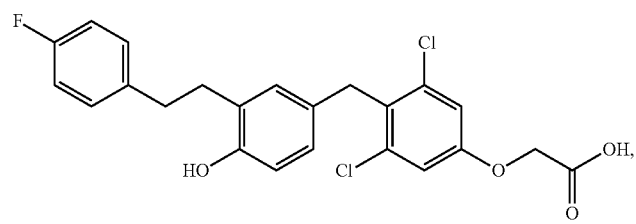 [SMILES: O=C(O)COc1cc(Cl)c(Cc2ccc(O)c(CCc3ccc(F)cc3)c2)c(Cl)c1] |

| Compound Number | Structure |
|---|---|
| 136 | 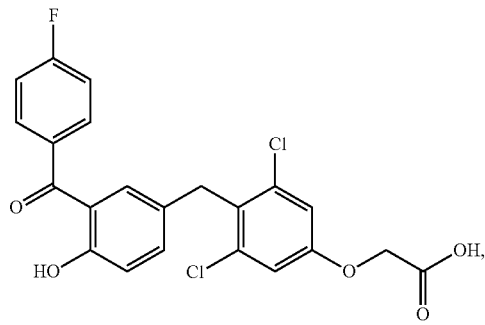 [SMILES: O=C(O)COc1cc(Cl)c(Cc2ccc(O)c(C(=O)c3ccc(F)cc3)c2)c(Cl)c1] |
| 137 | 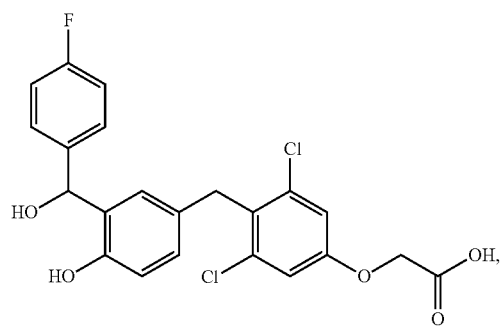 [SMILES: O=C(O)COc1cc(Cl)c(Cc2ccc(O)c(C(O)c3ccc(F)cc3)c2)c(Cl)c1] |
| 138 | 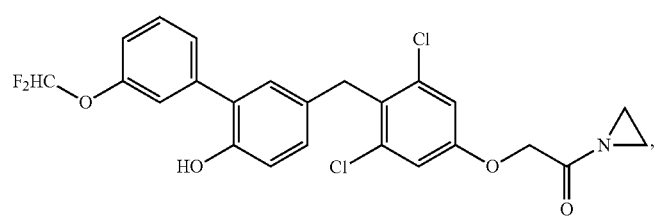 [SMILES: O=C(COc1cc(Cl)c(Cc2ccc(O)c(-c3cccc(OC(F)F)c3)c2)c(Cl)c1)N1CC1] |
| 139 | 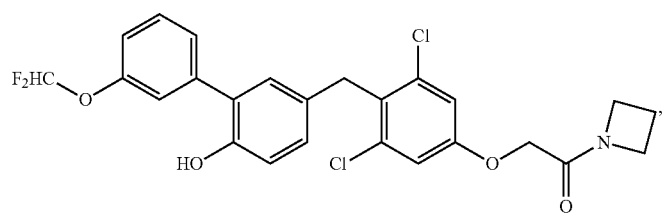 [SMILES: O=C(COc1cc(Cl)c(Cc2ccc(O)c(-c3cccc(OC(F)F)c3)c2)c(Cl)c1)N1CCC1] |
| 140 | 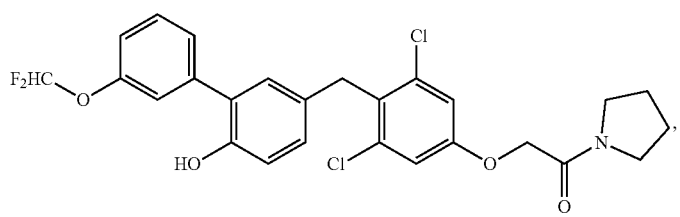 [SMILES: O=C(COc1cc(Cl)c(Cc2ccc(O)c(-c3cccc(OC(F)F)c3)c2)c(Cl)c1)N1CCCC1] |
| 141 | 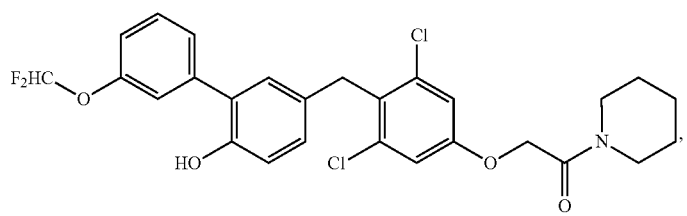 [SMILES: O=C(COc1cc(Cl)c(Cc2ccc(O)c(-c3cccc(OC(F)F)c3)c2)c(Cl)c1)N1CCCCC1] |

-continued
| Compound Number | Structure |
|---|---|
| 142 | 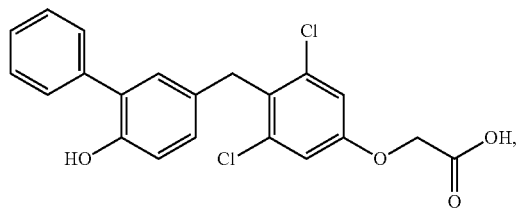 [SMILES: O=C(O)COc1cc(Cl)c(Cc2ccc(O)c(-c3ccccc3)c2)c(Cl)c1] |
| 143 | 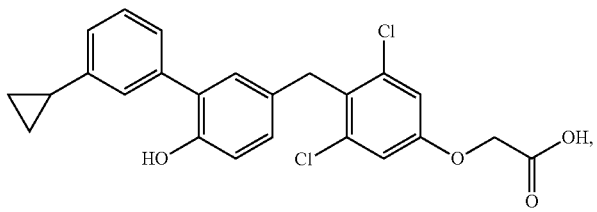 [SMILES: O=C(O)COc1cc(Cl)c(Cc2ccc(O)c(-c3cccc(C4CC4)c3)c2)c(Cl)c1] |
| 144 | 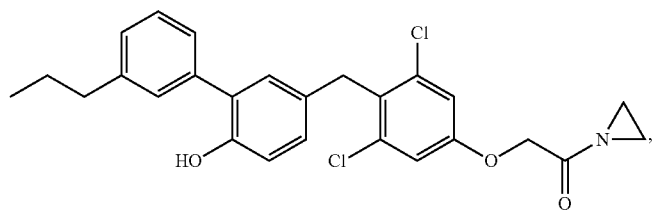 [SMILES: CCCc1cccc(-c2cc(Cc3c(Cl)cc(OCC(=O)N4CC4)cc3Cl)ccc2O)c1] |
| 145 | 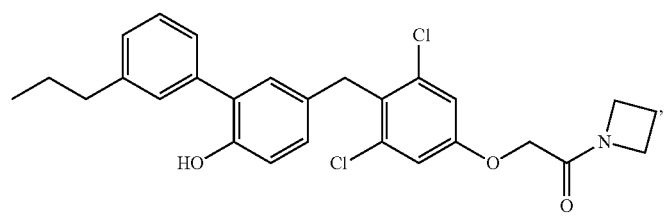 [SMILES: CCCc1cccc(-c2cc(Cc3c(Cl)cc(OCC(=O)N4CCC4)cc3Cl)ccc2O)c1] |
| 146 | 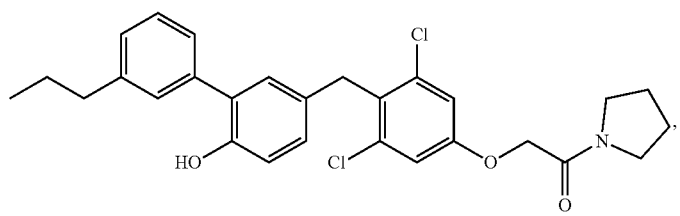 [SMILES: CCCc1cccc(-c2cc(Cc3c(Cl)cc(OCC(=O)N4CCCC4)cc3Cl)ccc2O)c1] |
| 147 | 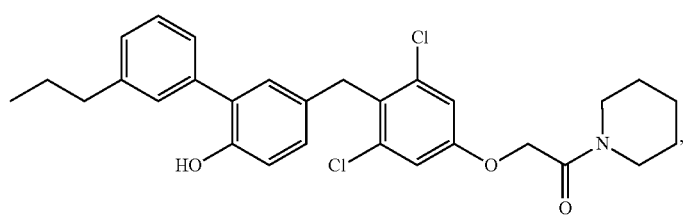 [SMILES: CCCc1cccc(-c2cc(Cc3c(Cl)cc(OCC(=O)N4CCCCC4)cc3Cl)ccc2O)c1] |
| 148 | 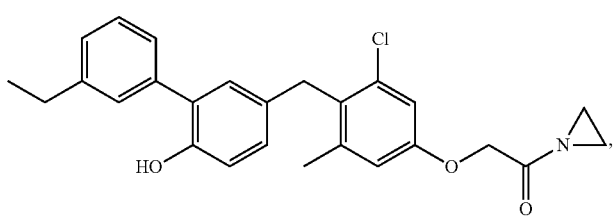 [SMILES: CCc1cccc(-c2cc(Cc3c(C)cc(OCC(=O)N4CC4)cc3Cl)ccc2O)c1] |

299
-continued
| Compound Number | Structure |
|---|---|
| 149 | 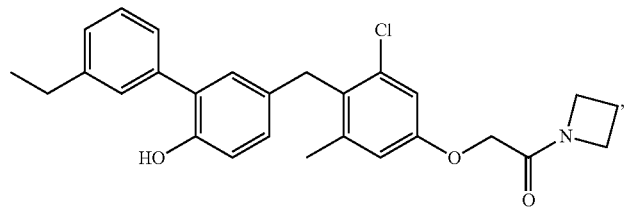 [SMILES: CCc1cccc(-c2cc(Cc3c(C)cc(OCC(=O)N4CCC4)cc3Cl)ccc2O)c1] |
| 150 | 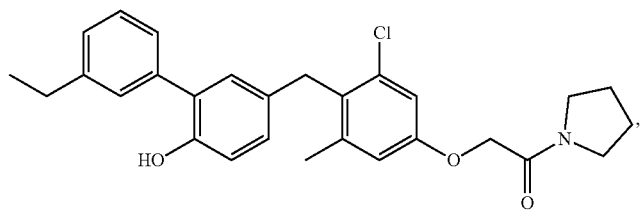 [SMILES: CCc1cccc(-c2cc(Cc3c(C)cc(OCC(=O)N4CCCC4)cc3Cl)ccc2O)c1] |
| 151 | 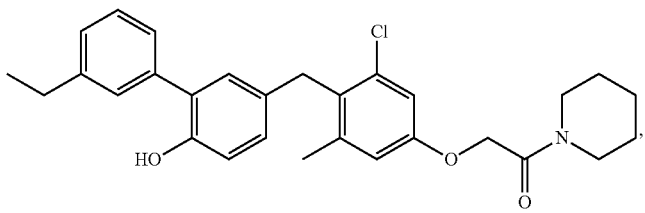 [SMILES: CCc1cccc(-c2cc(Cc3c(C)cc(OCC(=O)N4CCCCC4)cc3Cl)ccc2O)c1] |
| 152 | 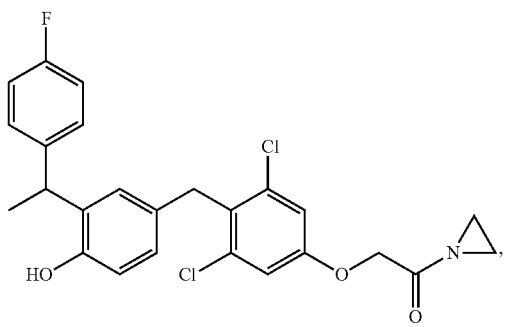 [SMILES: CC(c1ccc(F)cc1)c1cc(Cc2c(Cl)cc(OCC(=O)N3CC3)cc2Cl)ccc1O] |
| 153 | 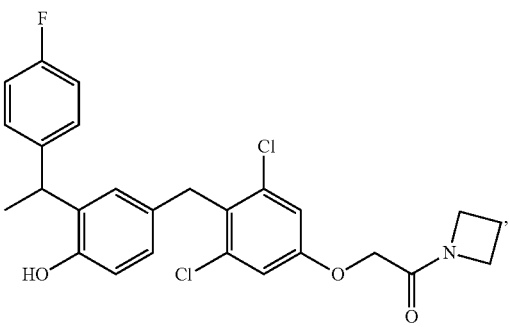 [SMILES: CC(c1ccc(F)cc1)c1cc(Cc2c(Cl)cc(OCC(=O)N3CCC3)cc2Cl)ccc1O] |
300

| Compound Number | Structure |
|---|---|
| 154 | 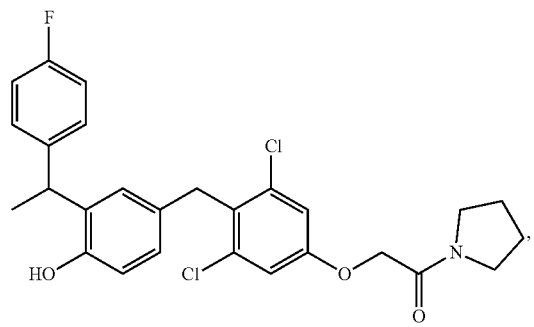 [SMILES: CC(c1ccc(F)cc1)c1cc(Cc2c(Cl)cc(OCC(=O)N3CCCC3)cc2Cl)ccc1O] |
| 155 | 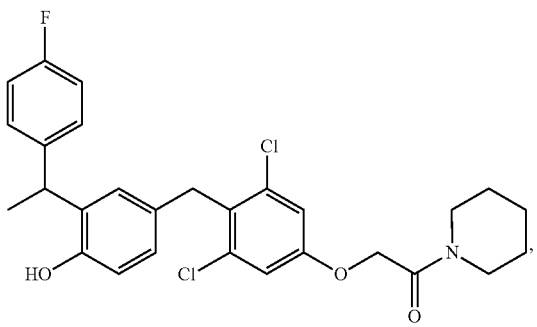 [SMILES: CC(c1ccc(F)cc1)c1cc(Cc2c(Cl)cc(OCC(=O)N3CCCCC3)cc2Cl)ccc1O] |
| 156 | 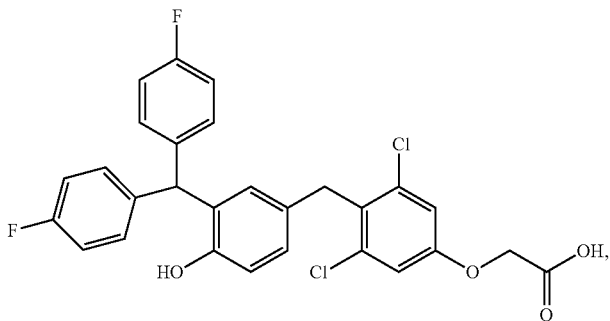 [SMILES: O=C(O)COc1cc(Cl)c(Cc2ccc(O)c(C(c3ccc(F)cc3)c3ccc(F)cc3)c2)c(Cl)c1] |
| 157 | 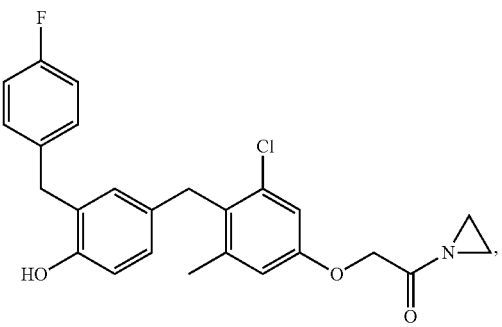 [SMILES: Cc1cc(OCC(=O)N2CC2)cc(Cl)c1Cc1ccc(O)c(Cc2ccc(F)cc2)c1] |

-continued
| Compound Number | Structure |
|---|---|
| 158 | 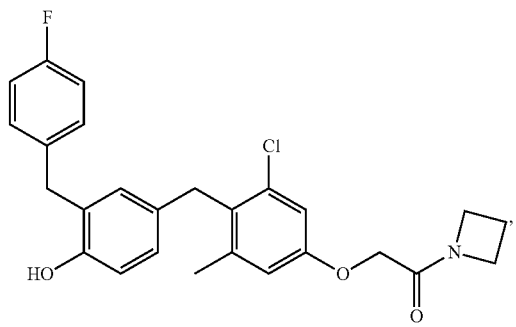 [SMILES: Cc1cc(OCC(=O)N2CCC2)cc(Cl)c1Cc1ccc(O)c(Cc2ccc(F)cc2)c1] |
| 159 | 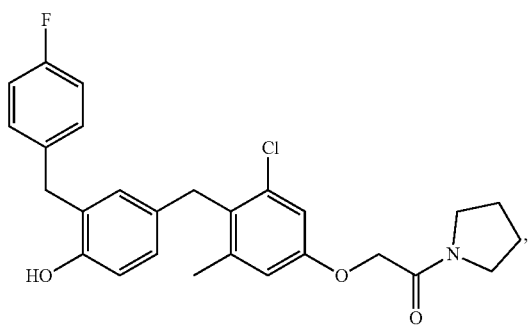 [SMILES: Cc1cc(OCC(=O)N2CCCC2)cc(Cl)c1Cc1ccc(O)c(Cc2ccc(F)cc2)c1] |
| 160 | 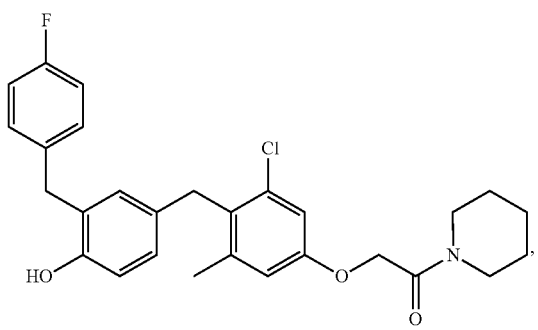 [SMILES: Cc1cc(OCC(=O)N2CCCCC2)cc(Cl)c1Cc1ccc(O)c(Cc2ccc(F)cc2)c1] |
| 161 | 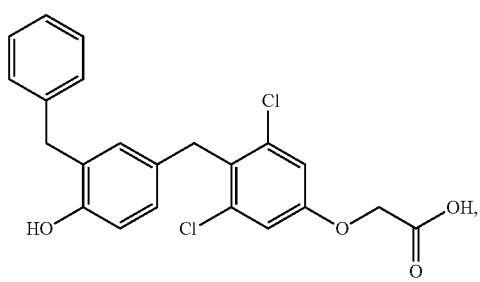 [SMILES: O=C(O)COc1cc(Cl)c(Cc2ccc(O)c(Cc3ccccc3)c2)c(Cl)c1] |
| 162 | 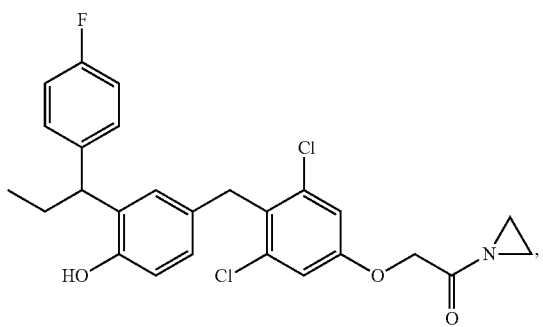 [SMILES: CCC(c1ccc(F)cc1)c1cc(Cc2c(Cl)cc(OCC(=O)N3CC3)cc2Cl)ccc1O] |

| Compound Number | Structure |
|---|---|
| 163 | 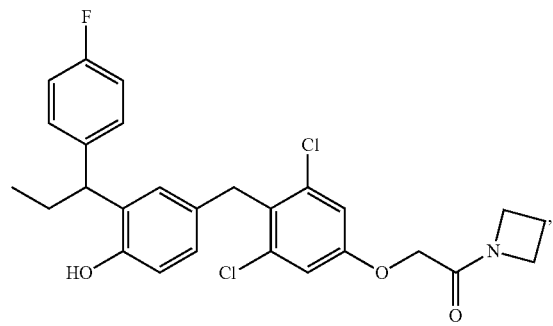 [SMILES: CCC(c1ccc(F)cc1)c1cc(Cc2c(Cl)cc(OCC(=O)N3CCC3)cc2Cl)ccc1O] |
| 164 | 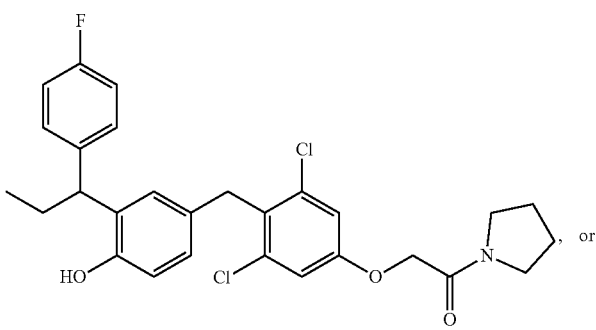 [SMILES: CCC(c1ccc(F)cc1)c1cc(Cc2c(Cl)cc(OCC(=O)N3CCCC3)cc2Cl)ccc1O], or |
| 165 | 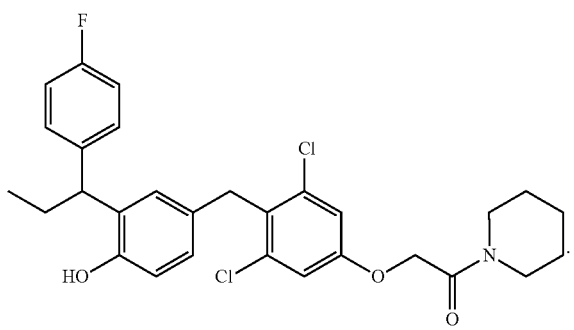 [SMILES: CCC(c1ccc(F)cc1)c1cc(Cc2c(Cl)cc(OCC(=O)N3CCCCC3)cc2Cl)ccc1O] |

28. A pharmaceutical composition comprising a compound of claim 1, or a pharmaceutically acceptable isomer, racemate, hydrate, solvate, isotope, or salt thereof, and a pharmaceutically acceptable excipient.

29. A method of treating a subject having NASH, NAFLD, NAFLD with hyperlipidemia, alcoholic liver disease/alcoholic steatohepatitis, liver fibrosis associated with viral infection (HBV, HCV), fibrosis associated with cholestatic diseases (primary biliary cholangitis, primary sclerosing cholangitis), (familial) hypercholesterolemia, dyslipidemia, genetic lipid disorders, cirrhosis, alcohol-induced fibrosis, hemochromatosis, glycogen storage diseases, alpha-1 antitrypsin deficiency, autoimmune hepatitis, Wilson's disease, Crigler-Najjar Syndrome, lysosomal acid lipase deficiency, liver disease in cystic fibrosis, the method comprising administering to the subject in need thereof a pharmaceutically effective amount of the compound of claim 1, or a pharmaceutically acceptable salt or composition thereof.

30. A method of treating a subject having Alport syndrome, diabetic nephropathy, FSGS, fibrosis associated with IgA nephropathy, chronic kidney diseases (CKD), post AKI, HIV associated CKD, chemotherapy induced CKD, CKD associated with nephrotoxic agents, nephrogenic systemic fibrosis, tubulointerstitial fibrosis, glomerulosclerosis, or polycystic kidney disease (PKD), the method comprising administering to the subject in need thereof a pharmaceutically effective amount of the compound of claim 1, or a pharmaceutically acceptable salt or composition thereof.

31. A method of treating a subject having IPF, ILD, pulmonary fibrosis, pulmonary fibrosis associated with autoimmune diseases like rheumatoid arthritis, scleroderma or Sjogren's syndrome, asthma-related pulmonary fibrosis, COPD, asbestos or silica induced PF, silicosis, respiratory bronchiolitis, Idiopathic interstitial pneumonias (IIP), Idiopathic nonspecific interstitial pneumonia, Respiratory bronchiolitis-interstitial lung disease, desquamative interstitial pneumonia, acute interstitial pneumonia, Rare IIPs: Idiopathic lymphoid interstitial pneumonia, idiopathic pleuroparenchymal fibroelastosis, unclassifiable idiopathic interstitial pneumonias, hypersensitivity pneumonitis, radiation-induced lung injury, progressive massive fibrosis— pneumoconiosis, bronchiectasis, byssinosis, chronic respiratory disease, chronic obstructive pulmonary disease (COPD), emphysema, pulmonary arterial hypertension (PAH), or Cystic fibrosis, the method comprising administering to the subject in need thereof a pharmaceutically effective amount of the compound of claim 1, or a pharmaceutically acceptable salt or composition thereof.

32. A method of treating a subject having scleroderma/systemic sclerosis, graft versus host disease, hypertrophic scars, keloids, nephrogenic systemic fibrosis, *porphyria cutanea tarda*, restrictive dermopathy, Dupuytren's contracture, dermal fibrosis, nephrogenic systemic fibrosis/nephrogenic fibrosing dermopathy, mixed connective tissue disease, scleromyxedema, eosinophilic fasciitis, fibrosis caused by exposure to chemicals or physical agents, GvHD induced fibrosis, *Scleredema adultorum*, Lipodermatosclerosis, or Progeroid disorders (progeria, acrogeria, Werner's syndrome), the method comprising administering to the subject in need thereof a pharmaceutically effective amount of the compound of claim 1, or a pharmaceutically acceptable salt or composition thereof.

33. A method of treating a subject having atrial fibrosis, endomyocardial fibrosis, cardiac fibrosis, *atherosclerosis*, restenosis, or arthrofibrosis, the method comprising administering to the subject in need thereof a pharmaceutically effective amount of the compound of claim 1, or a pharmaceutically acceptable salt or composition thereof.

34. A method of treating a subject having mediastinal fibrosis, myelofibrosis, post-polycythermia vera myelofibrosis, or post essential thrombocythemia, the method comprising administering to the subject in need thereof a pharmaceutically effective amount of the compound of claim 1, or a pharmaceutically acceptable salt or composition thereof.

35. A method of treating a subject having Crohn's disease, retroperitoneal fibrosis, intestinal fibrosis, fibrosis in inflammatory bowel disease, ulcerative colitis, GI fibrosis due to cystic fibrosis, or pancreatic fibrosis due to pancreatitis, the method comprising administering to the subject in need thereof a pharmaceutically effective amount of the compound of claim 1, or a pharmaceutically acceptable salt or composition thereof.

36. A method of treating a subject having endometrial fibrosis, uterine fibroids, or Peyronie's disease, the method comprising administering to the subject in need thereof a pharmaceutically effective amount of the compound of claim 1, or a pharmaceutically acceptable salt or composition thereof.

37. A method of treating a subject having macular degeneration, diabetic retinopathy, retinal fibrovascular diseases, or vitreal retinopathy, the method comprising administering to the subject in need thereof a pharmaceutically effective amount of the compound of claim 1, or a pharmaceutically acceptable salt or composition thereof.

38. A method of treating a subject having scarring associated with trauma, the method comprising administering to the subject in need thereof a pharmaceutically effective amount of the compound of claim 1, or a pharmaceutically acceptable salt or composition thereof.

* * * * *

UNITED STATES PATENT AND TRADEMARK OFFICE
CERTIFICATE OF CORRECTION

PATENT NO. : 11,667,606 B2
APPLICATION NO. : 16/803853
DATED : June 6, 2023
INVENTOR(S) : Thomas von Geldern et al.

Page 1 of 1

It is certified that error appears in the above-identified patent and that said Letters Patent is hereby corrected as shown below:

In the Claims

Columns 257-258
In Claim 27, delete the first compound 46 entry
" 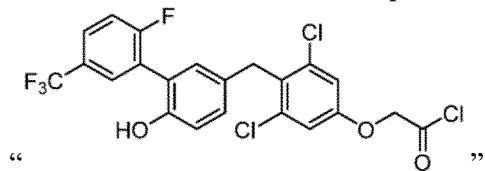 "

Columns 263-284
In Claim 27, delete the entries for compounds 69-109

Columns 285-296
In Claim 27, delete the entries for compounds 114-137

Columns 297-298
In Claim 27, delete the entry for compound 142
" 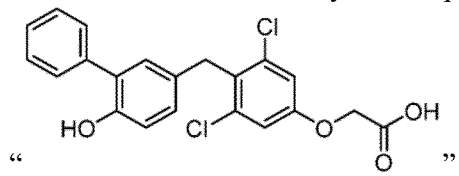 "

Columns 299-306
In Claim 27, delete the entries for compounds 152-165

Signed and Sealed this
Eighth Day of August, 2023

Katherine Kelly Vidal
*Director of the United States Patent and Trademark Office*